US012734259B2

(12) United States Patent
Osterkamp et al.

(10) Patent No.: US 12,734,259 B2
(45) **Date of Patent: *Sep. 15, 2026**

(54) COMPOUNDS COMPRISING A FIBROBLAST ACTIVATION PROTEIN LIGAND AND USE THEREOF

(71) Applicant: 3B PHARMACEUTICALS GMBH, Berlin (DE)

(72) Inventors: Frank Osterkamp, Berlin (DE); Dirk Zboralski, Berlin (DE); Eberhard Schneider, Brandenburg (DE); Christian Haase, Berlin (DE); Matthias Paschke, Berlin (DE); Aileen Höhne, Berlin (DE); Jan Ungewiss, Berlin (DE); Christiane Smerling, Berlin (DE); Ulrich Reineke, Berlin (DE); Anne Bredenbeck, Berlin (DE)

(73) Assignee: 3B PHARMACEUTICALS GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/392,245

(22) Filed: Nov. 18, 2025

(65) Prior Publication Data

US 2026/0061086 A1 Mar. 5, 2026

Related U.S. Application Data

(63) Continuation of application No. 19/328,329, filed on Sep. 15, 2025, which is a continuation of application No. 17/625,139, filed as application No. PCT/EP2020/069298 on Jul. 8, 2020, now Pat. No. 12,427,210.

(30) Foreign Application Priority Data

Jul. 8, 2019 (EP) .................................... 19000325
Sep. 20, 2019 (EP) .................................... 19198813

(51) Int. Cl.
*A61K 51/08* (2006.01)
*A61K 38/00* (2006.01)
*C07K 7/08* (2006.01)

(52) U.S. Cl.
CPC .............. *A61K 51/088* (2013.01); *C07K 7/08* (2013.01); *A61K 38/00* (2013.01)

(58) Field of Classification Search
CPC ...... A61K 51/00; A61K 51/08; A61K 51/088; A61K 38/00; C07K 7/08; C07K 7/06; A61P 1/00; A61P 1/16; A61P 9/00; A61P 11/00; A61P 29/00; A61P 35/00; A61P 37/03
See application file for complete search history.

(56) References Cited

U.S. PATENT DOCUMENTS

| | | | | |
|---|---|---|---|---|
| 6,890,904 | B1 | 5/2005 | Wallner et al. | |
| 8,450,275 | B2 | 5/2013 | Dockal et al. | |
| 8,466,108 | B2 | 6/2013 | Dockal et al. | |
| 8,962,563 | B2 | 2/2015 | Dockal et al. | |
| 9,018,167 | B2 | 4/2015 | Dockal et al. | |
| 9,556,230 | B2 | 1/2017 | Dockal et al. | |
| 9,777,051 | B2 | 10/2017 | Dockal et al. | |
| 9,873,720 | B2 | 1/2018 | Dockal et al. | |
| 10,201,586 | B2 | 2/2019 | Dockal et al. | |
| 10,370,433 | B2 | 8/2019 | Sahin et al. | |
| 10,799,605 | B2 | 10/2020 | Osterkamp et al. | |
| 10,800,816 | B2 | 10/2020 | Dockal et al. | |
| 10,961,199 | B2 | 3/2021 | Osterkamp et al. | |
| 11,001,613 | B2 | 5/2021 | Dockal et al. | |
| 12,427,210 | B2 * | 9/2025 | Osterkamp .......... | A61K 51/088 |
| 2006/0073518 | A1 | 4/2006 | Timmerman et al. | |
| 2008/0280856 | A1 | 11/2008 | Cohen et al. | |
| 2017/0066800 | A1 | 3/2017 | Mckee et al. | |
| 2017/0119913 | A1 | 5/2017 | Osterkamp et al. | |
| 2018/0022822 | A1 | 1/2018 | Brokopp et al. | |
| 2019/0134147 | A1 | 5/2019 | Dockal et al. | |
| 2021/0087149 | A1 | 3/2021 | Osterkamp et al. | |
| 2022/0315554 | A1 | 10/2022 | Osterkamp et al. | |
| 2023/0212549 | A1 | 7/2023 | Osterkamp et al. | |
| 2024/0115745 | A1 | 4/2024 | Osterkamp et al. | |

FOREIGN PATENT DOCUMENTS

| | | | |
|---|---|---|---|
| CN | 104837819 | A | 8/2015 |
| CN | 105949282 | A | 9/2016 |
| CN | 106046121 | A | 10/2016 |
| CN | 107531776 | A | 1/2018 |
| EP | 2 954 933 | A1 | 12/2015 |
| WO | 99/16864 | A1 | 4/1999 |
| WO | 99/57151 | A2 | 11/1999 |
| WO | 01/68708 | A2 | 9/2001 |
| WO | 2004/077062 | A2 | 9/2004 |
| WO | 2006/042282 | A2 | 4/2006 |
| WO | 2008/116054 | A1 | 9/2008 |
| WO | 2010/036814 | A1 | 4/2010 |
| WO | 2011/040972 | A1 | 4/2011 |
| WO | 2012/020006 | A2 | 2/2012 |
| WO | 2013/107820 | A1 | 7/2013 |
| WO | 2014/161845 | A1 | 10/2014 |
| WO | 2015/118030 | A2 | 8/2015 |
| WO | 2016/146174 | A1 | 9/2016 |
| WO | 2016/146639 | A1 | 9/2016 |
| WO | 2017/127007 | A1 | 7/2017 |
| WO | 2017/211809 | A1 | 12/2017 |
| WO | 2018/111989 | A1 | 6/2018 |
| WO | 2019/083990 | A2 | 5/2019 |
| WO | 2021/005131 | A1 | 1/2021 |

OTHER PUBLICATIONS

Smita B. Gunnoo et al, "Chemical Protein Modification Through Cysteine," 17(7) ChemBioChem 529-553 (Apr. 2016).

(Continued)

*Primary Examiner* — D. L. Jones
(74) *Attorney, Agent, or Firm* — Venable LLP

(57) ABSTRACT

The present invention is related to a compound comprising a cyclic peptide and a chelator, and its use.

30 Claims, 12 Drawing Sheets

Specification includes a Sequence Listing.

(56) References Cited

OTHER PUBLICATIONS

Claire M. Grison et al., “Double Quick, Double Click Reversible Peptide “Stapling”,” 8(7) Chem. Sci. 5166-5171 (Jan. 2017).
Mauricio Morais et al., “Site-Specific Chelator-Antibody Conjugation for PET and SPECT Imaging with Radiometals,” 30 Drug Discov. Today Technol. 91-104 (Oct. 2018).
Ben M. Dunn et al., “The Synthesis, Purification, and Evaluation of a Chromophoric Substrate for Pepsin and Other Aspartyl Proteases: Design of a Substrate Based on Subsite Preferences,” 138(1) 68-73 (Apr. 1984) (XP024764499).
Frederik L. Giesel et al., “68Ga-FAPI PET/CT: Biodistribution and Preliminary Dosimetry Estimate of 2 DOTA-Containing FAP-Targeting Agents in Patients with Various Cancers,” 60(3) J. Nucl. Med. 386-392 (Mar. 2019).

* cited by examiner

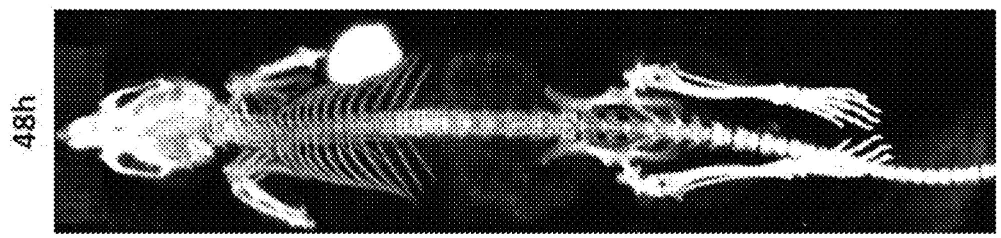
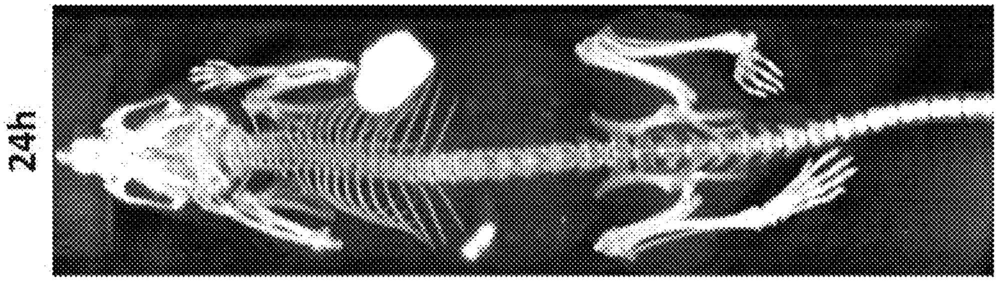
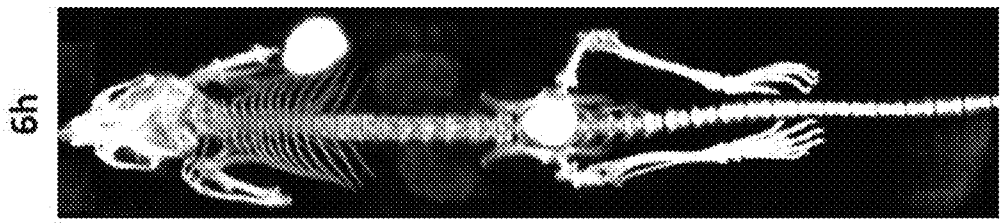
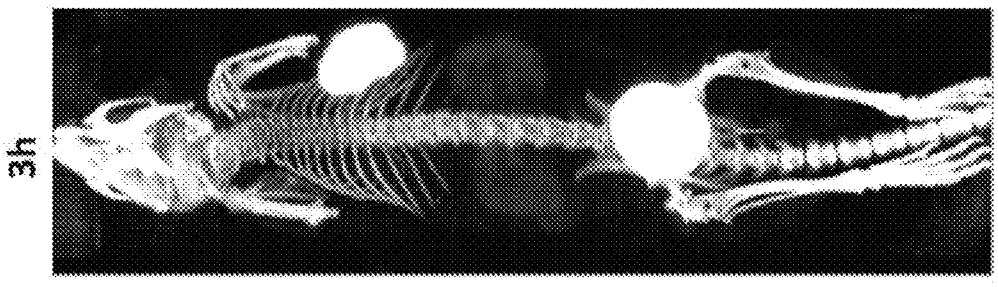
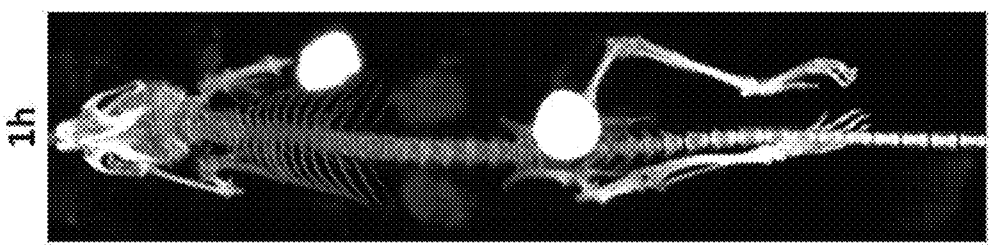
15
%ID/g
0.5
Fig. 7

Fibroblast activation protein (FAP), homo sapiens (UniProtKB - Q12884 (SEPR_HUMAN):

```
>sp|Q12884|SEPR_HUMAN Prolyl endopeptidase FAP OS=Homo sapiens OX=9606
GN=FAP PE=1 SV=5
MKTWVKIVFGVATSAVLALLVMCIVLRPSRVHNSEENTMRALTLKDILNGTFSYKTFFPN
WISGQEYLHQSADNNIVLYNIETGQSYTILSNRTMKSVNASNYGLSPDRQFVYLESDYSK
LWRYSYTATYYIYDLSNGEFVRGNELPRPIQYLCWSPVGSKLAYVYQNNIYLKQRPGDPP
FQITFNGRENKIFNGIPDWVYEEEMLATKYALWWSPNGKFLAYAEFNDTDIPVIAYSYYG
DEQYPRTINIPYPKAGAKNPVVRIFIIDTTYPAYVGPQEVPVPAMIASSDYYFSWLTWVT
DERVCLQWLKRVQNVSVLSICDFREDWQTWDCPKTQEHIEESRTGWAGGFFVSTPVFSYD
AISYYKIFSDKDGYKHIHYIKDTVENAIQITSGKWEAINIFRVTQDSLFYSSNEFEEYPG
RRNIYRISIGSYPPSKKCVTCHLRKERCQYYTASFSDYAKYYALVCYGPGIPISTLHDGR
TDQEIKILEENKELENALKNIQLPKEEIKKLEVDEITLWYKMILPPQFDRSKKYPLLIQV
YGGPCSQSVRSVFAVNWISYLASKEGMVIALVDGRGTAFQGDKLLYAVYRKLGVYEVEDQ
ITAVRKFIEMGFIDEKRIAIWGWSYGGYVSSLALASGTGLFKCGIAVAPVSSWEYYASVY
TERFMGLPTKDDNLEHYKNSTVMARAEYFRNVDYLLIHGTADDNVHFQNSAQIAKALVNA
QVDFQAMWYSDQNHGLSGLSTNHLYTHMTHFLKQCFSLSD
```

Dipeptidyl peptidase 4 (DPP4), homo sapiens (UniProtKB - P27487 (DPP4_HUMAN):

```
>sp|P27487|DPP4_HUMAN Dipeptidyl peptidase 4 OS=Homo sapiens OX=9606
GN=DPP4 PE=1 SV=2
MKTPWKVLLGLLGAAALVTIITVPVVLLNKGTDDATADSRKTYTLTDYLKNTYRLKLYSL
RWISDHEYLYKQENNILVFNAEYGNSSVFLENSTFDEFGHSINDYSISPDGQFILLEYNY
VKQWRHSYTASYDIYDLNKRQLITEERIPNNTQWVTWSPVGHKLAYVWNNDIYVKIEPNL
PSYRITWTGKEDIIYNGITDWVYEEEVFSAYSALWWSPNGTFLAYAQFNDTEVPLIEYSF
YSDESLQYPKTVRVPYPKAGAVNPTVKFFVVNTDSLSSVTNATSIQITAPASMLIGDHYL
CDVTWATQERISLQWLRRIQNYSVMDICDYDESSGRWNCLVARQHIEMSTTGWVGRFRPS
EPHFTLDGNSFYKIISNEEGYRHICYFQIDKKDCTFITKGTWEVIGIEALTSDYLYYISN
EYKGMPGGRNLYKIQLSDYTKVTCLSCELNPERCQYYSVSFSKEAKYYQLRCSGPGLPLY
TLHSSVNDKGLRVLEDNSALDKMLQNVQMPSKKLDFIILNETKFWYQMILPPHFDKSKKY
PLLLDVYAGPCSQKADTVFRLNWATYLASTENIIVASFDGRGSGYQGDKIMHAINRRLGT
FEVEDQIEAARQFSKMGFVDNKRIAIWGWSYGGYVTSMVLGSGSGVFKCGIAVAPVSRWE
YYDSVYTERYMGLPTPEDNLDHYRNSTVMSRAENFKQVEYLLIHGTADDNVHFQQSAQIS
KALVDVGVDFQAMWYTDEDHGIASSTAHQHIYTHMSHFIKQCFSLP
```

Prolyl endopeptidase (PREP), homo sapiens (UniProtKB - P48147 (PPCE_HUMAN):

```
>sp|P48147|PPCE_HUMAN Prolyl endopeptidase OS=Homo sapiens OX=9606 GN=PREP
PE=1 SV=2
MLSLQYPDVYRDETAVQDYHGHKICDPYAWLEDPDSEQTKAFVEAQNKITVPFLEQCPIR
GLYKERMTELYDYPKYSCHFKKGKRYFYFYNTGLQNQRVLYVQDSLEGEARVFLDPNILS
DDGTVALRGYAFSEDGEYFAYGLSASGSDWVTIKFMKVDGAKELPDVLERVKFSCMAWTH
DGKGMFYNSYPQQDGKSDGTETSTNLHQKLYYHVLGTDQSEDILCAEFPDEPKWMGGAEL
SDDGRYVLLSIREGCDPVNRLWYCDLQQESSGIAGILKWVKLIDNFEGEYDYVTNEGTVF
TFKTNRQSPNYRVINIDFRDPEESKWKVLVPEHEKDVLEWIACVRSNFLVLCYLHDVKNI
LQLHDLTTGALLKTFPLDVGSIVGYSGQKKDTEIFYQFTSFLSPGIIYHCDLTKEELEPR
VFREVTVKGIDASDYQTVQIFYPSKDGTKIPMFIVHKKGIKLDGSHPAFLYGYGGFNISI
TPNYSVSRLIFVRHMGGILAVANIRGGGEYGETWHKGGILANKQNCFDDFQCAAEYLIKE
GYTSPKRLTINGGSNGGLLVAACANQRPDLFGCVIAQVGVMDMLKFHKYTIGHAWTTDYG
CSDSKQHFEWLVKYSPLHNVKLPEADDIQYPSMLLLTADHDDRVVPLHSLKFIATLQYIV
GRSRKQSNPLLIHVDTKAGHGAGKPTAKVIEEVSDMFAFIARCLNVDWIP
```

Fig. 8

SEQUENCE LISTING

```
Sequence total quantity: 3
SEQ ID NO: 1            moltype = AA  length = 760
FEATURE                 Location/Qualifiers
REGION                  1..760
                        note = MISC_FEATURE - Fibroblast activation protein (FAP)
source                  1..760
                        mol_type = protein
                        organism = Homo sapiens
SEQUENCE: 1
MKTWVKIVFG VATSAVLALL VMCIVLRPSR VHNSEENTMR ALTLKDILNG TFSYKTFFPN  60
WISGQEYLHQ SADNNIVLYN IETGQSYTIL SNRTMKSVNA SNYGLSPDRQ FVYLESDYSK  120
LWRYSYTATY YIYDLSNGEF VRGNELPRPI QYLCWSPVGS KLAYVYQNNI YLKQRPGDPP  180
FQITFNGREN KIFNGIPDWV YEEEMLATKY ALWWSPNGKF LAYAEFNDTD IPVIAYSYYG  240
DEQYPRTINI PYPKAGAKNP VVRIFIIDTT YPAYVGPQEV PVPAMIASSD YYFSWLTWVT  300
DERVCLQWLK RVQNVSVLSI CDFREDWQTW DCPKTQEHIE ESRTGWAGGF FVSTPVFSYD  360
AISYYKIFSD KDGYKHIHYI KDTVENAIQI TSGKWEAINI FRVTQDSLFY SSNEFEEYPG  420
RRNIYRISIG SYPPSKKCVT CHLRKERCQY YTASFSDYAK YYALVCYGPG IPISTLHDGR  480
TDQEIKILEE NKELENALKN IQLPKEEIKK LEVDEITLWY KMILPPQFDR SKKYPLLIQV  540
YGGPCSQSVR SVFAVNWISY LASKEGMVIA LVDGRGTAFQ GDKLLYAVYR KLGVYEVEDQ  600
ITAVRKFIEM GFIDEKRIAI WGWSYGGYVS SLALASGTGL FKCGIAVAPV SSWEYYASVY  660
TERFMGLPTK DDNLEHYKNS TVMARAEYFR NVDYLLIHGT ADDNVHFQNS AQIAKALVNA  720
QVDFQAMWYS DQNHGLSGLS TNHLYTHMTH FLKQCFSLSD                         760

SEQ ID NO: 2            moltype = AA  length = 766
FEATURE                 Location/Qualifiers
REGION                  1..766
                        note = MISC_FEATURE - Dipeptidyl peptidase 4 (DPP4)
source                  1..766
                        mol_type = protein
                        organism = Homo sapiens
SEQUENCE: 2
MKTPWKVLLG LLGAAALVTI ITVPVVLLNK GTDDATADSR KTYTLTDYLK NTYRLKLYSL  60
RWISDHEYLY KQENNILVFN AEYGNSSVFL ENSTFDEFGH SINDYSISPD GQFILLEYNY  120
VKQWRHSYTA SYDIYDLNKR QLITEERIPN NTQWVTWSPV GHKLAYVWNN DIYVKIEPNL  180
PSYRITWTGK EDIIYNGITD WVYEEEVFSA YSALWWSPNG TFLAYAQFND TEVPLIEYSF  240
YSDESLQYPK TVRVPYPKAG AVNPTVKFFV VNTDSLSSVT NATSIQITAP ASMLIGDHYL  300
CDVTWATQER ISLQWLRRIQ NYSVMDICDY DESSGRWNCL VARQHIEMST TGWVGRFRPS  360
EPHFTLDGNS FYKIISNEEG YRHICYFQID KKDCTFITKG TWEVIGIEAL TSDYLYYISN  420
EYKGMPGGRN LYKIQLSDYT KVTCLSCELN PERCQYYSVS FSKEAKYYQL RCSGPGLPLY  480
TLHSSVNDKG LRVLEDNSAL DKMLQNVQMP SKKLDFIILN ETKFWYQMIL PPHFDKSKKY  540
PLLLDVYAGP CSQKADTVFR LNWATYLAST ENIIVASFDG RGSGYQGDKI MHAINRRLGT  600
FEVEDQIEAA RQFSKMGFVD NKRIAIWGWS YGGYVTSMVL GSGSGVFKCG IAVAPVSRWE  660
YYDSVYTERY MGLPTPEDNL DHYRNSTVMS RAENFKQVEY LLIHGTADDN VHFQQSAQIS  720
KALVDVGVDF QAMWYTDEDH GIASSTAHQH IYTHMSHFIK QCFSLP                  766

SEQ ID NO: 3            moltype = AA  length = 710
FEATURE                 Location/Qualifiers
REGION                  1..710
                        note = MISC_FEATURE - Prolyl endopeptidase (PREP)
source                  1..710
                        mol_type = protein
                        organism = Homo sapiens
SEQUENCE: 3
MLSLQYPDVY RDETAVQDYH GHKICDPYAW LEDPDSEQTK AFVEAQNKIT VPFLEQCPIR  60
GLYKERMTEL YDYPKYSCHF KKGKRYFYFY NTGLQNQRVL YVQDSLEGEA RVFLDPNILS  120
DDGTVALRGY AFSEDGEYFA YGLSASGSDW VTIKFMKVDG AKELPDVLER VKFSCMAWTH  180
DGKGMFYNSY PQQDGKSDGT ETSTNLHQKL YYHVLGTDQS EDILCAEFPD EPKWMGGAEL  240
SDDGRYVLLS IREGCDPVNR LWYCDLQQES SGIAGILKWV KLIDNFEGEY DYVTNEGTVF  300
TFKTNRQSPN YRVINIDFRD PEESKWKVLV PEHEKDVLEW IACVRSNFLV LCYLHDVKNI  360
LQLHDLTTGA LLKTFPLDVG SIVGYSGQKK DTEIFYQFTS FLSPGIIYHC DLTKEELEPR  420
VFREVTVKGI DASDYQTVQI FYPSKDGTKI PMFIVHKKGI KLDGSHPAFL YGYGGFNISI  480
TPNYSVSRLI FVRHMGGILA VANIRGGGEY GETWHKGGIL ANKQNCFDDF QCAAEYLIKE  540
GYTSPKRLTI NGGSNGGLLV AACANQRPDL FGCVIAQVGV MDMLKFHKYT IGHAWTTDYG  600
CSDSKQHFEW LVKYSPLHNV KLPEADDIQY PSMLLLTADH DDRVVPLHSL KFIATLQYIV  660
GRSRKQSNPL LIHVDTKAGH GAGKPTAKVI EEVSDMFAFI ARCLNVDWIP               710
```

COMPOUNDS COMPRISING A FIBROBLAST ACTIVATION PROTEIN LIGAND AND USE THEREOF

CROSS-REFERENCE TO RELATED APPLICATIONS

This application is a continuation application of U.S. patent application Ser. No. 19/328,329, filed Sep. 15, 2025, which is a continuation application of U.S. patent application Ser. No. 17/625,139, which was the U.S. National Stage Entry of International Application No. PCT/EP2020/069298, filed Jul. 8, 2020, now U.S. Pat. No. 12,427,210, which claims the benefit of European Application No. 19000325.1, filed Jul. 8, 2019, and European Application No. 19198813.8, filed Sep. 20, 2019. All prior applications are incorporated by reference herein in their entirety.

REFERENCE TO AN ELECTRONIC SEQUENCE LISTING

The contents of the electronic sequence listing (d 10026 pct_sequence listing_st26.xml; Size: 6,894 bytes; and Date of Creation: Sep. 5, 2025) are herein incorporated by reference in their entirety.

FIELD OF INVENTION

The present invention is related to a chemical compound; an inhibitor of fibroblast activation protein (FAP); a composition comprising the compound and inhibitor, respectively; the compound, the inhibitor and the composition, respectively, for use in a method for the diagnosis of a disease; the compound, the inhibitor and the composition, respectively, for use in a method for the treatment of a disease; the compound, the inhibitor and the composition, respectively, for use in a method of diagnosis and treatment of a disease which is also referred to as "thera(g)nosis" or "thera(g)nostics"; the compound, the inhibitor and the composition, respectively, for use in a method for delivering an effector to a FAP-expressing tissue; a method for the diagnosis of a disease using the compound, the inhibitor and the composition, respectively; a method for the treatment of a disease using the compound, the inhibitor and the composition, respectively; a method for the diagnosis and treatment of a disease which is also referred to as "thera(g)nosis" or "thera(g)nostics, using the compound, the inhibitor and the composition, respectively; a method for the delivery of an effector to a FAP-expressing tissue using the compound, the inhibitor and the composition, respectively.

BACKGROUND

Despite the increasing availability of therapeutic options, cancer is still the second leading cause of death globally. Therapeutic strategies mainly focus on targeting malignant cancer cells itself, ignoring the ever-present surrounding tumor microenvironment (TME) that limit the access of therapeutic cancer cell agents (Valkenburg, et al., *Nat Rev Clin Oncol,* 2018, 15:366). The TME is part of the tumor mass and consists not only of the heterogeneous population of cancer cells but also of a variety of resident and infiltrating host cells, secreted factors, and extracellular matrix proteins (Quail, et al., *Nat Med,* 2013, 19:1423). A dominant cell type found in the TME is the cancer associated fibroblast (CAF) (Kalluri, *Nat Rev Cancer,* 2016, 16:582). Many different cell types have been described as the source and origin for CAFs, such as e.g. fibroblasts, mesenchymal stem cells, smooth muscle cells, cells of epithelial origin, or endothelial cells (Madar, et al., *Trends Mol Med,* 2013, 19:447). CAFs exhibit mesenchymal-like features and often are the dominant cell type within a solid tumor mass. CAFs have attracted increasing attention as a player in tumor progression and homeostasis (Gascard, et al., *Genes Dev,* 2016, 30:1002; LeBleu, et al., *Dis Model Mech,* 2018, 11). During recent years, fibroblast activation protein (FAP) has gained notoriety as a marker of CAFs (Shiga, et al., *Cancers* (*Basel*), 2015, 7:2443; Pure, et al., *Oncogene,* 2018, 37:4343; Jacob, et al., *Curr Mol Med,* 2012, 12:1220). Due to the omnipresence of CAFs and stroma within tumors, FAP was discovered as a suitable marker for radiopharmaceutical diagnostics and as a suitable target for radiopharmaceutical therapy (Siveke, *J Nucl Med,* 2018, 59:1412).

Fibroblast activation protein a (FAP) is a type II transmembrane serine protease and a member of the S9 prolyl oligopeptidase family (Park, et al., *J Biol Chem,* 1999, 274:36505). The closest family member DPP4 shares 53% homology with FAP. Like other DPP enzymes (DPP4, DPP7, DPP8, DPP9), FAP has post-proline exopeptidase activity. In addition, FAP possesses endopeptidase activity, similar to prolyl oligopeptidase/endopeptidase (POP/PREP). The FAP gene is highly conserved across various species. The extracellular domain of human FAP shares 90% amino acid sequence identity with mouse and rat FAP. Mouse FAP has 97% sequence identity with rat FAP.

Structurally, FAP is a 760 amino acid transmembrane protein composed of a short N-terminal cytoplasmic tail (6 amino acids), a single transmembrane domain (20 amino acids), and a 734 amino acid extracellular domain (Aertgeerts, et al., *J Biol Chem,* 2005, 280:19441). This extracellular domain consists of an eight-bladed β-propeller and an α/β hydrolase domain. The catalytic triad is composed of Ser624, Asp702, and His734 and is located at the interface of the ß-propeller and the hydrolase domain. The active site is accessible through a central hole of the ß-propeller domain or through a narrow cavity between the β-propeller and the hydrolase domain. FAP monomers are not active, but form active homodimers as well as heterodimers with DPP4 (Ghersi, et al., *Cancer Res,* 2006, 66:4652). Soluble homodimeric FAP has also been described (Keane, et al., *FEBS Open Bio,* 2013, 4:43; Lee, et al., *Blood,* 2006, 107:1397).

FAP possesses dual enzyme activity (Hamson, et al., *Proteomics Clin Appl,* 2014, 8:454). Its dipeptidyl peptidase activity allows cleaving two amino acids of the N-terminus after a proline residue. FAP substrates that are cleaved rapidly via its dipeptidyl peptidase activity are neuropeptide Y, Peptide Y Y, Substance P, and B-type natriuretic peptide. Collagen I and III, FGF21 and $\alpha_2$-antiplasmin have been shown to be cleaved by the endopeptidase activity of FAP. While FAP is unable to cleave native collagens, pre-digestion by other proteases, such as matrix metalloproteinases, facilitates further collagen cleavage by FAP. Processing of collagen may influence migratory capacities of cancer cells. Besides increasing invasiveness of cancer cells through remodeling of the extracellular matrix, several other FAP-mediated tumor promoting roles have been proposed, including proliferation and increasing angiogenesis. Furthermore, stromal expression of FAP is linked to escape from immunosurveillance in various cancers, suggesting a role in anti-tumor immunity (Pure, et al., *Oncogene,* 2018, 37:4343).

FAP is transiently expressed during normal development, but only rarely in healthy adult tissues. In transgenic mice, it was demonstrated that FAP is expressed by adipose tissue, skeletal muscle, skin, bone and pancreas (Pure, et al., *Oncogene,* 2018, 37:4343; Roberts, et al., *J Exp Med,* 2013, 210:1137). However, a FAP knockout mouse has a healthy phenotype, suggesting a redundant role under normal conditions (Niedermeyer, et al., *Mol Cell Biol,* 2000, 20:1089). At sites of active tissue remodeling, including wound healing, fibrosis, arthritis, atherosclerosis and cancer, FAP becomes highly upregulated in stromal cells (Pure, et al., *Oncogene,* 2018, 37:4343).

FAP expression in the tumor stroma of 90% of epithelial carcinomas was first reported in 1990 under use of a monoclonal antibody, F19 (Garin-Chesa, et al., *Proc Natl Acad Sci USA,* 1990, 87:7235; Rettig, et al., *Cancer Res,* 1993, 53:3327). FAP-expressing stromal cells were further characterized as cancer-associated fibroblasts (CAF) and cancer-associated pericytes (Cremasco, et al., *Cancer Immunol Res,* 2018, 6:1472). FAP expression on malignant epithelial cells has also been reported but its significance remains to be defined (Pure, et al., *Oncogene,* 2018, 37:4343). The following Table 1, taken from Busek et al. (Busek, et al., *Front Biosci* (*Landmark Ed*), 2018, 23:1933), summarizes the expression of FAP in various malignancies indicating the tumor type and the cellular expression.

TABLE 1

FAP expression in human malignancies (from Busek et al.)

| Tumor Type | Expression of FAP in Malignant Cells | Expression of FAP in Stroma Cells | Notes |
|---|---|---|---|
| Basal cell carcinoma, squamous cell carcinoma of the skin | − | + | Expression in fibroblasts strongest in close proximity to cancer cells. FAP expression is absent in benign epithelial tumors, its positivity in the stroma may be a useful criterion for differentiating between morpheaform/infiltrative basal cell carcinomas FAP-negative desmoplastic trichoepithelioma. |
| Oral squamous cell carcinoma | + | + | FAP is a negative prognostic marker-elevated expression is associated with greater tumor size, lymph-node metastasis, advanced clinical stage, and worse overall survival. |
| Melanoma | − (in situ) | + | FAP expression present in a subset of melanocytes in 30% of benign melanocytic nevi, but not detectable in malignant melanoma cells in melanoma tissues. The quantity of FAP-positive stromal cells is positively associated with ECM content and inflammatory cell infiltration. Normal melanocytes express FAP in vitro. Conflicting data for FAP in melanoma cells: several human melanoma cell lines express FAP and FAP contributes to their invasiveness in vitro, but immunopositivity has not been detected in melanoma tissues. Mouse melanoma cell lines are FAP-negative and mouse FAP is a tumor suppressor independently of its enzymatic activity. |
| Esophageal cancer | + | + | FAP is expressed in cancer cells as well as in premalignant metaplastic cells of the esophagus in both adenocarcinoma and squamous cell carcinoma. |
| Gastric cancer | + | + (incl. low expression in endothelial cells) | A higher stromal FAP expression at the invasion front is associated with low tumor cell differentiation, more advanced TNM stage, serosal invasion, and poor survival. A higher stromal FAP is associated with worse survival. A higher FAP expression in intestinal-type gastric cancer (in stroma, moderately differentiated cancer cells, and endothelial cells) than in the diffuse type (mainly in cancer cells with poor cell-to-cell contacts, endothelial cells). A higher stromal FAP expression in the intestinal-type gastric cancer is associated with the presence of liver and lymph node metastases. |
| Colorectal cancer | + | + | A higher stromal FAP positivity found in earlier-stage disease, but in patients with stage IV tumors high FAP is associated with worse survival. A higher FAP expression is associated with advanced Duke stage. A high FAP expression in the tumor center is a negative prognostic factor. Stromal FAP expression in stage II/III rectal cancer after chemoradiotherapy is associated with a worse prognosis. A higher FAP mRNA expression is associated with worse disease-free survival and a trend for worse overall survival. |
| Pancreatic adenocarcinoma | + | + | FAP expression in carcinoma cells is associated with a larger tumor size, presence of a fibrotic focus, perineural invasion, and a worse prognosis. Stromal FAP expression correlates with lymph node metastasis and reduced survival. Nevertheless, a recent retrospective Korean study reports an association between a lower number of FAP+ fibroblasts and a decreased overall survival based on a univariate analysis. |

TABLE 1-continued

FAP expression in human malignancies (from Busek et al.)

| Tumor Type | Expression of FAP in Malignant Cells | Expression of FAP in Stroma Cells | Notes |
|---|---|---|---|
| Hepatocellular carcinoma | + | | FAP expression detected especially in tumors with abundant fibrous stroma. FAP mRNA expression increased in peritumoral tissue, positively correlating with the density of peritumoral activated HSCs. Higher levels are associated with more frequent early recurrence, larger tumor size, presence of vascular invasion, and an advanced TNM stage. |
| Non-small cell lung cancer | −/+ | + | Absence of stromal FAP expression (24% of cases) in NSCLC is associated with better survival. Reports regarding expression in cancer cells are inconsistent. |
| Mesothelioma | + | + | Expression, although to a variable extent, has been detected in all subtypes. |
| Breast tumors | + (ductal adenocarcinoma) | + (incl. endothelial cells | FAP positivity detected mainly in the stroma; another study proposes a predominant localization in cancer cells in ductal adenocarcinoma. Jung et al. observed expression in cancer and stromal cells in 50% of cases where stroma is rich in adipose tissue (approximately 1/3 of all tumors); in these cases, FAP expression was associated with a higher tumor grade. In tumors with fibrous stroma, FAP expression was virtually absent (2/3 of all tumors)<br>FAP expression is higher in cancer cells in lobular cancer than in ductal carcinoma. Stromal FAP and calponin positivity may be an ancillary marker for detecting microinvasion in ductal carcinoma. FAP expression increases with the malignant progression of phyllodes tumors, but a later study detected stromal FAP expression only in 12.5% of the malignant phyllodes tumors by IHC.<br>Conflicting data regarding a possible association with breast cancer survival: smaller studies have reported that a higher total FAP mRNA expression is associated with worse survival, while a higher stromal FAP expression detected by IHC was associated with a longer overall survival and disease-free survival. A recent larger study involving 939 breast cancer patients did not prove any association between FAP expression in the cancer or stromal cells and survival. |
| Renal cancer | − | + | Stromal FAP expression (detected in 23% of cases) associated with markers of aggressiveness and worse survival in clear cell renal cell carcinoma. In metastatic clear cell renal carcinoma, stromal FAP expression was detected in 36% of primary and 44% of metastatic lesions, and was associated with several parameters of tumor aggressiveness and worse survival. |
| Prostate cancer | − | + | Only small patient cohorts reported in literature. Expression in stromal cells detected in 7/7 cases, most intense in stromal cells adjacent to cancer cells. |
| Cervical cancer | + | + | No FAP expression was detected in preinvasive cervical neoplasia (CIN1, 2), occasional positivity in stroma in CIN3 with moderate or severe inflammatory infiltrates. Enhanced expression of FAP was found in cancer cells and subepithelial stromal cells in some of the microinvasive and all of the invasive carcinomas. |
| Ovary | + | + | FAP positivity increases with tumor stage; negative FAP expression is associated with longer disease-free survival. FAP positivity detected in cancer cells in 21% of tumors, stromal positivity in 61%. Another study reported stromal positivity in 92% of cancer tissues with extremely rare FAP expression in malignant cells; it also reported an association with advanced tumor stage and presence of lymph node metastases. FAP-positive malignant cells are present in malignant pleural and peritoneal effusions: strong positivity is associated with worse survival. |
| Glioma | + | + | FAP expression increased in glioblastoma, highest expression found in the mesenchymal subtype and gliosarcoma. Low expression in glioma stem-like cells. In glioblastoma, overall FAP quantity is not associated with survival. |
| Thyroid cancer | − | + | FAP upregulated in aggressive papillary thyroid carcinomas. In medullary thyroid carcinoma, FAP expression in the peritumoral and intratumoral stromal compartment correlates with the degree of desmoplasia and presence of lymph node metastases. |

TABLE 1-continued

| FAP expression in human malignancies (from Busek et al.) | | | |
|---|---|---|---|
| Tumor Type | Expression of FAP in Malignant Cells | Expression of FAP in Stroma Cells | Notes |
| Parathyroid tumors | n.d. | + | FAP mRNA expression was significantly higher in parathyroid carcinomas than in adenomas. |
| Sarcomas | + (see note) | + (reactive fibroblasts in Ewing's sarcomas) | FAP expression found in malignant cells in fibrosarcomas, leiomyosarcoma, malignant fibrous histiocytoma, low grade myofibroblastic sarcoma, fibroblastic areas in osteosarcomas, osteoid osteoma, and in osteosarcoma. FAP is negative in malignant cells with "small round cell" phenotype (embryonal rhabdomyosarcoma, Ewing sarcoma, or mesenchymal chondrosarcoma). A higher expression in osteosarcoma associated with more advanced clinical stage, presence of distant metastasis, high histological grade, and a worse progression-free and overall survival. FAP is expressed in both malignant and benign tumors and its positivity reflects their histogenetic origin rather than malignant potential. |
| Myeloma | − | + | FAP expression was detected in osteoclasts, endothelial cells, adipocytes, fibrotic stroma, but not in multiple myeloma cells. FAP is upregulated in osteoclasts co-cultured with myeloma cells. |

FAP expression in CAFs was shown for almost all carcinomas and sarcomas (Pure, et al., *Oncogene,* 2018, 37:4343; Busek, et al., *Front Biosci* (*Landmark Ed*), 2018, 23:1933). Furthermore, CAFs are present in hematological malignancies (Raffaghello, et al., *Oncotarget,* 2015, 6:2589). Utilization of FAP as a therapeutic target is therefore not limited to certain tumor entities.

The abundance of FAP-expressing CAFs is described to correlate with poor prognosis. Across a wide range of human tumor indications, FAP expression is described to correlate with higher tumor grade and worse overall survival (Pure, et al., *Oncogene,* 2018, 37:4343).

As described above, it is indicated that FAP as well as FAP-expressing cells present in the tumor microenvironment significantly influence tumor progression (Hanahan, et al., *Cancer Cell,* 2012, 21:309). Additionally, due to its relatively selective expression in tumors, FAP is regarded as a suitable target for therapeutic and diagnostic agents as described below (Siveke, *J Nucl Med,* 2018, 59:1412; Christiansen, et al., *Neoplasia,* 2013, 15:348; Zi, et al., *Mol Med Rep,* 2015, 11:3203).

Soon after its discovery, FAP was utilized as a therapeutic target in cancer. Until today, various strategies have been explored, including e.g. inhibition of FAP enzymatic activity, ablation of FAP-positive cells, or targeted delivery of cytotoxic compounds.

In 2007, an inhibitor of FAP and DPP4, Talabostat (Valboro-Pro, PT-100), was developed by Point Therapeutics (for example as described in U.S. Pat. No. 6,890,904, WO9916864). Pennisi et al. (Pennisi, et al., *Br J Haematol,* 2009, 145:775) observed a reduced tumor growth in a multiple myeloma animal model as well as in cancer syngeneic mouse models. Furthermore, several other prolyl boronic acid derivatives have been developed and reported as putative selective inhibitors for FAP. These derivatives show instability in aqueous environments at physiologic pH (Coutts, et al., *J Med Chem,* 1996, 39:2087) and a nonspecific reactivity with other enzymes.

WO 2008/116054 disclosed hexapeptide derivatives wherein compounds comprise a C-terminal bis-amino or boronic acid functional group.

US 2017/0066800 disclosed pseudopeptide inhibitors, such as M83, effective against FAP. These inhibitors were assessed in lung and colon cancer xenografts in immunodeficient mice. A suppression of tumor growth was observed (Jackson, et al., *Neoplasia,* 2015, 17:43). These pseudopeptides inhibit the activity of both prolyl oligopeptidase (POP/PREP) and FAP, thereby excluding their use as specific therapeutic FAP inhibitors.

US 2008/280856 disclosed a nanomolar boronic acid-based inhibitor. The inhibitor shows a bispecific inhibition of FAP and PREP, thereby excluding their use as specific therapeutic FAP inhibitors.

FAP inhibitors based on cyclic peptides were disclosed, e.g., in WO 2016/146174 and WO 2006/042282. WO 2016/146174 disclosed peptides for diagnosis and treatment of tumors expressing FAP showing specificity for FAP, whereby closely related homologue DPP4 was not recognized by said peptides. WO 2006/042282 disclosed polypeptides for treatment of melanoma. In nude mice, inhibition of melanoma growth and melanoma metastasis was shown.

WO 99/75151 and WO 01/68708 disclosed a humanized FAP monoclonal antibody, F19, (Sibrotuzumab). Furthermore, the anti-FAP antibody F19 and humanized versions thereof were disclosed in WO 99/57151 and WO 01/68708. Development approaches involved e.g. the generation of high affinity, species cross-reactive, FAP-specific scFvs converted into a bivalent derivative (Brocks, et al., *Mol Med,* 2001, 7:461). In Phase I and II clinical trials, Sibrotuzumab showed specific tumor enrichment whilst failing to demonstrate measurable therapeutic activity in patients with metastatic colorectal cancer, with only 2 out of 17 patients having stable disease (Hofheinz, et al., *Onkologie,* 2003, 26:44). This F19 antibody has not been shown to block any cellular or protease function of FAP, which might explain the lack of therapeutic effects (Hofheinz, et al., *Onkologie,* 2003, 26:44; Scott, et al., *Clin Cancer Res,* 2003, 9:1639).

US 2018/022822 disclosed novel molecules specifically binding to human FAP and epitopes thereof, as human-derived antibodies and chimeric antigen receptors (CARs) useful in the treatment of diseases and conditions induced by FAP. Treatment of mice bearing orthotopic syngeneic MC38 colorectal tumors with an anti-FAP antibody reduced the tumor diameter and number of metastasis. WO 2012/020006 disclosed glycoengineered antibodies that bear modified oligosaccharides in the Fc region. Subsequently, bispecific antibodies specific for FAP and DR5 were developed as subject to WO 2014/161845. These antibodies trigger tumor cell apoptosis in vitro and in in vivo preclinical tumor models with FAP-positive stroma (Brunker, et al., *Mol Cancer Ther,* 2016, 15:946). Antibody drug conjugates and immunotoxins that target FAP are described in WO 2015/118030. In vitro toxicity as well as in vivo inhibition of tumor growth was shown following application of anti-hu/moFAP hu36: cytolysin ADC candidates. It is unclear whether these antibodies were capable of inhibiting FAP activity.

Small molecule FAP inhibitors based on (4-quinolinoyl) glycyl-2-cyanopyrrolidine displaying low nanomolar inhibitory potency and high selectivity against related DPPs and PREP were described by Jansen et al. (Jansen, et al., *J Med Chem,* 2014, 57:3053; Jansen, et al., *ACS Med Chem Lett,* 2013, 4:491) and disclosed in WO 2013/107820. However, the compounds are structurally unrelated to the compounds of the present invention and include a war-head leading to covalent binding to FAP.

In recent years, several FAP-targeted radiopharmaceutical approaches were developed which are exemplarily described herein.

WO 2010/036814 disclosed small molecule inhibitors of FAP for use as therapeutic agents through inhibition of FAPs enzyme activity or as radiopharmaceuticals through binding to FAP.

WO 2019/083990 disclosed imaging and radiotherapeutic agents based on small molecule FAP-inhibitors described by Jansen et al. (Jansen, et al., *J Med Chem,* 2014, 57:3053; Jansen, et al., *ACS Med Chem Lett,* 2013, 4:491). Furthermore, several authors described selective uptake in tumors of cancer patients of imaging and radiotherapeutic agents (Lindner, et al., *J Nucl Med,* 2018, 59:1415; Loktev, et al., *J Nucl Med,* 2018, 59:1423; Giesel, et al., *J Nucl Med,* 2019, 60:386; Loktev, et al., *J Nucl Med,* 2019 March 8 (epub ahead of print); Giesel, et al., *Eur J Nucl Med Mol Imaging,* 2019, 46:1754; Kratochwil, et al., *J Nucl Med,* 2019, 60:801) based on FAP-inhibitors described by Jansen et al. (Jansen, et al., *J Med Chem,* 2014, 57:3053; Jansen, et al., *ACS Med Chem Lett,* 2013, 4:491).

Clinical assessments of a $^{131}$I-labeled, humanized form of the F19 antibody (sibrotuzumab) revealed a selective uptake by tumors but not by normal tissues in patients with colorectal carcinoma or non-small cell lung cancer (Scott, et al., *Clin Cancer Res,* 2003, 9:1639). This may be due to the long circulation time of antibodies that makes them unsuitable for a diagnostic, therapeutic, or theragnostic approach involving radionuclides.

WO 2011/040972 disclosed high-affinity antibodies recognizing both human and murine FAP antigen as potent radioimmunoconjugates. ESC11 lgG1 induces down modulation and internalization of surface FAP (Fischer, et al., *Clin Cancer Res,* 2012, 18:6208). WO 2017/211809 disclosed tissue targeting thorium-227 complexes wherein the targeting moiety has specificity for FAP. However, the long circulation time of antibodies makes them unsuitable for a diagnostic, therapeutic, or theragnostic approach involving radionuclides.

FAP has also been described as being involved in other diseases than oncology indications, examples of which are given below.

Fibroblast-like synoviocytes in rheumatoid arthritic joints of patients show a significantly increased expression of FAP (Bauer, et al., *Arthritis Res Ther,* 2006, 8: R171; Milner, et al., *Arthritis Res Ther,* 2006, 8: R23). In rheumatoid arthritis, stromal cells play an important role in organizing the structure of synovial tissue of joints by producing extracellular matrix components, recruiting infiltrating immune cells and secreting inflammatory mediators. Considerable evidence exists supporting a role for these cells in driving the persistence of inflammation and joint damage (Bartok, et al., *Immunol Rev,* 2010, 233:233; Turner, et al., *Curr Opin Rheumatol,* 2015, 27:175). In rheumatoid arthritis FAP has a pathological role in cartilage turnover at least by promotion of proteoglycan loss and subsequently cartilage degradation (Bauer, et al., *Arthritis Res Ther,* 2006, 8: R171; Waldele, et al., *Arthritis Res Ther,* 2015, 17:12). Therefore, it might serve as a marker for patient stratification, for evaluation and follow-up of treatment success, or as a therapeutic target (Bauer, et al., *Arthritis Res Ther,* 2006, 8: R171). In mice, a treatment response was demonstrated using SPECT/CT imaging of a $^{99m}$Tc-labeled anti-FAP antibody (van der Geest, et al., *Rheumatology* (*Oxford*), 2018, 57:737; Laverman, et al., *J Nucl Med,* 2015, 56:778; van der Geest, et al., *J Nucl Med,* 2017, 58:151).

Additionally, FAP was recognized not only as a marker of activated fibroblasts in the injury response (Tillmanns, et al., *Int J Cardiol,* 2013, 168:3926) but also as an important player in the healing process of wounds (Ramirez-Montagut, et al., *Oncogene,* 2004, 23:5435). Jing et al. demonstrated a time-dependent course of change in FAP expression following burn wounds in rats (Jing, et al., *Nan Fang Yi Ke Da Xue Xue Bao,* 2013, 33:615). Inhibiting of FAP activity in reactive wound fibroblasts in Keloid scars, common benign fibroproliferative reticular dermal lesions, might offer therapeutic option to prevent disease progression (Dienus, et al., *Arch Dermatol Res,* 2010, 302:725).

In fibrotic diseases, upregulated expression of FAP was observed e.g. in idiopathic pulmonary fibrosis, Crohn's disease, and liver fibrosis. In an ex vivo model for Crohn's disease, a chronic bowel inflammatory disease characterized by an excessive, misbalanced extracellular matrix (ECM) deposition, upregulated FAP expression was observed. FAP inhibition reconstituted extracellular matrix homeostasis (Truffi, et al., *Inflamm Bowel Dis,* 2018, 24:332). Similar observations were made by Egger et al. (Egger, et al., *Eur J Pharmacol,* 2017, 809:64) under use of a murine model of pulmonary fibrosis. Inhibition of FAP leads to reduced fibrotic pathology. FAP is also expressed in the tissue remodelling region in chronically injured liver (Wang, et al., *Front Biosci,* 2008, 13:3168), and FAP expression by hepatic stellate cells correlates with the histological severity of liver disease (Gorrell, et al., *Adv Exp Med Biol,* 2003, 524:235). Therefore, FAP is also a promising target in the treatment of liver fibrosis (Lay, et al., *Front Biosci* (*Landmark Ed*), 2019, 24:1).

FAP is expressed in arteriosclerotic lesions and upregulated in activated vascular smooth muscle cells (Monslow, et al., *Circulation,* 2013, 128: A17597). Monslow et al. showed that targeted inhibition of FAP in arteriosclerotic lesions may decrease overall lesion burden, inhibit inflammatory cell homing, and increase lesion stability through its ability to alter lesion architecture by favoring matrix-rich lesions over inflammation. More importantly, most of the arteriosclerotic pathologies share a common pathogenic feature: the rupture of an atherosclerotic plaque inducing arteriosclerotic lesions (Davies, et al., *Br Heart J,* 1985, 53:363; Falk, *Am J Cardiol,* 1989, 63: 114e). Rupture of the fibrous cap in advanced atherosclerotic plaques is a critical trigger of acute coronary syndromes that may lead to myocardial infarction and sudden cardiac death. One of the key events in promoting plaque instability is the degradation of the fibrous cap, which exposes the underlying thrombogenic plaque core to the bloodstream, thereby causing thrombosis and subsequent vessel occlusion (Farb, et al., Circulation, 1996, 93:1354; Virmani, et al., *J Am Coll Cardiol,* 2006, 47: C13). Brokopp et al. showed that FAP contributes to type I collagen breakdown in fibrous caps (Brokopp, et al., *Eur Heart J,* 2011, 32:2713). A radiolabeled tracer was developed and its applicability for atherosclerosis imaging shown (Meletta, et al., *Molecules,* 2015, 20:2081).

DETAILED DESCRIPTION OF THE INVENTION

The problem underlying the present invention is the provision of a compound which is suitable as a diagnostic agent and/or a pharmaceutical agent, particularly if conjugated to a diagnostically and/or therapeutically active effector. A further problem underlying the present invention is the provision of a compound which is suitable as a diagnostic agent and/or a pharmaceutical agent, particularly if conjugated to a diagnostically and/or therapeutically active effector, whereby the compound is a potent inhibitor of FAP activity; preferably the pIC50 of the compound is equal to or greater than 6.0. A further problem underlying the present invention is the provision of a compound which is suitable as a diagnostic agent and/or a pharmaceutical agent, particularly if conjugated to a diagnostically and/or therapeutically active effector, in the diagnosis and/or therapy of a disease where the diseased cells and/or diseased tissues express FAP. A still further problem underlying the instant invention is the provision of a compound which is suitable for delivering a diagnostically and/or therapeutically effective agent to a diseased cell and/or diseased tissue, respectively, and more particularly a FAP-expressing diseased cell and/or diseased tissue, preferably the diseased tissue comprises or contains cancer associated fibroblasts. Also, a problem underlying the present invention is the provision of a method for the diagnosis of a disease, of a method for the treatment and/or prevention of a disease, and a method for the combined diagnosis and treatment of a disease; preferably such disease is a disease involving FAP-expressing cells and/or tissues, more particularly a FAP-expressing diseased cell and/or diseased tissue, preferably the diseased tissue comprises or contains cancer associated fibroblasts. A still further problem underlying the present invention is the provision of a method for the identification of a subject, wherein the subject is likely to respond or likely not to respond to a treatment of a disease, a method for the selection of a subject from a group of subjects, wherein the subject is likely to respond or likely not to respond to a treatment of a disease. Also, a problem underlying the present invention is the provision of a pharmaceutical composition containing a compound having the characteristics as outlined above. Furthermore, a problem underlying the present invention is the provision of a kit which is suitable for use in any of the above methods.

There is a need for compounds that are suitable as a diagnostic agent and/or pharmaceutical agent, particularly if conjugated to a diagnostically and/or therapeutically active effector. Furthermore, there is a need for compounds that are suitable as a diagnostic agent and/or a pharmaceutical agent, particularly if conjugated to a diagnostically and/or therapeutically active effector, whereby the compound is a potent inhibitor of FAP activity; preferably the pIC50 of the compound is equal to or greater than 6.0. Further, there is a need for compounds suitable as diagnostic agents and/or pharmaceutical agents, particularly if conjugated to a diagnostically and/or therapeutically active effector, in the diagnosis and/or therapy of a disease where the diseased cells and/or diseased tissues express FAP. Furthermore, there is a need for a compound which is suitable for delivering a diagnostically and/or therapeutically effective agent to a diseased cell and/or diseased tissue, respectively, and more particularly a FAP-expressing diseased cell and/or diseased tissue, preferably the diseased tissue comprises or contains cancer associated fibroblasts. Also, there is a need for a method for the diagnosis of a disease, of a method for the treatment and/or prevention of a disease, and a method for the combined diagnosis and treatment of a disease; preferably such disease is a disease involving FAP-expressing cells and/or tissues, more particularly a FAP-expressing diseased cell and/or diseased tissue, preferably the diseased tissue comprises or contains cancer associated fibroblasts. Furthermore, there is a need for a method for the identification of a subject, wherein the subject is likely to respond or likely not to respond to a treatment of a disease, a method for the selection of a subject from a group of subjects, wherein the subject is likely to respond or likely not to respond to a treatment of a disease. Further, there is a need for a pharmaceutical composition containing a compound having the characteristics as outlined above. Furthermore, there is a need for a kit which is suitable for use in any of the above methods. The present invention satisfies these needs.

These and other problems are solved by the subject matter of the attached claims.

These and other problems underlying the present invention are also solved by the following embodiments.

Embodiment 1. A compound selected from the group consisting of compound Hex-[Cys(tMeBn(DOTA-AET))-Pro-Pro-Thr-Gln-Phe-Cys]-OH (3BP-3554) of the following formula
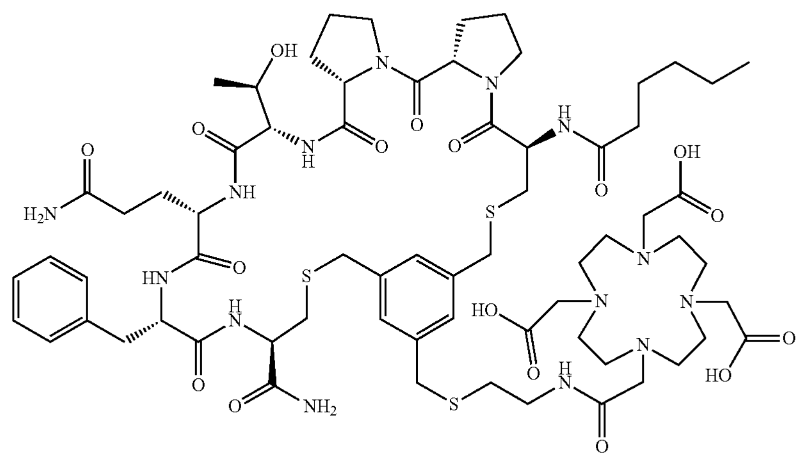 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(N)=O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]
and
compound Hex-[Cys(tMeBn(DOTA-PP))-Pro-Pro-Thr-Gin-Phe-Cys]-Asp-NH2 (3BP-3407) of the following formula
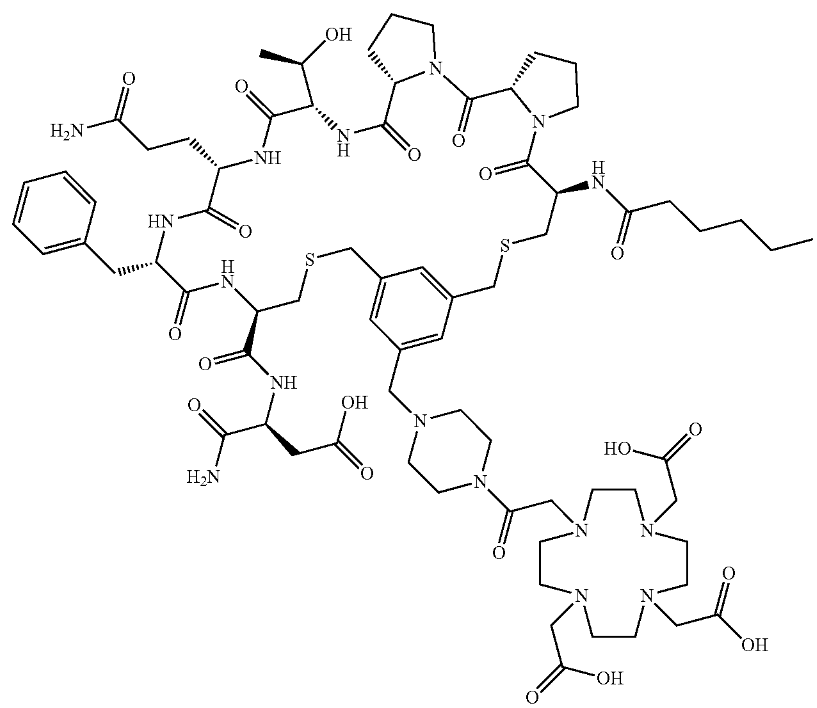 [SMILES: CCCCCC(=O)N[C@H]1CSCc2cc(cc(CN3CCN(C(=O)CN4CCN(CC(=O)O)CCN(CC(=O)O)CCN(CC(=O)O)CC4)CC3)c2)CSC[C@@H](C(=O)N[C@@H](CC(=O)O)C(N)=O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

Embodiment 2. The compound of Embodiment 1, wherein the compound is compound Hex-[Cys(tMeBn (DOTA-AET))-Pro-Pro-Thr-Gin-Phe-Cys]-OH (3BP-3554) of the following formula

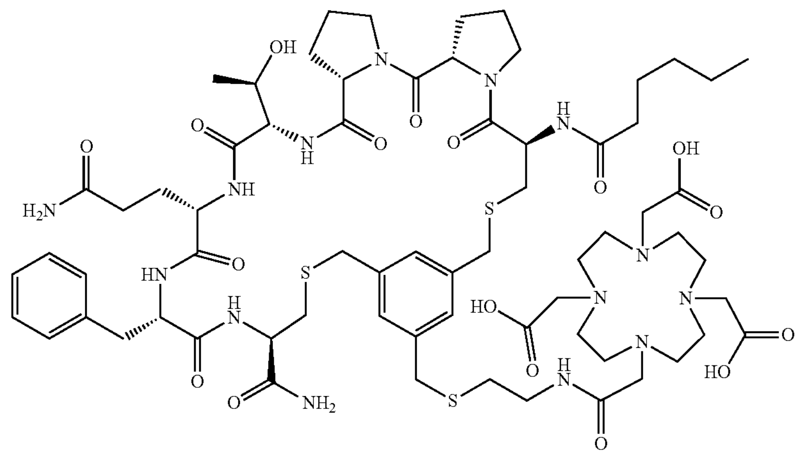 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(N)=O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

Embodiment 3. The compound of Embodiment 1, wherein the compound is compound Hex-[Cys(tMeBn (DOTA-PP))-Pro-Pro-Thr-Gln-Phe-Cys]-Asp-NH2 (3BP-3407) of the following formula

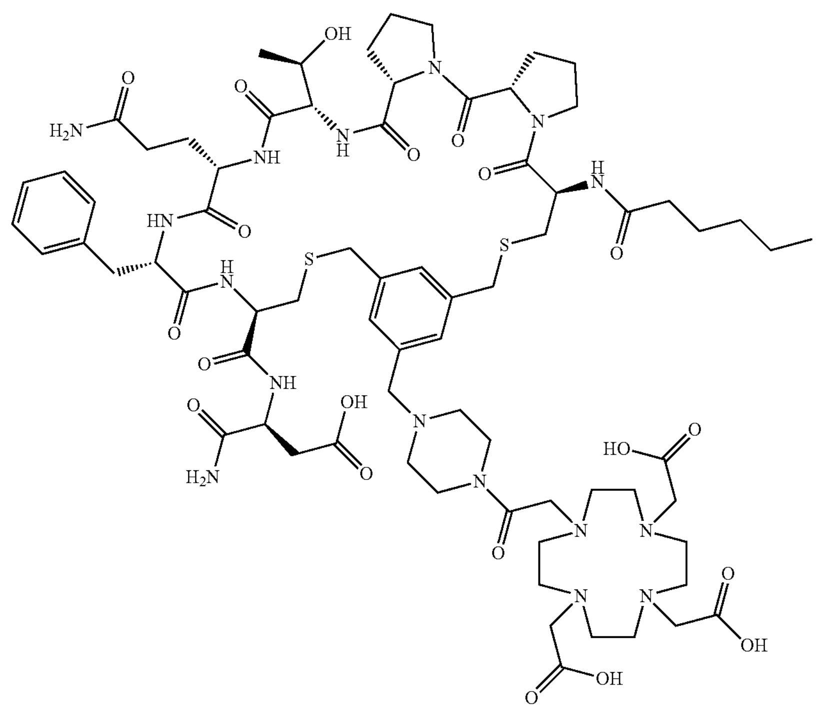 [SMILES: CCCCCC(=O)N[C@H]1CSCc2cc(cc(CN3CCN(C(=O)CN4CCN(CC(=O)O)CCN(CC(=O)O)CCN(CC(=O)O)CC4)CC3)c2)CSC[C@@H](C(=O)N[C@@H](CC(=O)O)C(N)=O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

Embodiment 4. The compound of any one of Embodiments 1 to 3, wherein any S atom which can be oxidized, preferably S atoms of thioether groups, is present as —S—, —S(O)— or —$S(O_2)$— or a mixture thereof.

Embodiment 5. The compound of any one of Embodiments 1 to 4, wherein the compound is capable of binding to fibroblast activation protein (FAP).

Embodiment 6. The compound of any one of Embodiments 1 to 5, wherein the compound comprises a diagnostically active nuclide or a therapeutically active nuclide.

Embodiment 7. The compound of Embodiment 6, wherein the compound is selected from the group comprising compound Hex-[Cys(tMeBn(InDOTA-PP))-Pro-Pro-Thr-Gln-Phe-Cys]-Asp-NH2 (3BP-3590) of the following formula

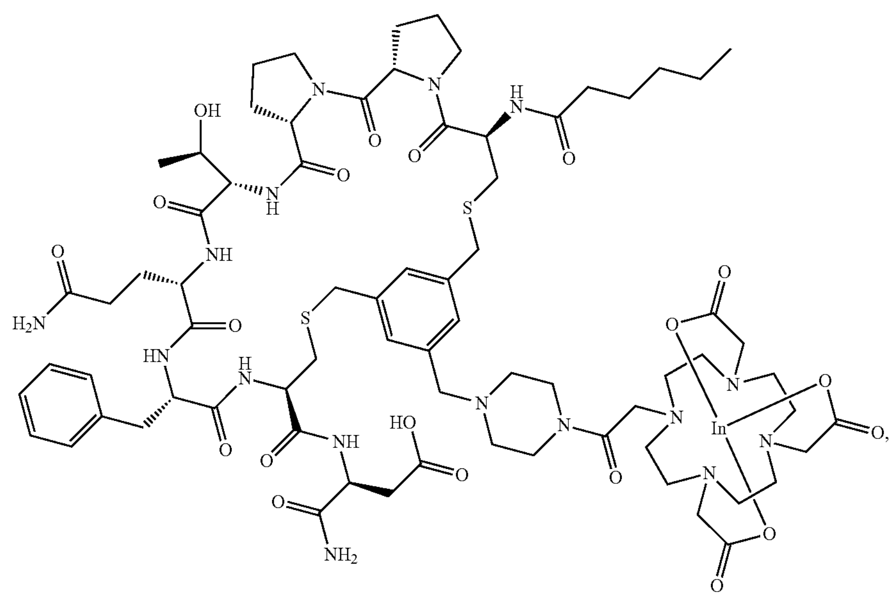
compound Hex-[Cys(tMeBn(LuDOTA-PP))-Pro-Pro-Thr-Gin-Phe-Cys]-Asp-NH2 (3BP-3591) of the following formula
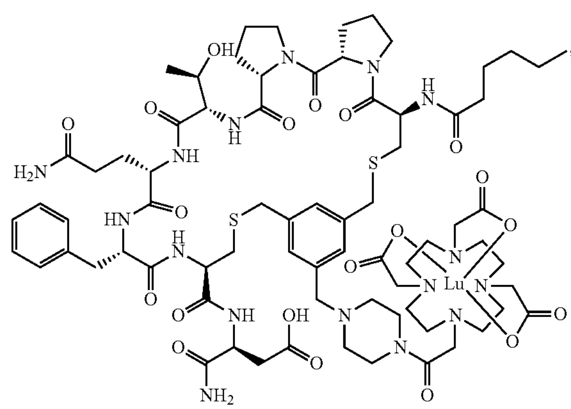
compound Hex-[Cys(tMcBn(GaDOTA-PP))-Pro-Pro-Thr-Gin-Phe-Cys]-Asp-NH2 (3BP-3592) of the following formula
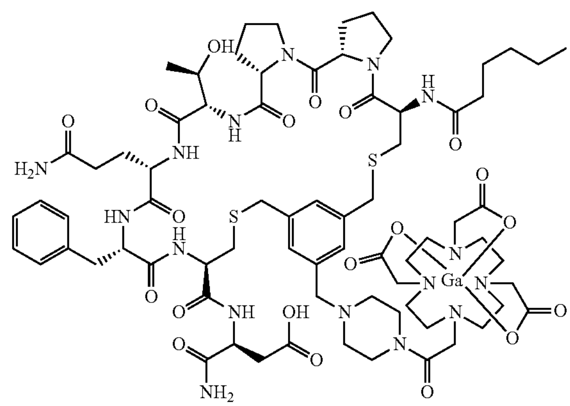
compound Hex-[Cys(tMeBn(EuDOTA-PP))-Pro-Pro-Thr-Gin-Phe-Cys]-Asp-NH2 (3BP-3661) of the following formula
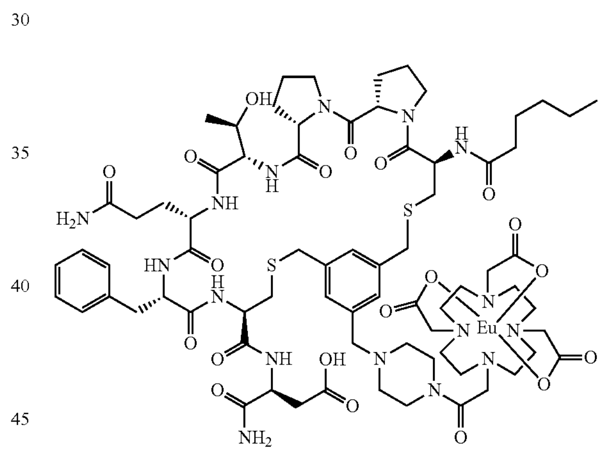
compound Hex-[Cys(tMeBn(InDOTA-AET))-Pro-Pro-Thr-Gin-Phe-Cys]-OH (3BP-3623) of the following formula
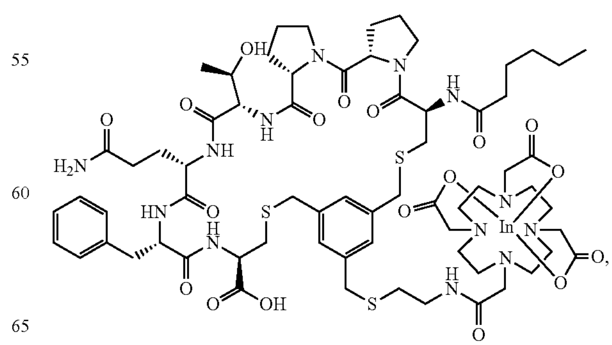

compound Hex-[Cys(tMeBn(LuDOTA-AET))-Pro-Pro-Thr-Gin-Phe-Cys]-OH (3BP-3624) of the following formula

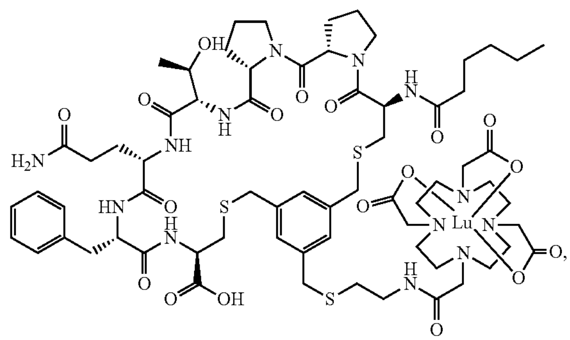

compound Hex-[Cys(tMeBn(EuDOTA-AET))-Pro-Pro-Thr-Gin-Phe-Cys]-OH (3BP-3662) of the following formula

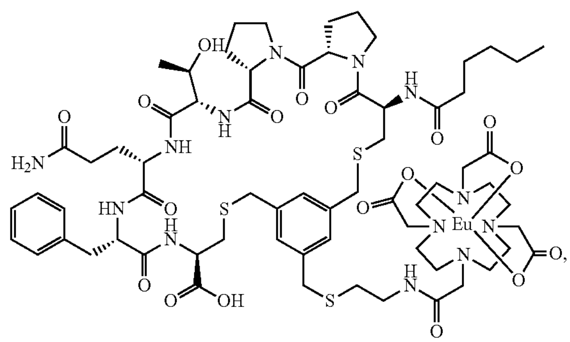

compound Hex-[Cys(tMeBn(GaDOTA-AET))-Pro-Pro-Thr-Gin-Phe-Cys]-OH (3BP-3949) of the following formula

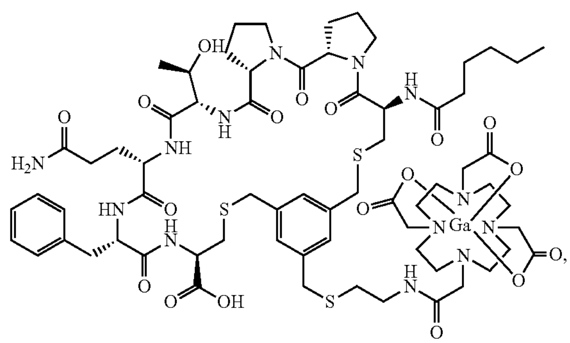

compound Hex-[Cys-(tMcBn(CuDOTA-AET))-Pro-Pro-Thr-Gin-Phe-Cys]-OH (3BP-4293) of the following formula

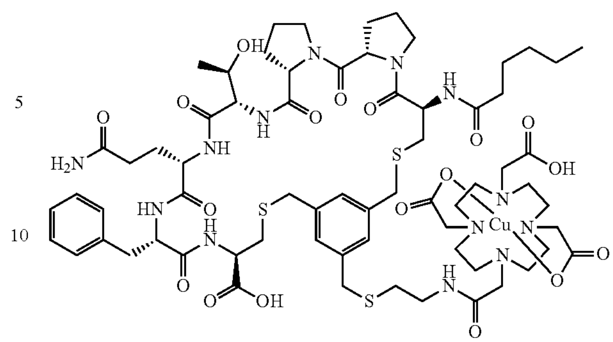

and compound Hex-[Cys-(tMeBn(ZnDOTA-AET))-Pro-Pro-Thr-Gin-Phe-Cys]-OH (3BP-4343) of the following formula

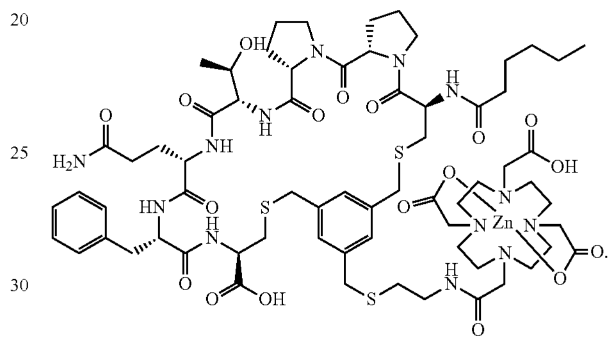

Embodiment 8. The compound of any one of Embodiments 6 and 7, wherein the diagnostically active nuclide is a diagnostically active radionuclide.

Embodiment 9. The compound of Embodiment 8, wherein the diagnostically active radionuclide is selected from the group consisting of $^{43}Sc$, $^{44}Sc$, $^{51}Mn$, $^{52}Mn$, $^{64}Cu$, $^{67}Ga$, $^{68}Ga$, $^{86}Y$, $^{89}Zr$, $^{94m}Tc$, $^{99m}Tc$, $^{111}In$, $^{152}Tb$, $^{155}Tb$, $^{201}Tl$, $^{203}Pb$, $^{18}F$, $^{76}Br$, $^{77}Br$, $^{123}I$, $^{124}I$, $^{125}I$, preferably $^{43}Sc$, $^{44}Sc$, $^{64}Cu$, $^{67}Ga$, $^{68}Ga$, $^{86}Y$, $^{89}Zr$, $^{99m}Tc$, $^{111}In$, $^{152}Tb$, $^{155}Tb$, $^{203}Pb$, $^{18}F$, $^{76}Br$, $^{77}Br$, $^{123}I$, $^{124}I$, $^{125}I$ and most preferably $^{64}Cu$, $^{68}Ga$, $^{89}Zr$, $^{99m}Tc$, $^{111}In$, $^{18}F$, $^{123}I$, and $^{124}I$.

Embodiment 10. The compound of any one of Embodiments 6 and 7, wherein the therapeutically active nuclide is a therapeutically active radionuclide.

Embodiment 11. The compound of Embodiment 10, wherein the therapeutically active radionuclide is selected from the group consisting of $^{47}Sc$, $^{67}Cu$, $^{89}Sr$, $^{90}Y$, $^{153}Sm$, $^{149}Tb$, $^{161}Tb$, $^{177}Lu$, $^{186}Re$, $^{188}Re$, $^{212}Pb$, $^{213}Bi$, $^{223}Ra$, $^{225}Ac$, $^{226}Th$, $^{227}Th$, $^{131}I$, $^{211}At$, preferably $^{47}Sc$, $^{67}Cu$, $^{90}Y$, $^{177}Lu$, $^{188}Re$, $^{212}Pb$, $^{213}Bi$, $^{225}Ac$, $^{227}Th$, $^{131}I$, $^{211}At$ and most preferably $^{90}Y$, $^{177}Lu$, $^{225}Ac$, $^{227}Th$, $^{131}I$ and $^{211}At$.

Embodiment 12. The compound of any one of Embodiments 1 to 11, wherein the compound interacts with a fibroblast activation protein (FAP), preferably with human FAP having an amino acid sequence of SEQ ID NO: 1 or a homolog thereof, wherein the amino acid sequence of the homolog has an identity of at least 85% to the amino acid sequence of SEQ ID NO: 1.

Embodiment 13. The compound of Embodiment 12, wherein the compound is an inhibitor of the fibroblast activation protein (FAP).

Embodiment 14. The compound of any one of Embodiments 1 to 13, for use in a method for the diagnosis of a disease.

Embodiment 15. The compound for use of Embodiment 14, wherein the disease is a disease involving fibroblast activation protein (FAP), preferably upregulated expression of fibroblast activation protein (FAP).

Embodiment 16. The compound for use of any one of Embodiments 14 to 15, wherein the disease involves cells showing upregulated expression of fibroblast activation protein (FAP), preferably diseased tissue containing cells showing upregulated expression of fibroblast activation protein (FAP), more preferably disease involving tumor associated fibroblasts.

Embodiment 17. The compound for use of any one of Embodiments 14 to 16, wherein the disease is a neoplasm, preferably a cancer or tumor.

Embodiment 18. The compound for use of Embodiment 17, wherein the neoplasm, cancer, and tumor are each and individually selected from the group comprising a solid tumor, an epithelial tumor, bladder cancer, breast cancer, cervical cancer, colorectal cancer, cholangiocarcinoma, endometrial cancer, esophageal cancer, gastric cancer, gastrointestinal stromal tumors, head and neck cancer, liver cancer, lung cancer, melanoma, mesothelioma, neuroendocrine tumors and carcinomas, ovarian cancer, pancreatic cancer, prostate cancer, renal cell carcinoma, salivary carcinoma, sarcoma, squamous cell carcinoma, and thyroid cancer.

Embodiment 19. The compound for use of Embodiment 18, wherein the neoplasm, cancer, and tumor are each and individually selected from the group comprising breast cancer, colorectal cancer, cholangiocarcinoma, head and neck cancer, lung cancer, mesothelioma, neuroendocrine tumors and carcinomas, ovarian cancer, pancreatic cancer, prostate cancer, sarcoma, and squamous cell carcinoma.

Embodiment 20. The compound for use of any one of Embodiments 14 to 16, wherein the disease is selected from the groups comprising inflammatory disease, cardiovascular disease, autoimmune disease, and fibrotic disease.

Embodiment 21. The compound for use of Embodiment 20, wherein the disease is an inflammatory disease.

Embodiment 22. The compound for use of Embodiment 21, wherein the disease is atherosclerosis, arthritis, or rheumatoid arthritis.

Embodiment 23. The compound for use of Embodiment 20, wherein the disease is a cardiovascular disease.

Embodiment 24. The compound for use of Embodiment 23, wherein the disease is a cardiovascular disease involving atherosclerotic plaques.

Embodiment 25. The compound for use of Embodiment 24, wherein the disease is an atherosclerotic pathology caused by rupture of plaques, acute coronary syndrome, myocardial infarction, thrombosis, or vessel occlusion.

Embodiment 26. The compound for use of Embodiment 20, wherein the disease is a fibrotic disease.

Embodiment 27. The compound for use of Embodiment 26, wherein the disease is selected form the group comprising idiopathic pulmonary fibrosis, Crohn's disease, and liver fibrosis.

Embodiment 28. The compound for use of any one of Embodiments 14 to 27, wherein the compound comprises a diagnostically active nuclide, preferably a diagnostically active radionuclide.

Embodiment 29. The compound for use of Embodiment 28, wherein the diagnostically active nuclide is selected from the group comprising $^{43}Sc$, $^{44}Sc$, $^{51}Mn$, $^{52}Mn$, $^{64}Cu$, $^{67}Ga$, $^{68}Ga$, $^{86}Y$, $^{89}Zr$, $^{94m}Tc$, $^{99m}Tc$, $^{111}In$, $^{152}Tb$, $^{155}Tb$, $^{201}Tl$, $^{203}Pb$, $^{18}F$, $^{76}Br$, $^{77}Br$, $^{123}I$, $^{124}I$, $^{125}I$, preferably $^{43}Sc$, $^{44}Sc$, $^{64}Cu$, $^{67}Ga$, $^{68}Ga$, $^{86}Y$, $^{89}Zr$, $^{99m}Tc$, $^{111}In$, $^{152}Tb$, $^{155}Tb$, $^{203}Pb$, $^{18}F$, $^{76}Br$, $^{77}Br$, $^{123}I$, $^{124}I$, $^{125}I$, and more preferably $^{64}Cu$, $^{68}Ga$, $^{89}Zr$, $^{99m}Tc$, $^{111}In$, $^{18}F$, $^{123}I$, and $^{124}I$.

Embodiment 30. The compound for use of any one of Embodiments 14 to 29, wherein the method for the diagnosis is an imaging method.

Embodiment 31. The compound for use of Embodiment 30, wherein the imaging method is selected from the group consisting of scintigraphy, Single Photon Emission Computed Tomography (SPECT) and Positron Emission Tomography (PET).

Embodiment 32. The compound for use of any one of Embodiments 14 to 31, wherein the method comprises the administration of a diagnostically effective amount of the compound to a subject, preferably to a mammal, wherein the mammal is selected from the group comprising man, companion animals, pets, and livestock, more preferably the subject is selected from the group comprising man, dog, cat, horse, and cow, and most preferably the subject is a human being.

Embodiment 33. The compound of any one of Embodiments 1 to 13, for use in a method for the treatment of a disease.

Embodiment 34. The compound for use of Embodiment 34, wherein the disease is a disease involving fibroblast activation protein (FAP), preferably upregulated expression of fibroblast activation protein (FAP).

Embodiment 35. The compound for use of any one of Embodiments 33 to 34, wherein the disease involves cells showing upregulated expression of fibroblast activation protein (FAP), preferably diseased tissue containing cells showing upregulated expression of fibroblast activation protein (FAP), more preferably disease involving tumor associated fibroblasts.

Embodiment 36. The compound for use of any one of Embodiments 33 to 35, wherein the disease is a neoplasm, preferably a cancer or tumor.

Embodiment 37. The compound for use of Embodiment 36, wherein the neoplasm, cancer, and tumor are each and individually selected from the group comprising a solid tumor, an epithelial tumor, bladder cancer, breast cancer, cervical cancer, colorectal cancer, cholangiocarcinoma, endometrial cancer, esophageal cancer, gastric cancer, gastrointestinal stromal tumors, head and neck cancer, liver cancer, lung cancer, melanoma, mesothelioma, neuroendocrine tumors and carcinomas, ovarian cancer, pancreatic cancer, prostate cancer, renal cell carcinoma, salivary carcinoma, sarcoma, squamous cell carcinoma, and thyroid cancer.

Embodiment 38. The compound for use of Embodiment 37, wherein the neoplasm, cancer, and tumor are each and individually selected from the group comprising breast cancer, colorectal cancer, cholangiocarcinoma, head and neck cancer, lung cancer, mesothelioma, neuroendocrine tumors and carcinomas, ovarian cancer, pancreatic cancer, prostate cancer, sarcoma, and squamous cell carcinoma.

Embodiment 39. The compound for use of any one of Embodiments 33 to 35, wherein the disease is selected from the groups comprising inflammatory disease, cardiovascular disease, autoimmune disease, and fibrotic disease.

Embodiment 40. The compound for use of Embodiment 39, wherein the disease is an inflammatory disease.

Embodiment 41. The compound for use of Embodiment 40, wherein the disease is atherosclerosis, arthritis, or rheumatoid arthritis.

Embodiment 42. The compound for use of Embodiment 39, wherein the disease is a cardiovascular disease.

Embodiment 43. The compound for use of Embodiment 42, wherein the diseases is a cardiovascular disease involving atherosclerotic plaques.

Embodiment 44. The compound for use of Embodiment 43, wherein the diseases is an atherosclerotic pathology caused by rupture of plaques, acute coronary syndrome, myocardial infarction, thrombosis, or vessel occlusion.

Embodiment 45. The compound for use of Embodiment 39, wherein the disease is a fibrotic disease.

Embodiment 46. The compound for use of Embodiment 45, wherein the disease is selected form the group comprising idiopathic pulmonary fibrosis, Crohn's disease, and liver fibrosis.

Embodiment 47. The compound for use of any one of Embodiments 33 to 38, wherein the compound comprises a therapeutically active nuclide, preferably a therapeutically active radionuclide.

Embodiment 48. The compound for use of Embodiment 47, wherein the therapeutically active nuclide is selected from the group comprising $^{47}Sc$, $^{67}Cu$, $^{89}Sr$, $^{90}Y$, $^{153}Sm$, $^{149}Tb$, $^{161}Tb$, $^{177}Lu$, $^{186}Re$, $^{188}Re$, $^{212}Pb$, $^{213}Bi$, $^{223}Ra$, $^{225}Ac$, $^{226}Th$, $^{227}Th$, $^{131}I$, $^{211}At$, preferably $^{47}Sc$, $^{67}Cu$, $^{90}Y$, $^{177}Lu$, $^{188}Re$, $^{212}Pb$, $^{213}Bi$, $^{225}Ac$, $^{227}Th$, $^{131}I$, $^{211}At$ and most preferably $^{90}Y$, $^{177}Lu$, $^{225}Ac$, $^{227}Th$, $^{131}I$ and $^{211}At$.

Embodiment 49. The compound for use of any one of Embodiments 33 to 48, wherein the method comprises the administration of a therapeutically effective amount of the compound to a subject, preferably to a mammal, wherein the mammal is selected from the group comprising man, companion animals, pets, and livestock, more preferably the subject is selected from the group comprising man, dog, cat, horse, and cow, and most preferably the subject is a human being.

Embodiment 50. The compound of any one of Embodiments 1 to 13, for use in a method for the identification of a subject, wherein the subject is likely to respond or likely not to respond to a treatment of a disease, wherein the method for the identification of a subject comprises carrying out a method of diagnosis using the compound of any one of Embodiments 1 to 13, preferably a method for the diagnosis of a disease as described in any one of Embodiments 14 to 33.

Embodiment 51. The compound of any one of Embodiments 1 to 13, for use in a method for the selection of a subject from a group of subjects, wherein the subject is likely to respond or likely not to respond to a treatment of a disease, wherein the method for the selection of a subject from a group of subjects comprises carrying out a method of diagnosis using the compound of any one of Embodiments 1 to 13, preferably a method for the diagnosis of a disease as described in any one of Embodiments 14 to 32.

Embodiment 52. The compound of any one of Embodiments 1 to 13, for use in a method for the stratification of a group of subjects into subjects which are likely to respond to a treatment of a disease, and into subjects which are not likely to respond to a treatment of a disease, wherein the method for the stratification of a group of subjects comprises carrying out a method of diagnosis using the compound of any one of Embodiments 1 to 13, preferably a method for the diagnosis of a disease as described in any one of Embodiments 14 to 32.

Embodiment 53. The compound for use of any one of Embodiments 50 to 52, wherein the disease is a disease involving fibroblast activation protein (FAP), preferably upregulated expression of fibroblast activation protein (FAP).

Embodiment 54. The compound for use of any one of Embodiments 50 to 53, wherein the disease involves cells showing upregulated expression of fibroblast activation protein (FAP), preferably diseased tissue containing cells showing upregulated expression of fibroblast activation protein (FAP), more preferably disease involving tumor associated fibroblasts.

Embodiment 55. The compound for use of any one of Embodiments 50 to 54, wherein the disease is a neoplasm, preferably a cancer or tumor.

Embodiment 56. The compound for use of Embodiment 55, wherein the neoplasm, cancer, and tumor are each and individually selected from the group comprising a solid tumor, an epithelial tumor, bladder cancer, breast cancer, cervical cancer, colorectal cancer, cholangiocarcinoma, endometrial cancer, esophageal cancer, gastric cancer, gastrointestinal stromal tumors, head and neck cancer, liver cancer, lung cancer, melanoma, mesothelioma, neuroendocrine tumors and carcinomas, ovarian cancer, pancreatic cancer, prostate cancer, renal cell carcinoma, salivary carcinoma, sarcoma, squamous cell carcinoma, and thyroid cancer.

Embodiment 57. The compound for use of Embodiment 56, wherein the neoplasm, cancer, and tumor are each and individually selected from the group comprising breast cancer, colorectal cancer, cholangiocarcinoma, head and neck cancer, lung cancer, mesothelioma, neuroendocrine tumors and carcinomas, ovarian cancer, pancreatic cancer, prostate cancer, sarcoma, and squamous cell carcinoma.

Embodiment 58. The compound for use of any one of Embodiments 50 to 54, wherein the disease is selected from the groups comprising inflammatory disease, cardiovascular disease, autoimmune disease, and fibrotic disease.

Embodiment 59. The compound for use of Embodiment 58, wherein the disease is an inflammatory disease.

Embodiment 60. The compound for use of Embodiment 59, wherein the disease is atherosclerosis, arthritis or rheumatoid arthritis.

Embodiment 61. The compound for use of Embodiment 58, wherein the disease is a cardiovascular disease.

Embodiment 62. The compound for use of Embodiment 61, wherein the disease is a cardiovascular disease involving atherosclerotic plaques.

Embodiment 63. The compound for use of Embodiment 62, wherein the disease is an atherosclerotic pathology caused by rupture of plaques, acute coronary syndrome, myocardial infarction, thrombosis, or vessel occlusion.

Embodiment 64. The compound for use of Embodiment 58, wherein the disease is a fibrotic disease.

Embodiment 65. The compound for use of Embodiment 64, wherein the disease is selected from the group comprising idiopathic pulmonary fibrosis, Crohn's disease, and liver fibrosis.

Embodiment 66. The compound for use of any one of Embodiments 50 to 65, wherein the method of diagnosis is an imaging method.

Embodiment 67. The compound for use of Embodiment 66, wherein the imaging method is selected from the group comprising scintigraphy, Single Photon Emission Computed Tomography (SPECT) and Positron Emission Tomography (PET).

Embodiment 68. The compound for use of any one of Embodiments 50 to 67, wherein the compound comprises a diagnostically active nuclide, preferably a diagnostically active radionuclide.

Embodiment 69. The compound for use of Embodiment 68, wherein the diagnostically active nuclide is selected from the group comprising $^{43}Sc$, $^{44}Sc$, $^{51}Mn$, $^{52}Mn$, $^{64}Cu$, $^{67}Ga$, $^{68}Ga$, $^{86}Y$, $^{89}Zr$, $^{94m}Tc$, $^{99m}Tc$, $^{111}In$, $^{152}Tb$, $^{155}Tb$, $^{201}Tl$, $^{203}Pb$, $^{18}F$, $^{76}Br$, $^{77}Br$, $^{123}I$, $^{124}I$, $^{125}I$, preferably $^{43}Sc$, $^{44}Sc$, $^{64}Cu$, $^{67}Ga$, $^{68}Ga$, $^{86}Y$, $^{89}Zr$, $^{99m}Tc$, $^{111}In$, $^{152}Tb$, $^{155}Tb$, $^{203}Pb$, $^{18}F$, $^{76}Br$, $^{77}Br$, $^{123}I$, $^{124}I$, $^{125}I$ and most preferably $^{64}Cu$, $^{68}Ga$, $^{89}Zr$, $^{99m}Tc$, $^{111}In$, $^{18}F$, $^{123}I$, and $^{124}I$.

Embodiment 70. The compound of any one of Embodiments 1 to 13, for use in a method for delivering an effector to fibroblast activation protein (FAP), preferably human fibroblast activation protein (FAP), wherein the effector is selected from the group comprising a diagnostically active agent and a therapeutically active agent.

Embodiment 71. The compound for use of Embodiment 70, wherein the effector is selected from the group comprising a diagnostically active nuclide and a therapeutically active nuclide.

Embodiment 72. The compound for use of Embodiment 71, wherein the diagnostically active nuclide is a diagnostically active radionuclide.

Embodiment 73. The compound for use of Embodiment 72, wherein the diagnostically active radionuclide is selected from the group consisting of $^{43}Sc$, $^{44}Sc$, $^{51}Mn$, $^{52}Mn$, $^{64}Cu$, $^{67}Ga$, $^{68}Ga$, $^{86}Y$, $^{89}Zr$, $^{94m}Tc$, $^{99m}Tc$, $^{111}In$, $^{152}Tb$, $^{155}Tb$, $^{201}Tl$, $^{203}Pb$, $^{18}F$, $^{76}Br$, $^{77}Br$, $^{123}I$, $^{124}I$, $^{125}I$, preferably $^{43}Sc$, $^{44}Sc$, $^{64}Cu$, $^{67}Ga$, $^{68}Ga$, $^{86}Y$, $^{89}Zr$, $^{99m}Tc$, $^{111}In$, $^{152}Tb$, $^{155}Tb$, $^{203}Pb$, $^{18}F$, $^{76}Br$, $^{77}Br$, $^{123}I$, $^{124}I$, $^{125}I$ and most preferably $^{64}Cu$, $^{68}Ga$, $^{89}Zr$, $^{99m}Tc$, $^{111}In$, $^{18}F$, $^{123}I$, and $^{124}I$.

Embodiment 74. The compound for use of any one of Embodiments 70 to 73, wherein the fibroblast activation protein (FAP) is expressed by a cell, preferably a fibroblast, a mesenchymal stem cell, smooth muscle cell, a cell of epithelial origin, or an endothelial cell, more preferably a human fibroblast, mesenchymal stem cell, smooth muscle cell, cell of epithelial origin, or endothelial cell, most preferably a human fibroblast, mesenchymal stem cell, smooth muscle cell, cell of epithelial origin, or endothelial cell each showing upregulated expression of fibroblast activation protein (FAP).

Embodiment 75. The compound for use of Embodiment 74, wherein the cell is contained in or part of a tissue, preferably a diseased tissue of a subject suffering from a disease.

Embodiment 76. The compound for use of Embodiment 75, wherein the disease involves cells showing upregulated expression of fibroblast activation protein (FAP), preferably diseased tissue containing cells showing upregulated expression of fibroblast activation protein (FAP), more preferably disease involving tumor associated fibroblasts.

Embodiment 77. The compound for use of any one of Embodiments 75 to 76, wherein the disease is a neoplasm, preferably a cancer or tumor.

Embodiment 78. The compound for use of Embodiment 77, wherein the neoplasm, cancer, and tumor are each and individually selected from the group comprising a solid tumor, an epithelial tumor, bladder cancer, breast cancer, cervical cancer, colorectal cancer, cholangiocarcinoma, endometrial cancer, esophageal cancer, gastric cancer, gastrointestinal stromal tumors, head and neck cancer, liver cancer, lung cancer, melanoma, mesothelioma, neuroendocrine tumors and carcinomas, ovarian cancer, pancreatic cancer, prostate cancer, renal cell carcinoma, salivary carcinoma, sarcoma, squamous cell carcinoma, and thyroid cancer.

Embodiment 79. The compound for use of Embodiment 78, wherein the neoplasm, cancer, and tumor are each and individually selected from the group comprising breast cancer, colorectal cancer, cholangiocarcinoma, head and neck cancer, lung cancer, mesothelioma, neuroendocrine tumors and carcinomas, ovarian cancer, pancreatic cancer, prostate cancer, sarcoma, and squamous cell carcinoma.

Embodiment 80. The compound for use of any one of Embodiments 75 to 76, wherein the disease is selected from the groups comprising inflammatory disease, cardiovascular disease, autoimmune disease, and fibrotic disease.

Embodiment 81. The compound for use of Embodiment 80, wherein the disease is an inflammatory disease.

Embodiment 82. The compound for use of Embodiment 81, wherein the disease is atherosclerosis, arthritis or rheumatoid arthritis.

Embodiment 83. The compound for use of Embodiment 80, wherein the disease is a cardiovascular disease.

Embodiment 84. The compound for use of Embodiment 83, wherein the diseases is a cardiovascular disease involving atherosclerotic plaques.

Embodiment 85. The compound for use of Embodiment 84, wherein the disease is an atherosclerotic pathology caused by rupture of plaques, acute coronary syndrome, myocardial infarction, thrombosis, or vessel occlusion.

Embodiment 86. The compound for use of Embodiment 80, wherein the disease is a fibrotic disease.

Embodiment 87. The compound for use of Embodiment 86, wherein the disease is selected form the group comprising idiopathic pulmonary fibrosis, Crohn's disease, and liver fibrosis.

Embodiment 88. The compound for use of Embodiment 71, wherein the therapeutically active nuclide is a therapeutically active radionuclide.

Embodiment 89. The compound for use of Embodiment 88, wherein the therapeutically active radionuclide is selected from the group consisting of $^{47}Sc$, $^{67}Cu$, $^{89}Sr$, $^{90}Y$, $^{153}Sm$, $^{149}Tb$, $^{161}Tb$, $^{177}Lu$, $^{186}Re$, $^{188}Re$, $^{212}Pb$, $^{213}Bi$, $^{223}Ra$, $^{225}Ac$, $^{226}Th$, $^{227}Th$, $^{131}I$, $^{211}At$, preferably $^{47}Sc$, $^{67}Cu$, $^{90}Y$, $^{177}Lu$, $^{188}Re$, $^{212}Pb$, $^{213}Bi$, $^{225}Ac$, $^{227}Th$, $^{131}I$, $^{211}At$ and most preferably $^{90}Y$, $^{177}Lu$, $^{225}Ac$, $^{227}Th$, $^{131}I$ and $^{211}At$.

Embodiment 90. The compound for use of any one of Embodiment 88 to 89, wherein the fibroblast activation protein (FAP) is expressed by a cell, preferably a fibroblast, a mesenchymal stem cell, smooth muscle cell, a cell of epithelial origin, or an endothelial cell, more preferably a human fibroblast, mesenchymal stem cell, smooth muscle cell, cell of epithelial origin, or endothelial cell, most preferably a human fibroblast, mesenchymal stem cell, smooth muscle cell, cell of epithelial origin, or endothelial cell showing upregulated expression of fibroblast activation protein (FAP).

Embodiment 91. The compound for use of Embodiment 90, wherein the cell is contained in or part of a tissue, preferably a diseased tissue of a subject suffering from a disease.

Embodiment 92. The compound for use of Embodiment 91, wherein the disease involves cells showing upregulated expression of fibroblast activation protein (FAP), preferably diseased tissue containing cells showing upregulated expression of fibroblast activation protein (FAP), more preferably disease involving tumor associated fibroblasts.

Embodiment 93. The compound for use of any one of Embodiments 90 to 92, wherein the disease is a neoplasm, preferably a cancer or tumor.

Embodiment 94. The compound for use of Embodiment 93, wherein the neoplasm, cancer, and tumor are each and individually selected from the group comprising a solid tumor, an epithelial tumor, bladder cancer, breast cancer, cervical cancer, colorectal cancer, cholangiocarcinoma, endometrial cancer, esophageal cancer, gastric cancer, gastrointestinal stromal tumors, head and neck cancer, liver cancer, lung cancer, melanoma, mesothelioma, neuroendocrine tumors and carcinomas, ovarian cancer, pancreatic cancer, prostate cancer, renal cell carcinoma, salivary carcinoma, sarcoma, squamous cell carcinoma, and thyroid cancer.

Embodiment 95. A composition, preferably a pharmaceutical composition, wherein the composition comprises a compound according to any one of Embodiment 1 to 13 and a pharmaceutically acceptable excipient.

Embodiment 96. The composition of Embodiment 95 for use in any method as defined in any of the preceding claims.

Embodiment 97. A method for the diagnosis of a disease in a subject, wherein the method comprises administering to the subject a diagnostically effective amount of a compound according to any one of Embodiments 1 to 13.

Embodiment 98. The method of Embodiment 97, wherein the compound comprises a diagnostically active agent, whereby the agent is preferably a radionuclide.

Embodiment 99. A method for the treatment of a disease in a subject, wherein the method comprises administering to the subject a therapeutically effective amount of a compound according to any one of Embodiment 1 to 13.

Embodiment 100. The method of Embodiment 99, wherein the compound comprises a therapeutically active agent, whereby the agent is preferably a radionuclide.

Embodiment 101. The method of any one of Embodiments 97 to 100, wherein the disease is a disease involving fibroblast activation protein (FAP), preferably upregulated expression of fibroblast activation protein (FAP).

Embodiment 102. The method of any one of Embodiments 97 to 101, wherein the disease involves cells showing upregulated expression of fibroblast activation protein (FAP), preferably diseased tissue containing cells showing upregulated expression of fibroblast activation protein (FAP), more preferably disease involving tumor associated fibroblasts.

Embodiment 103. The method of any one of Embodiments 97 to 102, wherein the disease is selected from the groups comprising neoplasms, preferably cancers or tumors, and inflammatory disease, cardiovascular disease, autoimmune disease, and fibrotic disease.

Embodiment 104. A kit comprising a compound according to any one of Embodiments 1 to 13, one or more optional excipient(s) and optionally one or more device(s), whereby the device(s) is/are selected from the group comprising a labeling device, a purification device, a handling device, a radioprotection device, an analytical device or an administration device.

Embodiment 105. The kit of Embodiment 104 for use in any method as defined in any of the preceding claims.

More specifically, the problem underlying the present invention is solved in a first aspect by a compound selected from the group consisting of compound Hex-[Cys(tMeBn(DOTA-AET))-Pro-Pro-Thr-Gln-Phe-Cys]-OH (3BP-3554) of the following formula

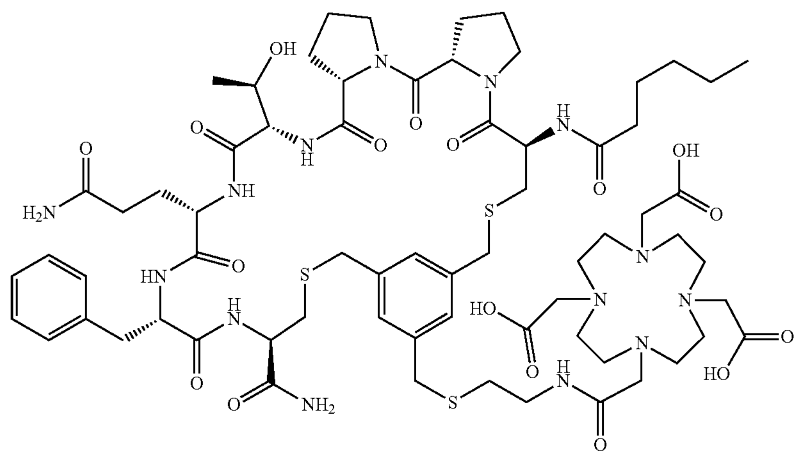 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(N)=O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

and compound Hex-[Cys(tMeBn(DOTA-PP))-Pro-Pro-Thr-Gln-Phe-Cys]-Asp-NH2 (3BP-3407) of the following formula

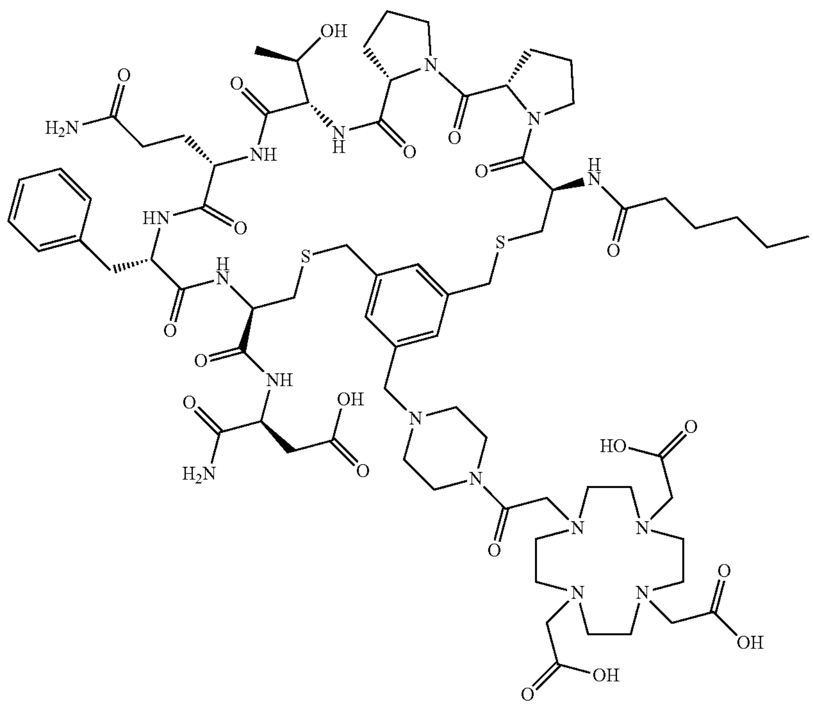 [SMILES: CCCCCC(=O)N[C@H]1CSCc2cc(cc(CN3CCN(C(=O)CN4CCN(CC(=O)O)CCN(CC(=O)O)CCN(CC(=O)O)CC4)CC3)c2)CSC[C@@H](C(=O)N[C@@H](CC(=O)O)C(N)=O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

More specifically, the problem underlying the present invention is solved in a second aspect by the compound according to the first aspect, including any embodiment thereof, for use in a method for the diagnosis of a disease.

More specifically, the problem underlying the present invention is solved in a third aspect by the compound according to the first aspect, including any embodiment thereof, for use in a method for the treatment of a disease.

More specifically, the problem underlying the present invention is solved in a fourth aspect by the compound according to the first aspect, including any embodiment thereof, for use in a method for the identification of a subject, wherein the subject is likely to respond or likely not to respond to a treatment of a disease, wherein the method for the identification of a subject comprises carrying out a method of diagnosis using the compound according to the first aspect including any embodiment thereof.

More specifically, the problem underlying the present invention is solved in a fifth aspect by the compound according to the first aspect, including any embodiment thereof, for use in a method for the selection of a subject from a group of subjects, wherein the subject is likely to respond or likely not to respond to a treatment of a disease, wherein the method for the selection of a subject from a group of subjects comprises carrying out a method of diagnosis using the compound according to the first aspect, including any embodiment thereof.

More specifically, the problem underlying the present invention is solved in a sixth aspect by the compound according to the first aspect, including any embodiment thereof, for use in a method for the stratification of a group of subjects into subjects which are likely to respond to a treatment of a disease, and into subjects which are not likely to respond to a treatment of a disease, wherein the method for the stratification of a group of subjects comprises carrying out a method of diagnosis using the compound according to the first aspect, including any embodiment thereof.

More specifically, the problem underlying the present invention is solved in a seventh aspect by a composition, preferably a pharmaceutical composition, wherein the composition comprises a compound according to the first aspect including any embodiment thereof and a pharmaceutically acceptable excipient.

More specifically, the problem underlying the present invention is solved in an eighth aspect by a method for the diagnosis of a disease in a subject, wherein the method comprises administering to the subject a diagnostically effective amount of a compound according to the first aspect, including any embodiment thereof.

More specifically, the problem underlying the present invention is solved in a ninth aspect by a method for the treatment of a disease in a subject, wherein the method comprises administering to the subject a therapeutically effective amount of a compound according to the first aspect including any embodiment thereof.

More specifically, the problem underlying the present invention is solved in a tenth aspect by a kit comprising a compound according to the first aspect, including any embodiment thereof, one or more optional excipient(s) and optionally one or more device(s), whereby the device(s) is/are selected from the group comprising a labeling device, a purification device, a handling device, a radioprotection device, an analytical device or an administration device.

It will be acknowledged by a person skilled in the art that a or the compound of the invention is any compound disclosed herein, including but not limited to any compound described in any of the above embodiments and any of the following embodiments.

It will be acknowledged by a person skilled in the art that a or the method of the invention is any method disclosed herein, including but not limited to any method described in any of the above embodiments and any of the following embodiments.

It will be acknowledged by a person skilled in the art that a or the composition of the invention is any composition disclosed herein, including but not limited to any composition described in any of the above embodiments and any of the following embodiments.

It will be acknowledged by a person skilled in the art that a or the kit of the invention is any kit disclosed herein, including but not limited to any kit described in any of the above embodiments and any of the following embodiments.

The present invention is based on the surprising finding of the present inventors that the compound of the invention and more specifically the cyclic peptide thereof provides for a highly specific binding of a compound comprising such cyclic peptide to fibroblast activation protein (FAP), since FAP-specific cyclic peptide-based inhibitors with nanomolar affinity have not been described so far.

Finally, the present inventors have found that the compounds of the invention are surprisingly stable in blood plasma, and are surprisingly useful as imaging agents and efficacious in shrinking tumors.

In an embodiment and as preferably used herein, a chelator is a compound which is capable of forming a chelate, whereby a chelate is a compound, preferably a cyclic compound where a metal or a moiety having an electron gap or a lone pair of electrons participates in the formation of the ring. More preferably, a chelator is this kind of compound where a single ligand occupies more than one coordination site at a central atom.

In an embodiment and as preferably used herein, a diagnostically active compound is a compound which is suitable for or useful in the diagnosis of a disease.

In an embodiment and as preferably used herein, a diagnostic agent or a diagnostically active agent is a compound which is suitable for or useful in the diagnosis of a disease.

In an embodiment and as preferably used herein, a therapeutically active compound is a compound which is suitable for or useful in the treatment of a disease.

In an embodiment and as preferably used herein, a therapeutic agent or a therapeutically active agent is a compound which is suitable for or useful in the treatment of a disease.

In an embodiment and as preferably used herein, a theragnostically active compound is a compound which is suitable for or useful in both the diagnosis and therapy of a disease.

In an embodiment and as preferably used herein, a theragnostic agent or a theragnostically active agent is a compound which is suitable for or useful in both the diagnosis and therapy of a disease.

In an embodiment and as preferably used herein, theragonstics is a method for the combined diagnosis and therapy of a disease; preferably, the combined diagnostically and therapeutically active compounds used in theragnostics are radiolabeled.

In an embodiment and as preferably used herein, treatment of a disease is treatment and/or prevention of a disease.

In an embodiment and as preferably used herein, a disease involving FAP is a disease where cells including but not limited to fibroblasts expressing, preferably in an upregulated manner, FAP and tissue either expressing FAP or containing or comprising cells such as fibroblasts, preferably expressing FAP in an upregulated manner respectively, are either a or the cause for the disease and/or the symptoms of the disease, or are part of the pathology underlying the disease. A preferred FAP-expressing cell is a cancer associated fibroblast (CAF). In an embodiment of the disease, preferably when used in connection with the treatment, treating and/or therapy of the disease, affecting the cells, the tissue and pathology, respectively, results in cure, treatment or amelioration of the disease and/or the symptoms of the disease. In an embodiment of the disease, preferably when used in connection with the diagnosis and/or diagnosing of the disease, labeling of the FAP-expressing cells and/or of the FAP-expressing tissue allows discriminating or distinguishing said cells and/or said tissue from healthy or FAP-non-expressing cells and/or healthy or FAP non-expressing tissue. More preferably such discrimination or distinction forms the basis for said diagnosis and diagnosing, respectively. In an embodiment thereof, labeling means the interaction of a detectable label either directly or indirectly with the FAP-expressing cells and/or with the FAP-expressing tissue or tissue containing such FAP-expressing cells; more preferably such interaction involves or is based on the interaction of the label or a compound bearing such label with FAP.

In an embodiment and as preferably used herein, a target cell is a cell which is expressing FAP and is a or the cause for a disease and/or the symptoms of a disease, or is part of the pathology underlying a disease.

In an embodiment and as preferably used herein, a non-target cell is a cell which is either not expressing FAP and/or is not a or the cause for a disease and/or the symptoms of a disease, or is part of the pathology underlying a disease.

In an embodiment and as preferably used herein, a neoplasm is an abnormal new growth of cells. The cells in a neoplasm grow more rapidly than normal cells and will continue to grow if not treated. A neoplasm may be benign or malignant.

In an embodiment and as preferably used herein, a tumor is a mass lesion that may be benign or malignant.

In an embodiment and as preferably used herein, a cancer is a malignant neoplasm.

The amino acid sequences of the peptides provided herein are depicted in typical peptide sequence format, as would be understood by the ordinary skilled artisan. For example, the three-letter code of a conventional amino acid, or the code for a non-conventional amino acid or the abbreviations for additional building blocks, indicates the presence of the amino acid or building block in a specified position within the peptide sequence. The code for each amino acid or building block is connected to the code for the next and/or previous amino acid or building block in the sequence by a hyphen which (typically represents an amide linkage).

Where an amino acid contains more than one amino and/or carboxy group all orientations of this amino acid are in principle possible, but in α-amino acid the utilization of the α-amino and the α-carboxy group is preferred and otherwise preferred orientations are explicitly specified.

For amino acids, in their abbreviations the first letter indicates the stereochemistry of the C-α-atom if applicable. For example, a capital first letter indicates that the L-form of the amino acid is present in the peptide sequence, while a lower case first letter indicating that the D-form of the correspondent amino acid is present in the peptide sequence.

In an embodiment and as preferably used herein, an aromatic L-α-amino acid is any kind of L-α-amino acid which comprises an aryl group.

In an embodiment and as preferably used herein, a heteroaromatic L-α-amino acid is any kind of L-α-amino acid which comprises a heteroaryl group.

Unless indicated to the contrary, the amino acid sequences are presented herein in N- to C-terminus direction.

Compounds of the invention typically contain amino acid sequences as provided herein. Conventional amino acids, also referred to as natural amino acids are identified according to their standard three-letter abbreviations and one-letter abbreviations, as set forth in Table 2.

TABLE 2

| Conventional amino acids and their abbreviations | | |
|---|---|---|
| Amino acid | 3-letter abbreviation | 1-letter abbreviation |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Non-conventional amino acids, also referred to as non-natural amino acids, are any kind of non-oligomeric compound which comprises an amino group and a carboxylic group and is not a conventional amino acid.

Examples of non-conventional amino acids and other building blocks as used for the construction of compounds of the invention are identified according to their abbreviation or name found in Table 3. The structures of some building blocks are depicted with an exemplary reagent for introducing the building block into the peptide (e.g., as carboxylic acid like) or these building blocks are shown as residue which is completely attached to another structure like a peptide or amino acid. The structures of the amino acids are shown as explicit amino acids and not as residues of the amino acids how they are presented after implementation in the peptide sequence. Some larger chemical moieties consisting of more than one moiety are also shown for the reason of clarity.

TABLE 3
| Abbreviation, name and structure of non-natural amino-acid and other building blocks and chemical moieties | | |
|---|---|---|
| Abbreviation | Name | Structure |
| 3MeBn | 3-Methylbenzylidene | 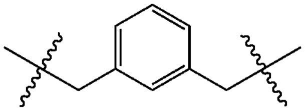 [SMILES: *Cc1cccc(C*)c1] |
| AET | 2-Aminoethanethiol | 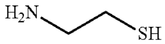 |
| CuDOTA | DOTA complexing Copper | 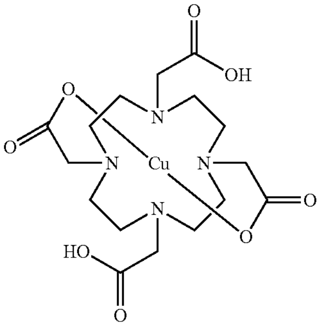 |
| Cy5SO3 | Cy5 dye (mono SO3) | 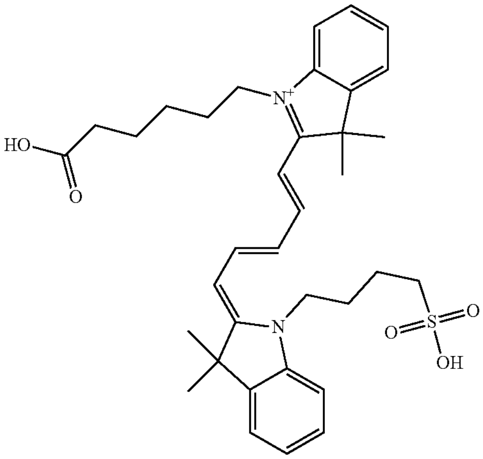 [SMILES: CC1(C)C(/C=C/C=C/C=C2\N(CCCCS(=O)(=O)O)c3ccccc3C2(C)C)=[N+](CCCCCC(=O)O)c2ccccc21] |
| Cys(3MeBn) | | 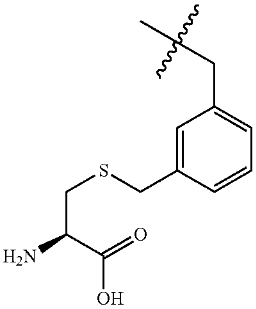 [SMILES: *Cc1cccc(CSC[C@H](N)C(=O)O)c1] |

TABLE 3-continued
| Abbreviation, name and structure of non-natural amino-acid and other building blocks and chemical moieties | | |
|---|---|---|
| Abbreviation | Name | Structure |
| Cys(tMeBn (DOTA-AET)) | | 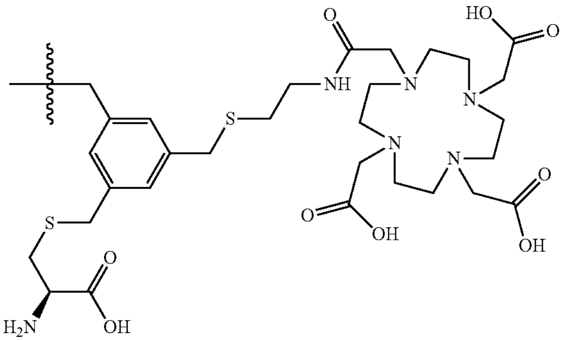 [SMILES: *Cc1cc(CSCCNC(=O)CN2CCN(CC(=O)O)CCN(CC(=O)O)CCN(CC(=O)O)CC2)cc(CSC[C@H](N)C(=O)O)c1] |
| Cys(tMeBn (DOTA-PP)) | | 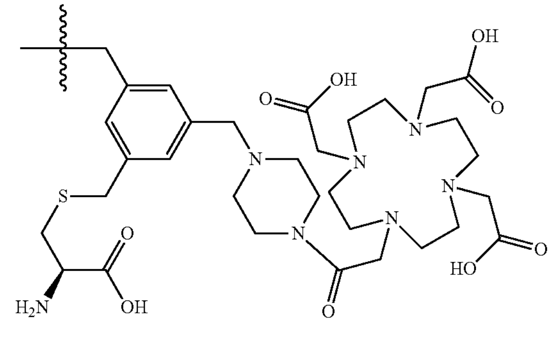 [SMILES: *Cc1cc(CSC[C@H](N)C(=O)O)cc(CN2CCN(C(=O)CN3CCN(CC(=O)O)CCN(CC(=O)O)CCN(CC(=O)O)CC3)CC2)c1] |
| Cys(tMeBn (H-AET)) | | 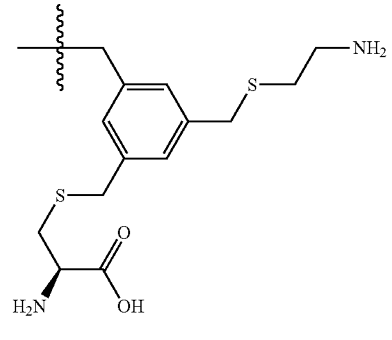 [SMILES: *Cc1cc(CSCCN)cc(CSC[C@H](N)C(=O)O)c1] |
| Cys(tMeBn (H-PP)) | | 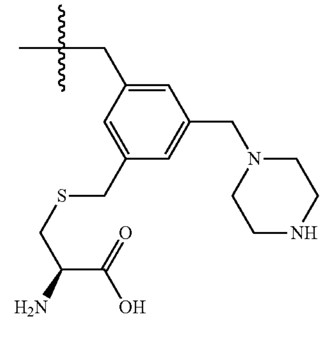 [SMILES: *Cc1cc(CSC[C@H](N)C(=O)O)cc(CN2CCNCC2)c1] |

TABLE 3-continued
| Abbreviation, name and structure of non-natural amino-acid and other building blocks and chemical moieties | | |
|---|---|---|
| Abbreviation | Name | Structure |
| DOTA | 1,4,7,10-Tetraazacyclododecane-1,4,7,10-tetraacetic acid | 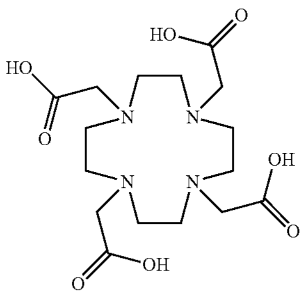 [SMILES: O=C(O)CN1CCN(CC(=O)O)CCN(CC(=O)O)CCN(CC(=O)O)CC1] |
| EuDOTA | DOTA complexing Europium | 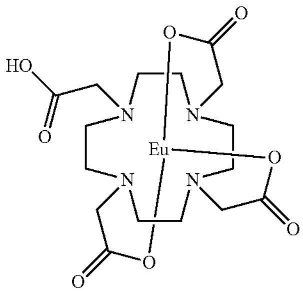 |
| GaDOTA | DOTA complexing Gallium | 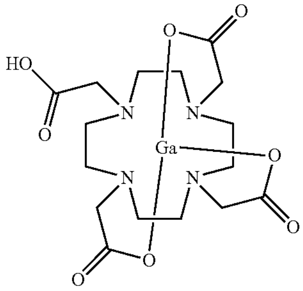 |
| Hex | Hexanoic acid | 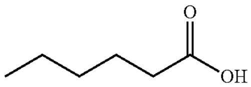 |
| Hex- | hexanoyl | 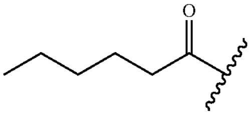 [SMILES: *C(=O)CCCCC] |
| InDOTA | DOTA complexing Indium | 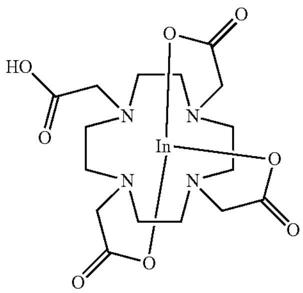 |

TABLE 3-continued
| Abbreviation, name and structure of non-natural amino-acid and other building blocks and chemical moieties | | |
|---|---|---|
| Abbreviation | Name | Structure |
| LuDOTA | DOTA complexing Lutetium | 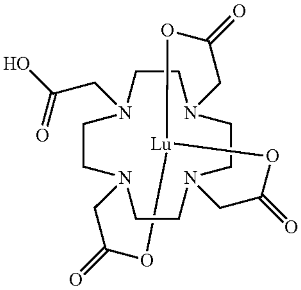 |
| PP | Piperazinyliden | 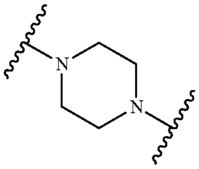 [SMILES: *N1CCN(*)CC1] |
| tMeBn | 1,3,5-Trimethylbenzyliden | 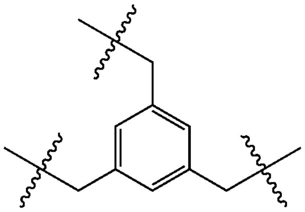 [SMILES: *Cc1cc(C*)cc(C*)c1] |
| tMeBn(H-AET) | | 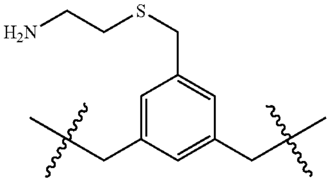 [SMILES: *Cc1cc(C*)cc(CSCCN)c1] |
| tMeBn(H-PP) | | 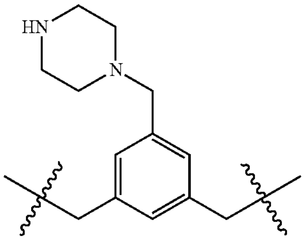 [SMILES: *Cc1cc(C*)cc(CN2CCNCC2)c1] |
| ZnDOTA | Zinc complex of DOTA | 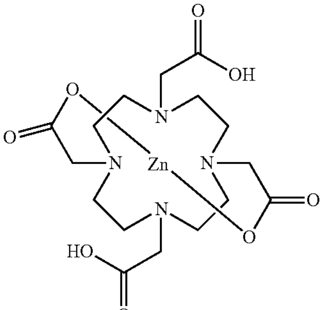 |

In accordance with the instant application, DOTA stands for 1,4,7,10-tetrazacyclododecane-1,4,7,10-tetraacetic acid.

It will be further acknowledged by the persons skilled in the art that the presence of a chelator in the compound of the invention includes, if not stated otherwise, the possibility that the chelator is complexed to any metal complex partner, i.e. any metal which, in principle, can be complexed by the chelator. An explicitly mentioned chelator of a compound of the invention or the general term chelator in connection with the compound of the invention refers either to the uncomplexed chelator as such or to the chelator to which any metal complex partner is bound, wherein the metal complex partner is any radioactive or non-radioactive metal complex partner. Preferably the chelator metal complex, i.e. the chelator to which the metal complex partner is bound, is a stable chelator metal complex.

Non-radioactive chelator metal complexes have several applications, e.g. for assessing properties like stability or activity which are otherwise difficult to determine. One aspect is that cold variants of the radioactive versions of the metal complex partner (e.g. non-radioactive Gallium, Lutetium or Indium complexes as described in the examples) can act as surrogates of the radioactive compounds. Furthermore, they are valuable tools for identifying metabolites in vitro or in vivo, as well as for assessing toxicity properties of the compounds of invention. Additionally, chelator metal complexes can be used in binding assays utilizing the fluorescence properties of some metal complexes with distinct ligands (e.g. Europium salts).

It will be acknowledged by a person skilled in the art that the radioactive nuclide which is or which is to be attached to the compound of the invention, is selected taking into consideration the disease to be treated and/or the disease to be diagnosed, respectively, and/or the particularities of the patient and patient group, respectively, to be treated and to be diagnosed, respectively.

In an embodiment of the present invention, the radioactive nuclide is also referred to as radionuclide. Radioactive decay is the process by which an atomic nucleus of an unstable atom loses energy by emitting ionizing particles (ionizing radiation). There are different types of radioactive decay. A decay, or loss of energy, results when an atom with one type of nucleus, called the parent radionuclide, transforms to an atom with a nucleus in a different state, or to a different nucleus containing different numbers of protons and neutrons. Either of these products is named the daughter nuclide. In some decays the parent and daughter are different chemical elements, and thus the decay process results in nuclear transmutation (creation of an atom of a new element). For example, the radioactive decay can be alpha decay, beta decay, and gamma decay. Alpha decay occurs when the nucleus ejects an alpha particle (helium nucleus). This is the most common process of emitting nucleons, but in rarer types of decays, nuclei can eject protons, or specific nuclei of other elements (in the process called cluster decay). Beta decay occurs when the nucleus emits an electron ($\beta^-$-decay) or positron ($\beta^+$-decay) and a type of neutrino, in a process that changes a proton to a neutron or the other way around. By contrast, there exist radioactive decay processes that do not result in transmutation. The energy of an excited nucleus may be emitted as a gamma ray in gamma decay, or used to eject an orbital electron by interaction with the excited nucleus in a process called internal conversion, or used to absorb an inner atomic electron from the electron shell whereby the change of a nuclear proton to neutron causes the emission of an electron neutrino in a process called electron capture (EC), or may be emitted without changing its number of proton and neutrons in a process called isomeric transition (IT). Another form of radioactive decay, the spontaneous fission (SF), is found only in very heavy chemical elements resulting in a spontaneous breakdown into smaller nuclei and a few isolated nuclear particles.

In a preferred embodiment of the present invention, the radionuclide can be used for labeling of the compound of the invention.

In an embodiment of the present invention, the radionuclide is suitable for complexing with a chelator, leading to a radionuclide chelate complex.

In a further embodiment one or more atoms of the compound of the invention are of non-natural isotopic composition, preferably these atoms are radionuclides; more preferably radionuclides of carbon, oxygen, nitrogen, sulfur, phosphorus and halogens: These radioactive atoms are typically part of amino acids, in some case halogen containing amino acids, and/or building blocks and in some cases halogenated building blocks each of the compound of the invention.

In a preferred embodiment of the present invention, the radionuclide has a half-life that allows for diagnostic and/or therapeutic medical use. Specifically, the half-life is between 1 min and 100 days.

In a preferred embodiment of the present invention, the radionuclide has a decay energy that allows for diagnostic and/or therapeutic medical use. Specifically, for $\gamma$-emitting isotopes, the decay energy is between 0.004 and 10 MeV, preferably between 0.05 and 4 MeV, for diagnostic use. For positron-emitting isotopes, the decay energy is between 0.6 and 13.2 MeV, preferably between 1 and 6 MeV, for diagnostic use. For particle-emitting isotopes, the decay energy is between 0.039 and 10 MeV, preferably between 0.4 and 6.5 MeV, for therapeutic use.

In a preferred embodiment of the present invention, the radionuclide is industrially produced for medical use. Specifically, the radionuclide is available in GMP quality.

In a preferred embodiment of the present invention, the daughter nuclide(s) after radioactive decay of the radionuclide are compatible with the diagnostic and/or therapeutic medical use. Furthermore, the daughter nuclides are either stable or further decay in a way that does not interfere with or even support the diagnostic and/or therapeutic medical use. Representative radionuclides which may be used in connection with the present invention are summarized in Table 4.

TABLE 4

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Carbon | | | | | | |
| C-11 | 20.4 | 0.34 | | ECβ+ | 1.982 | |
| Nitrogen | | | | | | |
| N-13 | 9.97 | 0.17 | | ECβ+ | 2.220 | |
| Oxygen | | | | | | |
| O-15 | 2.00 | | | ECβ+ | 2.754 | |
| Fluorine | | | | | | |
| F-18 | 110 | 1.83 | | β+ | 1.656 | |
| Mg-28 | | 20.9 | | β− | 1.832 | |
| Aluminum | | | | | | |
| Al-28 | 2.24 | 0.04 | | β− | 4.642 | |
| Al-29 | 6.56 | | | β− | 3.690 | |
| Silicon | | | | | | |
| Si-31 | 157 | 2.62 | | β− | 1.492 | |
| Phosphorus | | | | | | |
| P-30 | 2.50 | 0.04 | | β+ | 4.232 | |
| P-32 | | | 14.3 | β− | 1.170 | |
| P-33 | | | 25.4 | β− | 0.077 | |
| Sulphur | | | | | | |
| S-35 | | | 87.4 | β− | 0.167 | |
| S-37 | 5.00 | 0.08 | | | | |
| S-38 | | 2.80 | | β− | 2.937 | |
| Chlorine | | | | | | |
| Cl-34m1 | 32.0 | 0.53 | | EC | 5.693 | |
| Cl-38 | 37.2 | 0.62 | | β− | 4.917 | |
| Cl-39 | 55.6 | 0.93 | | β− | 3.422 | |
| Scandium | | | | | | |
| Sc-43 | | 3.89 | | EC | 2.221 | |
| Sc-44 | | 3.97 | | β+ | 0.632 | |
| Sc-44m1 | | 58.6 | 2.44 | IT | 0.271 | 98.8% IT (0.27086), 1.2% EC (3.924) |
| Sc-46 | | | 83.8 | β− | 2.367 | |
| Sc-47 | | 80.4 | 3.35 | β− | 0.601 | |
| Sc-48 | | 43.7 | 1.82 | β− | 3.988 | |
| Sc-49 | 57.4 | 0.96 | | β− | 2.002 | |
| Titanium | | | | | | |
| Ti-45 | 185 | 3.08 | | EC | 2.062 | |
| Ti-51 | 5.76 | | | β− | 2.472 | |
| Vanadium | | | | | | |
| V-47 | 32.6 | 0.54 | | β+ | 2.931 | |
| V-48 | | | 16.2 | EC | 4.013 | |
| V-49 | | | 330 | EC | 0.602 | |
| V-52 | 3.74 | | | β− | 3.975 | |
| Chromium | | | | | | |
| Cr-48 | | 23.0 | | EC | 1.655 | |
| Cr-49 | 42.1 | 0.70 | | β+ | 2.628 | |
| Cr-51 | | | 27.7 | EC | 0.753 | |
| Cr-55 | 3.50 | | | β− | 2.603 | |
| Cr-56 | 5.94 | | | β− | 1.630 | |
| Manganese | | | | | | |
| Mn-51 | 46.2 | 0.77 | | β+ | 2.185 | |
| Mn-52m1 | 21.1 | 0.35 | | EC | 5.091 | 98.25% EC (5.091), 1.75% IT (0.3796) |
| Mn-52 | | | 5.59 | β+ | 3.689 | |
| Mn-54 | | | 312 | EC | 1.377 | |
| Mn-56 | | 2.58 | | β− | 3.696 | |
| Iron | | | | | | |
| Fe-52 | | 8.28 | | EC | 2.375 | |
| Fe-53m1 | | 2.54 | | IT | 3.042 | |

TABLE 4-continued

| Key properties of relevant radionuclides - half life, decay types and decay energies | | | | | | |
|---|---|---|---|---|---|---|
| Radionuclide | Half-life (min) | Half-life (hours) | Half-life (days) | Decay | Energy (MeV) | Additional decays (energy [MeV]) |
| Fe-53 | | 8.51 | | EC | 3.742 | |
| Fe-59 | | | 44.5 | β− | 1.565 | |
| Fe-61 | | 5.98 | | β− | 3.977 | |
| Cobalt | | | | | | |
| Co-55 | | 17.5 | | EC | 3.451 | |
| Co-56 | | | 78.8 | EC | 4.567 | |
| Co-57 | | | 271 | EC | 0.836 | |
| Co-58m1 | | 9.15 | | IT | 0.026 | |
| Co-58 | | | 70.8 | EC | 2.308 | |
| Co-60m1 | 10.5 | 0.17 | | IT | 0.059 | 99.76% IT (0.05932), 0.24% β− (2.882) |
| Co-61 | | 1.65 | | β− | 1.324 | |
| Co-62m1 | 13.9 | 0.23 | | β− | 5.337 | |
| Nickel | | | | | | |
| Ni-56 | | 146 | 6.10 | EC | 2.133 | |
| Ni-57 | | 36.1 | 1.50 | β+ | 3.262 | |
| Ni-63 | | | | β− | 0.067 | |
| Ni-65 | | 2.52 | | β− | 2.138 | |
| Ni-66 | | 54.6 | 2.28 | β− | 0.252 | |
| Copper | | | | | | |
| Cu-60 | 23.2 | 0.39 | | EC | 6.128 | |
| Cu-61 | | 3.41 | | EC | 2.238 | |
| Cu-62 | 9.74 | 0.16 | | EC | 3.959 | |
| Cu-64 | | 12.7 | | β+ | 0.653 | 61.5% EC (1.674), 38.5% β− (0.5797) |
| Cu-66 | 5.10 | 0.09 | | β− | 2.641 | |
| Cu-67 | | | 2.58 | β− | 0.580 | |
| Cu-68m1 | 3.75 | | | IT | 0.722 | 84% IT (0.72163), 16% β− (5.162) |
| Cu-69 | 2.85 | | | β− | 2.681 | |
| Zinc | | | | | | |
| Zn-60 | 2.38 | | | EC | 4.171 | |
| Zn-62 | | 9.26 | | EC | 1.620 | |
| Zn-63 | 38.1 | 0.64 | | EC | 3.366 | |
| Zn-65 | | | 244 | EC | 1.352 | |
| Zn-69m1 | | 13.8 | | IT | 0.438 | 99.997% IT (0.43818), 0.003% $\beta^-$ (1.348) |
| Zn-69 | 57.0 | 0.95 | | β− | 0.910 | |
| Zn-71m1 | | 3.92 | | β− | 2.970 | 99.95% β− (2.97), 0.05% IT (0.15986) |
| Zn-71 | 2.45 | | | β− | 2.810 | |
| Zn-72 | | 46.5 | 1.94 | β− | 0.443 | |
| Gallium | | | | | | |
| Ga-65 | 15.2 | 0.25 | | EC | 3.255 | |
| Ga-66 | | 9.40 | | EC | 5.175 | |
| Ga-67 | | 78.2 | 3.26 | EC | 1.001 | |
| Ga-68 | 68.0 | 1.13 | | β+ | 2.921 | |
| Ga-70 | 21.1 | 0.35 | | β− | 1.652 | 99.59% β− (1.652), 0.41% EC (0.65456) |
| Ga-72 | | 14.1 | | β− | 3.998 | |
| Ga-73 | | 4.91 | | β− | 1.598 | |
| Ga-74 | 8.12 | 0.14 | | β− | 5.373 | |
| Selenium | | | | | | |
| Se-70 | 41.0 | 0.68 | | β+ | 2.412 | |
| Se-72 | 504 | 8.40 | | EC | 0.362 | |
| Se-73m | 39.0 | 0.65 | | IT | 2.761 | 27.4% EC (2.761), 72.6% IT (0.03608) |
| Se-73 | 429 | 7.15 | | EC | 2.725 | |
| Se-75 | | | 120 | EC | 0.865 | |
| Se-79m1 | 3.92 | | | IT | 0.096 | 99.94% IT (0.09622), 0.06% (0.247) |
| Se-81m1 | 57.2 | 0.95 | | IT | 0.103 | 99.95% IT (0.10253), 0.05% β− (1.689) |
| Se-81 | 18.5 | 0.31 | | β− | 1.587 | |
| Se-83 | 22.3 | 0.37 | | β− | 3.673 | |
| Se-84 | 3.26 | | | β− | 1.836 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Bromine | | | | | | |
| Br-73 | 3.40 | | | EC | 4.580 | |
| Br-74m1 | 41.5 | 0.69 | | EC | 9.921 | |
| Br-74 | 25.3 | 0.42 | | EC | 6.925 | |
| Br-75 | 98.0 | 1.63 | | EC | 3.062 | |
| Br-76 | | 16.2 | | β+ | 3.941 | |
| Br-77 | | 57.0 | 2.38 | β+ | 0.342 | |
| Br-78 | 6.64 | 0.11 | | EC | 3.574 | 99.99% EC (3.574), 0.01% $β^-$ (0.72746) |
| Br-80m1 | 265.20 | 4.42 | | IT | 0.085 | |
| Br-80 | 17.40 | 0.29 | | EC | 1.870 | 1.87 (EC), 2.004 (β−), EC = 91.7, β− = 8.3 |
| Br-82 | | 35.30 | 1.47 | β− | 3.090 | |
| Br-83 | 143.40 | 2.39 | | β− | 0.972 | |
| Br-84 | 31.80 | 0.53 | | β− | 4.656 | |
| Br-84m1 | 6.00 | | | β− | 4.960 | |
| Br-85 | 2.90 | | | β− | 2.905 | |
| Yttrium | | | | | | |
| Y-83 | 7.08 | | | EC | 4.470 | |
| Y-83m1 | 2.85 | | | EC | 4.532 | 4.532 (ECβ+), 0.062 (IT), ECβ+ = 60, IT = 40 |
| Y-84 | | | | | | |
| Y-84m1 | 39.50 | 0.66 | | EC | 6.490 | |
| Y-85 | 160.80 | 2.68 | | EC | 3.250 | |
| Y-85m1 | 291.60 | 4.86 | | EC | 3.270 | |
| Y-86m1 | 48.00 | 0.80 | | IT | 0.218 | |
| Y-86 | | 14.74 | | ECβ+ | 4.22 | |
| Y-87m1 | | 13.37 | | IT | 0.381 | 0.381 (IT), 2.243 (ECβ+), IT = 98.43, ECβ+ = 1.57 |
| Y-87 | | 80.30 | 3.35 | ECβ+ | 1.862 | |
| Y-88 | | | 106.64 | ECβ+ | 3.623 | |
| Y-90m1 | | 3.19 | | IT | 0.682 | |
| Y-90 | | 64.08 | 2.67 | β− | 2.280 | |
| Y-91m1 | 49.71 | 0.83 | | IT | | |
| Y-91 | | | 58.51 | β− | | |
| Y-92 | | 3.54 | | β− | 3.639 | |
| Y-93 | | 10.10 | | β− | 2.893 | |
| Y-94 | 19.10 | 0.32 | | β− | 4.919 | |
| Y-95 | 10.70 | 0.18 | | β− | 4.420 | |
| Zirconium | | | | | | |
| Zr-84 | 25.90 | | | ECβ+ | | |
| Zr-85 | 7.86 | | | ECβ+ | 4.690 | |
| Zr-86 | | 16.50 | | ECβ+ | 1.480 | |
| Zr-87 | 100.80 | 1.68 | | ECβ+ | 3.665 | |
| Zr-88 | | | 83.40 | EC | 0.670 | |
| Zr-89m1 | 4.18 | | | IT | 0.588 | 3.420 (ECβ+), 0.588 (IT), ECβ+ = 6.23, IT = 93.77 |
| Zr-89 | | 78.43 | 3.27 | β+ | 0.9 | |
| Zr-95 | | | 63.98 | β− | 1.125 | |
| Zr-97 | | 16.90 | | β− | 2.658 | |
| Niobium | | | | | | |
| Nb-87 | 2.60 | | | ECβ+ | 5.170 | |
| Nb-87m1 | 3.70 | | | ECβ+ | 5.170 | |
| Nb-88 | 14.50 | 0.24 | | ECβ+ | 7.200 | |
| Nb-88m1 | 7.80 | | | ECβ+ | 7.200 | |
| Nb-89 | 114.00 | 1.90 | | ECβ+ | 4.290 | |
| Nb-89m1 | 70.80 | 1.18 | | ECβ+ | 4.290 | |
| Nb-90 | | 14.60 | | ECβ+ | 6.111 | |
| Nb-91m1 | | | 60.86 | IT | 0.104 | 0.104 (IT), 1.357 (ECβ+), IT = 93, ECβ+ = 7 |
| Nb-95m1 | | 86.60 | 3.61 | IT | 0.236 | |
| Nb-95 | | | 35.15 | β− | 0.926 | |
| Nb-96 | | 23.35 | | β− | 3.187 | |
| Nb-97 | 72.10 | 1.20 | | β− | 1.934 | |
| Nb-98m1 | 51.50 | 0.86 | | β− | 4.585 | |
| Molybdenum | | | | | | |
| Mo-88 | 8.00 | | | ECβ+ | 3.720 | |
| Mo-89 | 2.04 | | | ECβ+ | 5.580 | |
| Mo-90 | | 5.67 | | ECβ+ | 2.489 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Mo-91 | 15.49 | | | ECβ+ | 4.434 | |
| Mo-93m1 | | 6.85 | | IT. ECβ+ | 2.830 | IT = 99.88, ECβ+ = 0.12 |
| Mo-99 | | 66.00 | 2.75 | β− | 1.375 | |
| Mo-101 | 14.62 | 0.24 | | β− | 2.824 | |
| Mo-102 | 11.30 | | | β− | 1.010 | |
| Technetium | | | | | | |
| Tc-91 | 3.14 | 0.05 | | ECβ+ | 6.220 | |
| Tc-91m1 | 3.30 | 0.06 | | ECβ+ | 6.570 | 6.57 (ECβ+), 0.35 (IT); ECβ+ ≈ 100, IT < 1 |
| Tc-92 | 4.23 | 0.07 | | ECβ+ | 7.870 | |
| Tc-93m1 | 43.50 | 0.73 | | IT | 0.392 | 3.593 (ECβ+), 0.392 (IT), IT = 76.6, ECβ+ = 23.4 |
| Tc-93 | | 2.75 | | EC | 3.201 | |
| Tc-94m1 | 52.00 | 0.87 | | β+ | 2.36 | 1.730 (ECβ+), 0.075 (IT); ECβ+ ≈ 100, IT < 0.1 |
| Tc-94 | | 4.90 | | ECβ+ | 4.256 | |
| Tc-95m1 | | | 61.00 | ECβ+ | 1.730 | 1.730 (ECβ+), 0.039 (IT); ECβ+ = 96.12, IT = 3.88 |
| Tc-95 | | 20.00 | | EC | 1.691 | |
| Tc-96m1 | 51.50 | 0.86 | | IT | 0.034 | 3.007 (ECβ+), 0.034 (IT), IT = 98.0, ECβ+ = 2.0 |
| Tc-96 | | 102.72 | 4.28 | EC | 2.973 | |
| Tc-97m1 | | | 87.00 | IT | 0.097 | |
| Tc-99m1 | | 6.02 | | IT | 0.143 | |
| Tc-101 | 14.20 | 0.24 | | β− | 1.614 | |
| Tc-102m1 | 4.35 | | | β− | 4.530 | 4.53 (β−), 0.0 (IT), β− = 98, IT = 2 |
| Tc-104 | 18.20 | 0.30 | | β− | 5.600 | |
| Tc-105 | 7.60 | 0.13 | | β− | 3.640 | |
| Ruthenium | | | | | | |
| Ru-92 | 3.65 | | | ECβ+ | 4.500 | |
| Ru-94 | 51.80 | 0.86 | | EC | 1.593 | |
| Ru-95 | | 1.64 | | ECβ+ | 2.572 | |
| Ru-97 | | 69.60 | 2.90 | EC | 1.115 | |
| Ru-103 | | | 39.28 | β− | 0.763 | |
| Ru-105 | | 4.44 | | β− | 1.917 | |
| Ru-106 | | | 368.20 | β− | 0.039 | |
| Ru-107 | 3.76 | 0.06 | | β− | 2.940 | |
| Ru-108 | 4.55 | 0.08 | | β− | 1.360 | |
| Rhodium | | | | | | |
| Rh-95 | 5.02 | 0.08 | | ECβ+ | 5.110 | |
| Rh-95m1 | 1.96 | 0.03 | | IT | 0.543 | 5.653 (ECβ+), 0.543 (IT); % ECβ+ = 12, IT = 88 |
| Rh-96 | 9.90 | 0.17 | | ECβ+ | 6.446 | |
| Rh-97 | 30.70 | 0.51 | | ECβ+ | 3.520 | |
| Rh-97m1 | 46.20 | 0.77 | | ECβ+ | 3.779 | 3.779 (ECβ+), 0.259 (IT); ECβ+ = 94.4, IT = 5.6 |
| Rh-98 | 8.70 | 0.15 | | ECβ+ | 5.057 | |
| Rh-98m1 | 3.50 | 0.06 | | ECβ+ | 5.057 | 5.057 (ECβ+), 0.0 (IT); ECβ+ > 0 |
| Rh-99m1 | | 4.70 | | ECβ+ | 2.167 | 2.167 (ECβ+), 0.064 (IT), ECβ+ > 99.84, IT < 0.16 |
| Rh-99 | | | 16.00 | ECβ+ | 2.130 | |
| Rh-100 | | 20.80 | | ECβ+ | 3.630 | |
| Rh-101m1 | | 104.16 | 4.34 | EC | 0.699 | 0.699 (EC), 0.157 (IT), EC = 92.8, IT = 7.2 |
| Rh-102 | | | 207.00 | ECβ+ | 2.323 | 2.323 (ECβ+), 1.150 (β−), ECβ+ = 80, β− = 20 |
| Rh-103m1 | 56.12 | 0.94 | | IT | 0.040 | |
| Rh-104m1 | 4.34 | | | IT | 0.129 | 0.129 (IT), 2.570 (β−), IT = 99.87, β$^-$ = 0.13 |
| Rh-105 | | 35.36 | 1.47 | β− | 0.567 | |
| Rh-106m1 | 132.00 | 2.20 | | β− | 3.678 | |
| Rh-107 | 21.70 | 0.36 | | β− | 1.511 | |
| Rh-108m1 | 6.00 | | | β− | 4.510 | |
| Palladium | | | | | | |
| Pd-97 | 3.10 | | | ECβ+ | 4.800 | |
| Pd-98 | 17.70 | | | ECβ+ | 1.873 | |
| Pd-99 | 21.40 | | | ECβ+ | 3.365 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Pd-100 | | 87.12 | 3.63 | EC | 0.361 | |
| Pd-101 | | 8.27 | | ECβ+ | 1.980 | |
| Pd-103 | | | 16.96 | EC | 0.543 | |
| Pd-109 | | 13.43 | | β− | 1.116 | |
| Pd-109m1 | 4.70 | | | IT | 0.189 | |
| Pd-111 | 23.40 | 0.39 | | β− | 2.190 | |
| Pd-111m1 | | 5.50 | | IT | 0.172 | 0.172 (IT), 2.362 ($\beta^-$); IT = 73, β− = 27 |
| Pd-112 | | 21.03 | | β− | 0.288 | |
| Pd-114 | 2.42 | 0.04 | | β− | 1.451 | |
| Silver | | | | | | |
| Ag-100 | 2.01 | | | ECβ+ | 7.050 | |
| Ag-100m1 | 2.24 | | | ECβ+ | 7.066 | 7.066 ($EC\beta^+$), 0.015 (IT) |
| Ag-101 | 11.10 | | | ECβ+ | 4.200 | |
| Ag-102 | 12.90 | 0.22 | | ECβ+ | 5.920 | |
| Ag-102m1 | 7.70 | | | ECβ+ | 5.929 | 5.929 (ECβ+), 0.009 (IT), ECβ+ = 51, IT = 49 |
| Ag-103 | 65.70 | 1.10 | | ECβ+ | 2.688 | |
| Ag-104m1 | 33.50 | 0.56 | | ECβ+ | 4.286 | 4.286 (ECβ+), 0.007 (IT), ECβ+ ≈ 100, IT < 0.07 |
| Ag-104 | 69.20 | 1.15 | | ECβ+ | 4.279 | |
| Ag-105 | | | 41.00 | ECβ+ | 1.346 | |
| Ag-106m1 | | 201.84 | 8.41 | EC | 3.055 | |
| Ag-106 | 23.96 | 0.40 | | ECβ+ | 2.965 | 2.965 (ECβ+), 0.195 (β−), ECβ+ = 99.5, β− < 1 |
| Ag-108 | 2.37 | 0.04 | | β− | 1.649 | 1.649 (β−), 1.918 (ECβ+), β− = 97.15, ECβ+ = 2.85 |
| Ag-110m1 | | | 249.90 | β− | 3.010 | 3.010 (β−), 0.188 (IT), $\beta^-$ = 98.64, IT = 1.,36 |
| Ag-111 | | 178.80 | 7.45 | β− | 0.810 | |
| Ag-112 | 187.20 | 3.12 | | β− | 3.956 | |
| Ag-113 | 322.20 | 5.37 | | β− | 2.016 | |
| Ag-115 | 20.00 | 0.33 | | β− | 3.100 | |
| Ag-116 | 2.68 | | | β− | 6.160 | |
| Cadmium | | | | | | |
| Cd-102 | 5.50 | | | ECβ+ | 2.587 | |
| Cd-103 | 7.30 | | | ECβ+ | 4.142 | |
| Cd-104 | 57.70 | 0.96 | | ECβ+ | 1.136 | |
| Cd-105 | 55.50 | | | ECβ+ | 2.739 | |
| Cd-107 | | 6.49 | | ECβ+ | 1.417 | |
| Cd-111 | 48.54 | | | IT | 0.396 | |
| Cd-115m1 | | | 44.60 | β− | 1.627 | |
| Cd-115 | | 53.46 | 2.23 | β− | 1.446 | |
| Cd-117m1 | 201.60 | 3.36 | | β− | 2.653 | |
| Cd-117 | 149.40 | 2.49 | | β− | 2.517 | |
| Cd-118 | 50.30 | | | β− | 0.520 | |
| Cd-119 | 2.69 | | | β− | 3.800 | |
| Cd-119m1 | 2.20 | | | β− | 3.947 | |
| Indium | | | | | | |
| In-105 | 5.07 | | | ECβ+ | 4.85 | |
| In-106 | 6.20 | | | ECβ+ | 6.52 | |
| In-106m1 | 5.20 | | | ECβ+ | 6.55 | |
| In-107 | 32.40 | | | ECβ+ | 3.43 | |
| In-108 | 58.00 | | | ECβ+ | 5.15 | |
| In-108m1 | 39.60 | | | ECβ+ | 5.18 | |
| In-109 | | 4.20 | | ECβ+ | 2.020 | |
| In-110 | | 4.9 | | ECβ+ | 3.878 | |
| In-110m1 | 69.10 | 1.15 | | ECβ+ | 3.940 | |
| In-111 | | 67.92 | 2.83 | EC | 0.245 | |
| In-112 | 14.40 | 0.24 | | ECβ+ | 2.586 | 2.586 (ECβ+), 0.664 (β−); ECβ+ = 56, β− = 44 |
| In-113m1 | | 1.66 | | IT | 0.392 | |
| In-114m1 | | | 49.51 | IT | 0.190 | 0.190 (IT), 1.642 (ECβ+), IT = 96.75, ECβ+ = 3.25 |
| In-115m1 | | 4.49 | | IT | 0.336 | 0.336 (IT), 0.831 (β−), IT = 95.0, $\beta^-$ = 5.0 |
| In-116m1 | 54.15 | 0.90 | | β− | 3.401 | |
| In-117m1 | 116.50 | 1.94 | | β− | 1.770 | 1.770 ($\beta^-$), 0.315 (IT); β− = 52.9, IT = 47.1 |
| In-117 | 43.80 | 0.73 | | β− | 1.455 | |
| In-118m1 | 4.45 | | | β− | 4.483 | |

TABLE 4-continued

| Key properties of relevant radionuclides - half life, decay types and decay energies | | | | | | |
|---|---|---|---|---|---|---|
| Radionuclide | Half-life (min) | Half-life (hours) | Half-life (days) | Decay | Energy (MeV) | Additional decays (energy [MeV]) |
| In-119m1 | 18.00 | 0.30 | | β− | 2.675 | 2.675 (β⁻), 0.311 (IT); β− = 94.4, IT = 5.6 |
| In-119 | 2.40 | 0.04 | | β− | 2.364 | |
| In-121m1 | 3.88 | 0.06 | | β− | 3.674 | 3.674 (β−), 0.314 (IT), β⁻ = 98.8, IT = 1.2 |
| Tin | | | | | | |
| Sn-107 | 2.90 | | | ECβ+ | 5.01 | |
| Sn-108 | 10.30 | | | ECβ+ | 2.092 | |
| Sn-109 | 18.00 | | | ECβ+ | 3.85 | |
| Sn-110 | | 4.11 | | EC | 0.638 | |
| Sn-111 | 35.30 | 0.59 | | ECβ+ | 2.445 | |
| Sn-113m1 | | 21.40 | | ECβ+ | 1.113 | 0.077 (IT), 1.113 (ECβ+), IT = 91.1, ECβ+ = 8.9 |
| Sn-113 | | | 115.09 | ECβ+ | 1.036 | |
| Sn-117m1 | | | 13.61 | IT | 0.135 | |
| Sn-119m1 | | | 293.00 | IT | 0.090 | |
| Sn-121 | | 27.06 | 1.13 | β− | 0.388 | |
| Sn-123m1 | 40.08 | 0.67 | | β− | 1.429 | |
| Sn-123 | | | 129.20 | β− | 1.404 | |
| Sn-125 | | 231.36 | 9.64 | β− | 2.364 | |
| Sn-125m1 | 9.52 | | | β⁻ | 2.364 | |
| Sn-127 | | 2.10 | | β− | 3.20 | |
| Sn-127m1 | 4.13 | | | β⁻ | 3.21 | |
| Sn-128 | 59.10 | 0.99 | | β− | 1.27 | |
| Sn-129 | 2.23 | | | β⁻ | 4.00 | |
| Sn-129m1 | 6.90 | | | β⁻ | 4.04 | 4.035 (β−), 0.035 (IT), β⁻ ≈ 100, IT ≈ $2 \cdot 10^{-4}$ |
| Sn-130 | 3.72 | | | β⁻ | 2.15 | |
| Antimony | | | | | | |
| Sb-113 | 6.67 | 0.11 | | β+ | 3.905 | |
| Sb-114 | 3.49 | 10.06 | | β+ | 5.880 | |
| Sb-155 | 32.10 | 0.54 | | β+ | 3.030 | |
| Sb-116 | 15.80 | 0.26 | | β+ | 4.707 | |
| Sb-116m1 | 60.30 | 1.01 | | β⁺ | 5.090 | |
| Sb-117 | 62.80 | 2.80 | | β⁺ | 1.757 | |
| Sb-118 | 3.60 | 0.06 | | β⁺ | 3.657 | |
| Sb-18m1 | | 5.00 | | β⁺ | 3.907 | |
| Sb-119 | | 38.19 | 1.59 | EC | 0.594 | |
| Sb-120m1 | | 138.24 | 5.76 | EC | 2.681 | |
| Sb-120 | 15.89 | 0.26 | | ECβ+ | 2.681 | |
| Sb-122 | | 65.28 | 2.72 | β− | 1.979 | 1.979 (β−), 1.620 (ECβ+), β− = 97.59, ECβ+ = 2.41 |
| Sb-122m2 | 4.19 | 0.07 | | IT | 0.164 | |
| Sb-124m2 | 20.20 | 0.34 | | IT | 0.037 | |
| Sb-124 | | | 60.20 | β− | 2.905 | |
| Sb-126m1 | 19.15 | 0.32 | | β− | 3.688 | 3.688 (β−), 0.016 (IT), β− = 86, IT = 14 |
| Sb-126 | | | 12.40 | β− | 3.670 | |
| Sb-127 | | 92.40 | 3.85 | β− | 1.581 | |
| Sb-128 | | 9.01 | | β⁻ | 4.380 | |
| Sb-128m1 | 10.40 | 0.17 | | β− | 4.380 | 4.380 (β−), 0.0 (IT), β− = 96.4, IT = 3.6 |
| Sb-129 | 259.20 | 4.32 | | β− | 2.380 | |
| Sb-129m1 | 17.70 | 0.30 | | β− | 4.231 | 4.231 (β−), 1.851 (IT), β− = 85, IT = 15 |
| Sb-130 | 40.00 | 0.67 | | β− | 4.960 | |
| Sb-130m1 | 6.30 | 0.11 | | β⁻ | 4.960 | |
| Sb-131 | 23.00 | 0.38 | | β− | 3.190 | |
| Sb-132 | 2.79 | | | β− | 5.290 | |
| Sb-132m1 | 4.15 | 0.07 | | β⁻ | 5.290 | |
| Sb-133 | 2.50 | 0.04 | | β⁻ | 4.003 | |
| Tellurium | | | | | | |
| Te-112 | 2.00 | | | ECβ+ | 4.35 | |
| Te-114 | 15.20 | | | ECβ+ | 2.8 | |
| Te-115 | 5.80 | | | ECβ+ | 4.64 | |
| Te-115m1 | 6.70 | | | ECβ+ | 4.66 | 4.66 (ECβ+), 0.02 (IT), ECβ+ < 100 |
| Te-116 | | 2.49 | | EC | 1.510 | |
| Te-117 | 62.00 | 1.00 | | ECβ+ | 3.535 | |
| Te-118 | 360.00 | 6 | | EC | 0.278 | |
| Te-119 | 961.80 | 16.03 | | ECβ+ | 2.293 | |

TABLE 4-continued

| Key properties of relevant radionuclides - half life, decay types and decay energies | | | | | | |
|---|---|---|---|---|---|---|
| Radionuclide | Half-life (min) | Half-life (hours) | Half-life (days) | Decay | Energy (MeV) | Additional decays (energy [MeV]) |
| Te-119m1 | 282.00 | 4.7 | | ECβ+ | 2.554 | 2.554 (ECβ+), 0.261 (IT), ECβ+ ≈ 100, IT < 0.008 |
| Te-121m1 | | | 154.00 | IT | 0.294 | 0.294 (IT), 1.334 (ECβ+), IT = 88.6, ECβ+ = 11.4 |
| Te-121 | | | 17.00 | EC | 1.040 | |
| Te-123m1 | | | 119.70 | IT | 0.248 | |
| Te-125m1 | | | 58.00 | IT | 0.145 | |
| Te-127m1 | | | 109.00 | IT | 0.088 | 0.088 (IT), 0.786 (β−), IT = 97.6, $β^-$ = 2.4 |
| Te-127 | | 9.35 | | β− | 0.698 | |
| Te-129m1 | | | 33.60 | IT | 0.105 | 0.105 (IT), 1.604 (β−), IT = 63, $β^-$ = 37 |
| Te-129 | 69.60 | 1.16 | | β− | 1.498 | |
| Te-131ml | | 30.00 | 1.25 | β− | 2.415 | |
| Te-131 | 25.00 | 0.42 | | β− | 2.233 | |
| Te-132 | | 78.20 | 3.26 | β− | 0.493 | |
| Te-133m1 | 55.40 | 0.92 | | β− | 3.254 | 3.254 (β−), 0.334 (IT), $β^-$ = 82.5, IT = 17.5 |
| Te-133 | 12.45 | 0.21 | | β− | 2.920 | |
| Te-134 | 41.80 | 0.70 | | β− | 1.560 | |
| Iodine | | | | | | |
| I-117 | 2.22 | | | ECβ+ | 4.67 | |
| I-118 | 13.70 | | | ECβ+ | 7.04 | |
| I-118m1 | 8.50 | | | ECβ+ | 7.14 | 7.144 (ECβ+), 0.104 (IT), ECβ+ < 100, IT > 0 |
| I-119 | 19.10 | | | ECβ+ | 3.51 | |
| I-120m1 | 53.00 | 0.88 | | ECβ+ | 5.615 | |
| I-120 | 81.00 | 1.35 | | ECβ+ | 5.615 | |
| I-121 | 127.20 | 2.12 | | ECβ+ | 2.270 | |
| I-122 | 3.62 | 0.06 | | ECβ+ | 4.234 | |
| I-123 | | 13.20 | | EC | 0.159 | |
| I-124 | | 100.32 | 4.18 | β+ | 2.14 | |
| I-125 | | | 59.408 | EC | 0.035 | |
| I-126 | | | 13.02 | ECβ+ | 2.155 | 2.155 (ECβ+), 1.258 (β−), ECβ+ = 56.3, β− = 43.7 |
| I-128 | 24.99 | 0.42 | | β− | 2.118 | 2118 (β−), 1.251 (ECβ+), β− = 93.1, ECβ+ = 6.9 |
| I-130 | | 12.36 | | β− | 2.949 | |
| I-130m1 | 9.00 | | | IT | 0.040 | 0.040 (IT), 2.989 ($β^-$), IT = 84, β− = 16 |
| I-131 | | 192.96 | 8.04 | β− | 0.806 | |
| I-132m1 | 83.60 | 1.39 | | IT | 0.120 | 0.120 (IT), 3.697 ($β^-$), IT = 86, β− = 14 |
| I-132 | | 2.30 | | β− | 3.577 | |
| I-133 | | 20.80 | | β− | 1.770 | |
| I-134 | 52.60 | 0.88 | | β− | 4.170 | |
| I-134m1 | 3.60 | | | IT | 0.316 | 0.316 (IT), 4.486 ($β^-$), IT = 97.7, β− = 2.3 |
| I-135 | | 6.61 | | β− | 2.648 | |
| Lanthanum | | | | | | |
| La-127 | 5.10 | | | ECβ+ | 4.69 | |
| La-127m1 | 3.70 | | | ECβ+ | 4.705 | |
| La-827 | 5.00 | | | ECβ+ | 6.7 | |
| La-129 | 11.60 | | | ECβ+ | 3.72 | |
| La-130 | 8.70 | | | ECβ+ | 5.6 | |
| La-131 | 59.00 | 0.98 | | ECβ+ | 2.960 | |
| La-132 | | 4.80 | | ECβ+ | 4.710 | |
| La-132m1 | 24.30 | | | IT | 0.188 | 0.188 (IT), 4.898 (ECβ+), IT = 76, ECβ+ = 24 |
| La-133 | 234.72 | 3.912 | | ECβ+ | 2.23 | |
| La-134 | 6.67 | 0.11 | | ECβ+ | 6.450 | |
| La-135 | | 19.50 | | ECβ+ | 1.200 | |
| La-136 | 9.87 | | | ECβ+ | 2.87 | |
| La-140 | | 40.27 | 1.68 | β− | 3.762 | |
| La-141 | | 3.93 | | β− | 2.502 | |
| La-142 | 92.50 | 1.54 | | β− | 4.505 | |
| La-143 | 14.23 | 0.24 | | β− | 3.425 | |
| Cerium | | | | | | |
| Ce-129 | 3.50 | 0.06 | | ECβ+ | 5.05 | |
| Ce-130 | 25.00 | 0.42 | | ECβ+ | 2.2 | |
| Ce-131 | 10.20 | 0.17 | | ECβ+ | 4 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Ce-131m1 | 5.00 | | | ECβ+ | 4 | |
| Ce-132 | 210.60 | 3.51 | | ECβ+ | 1.29 | 1.29 (ECβ+), 2.341 (IT) |
| Ce-133 | 97.00 | 1.62 | | ECβ+ | 2.9 | |
| Ce-133m1 | 294.00 | 4.9 | | ECβ+ | 2.937 | |
| Ce-134 | | 72.00 | 3.00 | EC | 0.500 | |
| Ce-135 | | 17.60 | | ECβ+ | 2.026 | |
| Ce-137m1 | | 34.40 | 1.43 | IT | 0.254 | 0.254 (IT), 1.476 (ECβ+), IT = 99.22, ECβ+ = 0.78 |
| Ce-137 | 540.00 | 9.00 | | EC | 1.222 | |
| Ce-139 | | | 137.66 | EC | 0.278 | |
| Ce-141 | | | 32.50 | β− | 0.581 | |
| Ce-143 | | 33.00 | 1.38 | β− | 1.462 | |
| Ce-144 | | | 284.30 | β− | 0.319 | |
| Ce-145 | 3.01 | | | $\beta^-$ | 2.54 | |
| Ce-146 | 13.52 | | | $\beta^-$ | 1.04 | |
| Praseodymium | | | | | | |
| Pr-133 | 6.50 | | | ECβ+ | 4.3 | |
| Pr-134 | 17.00 | | | ECβ+ | 6.2 | |
| Pr-134m1 | 11.00 | | | ECβ+ | 6.2 | |
| Pr-135 | 24.00 | | | ECβ+ | 3.72 | |
| Pr-136 | 13.10 | 0.22 | | ECβ+ | 5.126 | |
| Pr-137 | 76.60 | 1.28 | | ECβ+ | 2.702 | |
| Pr-138m1 | | 2.10 | | ECβ+ | 4.801 | |
| Pr-139 | | 4.51 | | ECβ+ | 2.129 | |
| Pr-140 | 3.39 | | | ECβ+ | 3.388 | |
| Pr-142m1 | 14.60 | 0.24 | | IT | 0.004 | |
| Pr-142 | | 19.12 | | β− | 2.162 | β− ≈ 100, EC = 0.0164 |
| Pr-143 | | | 13.56 | β− | 0.934 | |
| Pr-144m1 | 7.20 | 0.12 | | IT | 0.059 | IT ≈ 100, $\beta^-$ = 0.07 |
| Pr-144 | 17.28 | 0.29 | | β− | 2.997 | |
| Pr-145 | | 5.98 | | β− | 1.805 | |
| Pr-146 | 24.15 | | | $\beta^-$ | 4.2 | |
| Pr-147 | 13.60 | 0.23 | | β− | 2.69 | |
| Pr-148 | 2.27 | | | $\beta^-$ | 4.93 | |
| Pr-148m1 | 2.00 | | | $\beta^-$ | 5.02 | |
| Pr-149 | 2.26 | | | $\beta^-$ | 3.397 | |
| Neodymium | | | | | | |
| Nd-134 | 8.50 | | | ECβ+ | 2.77 | |
| Nd-135 | 12.40 | | | ECβ+ | 4.8 | |
| Nd-135m1 | 5.50 | | | ECβ+ | 4.856 | |
| Nd-136 | 50.65 | 0.84 | | ECβ+ | 2.210 | |
| Nd-137 | 38.50 | | | ECβ+ | 3.69 | |
| Nd-138 | 302.40 | 5.04 | | EC | 1.1 | |
| Nd-139m1 | 330.00 | 5.50 | | ECβ+ | 3.021 | 3.021 (ECβ+), 0.231 (IT), ECβ+ = 88.2, IT =11.8 |
| Nd-139 | 29.70 | 0.50 | | ECβ+ | 2.79 | |
| Nd-140 | 202.20 | 3.37 | | EC | 0.222 | |
| Nd-141 | | 2.49 | | ECβ+ | 1.823 | |
| Nd-147 | | | 10.98 | β− | 0.896 | |
| Nd-149 | | 1.73 | | β− | 1.691 | |
| Nd-151 | 12.44 | 0.21 | | β− | 2.442 | |
| Nd-152 | 11.40 | | | $\beta^-$ | 1.11 | |
| Promethium | | | | | | |
| Pm-137 | 2.40 | | | ECβ+ | | |
| Pm-138m1 | 3.24 | | | ECβ+, IT | 6.9 | |
| Pm-139 | 4.15 | | | ECβ+ | 4.52 | |
| Pm-140m1 | 5.95 | | | ECβ+ | 6.09 | |
| Pm-140m2 | 5.95 | | | ECβ+ | | |
| Pm-141 | 20.90 | 0.35 | | ECβ+ | 3.715 | |
| Pm-143 | | | 265.00 | EC | 1.041 | |
| Pm-148m1 | | | 41.30 | β− | 2.606 | 2.606 (β−), 0.138 (IT), β− = 95.0, IT = 5.0 |
| Pm-148 | | 128.88 | 5.37 | β− | 2.468 | |
| Pm-149 | | 53.08 | 2.21 | β− | 1.071 | |
| Pm-150 | | 2.68 | | β− | 3.454 | |
| Pm-151 | | 28.40 | 1.18 | β− | 1.187 | |
| Pm-152 | 4.12 | | | $\beta^-$ | 3.5 | |
| Pm-152m1 | 7.52 | | | $\beta^-$ | 3.56 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Pm-152m2 | 13.80 | | | $\beta^-$ | | $\beta^-$ < 100, IT > 0 |
| Pm-153 | 5.25 | | | $\beta^-$ | 1.9 | |
| Pm-154m1 | 2.68 | | | $\beta^-$ | 4.05 | |
| Samarium | | | | | | |
| Sm-138 | 3.10 | 0.05 | | ECβ+ | 3.900 | |
| Sm-139 | 2.57 | 0.04 | | ECβ+ | 5.460 | |
| Sm-140 | 14.80 | 0.25 | | ECβ+ | 3.020 | |
| Sm-141m1 | 22.60 | 0.38 | | ECβ+ | 4.719 | 4.719 (ECβ+), 0.176 (IT); ECβ+ = 99.69, IT = 0.31 |
| Sm-141 | 10.20 | 0.17 | | ECβ+ | 4.543 | |
| Sm-142 | 72.49 | 1.21 | | ECβ+ | 2.090 | |
| Sm-143 | 8.83 | | | ECβ+ | 3.443 | |
| Sm-145 | | | 340.00 | EC | 0.617 | |
| Sm-153 | | 46.80 | 1.95 | β– | 0.810 | |
| Sm-155 | 22.30 | 0.37 | | β– | 1.627 | |
| Sm-156 | | 9.40 | | β– | 0.722 | |
| Sm-158 | 5.30 | 0.09 | | β– | 1.999 | |
| Europium | | | | | | |
| Eu-143 | 2.63 | | | ECβ+ | 5.275 | |
| Eu-145 | | 142.56 | 5.94 | ECβ+ | 2.660 | |
| Eu-146 | | 110.64 | 4.61 | ECβ+ | 3.878 | |
| Eu-147 | | | 24.10 | ECβ+ | 1.722 | |
| Eu-148 | | | 54.50 | ECβ+ | 3.107 | |
| Eu-149 | | | 93.10 | EC | 0.692 | |
| Eu-150 | | 12.62 | | β– | 1.013 | ECβ+ = 11, β– = 89, IT < 5 · 10–8 |
| Eu-152m1 | | 9.32 | | β– | 1.865 | ECβ+ = 28, β– = 72, 1.920 (ECβ+), 1.865 (β–) |
| Eu-152m2 | 96.00 | 1.6 | | IT | 0.148 | |
| Eu-154m1 | 46.30 | 0.77 | | IT | 0.145 | |
| Eu-156 | | | 15.19 | β– | 2.451 | |
| Eu-157 | | 15.15 | | β– | 1.363 | |
| Eu-158 | 45.90 | 0.77 | | β– | 3.490 | |
| Eu-159 | 18.10 | | | $\beta^-$ | 2.514 | |
| Gadolinium | | | | | | |
| Gd-144 | 4.50 | | | ECβ+ | 3.74 | |
| Gd-145 | 22.90 | 0.38 | | ECβ+ | 5.050 | |
| Gd-146 | | | 48.30 | EC | 1.030 | |
| Gd-147 | | 38.10 | 1.59 | ECβ+ | 2.187 | |
| Gd-149 | | 225.60 | 9.40 | ECβ+ | 1.314 | |
| Gd-151 | | | 120.00 | EC | 0.464 | |
| Gd-153 | | | 242.00 | EC | 0.485 | |
| Gd-159 | | 18.49 | | β– | 0.971 | |
| Gd-161 | 3.66 | | | $\beta^-$ | 1.956 | |
| Gd-162 | 8.40 | | | $\beta^-$ | 1.39 | |
| Terbium | | | | | | |
| Tb-147 | | 1.65 | | ECβ+ | 4.609 | |
| Tb-148 | | 1.00 | | ECβ+ | 5.690 | |
| Tb-148m1 | 2.20 | | | ECβ+ | 5.78 | |
| Tb-149 | | 4.15 | | β+ | 2.62 | 3.636 (ECβ+), 4.113 (α); ECβ+ = 83.3, α = 16.7 |
| Tb-149m1 | 4.16 | | | ECβ+ | 3.672 | 3.672 (ECβ+), 4.077 (α), ECβ+ = 99.978, α = 0.022 |
| Tb-150 | | 3.27 | | ECβ+ | 4.656 | |
| Tb-150m1 | 5.80 | | | ECβ+ | 5.13 | |
| Tb-151 | | 17.60 | | β+ | 1.54 | 2.565 (ECβ+), 3.497 (α); ECβ+ ≈ 100, α = 9.5 · 10–3 |
| Tb-152m1 | 4.20 | | | IT | 0.052 | 0.502 (IT), 4.492 (ECβ+), IT = 78.8, ECβ+ = 21.2 |
| Tb-152 | | 17.50 | | ECβ+ | 3.990 | 3,.990 (ECβ+), 3.090 (α); ECβ+ ≈ 100, α < 7 · 10–7 |
| Tb-153 | | 56.16 | 2.34 | ECβ+ | 1.570 | |
| Tb-154 | | 21.40 | | ECβ+ | 3.560 | 3.56 (ECβ+), 0.25 (β–), ECβ+ ≈ 100, β– < 0.1 |
| Tb-154m1 | | 9.4 | | ECβ+ | 3.560 | 3.56 (ECβ+), 0.0 (IT), 0.25 (β–), ECβ+ = 78.2, IT = 21.8, β– < 0.1 |
| Tb-154m2 | | 22.7 | | ECβ+ | 3.560 | 3.56 (ECβ+), 0.0 (IT), ECβ+ = 98.2, IT = 1.8 |
| Tb-155 | | 127.68 | 5.32 | EC | 0.821 | |
| Tb-156m1 | | 24.40 | | IT | 0.050 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Tb-156m2 | | 5.00 | | IT | 0.088 | 0.088 (IT), 2.532 (ECβ+) |
| Tb-156 | | 128.40 | 5.35 | ECβ+ | 2.444 | 2.444 (ECβ+), 0.434 (β−); ECβ+ ≈ 100, β− = ? |
| Tb-160 | | | 72.30 | β− | 1.835 | |
| Tb-161 | | 165.84 | 6.91 | β− | 0.593 | |
| Tb-162 | 7.60 | 0.13 | | β− | 2.510 | |
| Tb-163 | 19.50 | 0.33 | | β− | 1.785 | |
| Tb-164 | 3.00 | | | $\beta^-$ | 3.89 | |
| Tb-165 | 2.11 | | | $\beta^-$ | 3 | |
| Dysprosium | | | | | | |
| Dy-148 | 3.10 | 186 | | ECβ+ | 2.678 | |
| Dy-149 | 4.20 | 252 | | ECβ+ | 3.812 | |
| Dy-150 | 7.17 | 430.2 | | ECβ+ | 1.794 | 4.351 (α), 1.794 (ECβ+), α = 36, ECβ+ = 64 |
| Dy-151 | 17.90 | | | ECβ+ | 2.870 | 2.87 (ECβ+), 4.180 (α), ECβ+ = 94.4, α = 5.6 |
| Dy-152 | | 2.38 | | ECβ+ | 0.600 | 0.60 (ECβ+), 3.727 (α), EC(?) = 99.900, α = 0.100 |
| Dy-153 | | 6.4 | | ECβ+ | 2.170 | 2.17 (ECβ+), 3.559 (α), ECβ+ ≈ 100, α = 0.0094 |
| Dy-155 | | 9.90 | | ECβ+ | 2.095 | |
| Dy-157 | | 8.14 | | ECβ+ | 1.341 | |
| Dy-159 | | | 144.40 | EC | 0.366 | |
| Dy-165 | | 2.33 | | β− | 1.290 | |
| Dy-166 | | 81.60 | 3.40 | β− | 0.486 | |
| Dy-167 | 6.20 | | | $\beta^-$ | 2.35 | |
| Dy-168 | 8.70 | | | $\beta^-$ | 1.6 | |
| Holmium | | | | | | |
| Ho-153 | 2.01 | | | ECβ+ | 4.129 | 4.129 (ECβ+), 4.015 (α), ECβ+ = 99.949, α = 0.051 |
| Ho-153m1 | 9.30 | | | ECβ+ | 4.179 | 4.179 (ECβ+), 4.119 (α), ECβ+ = 99.82, α = 0.18 |
| Ho-154 | 11.76 | | | ECβ+ | 5.751 | 5.751 (ECβ+), 4.042 (α), ECβ+ = 99.981, α = 0.019 |
| Ho-154m1 | 3.10 | | | ECβ+ | 6.071 | 6.071 (ECβ+), 4.362 (α), 0.320 (IT), ECβ+ ≈ 100, α < 0.001, IT ≈ 0 |
| Ho-155 | 48.00 | 0.80 | | ECβ+ | 3.102 | |
| Ho-156 | 56.00 | 0.93 | | ECβ+ | 5.060 | |
| Ho-157 | 12.60 | 0.21 | | ECβ+ | 2.540 | |
| Ho-158 | 11.30 | | | ECβ+ | 4.23 | |
| Ho-158m1 | 28.00 | | | IT | 0.067 | 4.297 (ECβ+), 0.067 (IT), ECβ+ < 19, IT > 81 |
| Ho-158m2 | 21.30 | | | ECβ+ | 4.410 | 4.41 (ECβ+), 0.18 (IT), ECβ+ > 93, IT < 7 |
| Ho-159 | 33.00 | 0.55 | | ECβ+ | 1.838 | |
| Ho-160 | 25.60 | | | ECβ+ | 3.29 | |
| Ho-160m1 | 301.20 | 5.02 | | IT | 0.060 | 0.06 (IT), 3.35 (ECβ+), IT = 65, ECβ+ = 35 |
| Ho-161 | 150.00 | 2.50 | | EC | 0.895 | |
| Ho-162m1 | 67.00 | 1.12 | | IT | 0.106 | 0.106 (IT), 2.246 (ECβ+), IT = 62, ECβ+ = 38 |
| Ho-162 | 15.00 | 0.25 | | ECβ+ | 2.140 | |
| Ho-164m1 | 37.50 | 0.63 | | IT | 0.140 | |
| Ho-164 | 29.00 | 0.48 | | EC | 0.987 | 0.987 (EC), 0.962 (β−); EC = 60, β− = 40 |
| Ho-166 | | 26.80 | 1.12 | β− | 1.855 | |
| Ho-167 | | 3.10 | | β− | 1.007 | |
| Ho-168 | 2.99 | | | $\beta^-$ | 2.91 | |
| Ho-169 | 4.70 | | | $\beta^-$ | 2.124 | |
| Ho-170 | 2.76 | | | $\beta^-$ | 3.87 | |
| Erbium | | | | | | |
| Er-154 | 3.73 | | | ECβ+ | 2.032 | 2.032 (ECβ+), 4.280 (α), ECβ+ = 99.53, α = 0.47 |
| Er-155 | 5.30 | | | ECβ+ | 3.84 | 3.84 (ECβ+), 4.12 (α), ECβ+ = 99.978, α = 0.022 |
| Er-156 | 19.50 | | | ECβ+ | 1.37 | |
| Er-157 | 18.65 | | | ECβ+ | 3.5 | 3.50 (ECβ+), 3.30 (α), ECβ+ ≈ 100, α < 0.02 |
| Er-158 | 137.40 | 2.29 | | EC | 0.9 | |
| Er-159 | 36.00 | | | ECβ+ | 2.769 | |
| Er-160 | | 28.58 | | EC | 0.33 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Er-161 | 192.60 | 3.21 | | ECβ+ | | |
| Er-163 | 75.00 | 1.25 | | ECβ+ | 1.21 | |
| Er-165 | 621.60 | 10.36 | | EC | 0.376 | |
| Er-169 | | 223.20 | 9.30 | β− | 0.340 | |
| Er-171 | 451.20 | 7.52 | | β− | 1.490 | |
| Er-172 | | 49.30 | 2.05 | β− | 0.891 | |
| Er-174 | 3.30 | | | $β^-$ | 1.8 | |
| Thulium | | | | | | |
| Tm-157 | 3.63 | | | ECβ+ | 4.48 | |
| Tm-158 | 3.98 | | | ECβ+ | 6.6 | |
| Tm-159 | 9.13 | | | ECβ+ | 3.85 | |
| Tm-160 | 9.40 | | | ECβ+ | 5.6 | |
| Tm-161 | 33.00 | | | ECβ+ | 3.16 | |
| Tm-162 | 21.70 | 0.36 | | ECβ+ | 4.810 | |
| Tm-163 | 108.60 | 1.81 | | ECβ+ | 2.439 | |
| Tm-164 | 2.00 | | | ECβ+ | 3.962 | |
| Tm-164m1 | 5.10 | | | ECβ+ | 3.962 | |
| Tm-165 | | 30.06 | | ECβ+ | 1.592 | |
| Tm-166 | 462.00 | 7.70 | | ECβ+ | 3.040 | |
| Tm-167 | | 221.76 | 9.24 | EC | 0.748 | |
| Tm-168 | | | 93.10 | ECβ+ | 1.679 | 1.679 (ECβ+), 0.257 (β−), ECβ+ = 99.990, β− = 0.010 |
| Tm-170 | | | 128.60 | β− | 0.968 | 0.314 (ECβ+), 0.968 (β−), EC, β−(99%) |
| Tm-172 | | 63.60 | 2.65 | β− | 1.880 | |
| Tm-173 | | 8.24 | | β− | 1.298 | |
| Tm-174 | 5.40 | | | $β^-$ | 3.08 | |
| Tm-175 | 15.20 | 0.25 | | β− | 2.39 | |
| Tm-176 | 1.90 | | | $β^-$ | 3.88 | |
| Ytterbium | | | | | | |
| Yb-160 | 4.80 | | | ECβ+ | 2.3 | |
| Yb-161 | 4.20 | | | ECβ+ | 4.15 | |
| Yb-162 | 18.90 | 0.32 | | EC | 1.660 | |
| Yb-163 | 11.05 | | | ECβ+ | 3.37 | |
| Yb-164 | 75.80 | | | EC | 1 | |
| Yb-165 | 9.90 | | | ECβ+ | 2.762 | |
| Yb-166 | | 56.70 | 2.36 | EC | 0.304 | |
| Yb-167 | 17.50 | 0.29 | | ECβ+ | 1.954 | |
| Yb-169 | | | 32.01 | EC | 0.909 | |
| Yb-175 | | 100.56 | 4.19 | β− | 0.47 | |
| Yb-177 | | 1.90 | | β− | 1.399 | |
| Yb-178 | 74.00 | 1.23 | | β− | 0.645 | |
| Yb-179 | 8.00 | | | $β^-$ | 2.4 | |
| Yb-180 | 2.40 | | | $β^-$ | | |
| Lutetium | | | | | | |
| Lu-162m2 | 1.90 | | | ECβ+ | | |
| Lu-164 | 3.14 | | | ECβ+ | 6.25 | |
| Lu-165 | 10.74 | | | ECβ+ | 3.92 | |
| Lu-166 | 2.65 | | | ECβ+ | 5.48 | |
| Lu-166m2 | 2.12 | | | ECβ+ | 5.523 | 5.523 (ECβ+), 0.043 (IT), ECβ+ > 80, IT < 20 |
| Lu-167 | 51.50 | 0.86 | | ECβ+ | 3.130 | |
| Lu-168 | 5.50 | | | ECβ+ | 4.48 | |
| Lu-168m1 | 6.70 | | | ECβ+ | 4.700 | 4.70 (ECβ+), 0.220 (IT), ECβ+ > 95, IT < 5 |
| Lu-169 | | 34.06 | 1.42 | ECβ+ | 2.293 | |
| Lu-170 | | 48.00 | 2.00 | ECβ+ | 3.459 | |
| Lu-171 | | 197.28 | 8.22 | ECβ+ | 1.479 | |
| Lu-172 | | 160.80 | 6.70 | ECβ+ | 2.519 | |
| Lu-174m1 | | | 142.00 | IT | 0.171 | 0.171 (IT), 1.545 (EC), IT = 99.38, EC = 0.62 |
| Lu-176m1 | | 3.68 | | β− | 1.316 | 1.316 (β−), 0.229 (EC), β− = 99.905, EC = 0.095 |
| Lu-177m1 | | | 160.90 | β− | 1.468 | 1.468 (β−), 0.970 (IT), β− = 78.3, IT = 21.7 |
| Lu-177 | | | 6.71 | β− | 0.490 | |
| Lu-178m1 | 22.70 | 0.38 | | β− | 2.219 | |
| Lu-178 | 28.40 | 0.47 | | β− | 2.099 | |
| Lu-179 | | 4.59 | | β− | 1.405 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Lu-180 | 5.70 | | | $\beta^-$ | 3.1 | |
| Lu-181 | 3.50 | | | $\beta^-$ | 2.5 | |
| Lu-182 | 2.00 | | | $\beta^-$ | | |
| Hafnium | | | | | | |
| Hf-166 | 6.77 | | | ECβ+ | 2.3 | |
| Hf-167 | 2.05 | | | ECβ+ | 4 | |
| Hf-168 | 25.95 | | | ECβ+ | 1.8 | |
| Hf-169 | 3.24 | | | ECβ+ | 3.27 | |
| Hf-170 | | 16.01 | | EC | 1.1 | |
| Hf-171 | | 12.1 | | ECβ+ | 2.4 | |
| Hf-173 | | 23.60 | 0.98 | ECβ+ | 1.610 | |
| Hf-175 | | | 70.00 | EC | 0.686 | |
| Hf-177m1 | 51.40 | 0.86 | | IT | 2.740 | |
| Hf-179m2 | | | 25.10 | IT | 1.106 | |
| Hf-180m1 | | 5.50 | | IT | 1.141 | 1.141 (IT), 1.287 (β−), IT = 99,.7, β− = 0.3 |
| Hf-181 | | | 42.40 | β− | 1.027 | |
| Hf-182m1 | 61.50 | 1.03 | | β− | 1.546 | 1.546 (β−), 1.173 (IT), β− = 58, IT = 42 |
| Hf-183 | 64.00 | 1.07 | | β− | 2.010 | |
| Hf-184 | | 4.12 | | β− | 1.340 | |
| Hf-185 | 3.50 | | | $\beta^-$ | | |
| Tantalum | | | | | | |
| Ta-168 | 2.00 | | | ECβ+ | 6.7 | |
| Ta-169 | 4.90 | | | ECβ+ | 4.44 | |
| Ta-170 | 6.76 | | | ECβ+ | 6 | |
| Ta-171 | 23.30 | | | ECβ+ | 3.7 | |
| Ta-172 | 36.80 | 0.61 | | ECβ+ | 4.920 | |
| Ta-173 | | 3.65 | | ECβ+ | 2.790 | |
| Ta-174 | | 1.20 | | ECβ+ | 3.850 | |
| Ta-175 | | 10.50 | | ECβ+ | 2.000 | |
| Ta-176 | | 8.08 | | ECβ+ | 3.110 | |
| Ta-177 | | 56.60 | 2.36 | EC | 1.166 | |
| Ta-178m1 | | 2.36 | | EC | 1.910 | |
| Ta-178 | 9.31 | 0.16 | | EC | 1.910 | |
| Ta-180 | | 8.15 | | EC | 0.854 | 0.854 (EC), 0.708 (β−), EC = 86, β− = 14 |
| Ta-182m1 | 15.84 | 0.26 | | IT | 0.52 | |
| Ta-182 | | | 115.00 | β− | 1814.000 | |
| Ta-183 | | 122.40 | 5.10 | β− | 1.070 | |
| Ta-184 | | 8.70 | | β− | 2.870 | |
| Ta-185 | 49.00 | 0.82 | | β− | 1.992 | |
| Ta-186 | 10.50 | 0.18 | | β− | 3.000 | |
| Tungsten | | | | | | |
| W-170 | 2.42 | | | ECβ+ | 3 | |
| W-171 | 2.38 | | | ECβ+ | 4.6 | |
| W-172 | 6.60 | | | ECβ+ | 2.5 | |
| W-173 | 7.60 | | | ECβ+ | 4 | |
| W-174 | 31.00 | | | ECβ+ | 1.9 | |
| W-175 | 35.20 | | | ECβ+ | 2.91 | |
| W-176 | | 2.50 | | EC | 0.790 | |
| W-177 | 135.00 | 2.25 | | ECβ+ | 2.000 | |
| W-178 | | | 21.70 | EC | 0.091 | |
| W-179m1 | 6.40 | | | IT | 0.222 | 0.222 (IT), 1.282 (ECβ+), IT = 99.72, ECβ+ = 0.28 |
| W-181 | | | 121.20 | EC | 0.188 | |
| W-185 | | | 75.10 | β− | 0.433 | |
| W-187 | | 23.72 | 0.99 | β− | 1.311 | |
| W-188 | | | 69.40 | β− | 0.349 | |
| W-189 | 11.50 | | | $\beta^-$ | 2.5 | |
| W-190 | 30.00 | | | $\beta^-$ | 1.27 | |
| Rhenium | | | | | | |
| Re-173 | 1.98 | | | ECβ+ | 4.8 | |
| Re-174 | 2.40 | | | ECβ+ | 6.5 | |
| Re-175 | 5.89 | | | ECβ+ | 4.3 | |
| Re-176 | 5.30 | | | ECβ+ | 5.6 | |
| Re-177 | 14.00 | 0.23 | | ECβ+ | 3.400 | |
| Re-178 | 13.20 | 0.22 | | ECβ+ | 13.200 | |
| Re-179 | 19.50 | | | ECβ+ | 2.71 | |
| Re-180 | 2.43 | 0.04 | | ECβ+ | 3.800 | |

TABLE 4-continued

| Key properties of relevant radionuclides - half life, decay types and decay energies | | | | | | |
|---|---|---|---|---|---|---|
| Radionuclide | Half-life (min) | Half-life (hours) | Half-life (days) | Decay | Energy (MeV) | Additional decays (energy [MeV]) |
| Re-181 | | 20.00 | | ECβ+ | 1.739 | |
| Re-182 | | 64.00 | | EC | 2.800 | |
| Re-182m1 | | 12.70 | | ECβ+ | 2.800 | |
| Re-183 | | | 70.00 | EC | 0.556 | |
| Re-184m1 | | | 169.00 | IT | 0.188 | 0.188 (IT), 1.671 (EC), IT = 75.4, EC = 24.6 |
| Re-184 | | | 38.00 | ECβ+ | 1.483 | |
| Re-186 | | 90.48 | 3.72 | β− | 1.07 | 0.582 (EC), 1.069 (β−); EC = 7.47, β− = 92.53 |
| Re-188m1 | 18.60 | 0.31 | | IT | 0.172 | |
| Re-188 | | 16.98 | | β− | 2.120 | |
| Re-189 | | 24.30 | 1.01 | β− | 1.009 | |
| Re-190 | 3.10 | | | $β^-$ | 3.15 | |
| Re-190m1 | 192.00 | 3.2 | | $β^-$ | 3.269 | 3.269 (β−), 0.119 (IT), $β^-$ = 54.4, IT = 45.6 |
| Re-191 | 9.80 | | | $β^-$ | 2.045 | |
| Osmium | | | | | | |
| Os-176 | 3.60 | | | ECβ+ | 3.2 | |
| Os-177 | 2.80 | | | ECβ+ | 4.5 | |
| Os-178 | 5.00 | | | ECβ+ | 2.3 | |
| Os-179 | 6.50 | | | ECβ+ | 3.68 | |
| Os-180 | 22.00 | 0.37 | | ECβ+ | 1.470 | |
| Os-181 | 105.00 | 1.75 | | ECβ+ | 2.930 | |
| Os-181m1 | 2.70 | | | ECβ+ | 2.979 | |
| Os-182 | | 22.00 | | EC | 0.91 | |
| Os-183 | 13.00 | | | ECβ+ | 2.13 | |
| Os-183m1 | 9.90 | | | ECβ+ | 2.301 | 2.301 (ECβ+), 0.171 (IT), ECβ+ = 85, IT = 15 |
| Os-185 | | | 94.00 | EC | 1.013 | |
| Os-189m1 | | 6.00 | | IT | 0.031 | |
| Os-190m1 | 9.90 | 0.17 | | IT | 1.705 | |
| Os-191m1 | | 13.03 | | IT | 0.074 | |
| Os-191 | | | 15.40 | β− | 0.314 | |
| Os-193 | | 30.00 | 1.25 | β− | 1.140 | |
| Os-195 | 6.50 | | | $β^-$ | 2 | |
| Os-196 | 34.90 | | | $β^-$ | 1.16 | |
| Iridium | | | | | | |
| Ir-181 | 4.90 | | | ECβ+ | 4.07 | |
| Ir-182 | 15.00 | 0.25 | | ECβ+ | 5.61 | |
| Ir-183 | 58.00 | | | ECβ+ | 3.45 | |
| Ir-184 | | 3.02 | | ECβ+ | 4.600 | |
| Ir-185 | | 14.00 | | ECβ+ | 2.370 | |
| Ir-186 | | 15.80 | | ECβ+ | 3.831 | |
| Ir-186m1 | | 1.90 | | ECβ+ | 3.831 | 3.831 (ECβ+), 0 (IT), ECβ+ ≈ 75, IT ≈ 25 |
| Ir-187 | | 10.50 | | EC | 1.502 | |
| Ir-188 | | 41.50 | 1.73 | ECβ+ | 2.809 | |
| Ir-189 | | | 13.30 | EC | 0.532 | |
| Ir-190m2 | | 3.25 | | ECβ+ | 2.149 | 2.149 (ECβ+), 0.140 (IT), ECβ+ = 94.4, IT = 5.6 |
| Ir-190m1 | | 1.20 | | IT | 0.026 | |
| Ir-190 | | | 12.10 | ECβ+ | 2.000 | |
| Ir-192 | | | 73.83 | β− | 1.460 | 1.46 (β−), 1.046 (EC), β− = 95.24, EC = 4.76 |
| Ir-193m1 | | | 10.53 | IT | 0.08 | |
| Ir-194m1 | | | 171.00 | β− | 2.437 | |
| Ir-194 | | 19.15 | | β− | 2.247 | |
| Ir-195m1 | | 3.80 | | β− | 1.220 | 1.22 (β−), 0.10 (IT), β− = 95, IT = 5 |
| Ir-195 | | 2.50 | | β− | 1.120 | |
| Ir-196m1 | 84.00 | 1.4 | | β− | 3.620 | |
| Ir-197 | 5.80 | | | β− | 2.155 | |
| Ir-197m1 | 8.90 | | | β− | 2.270 | 2.27 (β−), 0.115 (IT), $β^-$ = 99.75, IT = 0.25 |
| Platinum | | | | | | |
| Pt-182 | 3.00 | | | ECβ+ | 2.850 | 2.85 (ECβ+), 4.943 (α), ECβ+ = 99.969, α = 0.031 |
| Pt-183 | 6.50 | | | ECβ+ | 4.600 | |
| Pt-184 | 17.30 | | | ECβ+ | 2.300 | |
| Pt-185 | 70.90 | 1.1817 | | ECβ+ | 3.800 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Pt-185m1 | 33.00 | | | ECβ+ | 3.903 | 3.903 (ECβ+), 0.103 (IT), 4.643 (α), ECβ+ = 99, IT < 2 |
| Pt-186 | | 2.00 | | ECβ+ | 1.380 | |
| Pt-188 | | | 10.20 | EC | 0.507 | |
| Pt-187 | | 2.35 | | ECβ+ | 3.11 | |
| Pt-189 | | 10.87 | | ECβ+ | 1.971 | |
| Pt-191 | | 67.20 | 2.80 | EC | 1.019 | |
| Pt-193m1 | | 103.92 | 4.33 | IT | 0.150 | |
| Pt-195m1 | | 96.48 | 4.02 | IT | 0.259 | |
| Pt-197m1 | 95.41 | 1.59 | | IT | 0.399 | 0.399 (IT) 1.119 (β−), IT = 96.7, β− = 3.3 |
| Pt-197 | | 18.30 | | β− | 0.719 | |
| Pt-199 | 30.80 | 0.51 | | β− | 1.702 | |
| Pt-200 | | 12.50 | | β− | 0.660 | |
| Pt-201 | 2.50 | | | $\beta^-$ | 2.66 | |
| Pt-202 | | 44 | | $\beta^-$ | | |
| Gold | | | | | | |
| Au-185 | 4.25 | | | ECβ+ | 4.71 | 4.71 (ECβ+), 5.18 (α), ECβ+ = 99.74, α = 0.26 |
| Au-185m1 | 6.80 | | | ECβ+ | 4.71 | |
| Au-186 | 10.70 | | | ECβ+ | 6.04 | |
| Au-187 | 8.40 | | | ECβ+ | 3.6 | 3.6 (ECβ+), 4.79 (α), ECβ+ = 99.997, α = 0.003 |
| Au-188 | 8.84 | | | ECβ+ | 5.3 | |
| Au-189 | 28.70 | | | ECβ+ | 2.85 | ECβ+ ≈ 100, α < 3 · 10−5 |
| Au-189m1 | 4.59 | | | ECβ+ | 3.097 | ECβ+ ≈ 100, IT > 0 |
| Au-190 | 42.80 | | | ECβ+ | 4.442 | ECβ+ ≈ 100, α < 1 · 10−6 |
| Au-191 | 3.18 | | | ECβ+ | 1.83 | |
| Au-192 | 4.94 | | | ECβ+ | 3.516 | |
| Au-193 | | 17.65 | | EC | 1.069 | |
| Au-194 | | 398.02 | 16.58 | ECβ+ | 2.492 | |
| Au-195 | | | 183.00 | EC | 0.227 | |
| Au-196 | | 148.39 | 6.18 | ECβ+ | 1.500 | 1.506 (ECβ+), 0.686 (β−), ECβ+ = 92.80, β− = 7.20 |
| Au-196m2 | | 9.60 | | IT | 0.596 | |
| Au-198m1 | | 55.20 | 2.30 | IT | 0.812 | |
| Au-198 | | 64.70 | 2.70 | β− | 1.372 | |
| Au-199 | | 75.34 | 3.14 | β− | 0.453 | |
| Au-200m1 | | 18.70 | | β− | 3.202 | 3.202 (β−), 0.962 (IT), β− = 82, IT = 18 |
| Au-200 | 48.40 | 0.81 | | β− | 2.240 | |
| Au-201 | 26.40 | 0.44 | | β− | 1.275 | |
| Thallium | | | | | | |
| Tl-189 | 2.30 | | | ECβ+ | 5.18 | |
| Tl-190 | 2.60 | | | ECβ+ | 7 | |
| Tl-190m1 | 3.70 | | | ECβ+ | 7 | |
| Tl-191 | | | | ECβ+ | 4.49 | |
| Tl-191m1 | 5.22 | | | ECβ+ | 4.789 | |
| Tl-192 | 9.60 | | | ECβ+ | 6.12 | |
| Tl-192m1 | 10.80 | | | ECβ+ | 6.12 | |
| Tl-193 | 21.60 | | | ECβ+ | 3.64 | |
| Tl-193m1 | 2.11 | | | IT | 0.365 | 0.365 (IT), 4.005 (ECβ+), IT = 75, ECβ+ = 25 |
| Tl-194m1 | 32.80 | 0.55 | | ECβ+ | 5.280 | |
| Tl-194 | 33.00 | 0.55 | | EC | 5.280 | |
| Tl-195 | | 1.16 | | ECβ+ | 2.810 | |
| Tl-196 | | 1.84 | | ECβ+ | 4.38 | |
| Tl-196m1 | | 1.41 | | ECβ+ | 4.774 | 4.774 (ECβ+) 0.394 (IT), ECβ+ = 95.5, IT = 4.5 |
| Tl-197 | | 2.84 | | ECβ+ | 2.180 | |
| Tl-198m1 | | 1.87 | | ECβ+ | 4.004 | 4.004 (ECβ+), 0.544 (IT), ECβ+ = 54, IT = 46 |
| Tl-198 | | 5.30 | | ECβ+ | 3.460 | |
| Tl-199 | | 7.42 | | ECβ+ | 1.440 | |
| Tl-200 | | 26.10 | 1.09 | ECβ+ | 2.456 | |
| Tl-201 | | | 3.04 | EC | 0.483 | |
| Tl-202 | | | 12.23 | ECβ+ | 1.365 | |
| Tl-206 | 4.20 | 0.07 | | β− | 1.533 | |
| Tl-206m1 | 3.74 | | | IT | 2.643 | |
| Tl-207 | 4.77 | 0.08 | | β− | 1.423 | |
| Tl-208 | 3.07 | 0.05 | | β− | 5.001 | |
| Tl-209 | 2.20 | 0.04 | | β− | 3.980 | |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Lead | | | | | | |
| Pb-191m1 | 2.10 | | | ECβ+ | 6.038 | |
| Pb-192 | 3.50 | | | ECβ+ | 3.400 | 3.4 (ECβ+), 5.221 (α), ECβ+ = 99.9941, α = 0.0059 |
| Pb-193 | 2.00 | | | ECβ+ | | |
| Pb-193m1 | 5.80 | | | ECβ+ | 5.200 | |
| Pb-194 | 12.00 | | | ECβ+ | 2.700 | |
| Pb-195 | 15.00 | | | ECβ+ | 4.500 | |
| Pb-195m1 | 15.80 | 0.26 | | ECβ+ | 4.500 | |
| Pb-196 | 37.00 | | | ECβ+ | 2.050 | 2.05 (ECβ+), 4.2 (α), ECβ+ ≈ 100, α < 3 · 10−5 |
| Pb-197 | 8.00 | | | ECβ+ | 3.58 | |
| Pb-197m1 | 43.00 | | | ECβ+ | 3.889 | 3.889 (ECβ+), 0.319 (IT), ECβ+ = 81, IT = 19 |
| Pb-198 | | 2.40 | | ECβ+ | 1.410 | |
| Pb-199 | 90.00 | 1.50 | | ECβ+ | 2.880 | |
| Pb-199m1 | 12.20 | | | IT | 0.425 | 0.425 (IT), 3.305 (ECβ+), IT = 93, ECβ+ = 7 |
| Pb-200 | | 21.50 | | EC | 0.811 | |
| Pb-201 | | 9.33 | | ECβ+ | 1.900 | |
| Pb-202m1 | | 3.53 | | IT | 2.710 | |
| Pb-203 | | 51.87 | 2.16 | EC | 0.975 | |
| Pb-204m1 | 67.20 | 1.12 | | IT | 2.186 | |
| Pb-209 | | 3.25 | | β− | 0.644 | |
| Pb-211 | 36.10 | 0.60 | | β− | 1.373 | |
| Pb-212 | | 10.64 | | β− | 0.574 | |
| Pb-213 | 10.20 | 0.17 | | β− | 2.070 | |
| Pb-214 | 26.80 | 0.45 | | β− | 1.024 | |
| Bismuth | | | | | | |
| Bi-197 | 9.33 | | | ECβ+ | 5.200 | 5.2 (ECβ+), 5.39 (α), ECβ+ ≈ 100, α = 1 · 10−4 |
| Bi-197m1 | 5.04 | | | α | 5.890 | 5.89 (α), 5.7 (ECβ+), 0.50 (IT), α = 55, ECβ+ = 45, IT < 0.3 |
| Bi-198 | 10.30 | | | ECβ+ | 6.56 | |
| Bi-198m1 | 11.60 | | | ECβ+ | 6.56 | |
| Bi-199 | 27.00 | | | ECβ+ | 4.34 | |
| Bi-199m1 | 24.70 | | | ECβ+ | 5.020 | 5.02 (ECβ+), 5.64 (α), 0.68 (IT), ECβ+ = 99, α ≈ 0.01, IT < 2 |
| Bi-200 | 36.40 | | | ECβ+ | 5.89 | |
| Bi-200m1 | 31.00 | | | ECβ+ | 5.89 | ECβ+ > 90, IT < 10 |
| Bi-201 | 108.00 | 1.80 | | EC | 3.84 | |
| Bi-201m1 | 59.10 | 0.99 | | EC | 4.686 | 4.686 (EC), 5.346 (IT), 5.346 (α), EC > 93, IT < 6.8, α ≈ 0.3 |
| Bi-202 | | 1.67 | | ECβ+ | 5.150 | 5.15 (ECβ+), 4.29 (α), ECβ+ ≈ 100, α < 1 · 10−5 |
| Bi-203 | | 11.76 | | ECβ+ | 3.253 | 3.253 (ECβ+), 4.15 (α), ECβ+ ≈ 100, α ≈ 1 · 10−5 |
| Bi-204 | | 11.22 | | ECβ+ | 4.438 | |
| Bi-205 | | | 15.31 | ECβ+ | 2.708 | |
| Bi-206 | | 149.83 | 6.24 | ECβ+ | 3.758 | |
| Bi-210 | | 120.29 | 5.01 | β− | 1.163 | |
| Bi-211 | 2.14 | 0.04 | | α | 6.751 | 6.751 (α), 0.579 (β−), α = 99.724, β− = 0.276 |
| Bi-212 | 60.55 | 1.01 | | β− | 2.254 | 2.254 ($β^-$), 6.207 (α), 11.208 ($β^-$ + α); β− = 64.06, α = 35.94 |
| Bi-212m1 | 25.00 | | | α | 6.457 | 6.457 (α), 2.504 (β−), α = 67, $β^-$ = 33, $β^-α$ = 30 |
| Bi-212m2 | 7.00 | | | β− | 4.164 | |
| Bi-213 | 45.6 | 0.76 | | α | 5.98 | 1.464 ($β^-$), 5.932 (α); β− = 97.91, α = 2.09 |
| Bi-214 | 19.90 | 0.33 | | | 3.272 | 3.272 ($β^-$), 5.617 (α); β− = 99.979, α = 0.021 |
| Bi-215 | 7.60 | | | β− | 2.25 | |
| Bi-216 | 3.60 | | | β− | 4 | |
| Polonium | | | | | | |
| Po-199 | 5.48 | | | ECβ+ | 5.600 | 5.6 (ECβ+), 6.074 (α), ECβ+ = 88, α = 12 |
| Po-199m1 | 4.13 | | | ECβ+ | 5.910 | 5.91 (ECβ+), 6.384 (α), 0.310 (IT), ECβ+ = 59, α = 39, IT = 2.1 |
| Po-200 | 11.50 | | | ECβ+ | 3.350 | 3.35 (ECβ+), 5.982 (α), ECβ+ = 88.9, α = 11.1 |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Po-201 | 15.30 | | | ECβ+ | 4.880 | 4.88 (ECβ+), 5.799 (α), ECβ+ = 98.4, α = 1.6 |
| Po-201m1 | 8.90 | | | IT | 0.424 | 0.424 (IT), 5.304 (ECβ+), 6.223 (α), IT = 56, EC = 41, α ≈ 2.9 |
| Po-202 | 44.70 | 0.75 | | ECβ+ | 2.820 | 2.82 (ECβ+), 5.701 (α), ECβ+ = 98.08, α = 1.92 |
| Po-203 | 36.70 | 0.61 | | ECβ+ | 4.230 | 4.23 (ECβ+), 5.496 (α), ECβ+ = 99.89, α = 0.11 |
| Po-204 | | 3.53 | | ECβ+ | 2.340 | 2.34 (ECβ+), 5.485 (α), ECβ+ = 99.34, α = 0.,66 |
| Po-205 | | 1.66 | | ECβ+ | 3.530 | 3.53 (ECβ+), 5.324 (α), ECβ+ = 99.96, α = 0.04 |
| Po-206 | | 8.8 | | ECβ+ | 1.846 | 1.846 (ECβ+), 5.326 (α), ECβ+ = 94.55, α = 5.45 |
| Po-207 | | 5.8 | | ECβ+ | 2.909 | 2.909 (ECβ+), 5.216 (α), ECβ+ = 99.979, α = 0.021 |
| Po-210 | | | 138.38 | α | 5.307 | |
| Po-218 | 3.05 | 0.05 | | α | 6.115 | 6.115 (α), 0.265 (β−), α = 99.980, $β^-$ = 0.020 |
| Astatine | | | | | | |
| At-203 | 7.40 | | | ECβ+ | 5.060 | 5.06 (ECβ+), 6.21 (α), ECβ+ = 69, α = 31 |
| At-204 | 9.20 | | | ECβ+ | 6.480 | 6.48 (ECβ+), 6.07 (α), ECβ+ = 96.2, α = 3.8 |
| At-205 | 26.20 | 0.44 | | ECβ+ | 4.540 | 4.54 (ECβ+), 6.02 (α), ECβ+ = 90, α = 10 |
| At-206 | 30.00 | 0.50 | | ECβ+ | 5.720 | 5.72 (ECβ+), 5.888 (α), ECβ+ = 99.11, α = 0.89 |
| At-207 | | 1.80 | | ECβ+ | 3.910 | 3.91 (ECβ+), 5.873 (α), ECβ+ = 91.4, α = 8.6 |
| At-208 | | 1.63 | | ECβ+ | 4.973 | 4.973 (ECβ+), 5.751 (α), ECβ+ = 99.45, α = 0.55 |
| At-209 | | 5.41 | | ECβ+ | 3.486 | 3.486 (ECβ+), 5.757 (α), ECβ+ = 95.9, α = 4.1 |
| At-210 | | 8.1 | | ECβ+ | 3.981 | 3.981 (ECβ+), 5.631 (α), ECβ+ = 99.825, α = 0.175 |
| At-211 | | 7.21 | | α+ | 5.98 | 0.786 (ECβ+), 5.982 (α), EC = 58.2, α = 41.8 |
| At-220 | 3.71 | | | β− | | α = 8, β− = 92, 3.65 (ECβ+), 6.05 (α) |
| At-221 | 2.30 | | | β− | | |
| Radon | | | | | | |
| Rn-205 | 2.80 | | | ECβ+ | 5.240 | 5.24 (ECβ+), 6.39 (α), ECβ+ = 77, α = 23 |
| Rn-206 | 5.67 | | | α | 6.384 | 6.384 (α), 3.,31 (ECβ+), α = 63, ECβ+ = 37 |
| Rn-207 | 9.25 | | | ECβ+ | 4.610 | 4.61 (ECβ+), 6.251 (α), ECβ+ = 79, α = 21 |
| Rn-208 | 24.35 | 0.41 | | α | 6.260 | 6.26 (α), 2.85 (ECβ+), α = 62, ECβ+ = 38 |
| Rn-209 | 28.50 | 0.48 | | ECβ+ | 3.930 | 3.93 (ECβ+), 6.155 (α), ECβ+ = 83, α = 17 |
| Rn-210 | | 2.40 | | α | 6.159 | 6.159 (α), 2.374 (ECβ+), α = 96, ECβ+ = 4 |
| Rn-211 | | 14.60 | | EC | 2.892 | 2.892 (ECβ+), 5.965 (α), EC = 72.6, α = 27.4 |
| Rn-212 | 23.90 | 0.40 | | α | 6.385 | |
| Rn-221 | 25.00 | | | β− | 1.220 | 1.22 (β−), 6.146 (α), $β^-$ = 78, α = 22 |
| Rn-222 | | | 3.82 | α | 5.590 | |
| Rn-223 | 23.20 | | | β− | | $β^-$ ≈ 100, α = 0.0004 |
| Rn-224 | 107.00 | | | β− | 0.8 | |
| Rn-225 | 4.50 | | | β− | | |
| Rn-226 | 7.40 | | | β− | 1.4 | |
| Francium | | | | | | |
| Fr-210 | 3.18 | | | α | 6.700 | 6.7 (α), 6.262 (ECβ+), α = 60, ECβ+ = 40 |
| Fr-211 | 3.10 | | | α | 6.660 | 6.66 (α), 4.605 (ECβ+), α > 80, EC < 20 |
| Fr-212 | 20.00 | 0.33 | | ECβ+ | 5.117 | 5.117 (ECβ+), 6.529 (α), ECβ+ = 57, α = 43 |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Fr-221 | 4.80 | 0.08 | | α | 6.458 | α ≈ 100, $β^-$ = ?, $^{14}C$ = 8.8 · 10 |
| Fr-222 | 14.40 | 0.24 | | β− | 2.033 | |
| Fr-223 | 21.80 | 0.36 | | β− | 1.149 | |
| Fr-224 | 3.33 | | | $β^-$ | 2.83 | |
| Fr-225 | 4.00 | | | $β^-$ | 1.866 | |
| Fr-227 | 2.47 | | | $β^-$ | 2.49 | |
| Radium | | | | | | |
| Ra-213 | 2.74 | | | α | 6.859 | 6.859 (α), 3.88 (ECβ+), α = 80, ECβ+ = 20 |
| Ra-223 | | | 11.43 | α | 5.979 | |
| Ra-224 | | 87.84 | 3.66 | α | 5.789 | |
| Ra-225 | | | 14.80 | β− | 0.357 | |
| Ra-227 | 42.20 | 0.70 | | β− | 1.325 | |
| Ra-229 | 4.00 | | | $β^-$ | 1.76 | |
| Ra-230 | 93.00 | 1.55 | | β− | 0.990 | |
| Actinium | | | | | | |
| Ac-223 | 2.10 | 0.04 | | α | 6.783 | |
| Ac-224 | | 2.90 | | α | 1.403 | 1.403 (EC), 6.327 (α), 0.232 (β−), EC = 90.9, α = 9.1, β− < 1.6 |
| Ac-225 | | | 10.00 | α | 5.935 | |
| Ac-226 | | 29.00 | 1.21 | β− | 1.117 | 1.117 ($β^-$), 0.64 (EC), 5.563 (α), β− ≈ 83, EC = 17, α = 6 · 10−3 |
| Ac-228 | | 6.13 | | β− | 2.127 | |
| Ac-229 | 62.70 | | | $β^-$ | 1.1 | |
| Ac-231 | 7.50 | | | $β^-$ | 2.1 | |
| Thorium | | | | | | |
| Th-225 | 8.72 | | | α | 6.922 | 6.922 (α), 0.675 (EC), α ≈ 90, EC ≈ 10 |
| Th-226 | 30.90 | 0.52 | | α | 6.451 | |
| Th-227 | | | 18.72 | α | 6.051 | |
| Th-231 | | 25.52 | 1.06 | β− | 0.389 | |
| Th-233 | 22.30 | | | $β^-$ | 1.245 | |
| Th-234 | | | 24.10 | β− | 0.273 | |
| Th-235 | 7.10 | | | $β^-$ | 1.93 | |
| Th-236 | 37.00 | 0.62 | | $β^-$ | | |
| Th-237 | 5.00 | | | $β^-$ | | |
| Protactinium | | | | | | |
| Pa-227 | 38.30 | 0.64 | | α | 6.580 | 6.580 (α), 1.019 (EC), α = 85, EC = 15 |
| Pa-228 | | 22.00 | | ECβ+ | 2.148 | 2.148 (ECβ+), 6.265 (α), ECβ+ = 98.0, α = 2.0 |
| Pa-229 | | 36.00 | 1.50 | EC | 0.316 | |
| Pa-230 | | | 17.40 | ECβ+ | 1.310 | 1.310 (ECβ+), 0.563 (β−), 5.439 (α), ECβ+ = 91.6, β− = 8.4, α = 0.0032 |
| Pa-232 | | 31.44 | 1.31 | β− | 1337.000 | |
| Pa-233 | | | 27.00 | β− | 0.571 | |
| Pa-234 | | 6.70 | | β− | 2.197 | |
| Pa-235 | 24.50 | | | $β^-$ | 1.41 | |
| Pa-236 | 9.10 | | | $β^-$ | 2.9 | |
| Pa-237 | 8.70 | | | $β^-$ | 2.25 | |
| Pa-238 | 2.30 | | | $β^-$ | 3.46 | |
| Uranium | | | | | | |
| U-228 | 9.10 | | | α | 6.801 | 6.804 (α), 0.307 (EC), α > 95, EC < 5 |
| U-229 | 58.00 | 0.97 | | ECβ+ | 1.309 | 1.309 (ECβ+), 6.475 (α), ECβ+ ≈ 80, α ≈ 20 |
| U-230 | | | 20.80 | α | 5.993 | |
| U-231 | | 100.80 | 4.20 | EC | 0.360 | |
| U-235m1 | 25.00 | | | IT | | |
| U-237 | | 162.00 | 6.75 | β− | 0.519 | |
| U-239 | 23.54 | 0.39 | | β− | 1.265 | |
| U-240 | | 14.10 | | β− | 0.338 | |
| U-242 | 16.80 | | | $β^-$ | | |
| Neptunium | | | | | | |
| Np-229 | 4.00 | | | α | 2.560 | 7.01 (α), 2.56 (EC), α > 50, EC < 50 |

TABLE 4-continued

| Key properties of relevant radionuclides - half life, decay types and decay energies | | | | | | |
|---|---|---|---|---|---|---|
| Radionuclide | Half-life (min) | Half-life (hours) | Half-life (days) | Decay | Energy (MeV) | Additional decays (energy [MeV]) |
| Np-230 | 4.60 | | | ECβ+ | 3.610 | 3.,61 (ECβ+), 6.78 (α), ECβ+ < 97, α > 3 |
| Np-231 | 48.80 | | | ECβ+ | 1.840 | 1.84 (EC), 6.37 (α), EC = 98, α = 2 |
| Np-232 | 14.70 | 0.25 | | ECβ+ | 2.700 | |
| Np-233 | 36.20 | 0.60 | | EC | 1.230 | |
| Np-234 | | 105.60 | 4.40 | ECβ+ | 1.810 | |
| Np-236m1 | | 22.50 | | EC | 1.000 | 1.00 (EC), 0.55 (β−), EC = 52, β− = 48 |
| Np-238 | | 50.81 | 2.12 | β− | 1.292 | |
| Np-239 | | 56.52 | 2.36 | β− | 0.722 | |
| Np-240m1 | 7.40 | 0.12 | | β− | 2.200 | |
| Np-240 | 65.00 | 1.08 | | β− | 2.200 | |
| Np-241 | 13.90 | | | $β^-$ | 1.31 | |
| Np-242 | 5.50 | | | $β^-$ | 2.7 | |
| Np242m1 | 2.20 | | | $β^-$ | 2.7 | |
| Np-244 | 2.29 | | | $β^-$ | | |
| Plutonium | | | | | | |
| Pu-231 | 8.60 | | | ECβ+, α | | |
| Pu-232 | 34.10 | | | ECβ+ | 1.06 | 1.06 (ECβ+), 6.716 (α), EC = 77, α = 23 |
| Pu-233 | 20.90 | 0.35 | | ECβ+ | 1.900 | |
| Pu-234 | | 8.80 | | EC | 0.388 | 0.388 (ECβ+), 6.31 (α), EC ≈ 94, α ≈ 6 |
| Pu-235 | 25.30 | 0.42 | | ECβ+ | 1.170 | |
| Pu-237 | | | 45.30 | EC | 0.220 | |
| Pu-243 | | 4.96 | | β− | 0.528 | |
| Pu-245 | | 10.50 | | β− | 1.205 | |
| Pu-246 | | | 10.85 | β− | 0.401 | |
| Pu-247 | | | 2.27 | $β^-$ | | |
| Americium | | | | | | |
| Am-234 | 2.32 | | | | | EC ≈ 100, α = 0.039, ECSF = 0.0066 |
| Am-235 | 15.00 | | | | | |
| Am-237 | 73.00 | 1.22 | | EC | 1.730 | |
| Am-238 | 98.00 | 1.63 | | EC | 2.260 | |
| Am-239 | | 11.90 | | EC | 0.803 | |
| Am-240 | | 50.80 | 2.12 | EC | 1.379 | |
| Am-242 | | 16.02 | | β− | 0.665 | 0.665 (β−), 0.751 (EC), β− = 82.7, EC = 17.3 |
| Am-244m1 | 26.00 | 0.43 | | β− | 1.516 | |
| Am-244 | | 10.10 | | β− | 1.428 | |
| Am-245 | | 2.05 | | β− | 0.894 | |
| Am-246m1 | 25.00 | 0.42 | | β− | 2.376 | |
| Am-246 | 39.00 | 0.65 | | β− | 2.376 | |
| Am-247 | 23.00 | | | $β^-$ | 1.7 | |
| Am-248 | | | | $β^-$ | 3.1 | |
| Curium | | | | | | |
| Cm-236 | 10.00 | | | ECβ+ | 1.710 | |
| Cm-237 | 20.00 | | | | | |
| Cm-238 | | 2.40 | | EC | 0.970 | 0.97 (EC), 6.62 (α), EC = 96.16, α = 3.84 |
| Cm-239 | | 2.90 | | EC | 1.700 | |
| Cm-240 | | | 27.00 | α | 6.397 | |
| Cm-241 | | | 32.80 | EC | 0.767 | |
| Cm-242 | | | 162.80 | α | 6.216 | |
| Cm-249 | 64.15 | 1.07 | | β− | | |
| Cm-251 | 16.80 | | | $β^-$ | 1.42 | |
| Cm-252 | | | 2 | $β^-$ | | |
| Berkelium | | | | | | |
| Bk-240 | 4.80 | | | ECβ+ | 3.94 | |
| Bk-242 | 7.00 | 0.12 | | ECβ+ | 3.000 | |
| Bk-243 | | 4.50 | | EC | 1.508 | |
| Bk-244 | | 4.35 | | EC | 2.260 | |
| Bk-245 | | 118.56 | 4.94 | EC | 0.810 | |
| Bk-246 | | 43.92 | 1.83 | EC | 1.350 | 1.35 (EC), 6.07 (α), EC = 100, α < 0.2 |
| Bk-248m1 | | 23.7 | | β− | 0.870 | β− = 70, EC = 30, α < 0.001, 0.87 (β−), 0.717 (EC), 5.803 (α) |

TABLE 4-continued

Key properties of relevant radionuclides - half life, decay types and decay energies

| Radionuclide | Half-life (min) | Half-life (hours) | Half-life (days) | Decay | Energy (MeV) | Additional decays (energy [MeV]) |
|---|---|---|---|---|---|---|
| Bk-249 | | | 320.00 | β− | 0.125 | |
| Bk-250 | | 3.22 | | β− | 1.780 | |
| Bk-251 | 55.60 | | | β− | 1.093 | $\beta^- \approx 100$, $\alpha \approx 1 \cdot 10^{-5}$ |
| Californium | | | | | | |
| Cf-241 | 3.78 | | | EC | 3.300 | EC ≈ 75, a ≈ 25, 3.3 (EC), 7.66 (α) |
| Cf-242 | 3.49 | | | α | 7.516 | α = 65, SF < $1.4 \cdot 10^{-2}$ |
| Cf-243 | 10.70 | | | EC | 2.220 | EC ≈ 86, α ≈ 14, 2.22 (EC), 7.39 (α) |
| Cf-244 | 19.40 | 0.32 | | α | 7.329 | |
| Cf-245 | 45.00 | 0.75 | | EC | 1.569 | EC = 64, α = 36, 1.569 (EC), 7.256 (α) |
| Cf-246 | | 35.70 | 1.49 | α | 6.862 | α ≈ 100, SF = 2.3 · 10−4, EC < 5 · 10−4 |
| Cf-247 | | 3.11 | | EC | 0.646 | EC ≈ 100, α = 0.035 |
| Cf-248 | | | 333.50 | α | 6.361 | |
| Cf-253 | | | 17.81 | β− | 0.285 | |
| Cf-254 | | | 60.50 | SF | 5.926 | |
| Cf-255 | 85.00 | | | β− | 0.700 | |
| Cf-256 | 12.30 | | | α | 5.600 | SF = 100, $\beta^- < 1$, $\alpha \approx 1 \cdot 10^{-6}$ |
| Einsteinium | | | | | | |
| Es-246 | 7.70 | | | EC | 3.880 | EC = 90.1, α = 9.9, ECSF = 0.003 |
| Es-247 | 4.55 | | | EC | 2.480 | 2.48 (EC), 7.49 (α), EC ≈ 93, α ≈ 7 |
| Es-248 | 27.00 | 0.45 | | EC | | |
| Es-249 | 102.00 | 1.70 | | EC | 1.450 | |
| Es-250 | | 8.60 | | EC | 2.100 | |
| Es-250m1 | 132.00 | 2.2 | | EC | 2.100 | 2.10 (EC), 6.88 (α), EC ≈ 100, α < 1 |
| Es-251 | | 33.00 | 1.38 | EC | 0.376 | |
| Es-253 | | | 20.47 | α | 6.739 | |
| Es-254m1 | | 39.30 | 1.64 | α, β− | | |
| Es-254 | | | 275.70 | α | 6.618 | |
| Es-255 | | | 39.80 | β− | 0.288 | |
| Es-256 | 25.40 | | | β− | 1.67 | |
| Es-256m1 | 456.00 | 7.6 | | β− | 1.67 | $\beta^- \approx 100$, SF = 0.002 |
| Es-257 | | | 7.8 | | | |
| Fermium | | | | | | |
| FM-249 | 2.60 | | | EC | 2.440 | EC ≈ 85, α ≈ 15, 2.44 (EC), 7.81 (α) |
| Fm-250 | 30.00 | 0.50 | | α | 7.557 | 7.557 (α), 0.8 (EC), α > 90, EC < 10, SF = 0.0069 |
| Fm-251 | | 5.30 | | EC | 1.474 | 1.474 (EC), 7.425 (α), EC = 98.20, α = 1.80 |
| Fm-252 | | 22.70 | | α | 7.425 | |
| Fm-253 | | 72.00 | 3.00 | EC | 0.333 | 0.333 (EC), 7.197 (α), EC = 88, α = 12 |
| Fm-254 | | 3.24 | | α | 7.307 | α ≈ 100, SF = 0.0592 |
| Fm-255 | | 20.07 | | α | 7.241 | |
| Fm-256 | 157.60 | 2.60 | | α | 7.027 | SF = 91.9, α = 8.1 |
| Fm-257 | | | 100.50 | α | 6.864 | |
| Mendelevium | | | | | | |
| Md-251 | 4.00 | | | EC | 3.070 | 3.07 (EC), 8.02 (α), EC > 90, α < 10 |
| Md-252 | 2.30 | | | EC | 3.89 | EC > 50, α < 50 |
| Md-253 | 6.00 | | | ECβ+ | 1.96 | |
| Md-254 | 10.00 | | | EC | 2.68 | EC < 100 |
| Md-254m1 | 28.00 | | | EC | | EC < 100 |
| Md-255 | 27.00 | | | EC | 1.043 | 1.043 (EC), 7.907 (α), EC = 92, α = 8, SF < 1.4 |
| Md-256 | 78.10 | | | EC | 2.130 | 2.13 (EC), 7.897 (α), EC = 90.7, α = 9.3, SF < 2.8 |
| Md-257 | | 5.52 | | EC | 0.406 | 0.406 (EC), 7.271 (α), EC = 85, α = 15, SF < 1 |
| Md-258 | | | 51.50 | α | 7.241 | 7.271 (α), 1.23 (EC), α ≈ 100, SF < 0.003, β− < 0.003, EC < 0.003 |

TABLE 4-continued

| Key properties of relevant radionuclides - half life, decay types and decay energies | | | | | | |
|---|---|---|---|---|---|---|
| Radionuclide | Half-life (min) | Half-life (hours) | Half-life (days) | Decay | Energy (MeV) | Additional decays (energy [MeV]) |
| Md-258m1 | | 57.00 | | EC | 1.230 | EC > 70, SF < 30, α < 1.2, β− < 30 |
| Md-259 | 96.00 | 1.60 | | α | 7.100 | SF > 73, α < 25, β− < 10, 7.0 (α), 1.0 (β−) |
| Md-260 | | | 27.80 | α | 7.000 | SF > 73, α < 25, β⁻ < 10 |
| Nobelium | | | | | | |
| No-255 | 3.10 | | | α | 8.445 | α = 61.4, EC = 38.w6 |
| No-259 | 58.00 | | | α | 7.910 | α ≈ 100, EC = 25, SF < 10 |
| Lawrencium | | | | | | |
| Lr-261 | 39.00 | | | SF | | SF < 100 |
| Lr-262 | 216.00 | | | EC | 2.1 | EC > 10, SF < 10 |
| Rutherfordium | | | | | | |
| Rf-263 | 15.00 | | | SF | | |
| Seaborgium | | | | | | |
| Sg-271 | 2.40 | | | α, SF | | α > 50, SF < 50 |
| Hassium | | | | | | |
| Hs-278 | 11.00 | | | SF | | |
| Meitnerium | | | | | | |
| Mt-278 | 30.00 | | | α | 9.1 | |
| Roentgenium | | | | | | |
| Rg-282 | 4.00 | | | α, SF | 9.4 | |
| Nithonium | | | | | | |
| Nh-285 | 2.00 | | | α, SF | 10 | |
| Nh-286 | 5.00 | | | α | 9.7 | |
| Nh-287 | 20.00 | | | α, SF | 9.3 | |

In an embodiment of the present invention, the radionuclide is used for diagnosis. Preferably, the radioactive isotope is selected from the group, but not limited to, comprising $^{43}$Sc, $^{44}$Sc, $^{51}$Mn, $^{52}$Mn, $^{64}$Cu, $^{67}$Ga, $^{68}$Ga, $^{86}$Y, $^{89}$Zr, $^{94m}$Tc, $^{99m}$Tc, $^{111}$In, $^{152}$Tb, $^{155}$Tb, $^{177}$Lu, $^{201}$Tl, $^{203}$Pb, $^{18}$F, $^{76}$Br, $^{77}$Br, $^{123}$I, $^{124}$I, $^{125}$I. More preferably, the radionuclide is selected from the group comprising $^{43}$Sc, $^{44}$Sc, $^{64}$Cu, $^{67}$Ga, $^{68}$Ga, $^{86}$Y, $^{89}$Zr, $^{99m}$Tc, $^{111}$In, $^{152}$Tb, $^{155}$Tb, $^{203}$Pb, $^{18}$F, $^{76}$Br, $^{77}$Br, $^{123}$I, $^{124}$I, $^{125}$I. Even more preferably, the radionuclide is selected from the group comprising $^{64}$Cu, $^{68}$Ga, $^{89}$Zr, $^{99m}$Tc, $^{111}$In, $^{18}$F, $^{123}$I, and $^{124}$I. It will however, also be acknowledged by a person skilled in the art that the use of said radionuclide is not limited to diagnostic purposes, but encompasses their use in therapy and theragnostics when conjugated to the compound of the invention.

In an embodiment of the present invention, the radionuclide is used for therapy. Preferably, the radioactive isotope is selected from the group comprising $^{47}$Sc, $^{67}$Cu, $^{89}$Sr, $^{90}$Y, $^{111}$In, $^{153}$Sm, $^{149}$Tb, $^{161}$Tb, $^{177}$Lu, $^{186}$Re, $^{188}$Re, $^{212}$Pb, $^{213}$Bi, $^{223}$Ra, $^{225}$Ac, $^{226}$Th, $^{227}$Th, $^{131}$I, $^{211}$At. More preferably, the radioactive isotope is selected from the group comprising $^{47}$Sc, $^{67}$Cu, $^{90}$Y, $^{177}$Lu, $^{188}$Re, $^{212}$Pb, $^{213}$Bi, $^{225}$Ac, $^{227}$Th, $^{131}$I, $^{211}$At. Even more preferably, the radionuclide is selected from the group comprising $^{90}$Y, $^{177}$Lu, $^{225}$Ac, $^{227}$Th, $^{131}$I and $^{211}$At. It will however, also be acknowledged by a person skilled in the art that the use of said radionuclide is not limited to therapeutic purposes, but encompasses their use in diagnostic and theragnostics when conjugated to the compound of the invention.

In an embodiment the compound of the invention is present as a pharmaceutically acceptable salt.

A "pharmaceutically acceptable salt" of the compound of the present invention is preferably an acid salt or a base salt that is generally considered in the art to be suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Compounds of the invention are capable of forming internal salts which are also pharmaceutically acceptable salts.

Suitable pharmaceutically acceptable salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is any integer from 0 to 4, i.e., 0, 1, 2, 3, or 4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of non-aqueous media, such as ether, ethyl acetate, ethanol, isopropanol or acetonitrile, is preferred.

A "pharmaceutically acceptable solvate" of the compound of the invention is preferably a solvate of the compound of the invention formed by association of one or more solvent molecules to one or more molecules of a compound of the invention. Preferably, the solvent is one which is generally considered in the art to be suitable for use in contact with the tissues of human beings or animals without excessive toxicity or carcinogenicity, and preferably without irritation, allergic response, or other problem or complication. Such solvent includes an organic solvent such as alcohols, ethers, esters and amines.

A "hydrate" of the compound of the invention is formed by association of one or more water molecules to one or more molecules of a compound of the invention. Such hydrate includes but is not limited to a hemi-hydrate, monohydrate, dihydrate, trihydrate and tetrahydrate. Independent of the hydrate composition all hydrates are generally considered as pharmaceutically acceptable.

The compound of the invention has a high binding affinity to FAP and a high inhibitory activity on FAP. Because of this high binding affinity, the compound of the invention is effective as, useful as and/or suitable as a targeting agent and, if conjugated to another moiety, as a targeting moiety. As preferably used herein a targeting agent is an agent which interacts with the target molecule which is in the instant case said FAP. In terms of cells and tissues thus targeted by the compound of the invention any cell and tissue, respectively, expressing said FAP is or may be targeted.

In an embodiment, the compound interacts with a fibroblast activation protein (FAP), preferably with human FAP having an amino acid sequence of SEQ ID NO: 1 or a homolog thereof, wherein the amino acid sequence of the homolog has an identity of FAP that is at least 85% to the amino acid sequence of SEQ ID NO: 1. In preferred embodiments, the identity is 90%, preferably 95%, 96%, 97%, 98% or 99%.

The identity between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or protein or polypeptide which is said to be identical or to be tested whether it is identical, and if so, to what extent, to a different protein or polypeptide, whereby such different protein or polypepetide is also referred to as the reference sequence and is preferably the protein or polypeptide of wild type, more preferably the human FAP of SEQ ID NO: 1.

Optimal alignment of sequences for comparison can be conducted, e.g., by the local homology algorithm of Smith & Waterman (Smith, et al., *Advances in Applied Mathematics,* 1981, 2:482), by the homology alignment algorithm of Needleman & Wunsch (Needleman, et al., *J Mol Biol,* 1970, 48:443), by the search for similarity method of Pearson & Lipman (Pearson, et al., *Proc Natl Acad Sci USA,* 1988, 85:2444), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al., 1990 (Altschul, et al., *J Mol Biol,* 1990, 215:403) and Altschul et al., 1997 (Altschul, et al., *Nucleic Acids Res,* 1997, 25:3389). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al. (McGinnis, et al., *Nucleic Acids Res,* 2004, 32: W20).

It is within the present invention that the compound of the invention is used or is for use in a method for the treatment of a disease as disclosed herein. Such method, preferably, comprises the step of administering to a subject in need thereof a therapeutically effective amount of the compound of the invention. Such method includes, but is not limited to, curative or adjuvant cancer treatment. It is used as palliative treatment where cure is not possible and the aim is for local disease control or symptomatic relief or as therapeutic treatment where the therapy has survival benefit and it can be curative.

The method for the treatment of a disease as disclosed herein includes the treatment of the disease disclosed herein, including tumors and cancer, and may be used either as the primary therapy or as second, third, fourth or last line therapy. It is also within the present invention to combine the compound of the invention with further therapeutic approaches. It is well known to the person skilled in the art that the precise treatment intent including curative, adjuvant, neoadjuvant, therapeutic, or palliative treatment intent will depend on the tumor type, location, and stage, as well as the general health of the patient.

In an embodiment of the present invention, the disease is selected from the group comprising neoplasm nos, neoplasm benign, neoplasm uncertain whether benign or malignant, neoplasm malignant, neoplasm metastatic, neoplasm malignant uncertain whether primary or metastatic, tumor cells benign, tumor cells uncertain whether benign or malignant, tumor cells malignant, malignant tumor small cell type, malignant tumor giant cell type, malignant tumor fusiform cell type, epithelial neoplasms nos, epithelial tumor benign, carcinoma in situ nos, carcinoma nos, carcinoma metastatic nos, carcinomatosis, epithelioma benign, epithelioma malignant, large cell carcinoma nos, carcinoma undifferentiated type nos, carcinoma anaplastic type nos, pleomorphic carcinoma, giant cell and spindle cell carcinoma, giant cell carcinoma, spindle cell carcinoma, pseudosarcomatous carcinoma, polygonal cell carcinoma, spheroidal cell carcinoma, tumorlet, small cell carcinoma nos, oat cell carcinoma, small cell carcinoma, fusiform cell type, papillary and squamous cell neoplasms, papilloma nos, papillary carcinoma in situ, papillary carcinoma nos, verrucous papilloma, verrucous carcinoma nos, squamous cell papilloma, papillary squamous cell carcinoma, inverted papilloma, papillomatosis nos, squamous cell carcinoma in situ nos, squamous cell carcinoma nos, squamous cell carcinoma metastatic nos, squamous cell carcinoma, keratinizing type nos, squamous cell carcinoma large cell nonkeratinizing type, squamous cell carcinoma small cell nonkeratinizing type, squamous cell carcinoma spindle cell type, adenoid squamous cell carcinoma, squamous cell carcinoma in situ with questionable stromal invasion, squamous cell carcinoma microinvasive, queyrat's erythroplasia, bowen's disease, lymphoepithelial carcinoma, basal cell neoplasms, basal cell tumor, basal cell carcinoma nos, multicentric basal cell carcinoma, basal cell carcinoma morphea type, basal cell carcinoma fibroepithelial type, basosquamous carcinoma, metatypical carcinoma, intraepidermal epithelioma of jadassohn, trichoepithelioma, trichofolliculoma, tricholemmoma, pilomatrixoma, transitional cell papillomas and carcinomas, transitional cell papilloma nos, urothelial papilloma, transitional cell carcinoma in situ, transitional cell carcinoma nos, schneiderian papilloma, transitional cell papilloma, inverted type, schneiderian carcinoma, transitional cell carcinoma spindle cell type, basaloid carcinoma, cloacogenic carcinoma, papillary transitional cell carcinoma, adenomas and adenocarcinomas, adenoma nos, bronchial adenoma nos, adenocarcinoma in situ, adenocarcinoma nos, adenocarcinoma metastatic nos, scirrhous adenocarcinoma, linitis plastica, superficial spreading adenocarcinoma, adenocarcinoma intestinal type, carcinoma diffuse type, monomorphic adenoma, basal cell adenoma, islet cell adenoma, islet cell carcinoma, insulinoma nos, insulinoma malignant, glucagonoma nos, glucagonoma malignant, gastrinoma nos, gastrinoma malignant, mixed islet cell and exocrine adenocarcinoma, bile duct adenoma, cholangiocarcinoma, bile duct cystadenoma, bile duct cystadenocarcinoma, liver cell adenoma, hepatocellular carcinoma nos, hepatocholangioma benign, combined hepatocellular carcinoma and cholangiocarcinoma, trabecular adenoma, trabecular adenocarcinoma, embryonal adenoma, eccrine dermal cylindroma, adenoid cystic carcinoma, cribriform carcinoma, adenomatous polyp nos, adenocarcinoma in adenomatous polyp, tubular adenoma nos, tubular adenocarcinoma, adenomatous polyposis coli, adenocarcinoma in adenomatous polyposis coli, multiple adenomatous polyps, solid carcinoma nos, carcinoma simplex, carcinoid tumor nos, carcinoid tumor malignant, carcinoid tumor argentaffin nos, carcinoid tumor argentaffin malignant, carcinoid tumor nonargentaffin nos, carcinoid tumor nonargentaffin malignant, mucocarcinoid tumor malignant, composite carcinoid, pulmonary adenomatosis, bronchiolo-alveolar adenocarcinoma, alveolar adenoma, alveolar adenocarcinoma, papillary adenoma nos, papillary adenocarcinoma nos, villous adenoma nos, adenocarcinoma in villous adenoma, villous adenocarcinoma, tubulovillous adenoma, chromophobe adenoma, chromophobe carcinoma, acidophil adenoma, acidophil carcinoma, mixed acidophil-basophil adenoma, mixed acidophil-basophil carcinoma, oxyphilic adenoma, oxyphilic adenocarcinoma, basophil adenoma, basophil carcinoma, clear cell adenoma, clear cell adenocarcinoma nos, hypernephroid tumor, renal cell carcinoma, clear cell adenofibroma, granular cell carcinoma, chief cell adenoma, water-clear cell adenoma, water-clear cell adenocarcinoma, mixed cell adenoma, mixed cell adenocarcinoma, lipoadenoma, follicular adenoma, follicular adenocarcinoma nos, follicular adenocarcinoma well differentiated type, follicular adenocarcinoma trabecular type, microfollicular adenoma, macrofollicular adenoma, papillary and follicular adenocarcinoma, nonencapsulated sclerosing carcinoma, multiple endocrine adenomas, juxtaglomerular tumor, adrenal cortical adenoma nos, adrenal cortical carcinoma, adrenal cortical adenoma compact cell type, adrenal cortical adenoma heavily pigmented variant, adrenal cortical adenoma clear cell type, adrenal cortical adenoma glomerulosa cell type, adrenal cortical adenoma mixed cell type, endometrioid adenoma nos, endometrioid adenoma, borderline malignancy, endometrioid carcinoma, endometrioid adenofibroma nos, endometrioid adenofibroma borderline malignancy, endometrioid adenofibroma malignant, adnexal and skin appendage neoplasms, skin appendage adenoma, skin appendage carcinoma, sweat gland adenoma, sweat gland tumor nos, sweat gland adenocarcinoma, apocrine adenoma, apocrine adenocarcinoma, eccrine acrospiroma, eccrine spiradenoma, hidrocystoma, papillary hydradenoma, papillary syringadenoma, syringoma nos, sebaceous adenoma, sebaceous adenocarcinoma, ceruminous adenoma, ceruminous adenocarcinoma, mucoepidermoid neoplasms, mucoepidermoid tumor, mucoepidermoid carcinoma cystic, mucinous, and serous neoplasms, cystadenoma nos, cystadenocarcinoma nos, serous cystadenoma nos, serous cystadenoma borderline malignancy, serous cystadenocarcinoma nos, papillary cystadenoma nos, papillary cystadenoma borderline malignancy, papillary cystadenocarcinoma nos, papillary serous cystadenoma nos, papillary serous cystadenoma borderline malignancy, papillary serous cystadenocarcinoma, serous surface papilloma nos, serous surface papilloma borderline malignancy, serous surface papillary carcinoma, mucinous cystadenoma nos, mucinous cystadenoma borderline malignancy, mucinous cystadenocarcinoma nos, papillary mucinous cystadenoma nos, papillary mucinous cystadenoma borderline malignancy, papillary mucinous cystadenocarcinoma, mucinous adenoma, mucinous adenocarcinoma, pseudomyxoma peritonei, mucin-producing adenocarcinoma, signet ring cell carcinoma, metastatic signet ring cell carcinoma, ductal, lobular, and medullary neoplasms, intraductal carcinoma noninfiltrating nos, infiltrating duct carcinoma, comedocarcinoma, noninfiltrating comedocarcinoma nos, juvenile carcinoma of the breast, intraductal papilloma, noninfiltrating intraductal papillary adenocarcinoma, intracystic papillary adenoma, noninfiltrating intracystic carcinoma, intraductal papillomatosis nos, subareolar duct papillomatosis, medullary carcinoma nos, medullary carcinoma with amyloid stroma, medullary carcinoma with lymphoid stroma, lobular carcinoma in situ, lobular carcinoma nos, infiltrating ductular carcinoma, inflammatory carcinoma, paget's disease mammary, paget's disease and infiltrating duct carcinoma of breast, paget's disease extramammary, acinar cell neoplasms, acinar cell adenoma, acinar cell tumor, acinar cell carcinoma, complex epithelial neoplasms, adenosquamous carcinoma, adenolymphoma, adenocarcinoma with squamous metaplasia, adenocarcinoma with cartilaginous and osseous metaplasia, adenocarcinoma with spindle cell metaplasia, adenocarcinoma with apocrine metaplasia, thymoma benign, thymoma malignant, specialized gonadal neoplasms, sex cord-stromal tumor, thecoma nos, theca cell carcinoma, luteoma nos, granulosa cell tumor nos, granulosa cell tumor malignant, granulosa cell-theca cell tumor, androblastoma benign, androblastoma nos, androblastoma malignant, sertoli-leydig cell tumor, gynandroblastoma, tubular androblastoma nos, sertoli cell carcinoma, tubular androblastoma with lipid storage, leydig cell tumor benign, leydig cell tumor nos, leydig cell tumor malignant, hilar cell tumor, lipid cell tumor of ovary, adrenal rest tumor, paragangliomas and glomus tumors, paraganglioma nos, paraganglioma malignant, sympathetic paraganglioma, parasympathetic paraganglioma, glomus jugulare tumor, aortic body tumor, carotid body tumor, extra-adrenal paraganglioma nos, extra-adrenal paraganglioma malignant, pheochromocytoma nos, pheochromocytoma malignant, glomangiosarcoma, glomus tumor, glomangioma, nevi and melanomas, pigmented nevus nos, malignant melanoma nos, nodular melanoma, balloon cell nevus, balloon cell melanoma, halo nevus, fibrous papule of the nose, neuronevus, magnocellular nevus, nonpigmented nevus, amelanotic melanoma, junctional nevus, malignant melanoma in junctional nevus, precancerous melanosis nos, malignant melanoma in precancerous melanosis, hutchinson's melanotic freckle, malignant melanoma in hutchinson's melanotic freckle, superficial spreading melanoma, intradermal nevus, compound nevus, giant pigmented nevus, malignant melanoma in giant pigmented nevus, epithelioid and spindle cell nevus, epithelioid cell melanoma, spindle cell melanoma nos, spindle cell melanoma type a, spindle cell melanoma type b, mixed epithelioid and spindle cell melanoma, blue nevus nos, blue nevus malignant, cellular blue nevus, soft tissue tumors and sarcomas nos, soft tissue tumor benign, sarcoma nos, sarcomatosis nos, spindle cell sarcoma, giant cell sarcoma, small cell sarcoma, epithelioid cell sarcoma, fibromatous neoplasms, fibroma nos, fibrosarcoma nos, fibromyxoma, fibromyxosarcoma, periosteal fibroma, periosteal fibrosarcoma, fascial fibroma, fascial fibrosarcoma, infantile fibrosarcoma, elastofibroma, aggressive fibromatosis, abdominal fibromatosis, desmoplastic fibroma, fibrous histiocytoma nos, atypical fibrous histiocytoma, fibrous histiocytoma malignant, fibroxanthoma nos, atypical fibroxanthoma, fibroxanthoma malignant, dermatofibroma nos, dermatofibroma protuberans, dermatofibrosarcoma nos, myxomatous neoplasms, myxoma nos, myxosarcoma, lipomatous neoplasms, lipoma nos, liposarcoma nos, fibrolipoma, liposarcoma well differentiated type, fibromyxolipoma, myxoid liposarcoma, round cell liposarcoma, pleomorphic liposarcoma, mixed type liposarcoma, intramuscular lipoma, spindle cell lipoma, angiomyolipoma, angiomyoliposarcoma, angiolipoma nos, angiolipoma infiltrating, myelolipoma, hibernoma, lipoblastomatosis, myomatous neoplasms, leiomyoma nos, intravascular leiomyomatosis, leiomyosarcoma nos, epithelioid leiomyoma, epithelioid leiomyosarcoma, cellular leiomyoma, bizarre leiomyoma, angiomyoma, angiomyosarcoma, myoma, myosarcoma, rhabdomyoma nos, rhabdomyosarcoma nos, pleomorphic rhabdomyosarcoma, mixed type rhabdomyosarcoma, fetal rhabdomyoma, adult rhabdomyoma, embryonal rhabdomyosarcoma, alveolar rhabdomyosarcoma, complex mixed and stromal neoplasms, endometrial stromal sarcoma, endolymphatic stromal myosis, adenomyoma, pleomorphic adenoma, mixed tumor, malignant nos, mullerian mixed tumor, mesodermal mixed tumor, mesoblastic nephroma, nephroblastoma nos, epithelial nephroblastoma, mesenchymal nephroblastoma, hepatoblastoma, carcinosarcoma nos, carcinosarcoma embryonal type, myoepithelioma, mesenchymoma benign, mesenchymoma nos, mesenchymoma malignant, embryonal sarcoma, fibroepithelial neoplasms, brenner tumor nos, brenner tumor, borderline malignancy, brenner tumor malignant, fibroadenoma nos, intracanalicular fibroadenoma nos, pericanalicular fibroadenoma, adenofibroma nos, serous adenofibroma, mucinous adenofibroma, cellular intracanalicular fibroadenoma, cystosarcoma phyllodes nos, cystosarcoma phyllodes malignant, juvenile fibroadenoma, synovial neoplasms, synovioma benign, synovial sarcoma nos, synovial sarcoma spindle cell type, synovial sarcoma epithelioid cell type, synovial sarcoma biphasic type, clear cell sarcoma of tendons and aponeuroses, mesothelial neoplasms, mesothelioma benign, mesothelioma malignant, fibrous mesothelioma benign, fibrous mesothelioma malignant, epithelioid mesothelioma benign, epithelioid mesothelioma malignant, mesothelioma biphasic type benign, mesothelioma biphasic type malignant, adenomatoid tumor nos, germ cell neoplasms, dysgerminoma, seminoma nos, seminoma anaplastic type, spermatocytic seminoma, germinoma, embryonal carcinoma nos, endodermal sinus tumor, polyembryoma, gonadoblastoma, teratoma benign, teratoma nos, teratoma malignant nos, teratocarcinoma, malignant teratoma undifferentiated type, malignant teratoma intermediate type, dermoid cyst, dermoid cyst with malignant transformation, struma ovarii nos, struma ovarii malignant, strumal carcinoid, trophoblastic neoplasms, hydatidiform mole nos, invasive hydatidiform mole, choriocarcinoma, choriocarcinoma combined with teratoma, malignant teratoma trophoblastic, mesonephromas, mesonephroma benign, mesonephric tumor, mesonephroma malignant, endosalpingioma, blood vessel tumors, hemangioma nos, hemangiosarcoma, cavernous hemangioma, venous hemangioma, racemose hemangioma, kupffer cell sarcoma, hemangioendothelioma benign, hemangioendothelioma nos, hemangioendothelioma malignant, capillary hemangioma, intramuscular hemangioma, kaposi's sarcoma, angiokeratoma, verrucous keratotic hemangioma, hemangiopericytoma benign, hemangiopericytoma nos, hemangiopericytoma malignant, angiofibroma nos, hemangioblastoma, lymphatic vessel tumors, lymphangioma nos, lymphangiosarcoma, capillary lymphangioma, cavernous lymphangioma, cystic lymphangioma, lymphangiomyoma, lymphangiomyomatosis, hemolymphangioma, osteomas and osteosarcomas, osteoma nos, osteosarcoma nos, chondroblastic osteosarcoma, fibroblastic osteosarcoma, telangiectatic osteosarcoma, osteosarcoma in paget's disease of bone, juxtacortical osteosarcoma, osteoid osteoma nos, osteoblastoma, chondromatous neoplasms, osteochondroma, osteochondromatosis nos, chondroma nos, chondromatosis nos, chondrosarcoma nos, juxtacortical chondroma, juxtacortical chondrosarcoma, chondroblastoma nos, chondroblastoma malignant, mesenchymal chondrosarcoma, chondromyxoid fibroma, giant cell tumors, giant cell tumor of bone nos, giant cell tumor of bone malignant, giant cell tumor of soft parts nos, malignant giant cell tumor of soft parts, miscellaneous bone tumors, ewing's sarcoma, adamantinoma of long bones, ossifying fibroma, odontogenic tumors, odontogenic tumor benign, odontogenic tumor nos, odontogenic tumor malignant, dentinoma, cementoma nos, cementoblastoma benign, cementifying fibroma, gigantiform cementoma, odontoma nos, compound odontoma, complex odontoma, ameloblastic fibro-odontoma, ameloblastic odontosarcoma, adenomatoid odontogenic tumor, calcifying odontogenic cyst, ameloblastoma nos, ameloblastoma malignant, odontoameloblastoma, squamous odontogenic tumor, odontogenic myxoma, odontogenic fibroma nos, ameloblastic fibroma, ameloblastic fibrosarcoma, calcifying epithelial odontogenic tumor, miscellaneous tumors, craniopharyngioma, pinealoma, pineocytoma, pineoblastoma, melanotic neuroectodermal tumor, chordoma, gliomas, glioma malignant, gliomatosis cerebri, mixed glioma, subependymal glioma, subependymal giant cell astrocytoma, choroid plexus papilloma nos, choroid plexus papilloma malignant, ependymoma nos, ependymoma anaplastic type, papillary ependymoma, myxopapillary ependymoma, astrocytoma nos, astrocytoma, anaplastic type, protoplasmic astrocytoma, gemistocytic astrocytoma, fibrillary astrocytoma, pilocytic astrocytoma, spongioblastoma nos, spongioblastoma polare, astroblastoma, glioblastoma nos, giant cell glioblastoma, glioblastoma with sarcomatous component, primitive polar spongioblastoma, oligodendroglioma nos, oligodendroglioma, anaplastic type, oligodendroblastoma, medulloblastoma nos, desmoplastic medulloblastoma, medullomyoblastoma, cerebellar sarcoma nos, monstrocellular sarcoma, neuroepitheliomatous neoplasms, ganglioneuroma, ganglioneuroblastoma, ganglioneuromatosis, neuroblastoma nos, medulloepithelioma nos, teratoid medulloepithelioma, neuroepithelioma nos, spongioneuroblastoma, ganglioglioma, neurocytoma, pacinian tumor, retinoblastoma nos, retinoblastoma differentiated type, retinoblastoma undifferentiated type, olfactory neurogenic tumor, esthesioneurocytoma, esthesioneuroblastoma, esthesioneuroepithelioma, meningiomas, meningioma nos, meningiomatosis nos, meningioma malignant, meningotheliomatous meningioma, fibrous meningioma, psammomatous meningioma, angiomatous meningioma, hemangioblastic meningioma, hemangiopericytic meningioma, transitional meningioma, papillary meningioma, meningeal sarcomatosis, nerve sheath tumor, neurofibroma nos, neurofibromatosis nos, neurofibrosarcoma, melanotic neurofibroma, plexiform neurofibroma, neurilemmoma nos, neurinomatosis, neurilemmoma malignant, neuroma nos, granular cell tumors and alveolar soft part sarcoma, granular cell tumor nos, granular cell tumor malignant, alveolar soft part sarcoma, lymphomas nos or diffuse, lymphomatous tumor benign, malignant lymphoma nos, malignant lymphoma non hodgkin's type, malignant lymphoma undifferentiated cell type nos, malignant lymphoma stem cell type, malignant lymphoma convoluted cell type nos, lymphosarcoma nos, malignant lymphoma lymphoplasmacytoid type, malignant lymphoma immunoblastic type, malignant lymphoma mixed lymphocytic-histiocytic nos, malignant lymphoma centroblastic-centrocytic diffuse, malignant lymphoma follicular center cell nos, malignant lymphoma lymphocytic well differentiated nos, malignant lymphoma lymphocytic intermediate differentiation nos, malignant lymphoma centrocytic, malignant lymphoma follicular center cell cleaved nos, malignant lymphoma lymphocytic poorly differentiated nos, prolymphocytic lymphosarcoma, malignant lymphoma centroblastic type nos, malignant lymphoma follicular center cell noncleaved nos, reticulosarcomas, reticulosarcoma nos, reticulosarcoma pleomorphic cell type, reticulosarcoma nodular, hodgkin's disease, hodgkin's disease nos, hodgkin's disease lymphocytic predominance, hodgkin's disease mixed cellularity, hodgkin's disease lymphocytic depletion nos, hodgkin's disease lymphocytic depletion diffuse fibrosis, hodgkin's disease lymphocytic depletion reticular type, hodgkin's disease nodular sclerosis nos, hodgkin's disease nodular sclerosis cellular phase, hodgkin's paragranuloma, hodgkin's granuloma, hodgkin's sarcoma, lymphomas nodular or follicular, malignant lymphoma nodular nos, malignant lymphoma mixed lymphocytic-histiocytic nodular, malignant lymphoma centroblastic-centrocytic follicular, malignant lymphoma lymphocytic well differentiated nodular, malignant lymphoma lymphocytic intermediate differentiation nodular, malignant lymphoma follicular center cell cleaved follicular, malignant lymphoma lymphocytic poorly differentiated nodular, malignant lymphoma centroblastic type follicular, malignant lymphoma follicular center cell noncleaved follicular, mycosis fungoides, mycosis fungoides, sezary's disease, miscellaneous reticuloendothelial neoplasms, microglioma, malignant histiocytosis, histiocytic medullary reticulosis, letterer-siwe's disease, plasma cell tumors, plasma cell myeloma, plasma cell tumor benign, plasmacytoma nos, plasma cell tumor malignant, mast cell tumors, mastocytoma nos, mast cell sarcoma, malignant mastocytosis, burkitt's tumor, burkitt's tumor, leukemias, leukemias nos, leukemia nos, acute leukemia nos, subacute leukemia nos, chronic leukemia nos, aleukemic leukemia nos, compound leukemias, compound leukemia, lymphoid leukemias, lymphoid leukemia nos, acute lymphoid leukemia, subacute lymphoid leukemia, chronic lymphoid leukemia, aleukemic lymphoid leukemia, prolymphocytic leukemia, plasma cell leukemias, plasma cell leukemia, erythroleukemias, erythroleukemia, acute erythremia, chronic erythremia, lymphosarcoma cell leukemias, lymphosarcoma cell leukemia, myeloid leukemias, myeloid leukemia nos, acute myeloid leukemia, subacute myeloid leukemia, chronic myeloid leukemia, aleukemic myeloid leukemia, neutrophilic leukemia, acute promyelocytic leukemia, basophilic leukemias, basophilic leukemia, eosinophilic leukemias, eosinophilic leukemia, monocytic leukemias, monocytic leukemia nos, acute monocytic leukemia, subacute monocytic leukemia, chronic monocytic leukemia, aleukemic monocytic leukemia, miscellaneous leukemias, mast cell leukemia, megakaryocytic leukemia, megakaryocytic myelosis, myeloid sarcoma, hairy cell leukemia, miscellaneous myeloproliferative and lymphoproliferative disorders, polycythemia vera, acute panmyelosis, chronic myeloproliferative disease, myelosclerosis with myeloid metaplasia, idiopathic thrombocythemia, chronic lymphoproliferative disease.

In an embodiment of the present invention, the disease is selected from the group comprising tumors of pancreas, pancreatic adenocarcinoma, tumors of head of pancreas, of body of pancreas, of tail of pancreas, of pancreatic duct, of islets of langerhans, neck of pancreas, tumor of prostate, prostate adenocarcinoma, prostate gland, neuroendocrine tumors, breast cancer, tumor of central portion of breast, upper inner quadrant of breast, lower inner quadrant of breast, upper outer quadrant of breast, lower outer quadrant of breast, axillary tail of breast, overlapping lesion of breast, juvenile carcinoma of the breast, tumors of parathyroid gland, myeloma, lung cancer, small cell lung cancer, non-small cell lung cancer, tumor of main bronchus, of upper lobe lung, of middle lobe lung, of lower lobe lung, colorectal carcinoma, tumor of ascending colon, of hepatic flexure of colon, of transverse colon, of splenic flexure of colon, of descending colon, of sigmoid colon, of overlapping lesion of colon, of small intestine, tumors of liver, liver cell adenoma, hepatocellular carcinoma, hepatocholangioma, ombined hepatocellular carcinoma and cholangiocarcinoma, hepatoblastoma, ovarian carcinoma, sarcoma, osteosarcoma, fibrosarcoma, gastrointestinal stroma tumors, gastrointestinal tract, gastric carcinoma, thyroid carcinoma, medullary thyroid carcinoma, thyroid gland, renal cell carcinoma, renal pelvis, tumors of bladder, bladder carcinoma, tumors of trigone bladder, of dome bladder, of lateral wall bladder, of posterior wall bladder, of ureteric orifice, of urachus, overlapping lesion of bladder, basal cell carcinoma, basal cell neoplasms, basal cell tumor, basal cell carcinoma, multicentric basal cell carcinoma, basaloid carcinoma, basal cell adenoma, squamous cell carcinoma, oral squamous cell carcinoma, squamous cell carcinoma of the larynx, cervical carcinoma, tumors of exocervix, of overlapping lesion of cervix uteri, of cervix uteri, of isthmus uteri, tumors of uterus, tumors of ovary, tumors of cervical esophagus, of thoracic esophagus, of abdominal esophagus, of upper third of esophagus, of esophagus middle third, of esophagus lower third, of overlapping lesion of esophagus, endometrial carcinoma, head and neck cancer, lymphoma, malignant mesothelioma, mesothelial neoplasms, mesothelioma, fibrous mesothelioma, fibrous mesothelioma, epithelioid mesothelioma, epithelioid mesothelioma, duodenal carcinoma, neuroendocrine tumors, neuroendocrine tumors of the lung, neuroendocrine tumors of the pancreas, neuroendocrine tumors of the foregut, neuroendocrine tumors of the midgut, neuroendocrine tumors of the hindgut, gastroenteropancreatic neuroendocrine tumors, neuroendocrine carcinomas, neuroendocrine tumors of the breast, neuroendocrine tumors o the ovaries, testicular cancer, thymic carcinoma, tumors of stomach, fundus stomach, body stomach, gastric antrum, pylorus, lesser curvature of stomach, greater curvature of stomach, overlapping lesion of stomach, paragangliomas, ganglioma, melanomas, malignant melanoma, nodular melanoma, amelanotic melanoma, superficial spreading melanoma, epithelioid cell melanoma, spindle cell melanoma, mixed epithelioid and spindle cell melanoma.

In a still further embodiment, the aforementioned indications may occur in organs and tissues selected from the group comprising external upper lip, external lower lip, external lip nos, upper lip mucosa, lower lip mucosa, mucosa lip nos, commissure lip, overlapping lesion of lip, base of tongue nos, dorsal surface tongue nos, border of tongue, ventral surface of tongue nos, anterior ⅔ of tongue nos, lingual tonsil, overlapping lesion of tongue, tongue nos, upper gum, lower gum, gum nos, anterior floor of mouth, lateral floor of mouth, overlapping lesion of floor of mouth, floor of mouth nos, hard palate, soft palate nos, uvula, overlapping lesion of palate, palate nos, cheek mucosa, vestibule of mouth, retromolar area, overlapping lesion of other and unspecified parts of mouth, mouth nos, parotid gland, submaxillary gland, sublingual gland, overlapping lesion of major salivary glands, major salivary gland nos, tonsillar fossa, tonsillar pillar, overlapping lesion of tonsil, tonsil nos, vallecula, anterior surface of epiglottis, lateral wall oropharynx, posterior wall oropharynx, branchial cleft, overlapping lesion of oropharynx, oropharynx nos, superior wall of nasopharynx, posterior wall nasopharynx, lateral wall nasopharynx, anterior wall nasopharynx, overlapping lesion of nasopharynx, nasopharynx nos, pyriform sinus, postcricoid region, hypopharyngeal aspect of aryepiglottic fold, posterior wall hypopharynx, overlapping lesion of hypopharynx, hypopharynx nos, pharynx nos, laryngopharynx, waldeyer's ring, overlapping lesion of lip oral cavity and pharynx, cervical esophagus, thoracic esophagus, abdominal esophagus, upper third of esophagus, middle third of esophagus, esophagus lower third, overlapping lesion of esophagus, esophagus nos, cardia nos, fundus stomach, body stomach, gastric antrum, pylorus, lesser curvature of stomach nos, greater curvature of stomach nos, overlapping lesion of stomach, stomach nos, duodenum, jejunum, ileum, meckel's diverticulum, overlapping lesion of small intestine, small intestine nos, cecum, appendix, ascending colon, hepatic flexure of colon, transverse colon, splenic flexure of colon, descending colon, sigmoid colon, overlapping lesion of colon, colon nos, rectosigmoid junction, rectum nos, anus nos, anal canal, cloacogenic zone, overlapping lesion of rectum anus and anal canal, liver, intrahepatic bile duct, gallbladder, extrahepatic bile duct, ampulla of vater, overlapping lesion of biliary tract, biliary tract nos, head of pancreas, body pancreas, tail pancreas, pancreatic duct, islets of langerhans, neck of pancreas, overlapping lesion of pancreas, pancreas nos, intestinal tract nos, overlapping lesion of digestive system, gastrointestinal tract nos, nasal cavity, middle ear, maxillary sinus, ethmoid sinus, frontal sinus, sphenoid sinus, overlapping lesion of accessory sinuses, accessory sinus nos, glottis, supraglottis, subglottis, laryngeal cartilage, overlapping lesion of larynx, larynx nos, trachea, main bronchus, upper lobe lung, middle lobe lung, lower lobe lung, overlapping lesion of lung, lung nos, thymus, heart, anterior mediastinum, posterior mediastinum, mediastinum nos, pleura nos, overlapping lesion of heart mediastinum and pleura, upper respiratory tract nos, overlapping lesion of respiratory system and intrathoracic organs, respiratory tract nos, upper limb long bones joints, upper limb short bones joints, lower limb long bones joints, lower limb short bones joints, overlapping lesion of bones joints and articular cartilage of limbs, bone limb nos, skull and facial bone, mandible, vertebral column, rib sternum clavicle, pelvic bone, overlapping lesion of bones joints and articular cartilage, bone nos, blood, bone marrow, spleen, reticuloendothelial system nos, hematopoietic system nos, skin lip nos, eyelid nos, external ear, skin face, skin scalp neck, skin trunk, skin limb upper, skin limb lower, peripheral nerve head neck, peripheral nerve shoulder arm, peripheral nerve leg, peripheral nerve thorax, peripheral nerve abdomen, peripheral nerve pelvis, peripheral nerve trunk, overlapping lesion of peripheral nerves and autonomic nervous system, autonomic nervous system nos, retroperitoneum, peritoneum, peritoneum nos, overlapping lesion of retroperitoneum and peritoneum, connective tissue head, connective tissue arm, connective tissue leg, connective tissue thorax, connective tissue abdomen, connective tissue pelvis, connective tissue trunk nos, overlapping lesion of connective subcutaneous and other soft tissues, connective tissue nos, nipple, central portion of breast, upper inner quadrant of breast, lower inner quadrant of breast, upper outer quadrant of breast, lower outer quadrant of breast, axillary tail of breast, overlapping lesion of breast, breast nos, labium majus, labium minus, clitoris, overlapping lesion of vulva, vulva nos, vagina nos, endocervix, exocervix, overlapping lesion of cervix uteri, cervix uteri, isthmus uteri, endometrium, myometrium, fundus uteri, overlapping lesion of corpus uteri, corpus uteri, uterus nos, ovary, fallopian tube, broad ligament, round ligament, parametrium, uterine adnexa, wolffian body, overlapping lesion of female genital organs, female genital tract nos, prepuce, glans penis, body penis, overlapping lesion of penis, penis nos, prostate gland, undescended testis, descended testis, testis nos, epididymis, spermatic cord, scrotum nos, tunica vaginalis, overlapping lesion of male genital organs, male genital organs nos, kidney nos, renal pelvis, ureter, trigone bladder, dome bladder, lateral wall bladder, posterior wall bladder, ureteric orifice, urachus, overlapping lesion of bladder, bladder nos, urethra, paraurethral gland, overlapping lesion of urinary organs, urinary system nos, conjunctiva, cornea nos, retina, choroid, ciliary body, lacrimal gland, orbit nos, overlapping lesion of eye and adnexa, eye nos, cerebral meninges, spinal meninges, meninges nos, cerebrum, frontal lobe, temporal lobe, parietal lobe, occipital lobe, ventricle nos, cerebellum nos, brain stem, overlapping lesion of brain, brain nos, spinal cord, cauda *equina*, olfactory nerve, optic nerve, acoustic nerve, cranial nerve nos, overlapping lesion of brain and central nervous system, nervous system nos, thyroid gland, adrenal gland cortex, adrenal gland medulla, adrenal gland nos, parathyroid gland, pituitary gland, craniopharyngeal duct, pineal gland, carotid body, aortic body, overlapping lesion of endocrine glands and related structures, endocrine gland nos, head face or neck nos, thorax nos, abdomen nos, pelvis nos, upper limb nos, lower limb nos, other illdefined sites, overlapping lesion of ill-defined sites, lymph node face head neck, intrathoracic lymph node, intra-abdominal lymph nodes, lymph node axilla arm, lymph node inguinal region leg, lymph node pelvic, lymph nodes of multiple regions, lymph node nos, unknown primary site, The subjects treated with the presently disclosed and claimed compounds may be treated in combination with other non-surgical anti-proliferative (e.g., anti-cancer) drug therapy. In one embodiment, the compounds may be administered in combination with an anti-cancer compound such as a cytostatic compound. A cytostatic compound is a compound (e.g., a small molecule, a nucleic acid, or a protein) that suppresses cell growth and/or proliferation. In some embodiments, the cytostatic compound is directed towards the malignant cells of a tumor. In yet other embodiments, the cytostatic compound is one which inhibits the growth and/or proliferation of vascular smooth muscle cells or fibroblasts.

Suitable anti-proliferative drugs or cytostatic compounds to be used in combination with the presently disclosed and claimed compounds include anti-cancer drugs. Numerous anti-cancer drugs which may be used are well known and include, but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Niraparib; Nocodazole; Nogalamycin; Olaparib; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Rucaparib; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talazoparib; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Tubulozole Hydrochloride; Uracil Mustard; Uredepa; Vapreotide; Velaparib; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Other anti-cancer drugs include, but are not limited to: 20-epi-1,25 dihydroxyvitamin D3; 5-ethynyluracil; abiraterone; acylfulvene; adecypenol; adozelesin; ALL-TK antagonists; ambamustine; amidox; amifostine; aminolevulinic acid; amrubicin; anagrelide; andrographolide; angiogenesis inhibitors; antagonist D; antagonist G; antarelix; anti-dorsalizing morphogenetic protein-1; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bisaziridinylspermine; bisnafide; bistratene A; breflate; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; casein kinase inhibitors (ICOS); castanospermine; cecropin B; cetrorelix; chlorins; chloroquinoxaline sulfonamide; cicaprost; cis-porphyrin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; dehydrodidemnin B; deslorelin; dexifosfamide; dexrazoxane; dexverapamil; didemnin B; didox; diethylnorspermine; dihydro-5-azacytidine; dihydrotaxol, 9-; dioxamycin; diphenyl spiromustine; docosanol; dolasetron; doxifluridine; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; filgrastim; finasteride; flavopiridol; flezelastine; fluasterone; fludarabine; fluorodaunorunicin hydrochloride; forfenimex; formestane; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine;

napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; saintopin; SarCNU; sarcophytol A; sargramostim; Sdi 1 mimetics; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temozolomide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; titanocene dichloride; topsentin; toremifene; totipotent stem cell factor; translation inhibitors; tretinoin; triacetyluridine; triciribine; tropisetron; turosteride; tyrosine kinase inhibitors; tyrphostins; UBC inhibitors; ubenimex; urogenital sinus-derived growth inhibitory factor; urokinase receptor antagonists; variolin B; vector system, erythrocyte gene therapy; velaresol; veramine; verdins; vinorelbine; vinxaltine; vitaxin; zanoterone; zilascorb; and zinostatin stimalamer.

The presently disclosed and claimed compounds can also be used in combination with any of the following treatments:

Therapy in combination with inhibitors of Poly(ADP-ribose) polymerases (PARP), a class of chemotherapeutic agents directed at targeting cancers with defective DNA-damage repair (Yuan, et al., *Expert Opin Ther Pat,* 2017, 27:363). Such PARP inhibitors include but are not limited to olaparib, rupacarib, velaparib, niraparib, talazoparib, pamiparib, iniparib, E7449, and A-966492.

Therapy in combination with inhibitors of signaling pathways and mechanisms leading to repair of DNA single and double strand breaks as e.g. nuclear factor-kappaB signaling (Pilie, et al., *Nat Rev Clin Oncol,* 2019, 16:81; Zhang, et al., *Chin J Cancer,* 2012, 31:359). Such inhibitors include but are not limited to inhibitors of ATM and ATR kinases, checkpoint kinase 1 and 2, DNA-dependen protein kinase, and WEEl kinase (Pilie, et al., *Nat Rev Clin Oncol,* 2019, 16:81).

Therapy in combination with an immunomodulator (Khalil, et al., *Nat Rev Clin Oncol,* 2016, 13:394), a cancer vaccine (Hollingsworth, et al., *NPJ Vaccines,* 2019, 4:7), an immune checkpoint inhibitor (e.g. PD-1, PD-L1, CTLA-4-inhibitor) (Wei, et al., *Cancer Discov,* 2018, 8:1069), a Cyclin-D-Kinase 4/6 inhibitor (Goel, et al., *Trends Cell Biol,* 2018, 28:911), an antibody being capable of binding to a tumor cell and/or metastases and being capable of inducing antibody-dependent cellular cytotoxicity (ADCC) (Kellner, et al., *Transfus Med Hemother,* 2017, 44:327), a T cell- or NK cell engager (e.g. bispecific antibodies) (Yu, et al., *J Cancer Res Clin Oncol,* 2019, 145:941), a cellular therapy using expanded autologous or allogeneic immune cells (e.g. chimeric antigen receptor T (CAR-T) cells) (Khalil, et al., *Nat Rev Clin Oncol,* 2016, 13:394). Immune checkpoint inhibitors incluce but are not limited to nivolumab, ipilimumab, pembrolizumab, atezolizumab, avelumab, durvalumab, and cemiplimab.

According to the present invention, the compounds may be administered prior to, concurrent with, or following other anti-cancer compounds. The administration schedule may involve administering the different agents in an alternating fashion. In other embodiments, the compounds may be delivered before and during, or during and after, or before and after treatment with other therapies. In some cases, the compound is administered more than 24 hours before the administration of the other anti-proliferative treatment. In other embodiments, more than one anti-proliferative therapy may be administered to a subject. For example, the subject may receive the present compounds, in combination with both surgery and at least one other anti-proliferative compound. Alternatively, the compound may be administered in combination with more than one anti-cancer drug.

In an embodiment, the compounds of the present invention are used to detect cells and tissues overexpressing FAP, whereby such detection is achieved by conjugating a detectable label to the compounds of the invention, preferably a detectable radionuclide. In a preferred embodiment, the cells and tissues detected are diseased cells and tissues and/or are either a or the cause for the disease and/or the symptoms of the disease, or are part of the pathology underlying the disease. In a further preferred embodiment, the diseased cells and tissues are causing and/or are part of an oncology indication (e.g. neoplasms, tumors, and cancers) or a non-oncology indication (e.g. inflammatory disease, cardiovascular disease, autoimmune disease, and fibrotic disease).

In another embodiment, the compounds of the present invention are used to treat cells and tissues overexpressing FAP. In a preferred embodiment, the cells and tissues treated are diseased cells and tissues and/or are either a or the cause for the disease and/or the symptoms of the disease, or are part of the pathology underlying the disease. In a further preferred embodiment, the diseased cells and tissues are causing and/or are part of an oncology indication (e.g. neoplasms, tumors, and cancers) and the therapeutic activity is achieved by conjugating therapeutically active effector to the compounds of the present invention, preferably a therapeutically active radionuclide. In a further preferred embodiment, the diseased cells and tissues are causing and/or are part of a non-oncology indication (e.g. inflammatory disease, cardiovascular disease, autoimmune disease, and fibrotic disease) and the therapeutic activity is achieved by inhibition of the enzymatic activity of FAP.

In a further embodiment, particularly if the disease is a non-oncology disease or a non-oncology indication (e.g. inflammatory disease, cardiovascular disease, autoimmune disease, and fibrotic disease), the compounds of the present invention are administered in therapeutically effective amounts; preferably the compound of the present invention does not comprise a therapeutically active nuclide. An effective amount is a dosage of the compound sufficient to provide a therapeutically or medically desirable result or effect in the subject to which the compound is administered. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. For example, in connection with methods directed towards treating subjects having a condition characterized by abnormal cell proliferation, an effective amount to inhibit proliferation would be an amount sufficient to reduce or halt altogether the abnormal cell proliferation so as to slow or halt the development of or the progression of a cell mass such as, for example, a tumor. As used in the embodiments, “inhibit” embraces all of the foregoing.

In other embodiments, a therapeutically effective amount will be an amount necessary to extend the dormancy of micrometastases or to stabilize any residual primary tumor cells following surgical or drug therapy.

Generally, when using an unconjugated compound without a therapeutically active radionuclide, a therapeutically effective amount will vary with the subject’s age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount is typically, but not limited to, an amount in a range from 0.1 μg/kg to about 2000 mg/kg, or from 1.0 μg/kg to about 1000 mg/kg, or from about 0.1 mg/kg to about 500 mg/kg, or from about 1.0 mg/kg to about 100 mg/kg, in one or more dose administrations daily, for one or more days. If desired, the effective daily dose of the active compound may be administered as two, three, four, five, six, or more sub-doses for example administered separately at appropriate intervals throughout the day, optionally, in unit dosage forms. In some embodiments, the compounds are administered for more than 7 days, more than 10 days, more than 14 days and more than 20 days. In still other embodiments, the compound is administered over a period of weeks, or months. In still other embodiments, the compound is delivered on alternate days. For example, the agent is delivered every two days, or every three days, or every four days, or every five days, or every six days, or every week, or every month.

In a preferred embodiment, the compound of the present invention is for use in the treatment and/or prevention of a disease, whereby such treatment is radionuclide therapy.

Preferably, radionuclide therapy makes use of or is based on different forms of radiation emitted by a radionuclide. Such radiation can, for example, be any one of radiation of photons, radiation of electrons including but not limited to $\beta^-$-particles and Auger-electrons, radiation of protons, radiation of neutrons, radiation of positrons, radiation of α-particles or an ion beam. Depending on the kind of particle or radiation emitted by said radionuclide, radionuclide therapy can, for example, be distinguished as photon radionuclide therapy, electron radionuclide therapy, proton radionuclide therapy, neutron radionuclide therapy, positron radionuclide therapy, α-particle radionuclide therapy or ion beam radionuclide therapy. All of these forms of radionuclide therapy are encompassed by the present invention, and all of these forms of radionuclide therapy can be realized by the compound of the invention, preferably under the proviso that the radionuclide attached to the compound of the invention, more preferably as an effector, is providing for this kind of radiation.

Radionuclide therapy preferably works by damaging the DNA of cells. The damage is caused by a photon, electron, proton, neutron, positron, α-particle or ion beam directly or indirectly ionizing the atoms which make up the DNA chain. Indirect ionization happens as a result of the ionization of water, forming free radicals, notably hydroxyl radicals, which then damage the DNA.

In the most common forms of radionuclide therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly.

Oxygen is a potent radiosensitizer, increasing the effectiveness of a given dose of radiation by forming DNA-damaging free radicals. Therefore, use of high pressure oxygen tanks, blood substitutes that carry increased oxygen, hypoxic cell radiosensitizers such as misonidazole and metronidazole, and hypoxic cytotoxins, such as tirapazamine may be applied.

Other factors that are considered when selecting a radioactive dose include whether the patient is receiving chemotherapy, whether radiation therapy is being administered before or after surgery, and the degree of success of surgery.

The total radioactive dose may be fractionated, i.e. spread out over time in one or more treatments for several important reasons. Fractionation allows normal cells time to recover, while tumor cells are generally less efficient in repair between fractions. Fractionation also allows tumor cells that were in a relatively radio-resistant phase of the cell cycle during one treatment to cycle into a sensitive phase of the cycle before the next fraction is given. Similarly, tumor cells that were chronically or acutely hypoxic and, therefore, more radioresistant, may reoxygenate between fractions, improving the tumor cell kill.

It is generally known that different cancers respond differently to radiation therapy. The response of a cancer to radiation is described by its radiosensitivity. Highly radiosensitive cancer cells are rapidly killed by modest doses of radiation. These include leukemias, most lymphomas, and germ cell tumors.

It is important to distinguish radiosensitivity of a particular tumor, which to some extent is a laboratory measure, from “curability” of a cancer by an internally delivered radioactive dose in actual clinical practice. For example, leukemias are not generally curable with radiotherapy, because they are disseminated through the body. Lymphoma may be radically curable if it is localized to one area of the body. Similarly, many of the common, moderately radioresponsive tumors can be treated with curative doses of radioactivity if they are at an early stage. This applies, for example, to non-melanoma skin cancer, head and neck cancer, non-small cell lung cancer, cervical cancer, anal cancer, prostate cancer.

The response of a tumor to radiotherapy is also related to its size. For complex reasons, very large tumors respond less well to radiation than smaller tumors or microscopic disease. Various strategies are used to overcome this effect. The most common technique is surgical resection prior to radiotherapy. This is most commonly seen in the treatment of breast cancer with wide local excision or mastectomy followed by adjuvant radiotherapy. Another method is to shrink the tumor with neoadjuvant chemotherapy prior to radical radionuclide therapy. A third technique is to enhance the radiosensitivity of the cancer by giving certain drugs during a course of radiotherapy. Examples of radiosensiting drugs include, but are not limited to Cisplatin, Nimorazole, and Cetuximab.

Introperative radiotherapy is a special type of radiotherapy that is delivered immediately after surgical removal of the cancer. This method has been employed in breast cancer (TARGeted Introperative radioTherapy), brain tumors and rectal cancers.

Radionuclide therapy is in itself painless. Many low-dose palliative treatments cause minimal or no side effects. Treatment to higher doses may cause varying side effects during treatment (acute side effects), in the months or years following treatment (long-term side effects), or after re-treatment (cumulative side effects). The nature, severity, and longevity of side effects depends on the organs that receive the radiation, the treatment itself (type of radionuclide, dose, fractionation, concurrent chemotherapy), and the patient.

It is within the present inventions that the method for the treatment of a disease of the invention may realize each and any of the above strategies which are as such known in the art, and which insofar constitute further embodiments of the invention.

It is also within the present invention that the compound of the invention is used in a method for the diagnosis of a disease as disclosed herein. Such method, preferably, comprises the step of administering to a subject in need thereof a diagnostically effective amount of the compound of the invention.

In accordance with the present invention, an imaging method is selected from the group consisting of scintigraphy, Single Photon Emission Computed Tomography (SPECT) and Positron Emission Tomography (PET).

Scintigraphy is a form of diagnostic test or method used in nuclear medicine, wherein radiopharmaceuticals are internalized by cells, tissues and/or organs, preferably internalized in vivo, and radiation emitted by said internalized radiopharmaceuticals is captured by external detectors (gamma cameras) to form and display two-dimensional images. In contrast thereto, SPECT and PET forms and displays three-dimensional images. Because of this, SPECT and PET are classified as separate techniques to scintigraphy, although they also use gamma cameras to detect internal radiation. Scintigraphy is unlike a diagnostic X-ray where external radiation is passed through the body to form an image.

Single Photon Emission Tomography (SPECT) scans are a type of nuclear imaging technique using gamma rays. They are very similar to conventional nuclear medicine planar imaging using a gamma camera. Before the SPECT scan, the patient is injected with a radiolabeled chemical emitting gamma rays that can be detected by the scanner. A computer collects the information from the gamma camera and translates this into two-dimensional cross-sections. These cross-sections can be added back together to form a three-dimensional image of an organ or a tissue. SPECT involves detection of gamma rays emitted singly, and sequentially, by the radionuclide provided by the radiolabeled chemical. To acquire SPECT images, the gamma camera is rotated around the patient. Projections are acquired at defined points during the rotation, typically every 3-6 degrees. In most cases, a full 360 degree rotation is used to obtain an optimal reconstruction. The time taken to obtain each projection is also variable, but 15-20 seconds is typical. This gives a total scan time of 15-20 minutes. Multi-headed gamma cameras are faster. Since SPECT acquisition is very similar to planar gamma camera imaging, the same radiopharmaceuticals may be used.

Positron Emitting Tomography (PET) is a non-invasive, diagnostic imaging technique for measuring the biochemical status or metabolic activity of cells within the human body. PET is unique since it produces images of the body's basic biochemistry or functions. Traditional diagnostic techniques, such as X-rays, CT scans, or MRI, produce images of the body's anatomy or structure. The premise with these techniques is that any changes in structure or anatomy associated with a disease can be seen. Biochemical processes are also altered by a disease, and may occur before any gross changes in anatomy. PET is an imaging technique that can visualize some of these early biochemical changes. PET scanners rely on radiation emitted from the patient to create the images. Each patient is given a minute amount of a radioactive pharmaceutical that either closely resembles a natural substance used by the body or binds specifically to a receptor or molecular structure. As the radioisotope undergoes positron emission decay (also known as positive beta decay), it emits a positron, the antiparticle counterpart of an electron. After traveling up to a few millimeters, the positron encounters an electron and annihilates, producing a pair of annihilation (gamma) photons moving in opposite directions. These are detected when they reach a scintillation material in the scanning device, creating a burst of light, which is detected by photomultiplier tubes or silicon avalanche photodiodes. The technique depends on simultaneous or coincident detection of the pair of photons. Photons that do not arrive in pairs, i.e., within a few nanoseconds, are ignored. All coincidences are forwarded to the image processing unit where the final image data is produced using image reconstruction procedures.

SPECT/CT and PET/CT is the combination of SPECT and PET with computed tomography (CT). The key benefits of combining these modalities are improving the reader's confidence and accuracy. With traditional PET and SPECT, the limited number of photons emitted from the area of abnormality produces a very low-level background that makes it difficult to anatomically localize the area. Adding CT helps determine the location of the abnormal area from an anatomic perspective and categorize the likelihood that this represents a disease.

It is within the present inventions that the method for the diagnosis of a disease of the invention may realize each and any of the above strategies which are as such known in the art, and which insofar constitute further embodiments of the invention.

Compounds of the present invention are useful to stratify patients, i.e. to create subsets within a patient population that provide more detailed information about how the patient will respond to a given drug. Stratification can be a critical component to transforming a clinical trial from a negative or neutral outcome to one with a positive outcome by identifying the subset of the population most likely to respond to a novel therapy.

Stratification includes the identification of a group of patients with shared "biological" characteristics to select the optimal management for the patients and achieve the best possible outcome in terms of risk assessment, risk prevention and achievement of the optimal treatment outcome A compound of the present invention may be used to assess or detect, a specific disease as early as possible (which is a diagnostic use), the risk of developing a disease (which is a susceptibility/risk use), the evolution of a disease including indolent vs. aggressive (which is a prognostic use) and it may be used to predict the response and the toxicity to a given treatment (which is a predictive use).

It is also within the present invention that the compound of the invention is used in a theragnostic method. The concept of theragnostics is to combine a therapeutic agent with a corresponding diagnostic test that can increase the clinical use of the therapeutic drug. The concept of theragnostics is becoming increasingly attractive and is widely considered the key to improving the efficiency of drug treatment by helping doctors identify patients who might profit from a given therapy and hence avoid unnecessary treatments.

The concept of theragnostics is to combine a therapeutic agent with a diagnostic test that allows doctors to identify those patients who will benefit most from a given therapy. In an embodiment and as preferably used herein, a compound of the present invention is used for the diagnosis of a patient, i.e. identification and localization of the primary tumor mass as well as potential local and distant metastases. Furthermore, the tumor volume can be determined, especially utilizing three-dimensional diagnostic modalities such as SPECT or PET. Only those patients having FAP-positive tumor masses and who, therefore, might profit from a given therapy are selected for a particular therapy and hence unnecessary treatments are avoided. Preferably, such therapy is a FAP-targeted therapy using a compound of the present invention. In one particular embodiment, chemically identical tumor-targeted diagnostics, preferably imaging diagnostics for scintigraphy, PET or SPECT and radiotherapeutics are applied. Such compounds only differ in the radionuclide and therefore usually have a very similar if not identical pharmacokinetic profile. This can be realized using a chelator and a diagnostic or therapeutic radiometal. Alternatively, this can be realized using a precursor for radiolabeling and radiolabeling with either a diagnostic or a therapeutic radionuclide. In one embodiment diagnostic imaging is used preferably by means of quantification of the radiation of the diagnostic radionuclide and subsequent dosimetry which is known to those skilled in the art and the prediction of drug concentrations in the tumor compared to vulnerable side effect organs. Thus, a truly individualized drug dosing therapy for the patient is achieved.

In an embodiment and as preferably used herein, the theragnostic method is realized with only one theragnostically active compound such as a compound of the present invention labeled with a radionuclide emitting diagnostically detectable radiation (e.g. positrons or gamma rays) as well as therapeutically effective radiation (e.g. electrons or alpha particles).

The invention also contemplates a method of intraoperatively identifying/disclosing diseased tissues expressing FAP in a subject. Such method uses a compound of the invention, whereby such compound of the invention preferably comprises as Effector a diagnostically active agent.

According to a further embodiment of the invention, the compound of the invention, particularly if complexed with a radionuclide, may be employed as adjunct or adjuvant to any other tumor treatment including, surgery as the primary method of treatment of most isolated solid cancers, radiation therapy involving the use of ionizing radiation in an attempt to either cure or improve the symptoms of cancer using either sealed internal sources in the form of brachytherapy or external sources, chemotherapy such as alkylating agents, antimetabolites, anthracyclines, plant alkaloids, topoisomerase inhibitors, and other antitumor agents, hormone treatments that modulate tumor cell behavior without directly attacking those cells, targeted agents which directly target a molecular abnormality in certain types of cancer including monoclonal antibodies and tyrosine kinase inhibitors, angiogenesis inhibitors, immunotherapy, cancer vaccination, palliative care including actions to reduce the physical, emotional, spiritual, and psycho-social distress to improve the patient's quality of life and alternative treatments including a diverse group of health care systems, practices, and products that are not part of conventional medicine.

In an embodiment of the methods of the invention, the subject is a patient. In an embodiment, a patient is a subject which has been diagnosed as suffering from or which is suspected of suffering from or which is at risk of suffering from or developing a disease, whereby the disease is a disease as described herein and preferably a disease involving FAP.

Dosages employed in practicing the methods for treatment and diagnosis, respectively, where a radionuclide is used and more specifically attached to or part of the compound of the invention will vary depending e.g. on the particular condition to be treated, for example the known radiosensitivity of the tumor type, the volume of the tumor and the therapy desired. In general, the dose is calculated on the basis of radioactivity distribution to each organ and on observed target uptake. A γ-emitting complex may be administered once or at several times for diagnostic imaging. In animals, an indicated dose range may be from 0.1 μg/kg to 5 mg/kg of the compound of the invention complexed e.g. with 1 to 200 MBq of 111In or 89Zr. A β-emitting complex of the compound of the invention may be administered at several time points e.g. over a period of 1 to 3 weeks or longer. In animals, an indicated dosage range may be of from 0.1 μg/kg to 5 mg/kg of the compound of the invention complexed e.g. with 1 to 200 MBq 90Y or 177Lu. In larger mammals, for example humans, an indicated dosage range is from 0.1 to 100 μg/kg of the compound of the invention complexed with e.g. 10 to 400 MBq 111In or 89Zr. In larger mammals, for example humans, an indicated dosage range is of from 0.1 to 100 μg/kg of the compound of the invention complexed with e.g. 10 to 5000 MBq 90Y or 177Lu.

In a further aspect, the instant invention is related to a composition and a pharmaceutical composition in particular, comprising the compound of the invention.

The pharmaceutical composition of the present invention comprises at least one compound of the invention and, optionally, one or more carrier substances, excipients and/or adjuvants. The pharmaceutical composition may additionally comprise, for example, one or more of water, buffers such as, e.g., neutral buffered saline or phosphate buffered saline, ethanol, mineral oil, vegetable oil, dimethylsulfoxide, carbohydrates such as e.g., glucose, mannose, sucrose or dextrans, mannitol, proteins, adjuvants, polypeptides or amino acids such as glycine, antioxidants, chelating agents such as EDTA or glutathione and/or preservatives. Furthermore, one or more other active ingredients may, but need not, be included in the pharmaceutical composition of the invention.

The pharmaceutical composition of the invention may be formulated for any appropriate route of administration, including, for example, topical such as, e.g., transdermal or ocular, oral, buccal, nasal, vaginal, rectal or parenteral administration. The term parenteral as used herein includes subcutaneous, intradermal, intravascular such as, e.g., intravenous, intramuscular, intrathecal and intraperitoneal injection, as well as any similar injection or infusion technique. A preferred route of administration is intravenous administration.

In an embodiment of the invention the compound of the invention comprising a radionuclide is administered by any conventional route, in particular intravenously, e.g. in the form of injectable solutions or suspensions. The compound of the invention may also be administered advantageously by infusion, e.g., by an infusion of 30 to 60 min.

Depending on the site of the tumor, the compound of the invention may be administered as close as possible to the tumor site, e.g. by means of a catheter. Such administration may be carried out directly into the tumor tissue or into the surrounding tissue or into the afferent blood vessels. The compound of the invention may also be administered repeatedly in doses, preferably in divided doses.

According to a preferred embodiment of the invention, a pharmaceutical composition of the invention comprises a stabilizer, e.g. a free radical scavenger, which inhibits autoradiolysis of the compound of the invention. Suitable stabilizers include, e.g., serum albumin, ascorbic acid, retinol, gentisic acid or a derivative thereof, or an amino acid infusion solution such, e.g., used for parenteral protein feeding, preferably free from electrolyte and glucose, for example a commercially available amino acid infusion such as Proteinsteril® KE Nephro. Ascorbic acid and gentisic acid are preferred.

A pharmaceutical composition of the invention may comprise further additives, e.g. an agent to adjust the pH between 7.2 and 7.4, e.g. sodium or ammonium acetate or Na2HP04. Preferably, the stabilizer is added to the non-radioactive compound of the invention and introduction of the radionuclide, for instance the complexation with the radionuclide, is performed in the presence of the stabilizer, either at room temperature or, preferably, at a temperature of from 40 to 120° C. The complexation may conveniently be performed under air free conditions, e.g. under $N_2$ or Ar. Further stabilizer may be added to the composition after complexation.

Excretion of the compound of the invention, particularly if the Effector is a radionuclide, essentially takes place through the kidneys. Further protection of the kidneys from radioactivity accumulation may be achieved by administration of lysine or arginine or an amino acid solution having a high content of lysine and/or arginine, e.g. a commercially available amino acid solution such as Synthamin®-14 or -10, prior to the injection of or together with the compound of the invention, particularly if the Effector is a radionuclide. Protection of the kidneys may also be achieved by administration of plasma expanders such as e.g. gelofusine, either instead of or in addition to amino acid infusion. Protection of the kidneys may also be achieved by administration of diuretics providing a means of forced diuresis which elevates the rate of urination. Such diuretics include high ceiling loop diuretics, thiazides, carbonic anhydrase inhibitors, potassium-sparing diuretics, calcium-sparing diuretics, osmotic diuretics and low ceiling diuretics. A pharmaceutical composition of the invention may contain, apart from a compound of the invention, at least one of these further compounds intended for or suitable for kidney protection, preferably kidney protection of the subject to which the compound of the invention is administered.

It will be understood by a person skilled in the art that the compound of the invention is disclosed herein for use in various methods. It will be further understood by a person skilled in the art that the composition of the invention and the pharmaceutical composition of the invention can be equally used in said various methods. It will also be understood by a person skilled in the art that the composition of the invention and the pharmaceutical composition are disclosed herein for use in various methods. It will be equally understood by a person skilled in the art that the compound of the invention can be equally used in said various methods.

It will be acknowledged by a person skilled in the art that the composition of the invention and the pharmaceutical composition of the invention contain one or more further compounds in addition to the compound of the invention. To the extent that such one or more further compounds are disclosed herein as being part of the composition of the invention and/or of the pharmaceutical composition of the invention, it will be understood that such one or more further compounds can be administered separately from the compound of the invention to the subject which is exposed to or the subject of a method of the invention. Such administration of the one or more further compounds can be performed prior, concurrently with or after the administration of the compound of the invention. It will also be acknowledged by a person skilled in the art that in a method of the invention, apart from a compound of the invention, one or more further compound may be administered to a subject. Such administration of the one or more further compounds can be performed prior, concurrently with or after the administration of the compound of the invention. To the extent that such one or more further compounds are disclosed herein as being administered as part of a method of the invention, it will be understood that such one or more further compounds are part of a composition of the invention and/or of a pharmaceutical composition of the invention. It is within the present invention that the compound of the invention and the one or more further compounds may be contained in the same or a different formulation. It is also within the present invention that the compound of the invention and the one or more further compounds are not contained in the same formulation, but are contained in the same package containing a first formulation comprising a compound of the invention, and a second formulation comprising the one or more further compounds, whereby the type of formulation may be the same or may be different.

It is within the present invention that more than one type of a compound of the invention is contained in the composition of the invention and/or the pharmaceutical composition of the invention. It is also within the present invention that more than one type of a compound of the invention is used, preferably administered, in a method of the invention.

It will be acknowledged that a composition of the invention and a pharmaceutical composition of the invention may be manufactured in conventional manner.

Radiopharmaceuticals have decreasing content of radioactivity with time, as a consequence of the radioactive decay. The physical half-life of the radionuclide is often short for radiopharmaceutical diagnostics. In these cases, the final preparation has to be done shortly before administration to the patient. This is in particular the case for positron emitting radiopharmaceuticals for tomography (PET radiopharmaceuticals). It often leads to the use of semi-manufactured products such as radionuclide generators, radioactive precursors and kits.

Preferably, a kit of the invention comprises apart from one or more than one compounds of the invention typically at least one of the followings: instructions for use, final preparation and/or quality control, one or more optional excipient(s), one or more optional reagents for the labeling procedure, optionally one or more radionuclide(s) with or without shielded containers, and optionally one or more device(s), whereby the device(s) is/are selected from the group comprising a labeling device, a purification device, an analytical device, a handling device, a radioprotection device or an administration device.

Shielded containers known as "pigs" for general handling and transport of radiopharmaceutical containers come in various configurations for holding radiopharmaceutical containers such as bottles, vials, syringes, etc. One form often includes a removable cover that allows access to the held radiopharmaceutical container. When the pig cover is in place, the radiation exposure is acceptable.

A labeling device is selected from the group of open reactors, closed reactors, microfluidic systems, nanoreactors, cartridges, pressure vessels, vials, temperature controllable reactors, mixing or shaking reactors and combinations thereof.

A purification device is preferably selected from the group of ion exchange chromatography columns or devices, size-exclusion chromatography columns or devices, affinity chromatography columns or devices, gas or liquid chromatography columns or devices, solid phase extraction columns or devices, filtering devices, centrifugations vials columns or devices.

An analytical device is preferably selected from the group of tests or test devices to determine the identity, radiochemical purity, radionuclidic purity, content of radioactivity and specific radioactivity of the radiolabelled compound.

A handling device is preferably selected from the group consisting of devices for mixing, diluting, dispensing, labeling, injecting and administering radiopharmaceuticals to a subject.

A radioprotection device is used in order to protect doctors and other personnel from radiation when using therapeutic or diagnostic radionuclides. The radioprotection device is preferably selected from the group consisting of devices with protective barriers of radiation-absorbing material selected from the group consisting of aluminum, plastics, wood, lead, iron, lead glass, water, rubber, plastic, cloth, devices ensuring adequate distances from the radiation sources, devices reducing exposure time to the radionuclide, devices restricting inhalation, ingestion, or other modes of entry of radioactive material into the body and devices providing combinations of these measures.

An administration device is preferably selected from the group of syringes, shielded syringes, needles, pumps, and infusion devices. Syringe shields are commonly hollow cylindrical structures that accommodate the cylindrical body of the syringe and are constructed of lead or tungsten with a lead glass window that allows the handler to view the syringe plunger and liquid volume within the syringe.

BRIEF DESCRIPTION OF THE DRAWINGS

The present invention is now further illustrated by reference to the following figures and examples from which further features, embodiments and advantages, may be taken, wherein

FIG. 7 shows SPECT-images of $^{111}$In-3BP-3554 1 h, 3 h, 6 h, 24 h and 48 h post injection into mice with HEK-FAP tumors;

FIG. 8 shows the amino acid sequences of human fibroblast activating protein (FAP), human dipeptidyl peptidase 4 (DDP4) and human prolyl endopeptidase (PREP);

FIG. 11 B shows % ID/g uptake of $^{111}$In-3BP-3554 in four different sarcoma PDX models, 3 hours post injection;

FIG. 12 B shows body weight changes over time in mice with sarcoma Sarc4809 PDX tumors treated with vehicle, cold compound $^{nat}$Lu-3BP-3554, 30 MBq $^{177}$Lu-3BP-3554, or 60 MBq $^{177}$Lu-3BP-3554.

Figure 1:
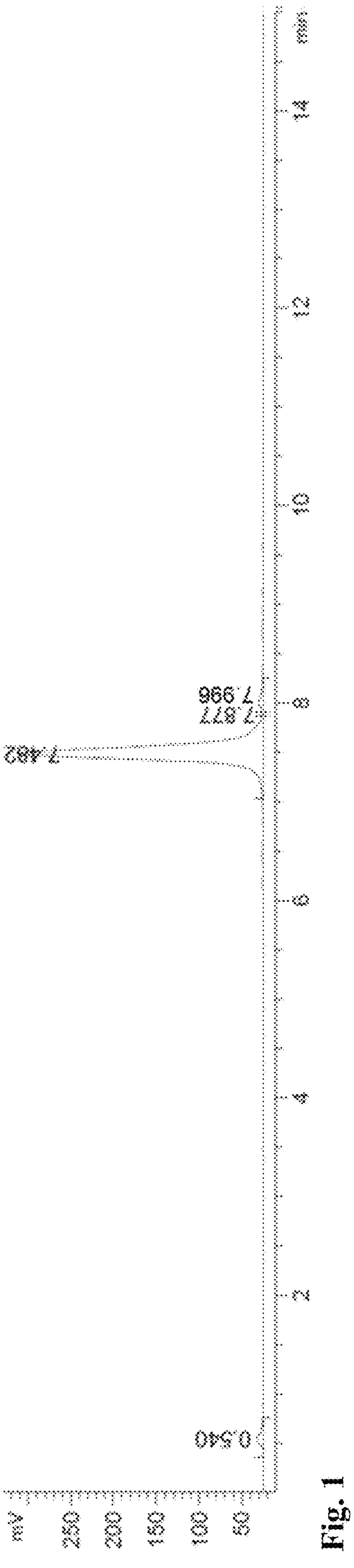
FIG. 1 shows a radiochromatogram of $^{177}$Lu-3BP-3407 in formulation buffer containing 100 mg/mL ascorbate and 5 mg/mL L-methionine analyzed immediately after synthesis.

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration and are not to be construed as limiting in any manner to make compounds of the disclosure by other methods.

EXAMPLES

Abbreviations used in the instant application and the following examples in particular are as follows:

4PL means four parameter logistic curve fitting
Å means ångström
ACN means acetonitrile
Ahx means 6-Aminohexanoic acid
AMC means 7-amino-4-methylcoumarin
amu means atomic mass unit
aq. means aqueous
$AUC_{inf}$ means area under the curve extrapolated to infinity
BSA means bovine serum albumin
$C_0$ means initial concentration of the compound
CAF means cancer associated fibroblasts
CL means clearance
CM means ChemMatrix™
CT means computed tomography
Cy5 means Cyanine-5
DAD means Diode Array Detector
DCM means dichloromethane
Dde means N-(1-(4,4-dimethyl-2,6-dioxocyclohexylidene)ethyl)
DEG means di ethylene glycol dimethacrylate
DIC means N,N'-Diisopropylcarbodiimide
DICOM means Digital Imaging and Communications in Medicine
DIPEA means diisopropylethylamine
DMF means N,N-dimethylformamide
DMSO means dimethyl sulfoxide
DOTA means 1,4,7,10-tetraazacyclododecane-1,4,7,10-tetraacetic acid
$DOTA(tBu)_3$-OH means Tri-tert-butyl-1,4,7,10-tetraaza-cyclo-dodecane-1,4,7,10-tetraacetate
DPP means dipeptidyl peptidase
EC means electron capture
$EC_{50}$ means half-maximal excitatory concentration
ECACC means European Collection of Authenticated Cell Cultures
EDC means 1-ethyl-3-(3-dimethylaminopropyl)carbodiimide
EMEM means Eagle's Minimum Essential Medium
eq or eq. means equivalent
ESI means electrospray ionization
$Et_2O$ means Diethylether
EtOAc means ethylacetate
FACS means fluorescence-activated cell sorting
FAP means fibroblast activation protein
Fb means background fluorescent intensity
FBS means fetal bovine serum
FGF21 means fibroblast growth factor 21
FITC means 5(6)-fluorescein isothiocyanate
Fmoc means 9-Fluorenylmethoxycarbonyl
FRET means Fluorescence Resonance Energy Transfer
Ft means fluorescent intensity
Gab means gamma-amino butyric acid
GABA means gamma-amino butyric acid
h means hour(s)
HATU means O-(7-azabenzotriazol-1-yl)-N,N,N',N'-tetramethyluronium hexafluorophosphate
HBST means SPR running buffer
HEK-FAP means human embryonic kidney 293 cells expressing human FAP
HEPES means 4-(2-hydroxyethyl)-1-piperazineethanesulfonic acid
HFIP means hexafluoro-2-isopanol
HOAc means acetic acid
HOAt means 1-Hydroxy-7-azabenzotriazole
HPLC means high performance liquid chromatography
HPLC/MS means high performance liquid chromatography/mass spectrometry
$IC_{50}$ means half-maximal inhibitory concentration
ID/g means injected dose per gram
IS means isomeric transition
iTLC-SG means instant thin layer chromatography-silica-gel
K2EDTA means ethylenediaminetetraacetic acid dipotassium
$K_D$ means dissociation constant
kDa means 1000 Dalton
$K_i$ means inhibitory constant
$k_{off}$ means dissociation rate
$k_{on}$ means association rate
LC/TOF-MS means Liquid chromatography/time-of-flight/mass spectrometry
LC-MS means high performance liquid chromatography coupled with mass spectrometry
LDH means lactate dehydrogenase
Leu means leucine
LiOH means lithium hydroxide
M means molar or mol per Liter
m/z means mass divided by charge
max. means maximum
MeOH means Methanol
MeV means mega electron volt
min means minute(s)
MMP means matrix metalloproteinase
MRM means multiple reaction monitoring
MTBE means Methyl-tert-butylether
Mtt means Methyltrityl
MTV means mean tumor volume
MW means molecular weight
n.d. means not determined
$Na_2SO_4$ means sodium sulfate
NaCl means sodium chloride
$NaHCO_3$ means sodium hydrogencarbonate
NCA means non-compartmental analysis
NHS means N-Hydroxysuccinimide
NMP means 1-methyl-2-pyrrolidone
NOS means not otherwise specified
Oic means L-octahydroindol-2-carbonsäure
p.a. means: for analytical purpose (quality grade)
p.i. means post injection
Pbf means 2,2,4,6,7-pentamethyl-2,3-dihydrobenzofuran-5-sulfonyl
PBS means phosphate buffered saline
PDX means patient-derived xenograft
PET means positron emission tomography
pIC50 means the negative log of the IC50 value when converted to molar
POP means prolyl oligopeptidase
ppm means parts per million
PREP means prolyl endopeptidase
prep. means preparative
PS means polystyrene
Q-TOF means quadrupole time of flight
Ref means reference
RFU means relative fluorescence unit
RLB means radioligand binding assay
RMCE means recombinase-mediated cassette exchange
RP means reversed phase
$R_t$ means retention time
RT means room temperature RU means resonance units
SAR means structure activity relationship
sat. means saturated
SCID means severe combined immunodeficiency
SCK means single cycle kinetics
sec or s means second
SF means spontaneous fission
SPECT means single photon emission computed tomography
SPPS means Solid Phase Peptide Synthesis
$t_{1/2}$ means terminal half-life
tBu means tert. butyl
TFA means trifluoroacetate or trifluoroacetic acid
TG means TentaGel
TGI means tumor growth inhibition
THE means Tetrahydrofuran
TIPS means triisopropylsilane
TLC means thin layer chromatography
TME means tumor microenvironment
$t_R$ means retention time
UHPLC means ultrahigh performance liquid chromatography
UV means ultraviolet
$V_{SS}$ means volume of distribution at steady state
$V_Z$ means volume of distribution in the terminal phase Example 1: Material and Methods The materials and methods as well as general methods are further illustrated by the following examples.

Solvents:

Solvents were used in the specified quality without further purification. Acetonitrile (Super Gradient, HPLC, VWR—for analytical purposes; PrepSolv, Merck—for preparative purposes); dichloromethane (synthesis, Roth); ethyl acetate (synthesis grade, Roth); N,N-dimethylformamide (peptide synthesis grade, Biosolve); 1-methyl-2-pyrolidone (peptide grade, IRIS BioTech) 1,4-dioxane (reinst, Roth); methanol (p. a., Merck).

Water: Milli-Q Plus, Millipore, demineralized.

Chemicals:

Chemicals were synthesized according to or in analogy to literature procedures or purchased from Sigma-Aldrich-Merck (Deisenhofen, Germany), Bachem (Bubendorf, Switzerland), VWR (Darmstadt, Germany), Novabiochem (Merck Group, Darmstadt, Germany), Acros Organics (distribution company Fisher Scientific GmbH, Schwerte, Germany), Iris Biotech (Marktredwitz, Germany), Amatek Chemical (Jiangsu, China), Roth (Karlsruhe, Deutschland), Molecular Devices (Chicago, USA), Biochrom (Berlin, Germany), Peptech (Cambridge, MA, USA), Synthetech (Albany, OR, USA), Pharmacore (High Point, NC, USA), PCAS Biomatrix Inc (Saint-Jean-sur-Richelieu, Quebec, Canada), Alfa Aesar (Karlsruhe, Germany), Tianjin Nankai Hecheng S&T Co., Ltd (Tianjin, China), CheMatech (Dijon, France) and Anaspec (San Jose, CA, USA) or other companies and used in the assigned quality without further purification.

Cells:

HT29 (ECACC Cat. No. 91072201) and WI-38 (ECACC Cat. No. 90020107) were purchased from ECACC and HEK293 cells expressing human FAP (Q12884) were produced by InSCREENeX GmbH (Braunschweig, Germany) using recombinase-mediated cassette exchange (RMCE). The RMCE procedure is described by Nehlsen et al. (Nehlsen, et al., *BMC Biotechnol,* 2009, 9:100).

HPLC/MS Analyses

HPLC/MS analyses were performed by injection of 5 μl of a solution of the sample, using a 2 step gradient for all chromatograms (5-65% B in 12 min, followed by 65-90% in 0.5 min, A: 0.1% TFA in water and B: 0.1% TFA in ACN). RP columns were from Agilent (Type Poroshell 120, 2.7 μm, EC-C18, 50×3.00 mm, flow 0.8 ml, HPLC at room temperature); Mass spectrometer: Agilent 6230 LC/TOF-MS, ESI ionization. MassHunter Qualitative Analysis B.07.00 SP2 was used as software. UV detection was done at 2=230 nm. Retention times (Rt) are indicated in the decimal system (e.g. 1.9 min=1 min 54 s) and are referring to detection in the UV spectrometer. For the evaluation of observed compound masses the 'Find Compounds by Formula'-feature was used. In particular, the individual 'neutral mass of a compound (in units of Daltons)'-values and the corresponding isotope distribution pattern were used to confirm compound identity. The accuracy of the mass spectrometer was approx. #5 ppm.

Preparative HPLC:

Preparative HPLC separations were done with reversed phase columns (Kinetex 5μ XB-C18 100 Å, 150×30 mm from Phenomenex or RLRP-S 8μ, 100 Å, 150×25 mm) as stationary phase. As mobile phase 0.1% TFA in water (A) and 0.1% TFA in ACN (B) were used which were mixed in linear binary gradients. The gradients are described as: "10 to 40% B in 30 min", which means a linear gradient from 10% B (and correspondingly 90% A) to 40% B (and correspondingly 60% A) was run within 30 min. Flow-rates were within the range of 30 to 50 ml/min. A typical gradient for the purification of the compounds of the invention started at 5-25% B and ended after 30 min at 35-50% B and the difference between the percentage B at end and start was at least 10%. A commonly used gradient was "15 to 40% B in 30 min".

General Procedures for Automated/Semi-Automated Solid-Phase Synthesis:

Automated solid-phase of peptides and polyamides was performed on a Tetras Peptide Synthesizer (Advanced ChemTech) in 50 μmol and 100 μmol scales. Manual steps were performed in plastic syringes equipped with frits (material PE, Roland Vetter Laborbedarf OHG, Ammerbuch, Germany). The amount of reagents in the protocols described corresponds to the 100 μmol scale, unless stated otherwise.

Solid-phase synthesis was performed on polystyrene (cross linked with 1,4-divinylbenzene (PS) or di (ethylene glycol) dimethacrylate (DEG)), ChemMatrix (CM) or TentaGel (TG) resin. Resin linkers were trityl, wang and rink amide.

Resin Loading:

In case of the trityl linker the attachment of the first building block (resin loading) was performed as follows. The resin (polystyrene (PS) trityl chloride, initial loading: 1.8 mmol/g) was swollen in DCM (5 ml) for 30 minutes and subsequently washed with DCM (3 ml, 1 minute). Then the resin was treated with a mixture of the corresponding building block (0.5 mmol, 5 eq.) and DIPEA (350 μl, 3.5 mmol, 35 eq.) in DCM (4 ml) for 1 hour. Afterwards the resin was washed with methanol (5 ml, 5 minutes) and DMF (3 ml, 2×1 minute).

In case of the Wang linker pre-loaded resins (polystyrene (PS) and TentaGel (TG)) were employed.

In case of the rink amide linker the attachment of the first residue the resin (CM, DEG) was performed with the same procedure as for the chain assembly as described below.

Alloc Allyl-Deprotection:

After swelling in DMF, the resin was washed with DMF and DCM. DCM was de-oxygenated by passing a stream of nitrogen through the stirred solvent. The oxygen-free solvent was used to wash the resin trice. Then 2 ml of a 2 M solution of barbituric acid in oxygen-free DCM and 1 ml of a 25 μM solution of Tetrakis(triphenylphosphine)palladium (0) in oxygen-free DCM were added to the resin. The resin was agitated for 1 hour and then washed with DCM, MeOH, DMF, 5% DIPEA in DMF, 5% dithiocarbamate in DMF, DMF and DCM (each washing step was repeated 3 times with 3 ml, 1 minute).

Fmoc-Deprotection:

After swelling in DMF, the resin was washed with DMF and then treated with piperidine/DMF (1:4, 3 ml, 2 and 20 minutes) and subsequently washed with DMF (3 ml, 5×1 minute).

Dde-Deprotection:

After swelling in DMF, the resin was washed with DMF and then treated with hydrazine-hydrate/DMF (2/98, 3 ml 2×10 minutes) and subsequently washed with DMF (3 ml, 5×1 minute).

Mtt-Deprotection:

After swelling in DCM, the resin was washed with DCM and then treated with HFIP/DCM (7/3, 4-6 ml, 4 hours) and subsequently washed with DCM (3 ml, 3×1 minute), DMF (3 ml, 3×1 ml) and DIPEA (0.9 M in DMF, 3 ml, 1 minute).

Solutions of Reagents:

Building Blocks (0.3 M in DMF or NMP), DIPEA (0.9 M in DMF), HATU (0.4 M in DMF), Acetic anhydride (0.75 M in DMF)

Coupling: Coupling of Building Blocks Amino Acids (Chain Assembly):

Unless otherwise stated, coupling of building blocks was performed as follows: After subsequent addition of solutions of the corresponding building block (1.7 ml, 5 eq.), DIPEA solution (1.15 ml, 10 eq.) and HATU solution (1.25 ml, 5 eq.) the resin was shaken for 45 min. If necessary, the resin was washed with DMF (3 ml, 1 minute) and the coupling step was repeated.

Terminal Acetylation:

After addition of DIPEA solution (1.75 ml, 16 eq.) and acetic anhydride solution (1.75 ml, 13 eq.) the resin was shaken for 10 minutes. Afterwards the resin was washed with DMF (3 ml, 6×1 minutes).

Cleavage Method A: Cleavage of Protected Fragments from Hyper-Acid Labile Resin:

After the completion of the assembly of the sequence the resin was finally washed with DCM (3 ml, 4×1 minute) and then dried in the vacuum. Then the resin was treated with HFIP/DCM (7/1, 4 ml, 4 hours) and the collected solution evaporated to dryness. The residue was purified with preparative HPLC or used without further purification.

Cleavage Method B: Cleavage of Unprotected Fragments (Complete Resin Cleavage):

After the completion of the assembly of the sequence the resin was finally washed with DCM (3 ml, 4×1 minute), dried in the vacuum overnight and treated with TFA, EDT, water and TIPS (94/2.5/2.5/1) for 2 h (unless otherwise stated). Afterwards the cleavage solution was poured into a chilled mixture of MTBE and cyclohexane (1/1, 10-fold excess compared to the volume of cleavage solution), centrifuged at 4° C. for 5 minutes and the precipitate collected and dried in the vacuum. The residue was lyophilized from water/acetonitrile prior to purification or further modification.

Cleavage Method C: Cleavage of Protective Groups of Peptides in Solution

The protected/partially protected compound was dissolved in TFA, water and TIPS (95/2.5/2.5) for 2 h (unless otherwise stated). Afterwards the cleavage solution was poured into a chilled mixture of MTBE and cyclohexane (1/1, 10-fold excess compared to the volume of cleavage solution), centrifuged at 4° C. for 5 minutes and the precipitate collected and dried in the vacuum. The residue was lyophilized from water/acetonitrile prior to purification or further modification.

More relevant Fmoc-solid-phase-peptide synthesis methods are described in detail in "Fmoc Solid Phase Peptide Synthesis" Editors W. Chan, P. White, Oxford University Press, USA, 2000. Compounds were named using MestreNova version 12 Mnova IUPAC Name plugin (Mestrelab Research, S.L.), or AutoNom version 2.2 (Beilstein Informationssysteme Copyright 1988-1998, Beilstein Institut für Literatur der Organischen Chemie licensed to Beilstein Chemiedaten and Software GmbH, where appropriate.

Preparation of Compounds:

Specific embodiments for the preparation of compounds of the invention are provided in the following examples. Unless otherwise specified, all starting materials and reagents are of standard commercial grade, and are used without further purification, or are readily prepared from such materials by routine methods. Those skilled in the art of organic synthesis will recognize in light of the instant disclosure that starting materials and reaction conditions may be varied including additional steps employed to produce compounds encompassed by the present invention.

One general synthesis route for compounds of the invention comprises

1. Solid Phase Peptide Synthesis (SPPS) of a linear peptide precursor with two thiol moieties.
2. the thiol-site specific cyclization of this linear peptide precursor with
   a. a bis(bromomethyl)benzene derivative or
   b. a tris(bromomethyl)benzene derivative.
3. In case of cyclizations with a tris(bromomethyl)benzene derivative the intermediate formed in the cyclization reaction was further reacted with a linker that enabled the attachment of a chelator.

Example 2: Synthesis of Hex-[Cys(tMeBn(DOTA-AET))-Pro-Pro-Thr-Gln-Phe-Cys]-OH (3BP-3554)

The synthesis of the title compound was either performed by initially synthesizing the linear peptide precursor on solid phase and by subsequent solution phase cyclizations (Example 2a, either in non-aqueous solution (Method A) or in aqueous solution (Method B)) or alternatively by performing all steps on solid phase including a solid phase cyclization (Example 2b).

Example 2a: Synthesis by Two Alternative Cyclization Methods in Solution

Fmoc-Cys(Trt)-OH was loaded onto the trityl resin as described in the 'General procedures for Automated/Semi-automated Solid-Phase Synthesis' in a 50 μmol scale. Onto this resin the sequence (Hex-Cys-Pro-Pro-Thr-Gln-Phe-Cys-OH) of the peptide was assembled according to the 'General procedures for Automated/Semi-automated Solid-Phase Synthesis'. After performing the steps of 'Cleavage method B' the crude peptide was lyophilized and cyclized by two alternative methods in solution.

Cyclization Method A:

The crude peptide (based on 50 μmol resin loading) was dissolved in 10 ml of a 1:1 mixture of ethanol and acetonitrile. To this mixture first 35 µl DIPEA and then 23.7 mg of 1,3,5-tris(bromomethyl)benzene (66.6 µmol, 1.3 eq compared to initial resin loading) were added. The solution was stirred for 1 hour and then 42.8 mg cysteamine (555 µmol, 11 eq compared to initial resin loading) were added. After 1 hour the solvents was removed in vacuo and 25 ml of a 1:1 mixture of acetonitrile and water (containing 50 µl TFA) were added. The solvents were removed by lyophilization. The remainder was subjected to HPLC purification (15 to 45% B in 30 min-Kinetex) to yield 17.8 mg (16.4 µmol) of the intermediate Hex-[Cys(tMeBn(H-AET))-Pro-Pro-Thr-Gln-Phe-Cys]-OH (32.8%).

Cyclization Method B:

The crude peptide (based on 50 µmol resin loading) was dissolved in 60 ml of a 1:1 mixture of ammonium bicarbonate solution (50 mM, pH=8.5) and acetonitrile. To this mixture a solution of 26.8 mg 1,3,5-tris(bromomethyl)benzene (75 µmol, 1.5 eq compared to initial resin loading) in 0.5 ml acetonitrile was added. The solution was stirred for 1 hour and then 38.6 mg cysteamine (500 µmol, 10 eq compared to initial resin loading) were added. After 2 hours 50 µl TFA were added and the solvent removed by lyophilization. The remainder was subjected to HPLC purification (15 to 45% B in 30 min-Kinetex) to yield 19.47 mg (18 µmol) of the intermediate Hex-[Cys(tMeBn(H-AET))-Pro-Pro-Thr-Gln-Phe-Cys]-OH (35.9%).

Both cyclization methods perform similarly and achieve comparable yields and similar purities.

To the solution of the intermediate Hex-[Cys(tMeBn(H-AET))-Pro-Pro-Thr-Gln-Phe-Cys]-OH (in this example obtained by cyclization method B) in 300 µl DMSO, 5 µl DIPEA were added to adjust the pH value to approximately 7.5-8. Then 20.5 mg of DOTA-NHS (27 µmol, 1.5 eq compared to the peptide intermediate) in 200 µl DMSO were added. During the course of the LC/TOF-MS monitored reaction 5 µl DIPEA were added 3 times to re-adjust the pH value to the starting value. After reaction completion the solution was subjected to HPLC purification (15 to 45% B in 30 min-Kinetex) to yield 20.44 mg of the pure title compound (27.8% overall yield). HPLC: $R_t$=5.9 min. LC/TOF-MS: exact mass 1469.640 (calculated 1469.639). $C_{67}H_{99}N_{13}O_{18}S_3$ (MW=1470.780).

Example 2b: Synthesis Including Solid Phase Cyclization Method

For the synthesis of the resin bound title compound a Fmoc-Cys(Trt)-WANG Tentagel resin was used as starting material. Onto the latter the sequence (Hex-Cys(Trt)-Pro-Pro-Thr (tBu)-Gln (Trt)-Phe-Cys-OH) of the peptide was assembled according to the 'General procedures for Automated/Semi-automated Solid-Phase Synthesis' in a 1 mmol scale. After completion of the sequence assembly the resin was washed with DCM (3×1 min). Then the trityl protecting groups were selectively removed from the resin by treatment with a solution of TFA, TIPS and DCM (5/5/90, 5×5 min). The resin was washed with DCM, DMF, 0.9 M DIPEA in DMF, DMF, DCM (3/3/2/3/3) and dried in the vaccum. The following cyclization was performed in 200 µmol portions. To this end, the resin was swollen in DMF and then treated with a solution of 1,3,5-Tris(bromomethyl)benzene (86 mg, 240 µmol, 1.2 eq), DIPEA (235 µL, 1 mmol, 5 eq) in 2 mL DMF at 50° C. for 90 minutes. The solution was removed, the resin washed with DMF and then a solution of cysteamine (154.3 mg, 2 mmol, 10 eq) added to the resin. The resin was agited for another 90 minutes at 50° C. After washing the resin with DMF and DCM (3/3) the peptide resin (Hex-[Cys(tMeBn(H-AET))-Pro-Pro-Thr (tBu)-Gln (Trt)-Phe-Cys]-O-WANG-Tentagel) was dried. By this procedure it may happen that the Trityl group at Glutamine is either partially or fully deprotected. In any case, this does not interfer with the optional derivatization of the free amino group of AET.

For the final derivatisation with DOTA the peptide resin (Hex-[Cys(tMeBn(H-AET))-Pro-Pro-Thr (tBu)-Gln (Trt)-Phe-Cys]-O-WANG-Tentagel) was used in a 50 µmol scale. According to the 'General procedures for Automated/Semi-automated Solid-Phase Synthesis' DOTA (tBu) 3-OH was coupled. After drying the resin was subjected to 'Cleavage method B'. The crude peptide was lyophilized and subsequently purified by preparative HPLC (15 to 45% B in 30 min-Kinetex) to yield 11.0 mg (7.5 µmol) of the pure title compound (15%). HPLC: $R_t$=5.9 min. LC/TOF-MS: exact mass 1469.640 (calculated 1469.639). $C_{67}H_{99}N_{13}O_{18}S_3$ (MW=1470.780).

Example 3: Synthesis of Hex-[Cys(tMeBn(DOTA-PP))-Pro-Pro-Thr-Gln-Phe-Cys]-Asp-NH2 (3BP-3407)

a) Synthesis of Intermediate Hex-[Cys(tMeBn(H—PP))-Pro-Pro-Thr-Gln-Phe-Cys]-Asp-$NH_2$ by Two Different Cyclization Methods The sequence (Hex-Cys-Pro-Pro-Thr-Gln-Phe-Cys-Asp-NH2) of the peptide was assembled according to the 'General procedures for Automated/Semi-automated Solid-Phase Synthesis' in a 50 µmol scale on a Rink amide resin. After performing the steps of 'Cleavage method B' the crude peptide was lyophilized and cyclized by two alternative methods.

Cyclization Method A:

The crude peptide (based on 50 µmol resin loading) was dissolved in 10 ml of a 1:1 mixture of ethanol and acetonitrile. To this mixture first 30 µl DIPEA and then 26.8 mg of 1,3,5-tris(bromomethyl)benzene (75 µmol, 1.5 eq compared to initial resin loading) were added. After stirring the solution for 45 minutes a solution of 43 mg piperazine (500 µmol, 10 eq compared to intial resin loading) in 200 µl of a 1:1 mixture of ethanol/acetonitrile was added. After 1 hour the solvents were removed in vacuo, 25 ml of a 1:1 mixture of acetonitrile and water (containing 50 µl TFA) was added and the solvents were removed by lyophilization. The remainder was subjected to HPLC purification (15 to 40% B in 30 min—Kinetex) to yield 15.3 mg (12.7 µmol) of the peptide intermediate Hex-Cys(tMeBn(H—PP))-Pro-Pro-Thr-Gln-Phe-Cys]-Asp-$NH_2$ (25.3%).

Cyclization Method B:

The crude peptide (based on 50 µmol resin loading) was dissolved in 60 ml of a 1:1 mixture of ammonium bicarbonate solution (50 mM, pH=8.5) and acetonitrile. To this mixture 26.8 mg of 1,3,5-tris(bromomethyl)benzene (75 µmol, 1.5 eq compared to initial resin loading) were added. The solution was stirred for 1 hour and 43 mg piperazine (500 µmol, 10 eq compared to intial resin loading) were added. After 6 hours 100 µl TFA were added and the solvent removed by lyophilization. The remainder was subjected to HPLC purification (15 to 40% B in 30 min-Kinetex) to yield 17.2 mg (14.2 µmol) of the peptide intermediate Hex-Cys (tMeBn(H—PP))-Pro-Pro-Thr-Gln-Phe-Cys]-Asp-NH2 (28.4%).

Both cyclization methods perform similar and achieve comparable yields and similar purities.

b) Final Steps of Synthesis of Hex-[Cys(tMeBn(DOTA-PP))-Pro-Pro-Thr-Gln-Phe-Cys]-Asp-$NH_2$ (3BP-3407): DOTA-Coupling and Purification To the solution of the intermediate (obtained by cyclization method B) in 200 μl DMSO 2.5 μl DIPEA were added to adjust the pH value to approximately 7.5-8. Then 16.3 mg of DOTA-NHS (21.4 μmol, 1.5 eq compared to the peptide intermediate) in 100 μl DMSO were added. During the course of the LC/TOF-MS monitored reaction 2.5 μl DIPEA was added 5 times to re-adjust the pH value to the starting value. After reaction completion the solution was subjected to HPLC purification (15 to 40% B in 30 min-Kinetex) to yield 19.1 mg (12.0 μmol) of the pure title compound (85%). HPLC: $R_t$=5.70 min. LC/TOF-MS: exact mass 1592.737 (calculated 1592.737). $C_{73}H_{108}N_{16}O_{20}S_2$ (MW=1593.866).

Example 4: Preparation of DOTA-Transition Metal Complexes of Compounds of the Invention A. General Procedure for the Preparation of a Peptide Comprising DOTA-Transition Metal-Complexes from Corresponding Peptides Comprising Uncomplexed DOTA A 0.1 mM solution of the peptide comprised by uncomplexed DOTA in

- 0.4 M sodium acetate, pH=5 (Buffer A) (in case of Cu(II), Zn(II), In(III), Lu(III) or Ga(III) complexes) or.
- 0.1 M ammonium acetate, pH=8 (Buffer B) (in case of Eu(III) complexes)

was diluted with a solution 0.1 mM solution of the corresponding metal salt in water whereby the molar ratio of peptide to metal was adjusted to 1:3. The solution was stirred.

- at 50° C. for 20 minutes (also referred to herein as Condition A) (in case of In(III), Lu(III), Ga(III), Zn(II) or Cu(II) complexes) or.
- at room temperature overnight (also referred to herein as Condition B) (in case of Eu(III) complexes).

The solution was then applied to

- HPLC purification (also referred to herein as Purification A) or
- solid phase extraction (also referred to herein as Purification B).

In case of solid phase extraction 250 mg Varian Bondesil-ENV was placed in a 15 ml polystyrene syringe, pre-washed with methanol (1×5 ml) and water (2×5 ml). Then the reaction solution was applied to the column. Thereafter elution was performed with water (2×5 ml—to remove excess salt), 5 ml of 50% ACN in water as first fraction and each of the next fractions were eluted with 5 ml of 50% ACN in water containing 0.1% TFA.

In either case (HPLC purification or solid phase extraction) fractions containing the pure product were pooled and freeze dried.

B. Indium-Complex of Hex-[Cys(tMeBn(DOTA-PP))-Pro-Pro-Thr-Gln-Phe-Cys]-Asp-$NH_2$ (3BP-3590)

The complex was prepared starting from 25 mg peptide 3BP-3407 (15.7 μmol) dissolved in Buffer A, diluted with a solution of $InCl_3$×4$H_2O$ which was treated with Condition A. In the purification step 'Purification A' was employed (15 to 40% B in 30 min-RLRP-S) to yield 18.24 mg of the pure title compound (68.1% yield). HPLC: $R_t$=5.6 min. LC/TOF-MS: exact mass 1702.622 (calculated 1702.617). $C_{73}H_{105}InN_{16}O_{20}S_2$ (MW=1705.663).

C. Gallium-Complex of Hex-[Cys(tMeBn(DOTA-PP))-Pro-Pro-Thr-Gln-Phe-Cys]-Asp-$NH_2$ (3BP-3592)

The complex was prepared starting from 25 mg peptide 3BP-3407 (15.7 μmol) dissolved in Buffer A, diluted with a solution of $Ga(NO_3)_3$×$H_2O$ which was treated with Condition A. In the purification step 'Purification A' was employed (15 to 40% B in 30 min—RLRP-S) to yield 16.78 mg of the pure title compound (69.3% yield). HPLC: $R_t$=5.7 min. LC/TOF-MS: exact mass 1658.664 (calculated 1658.639). $C_{73}H_{105}GaN_{16}O_{20}S_2$ (MW=1660.568).

D. Lutetium-Complex of Hex-[Cys(tMeBn(DOTA-PP))-Pro-Pro-Thr-Gln-Phe-Cys]-Asp-$NH_2$ (3BP-3591)

The complex was prepared starting from 25 mg peptide 3BP-3407 (15.7 μmol) dissolved in Buffer A, diluted with a solution of $LuCl_3$ which was treated with Condition A. In the purification step 'Purification A' was employed (15 to 40% B in 30 min-RLRP-S) to yield 16.66 mg of the pure title compound (60.1% yield). HPLC: $R_t$=5.6 min. LC/TOF-MS: exact mass 1764.654 (calculated 1764.654). $C_{73}H_{105}LuN_{16}O_{20}S_2$ (MW=1765.812).

E. Europium-Complex of Hex-[Cys(tMeBn(DOTA-PP))-Pro-Pro-Thr-Gln-Phe-Cys]-Asp-$NH_2$ (3BP-3661)

The complex was prepared starting from 9.5 mg peptide (6 μmol) 3BP-3407 dissolved in Buffer B, diluted with a solution of $EuCl_3$×6$H_2O$ which was treated with Condition B. In the purification step 'Purification B' was employed to yield 8.24 mg of the pure title compound (79.3% yield). HPLC: $R_t$=5.7 min. LC/TOF-MS: exact mass 1740.636 (calculated 1740.633). $C_{73}H_{105}EuN_{16}O_{20}S_2$ (MW=1742.809).

F. Indium-Complex of Hex-[Cys(tMeBn(DOTA-AET))-Pro-Pro-Thr-Gln-Phe-Cys]-OH (3BP-3623)

The complex was prepared starting from 6 mg peptide 3BP-3554 (4.1 μmol) dissolved in Buffer A, diluted with a solution of $InCl_3$×4$H_2O$ which was treated with Condition A. In the purification step 'Purification B' was employed to yield 5.26 mg of the pure title compound (81% yield). HPLC: $R_t$=5.8 min. LC/TOF-MS: exact mass 1579.524 (calculated 1579.520). $C_{67}H_{96}InN_{13}O_{18}S_3$ (MW=1582.574).

G. Lutetium-Complex of Hex-[Cys(tMeBn(DOTA-AET))-Pro-Pro-Thr-Gln-Phe-Cys]-OH (3BP-3624)

The complex was prepared starting from 6 mg peptide 3BP-3554 (4.1 μmol) dissolved in Buffer A, diluted with a solution of $LuCl_3$ which was treated with Condition A. In the purification step 'Purification B' was employed to yield 5.5 mg of the pure title compound (82% yield). HPLC: $R_t$=5.9 min. LC/TOF-MS: exact mass 1641.560 (calculated 1641.557). $C_{67}H_{96}LuN_{13}O_{18}S_3$ (MW=1642.723).

H. Gallium-Complex of Hex-[Cys(tMeBn(DOTA-AET))-Pro-Pro-Thr-Gln-Phe-Cys]-OH (3BP-3949)

The complex was prepared starting from 7.9 mg peptide 3BP-3554 (5.4 μmol) dissolved in Buffer A, diluted with a solution of $Ga(NO_3)_3 \times H_2O$ which was treated with Condition A. In the purification step 'Purification B' was employed to yield 4.2 mg of the pure title compound (51% yield). HPLC: $R_t$=6.6 min. LC/TOF-MS: exact mass 1535.543 (calculated 1535.541). $C_{67}H_{96}GaN_{13}O_{18}S_3$ (MW=1537.479).

I. Europium-Complex of Hex-[Cys(tMeBn(DOTA-AET))-Pro-Pro-Thr-Gln-Phe-Cys]-OH (3BP-3662)

The complex was prepared starting from 3.4 mg peptide 3BP-3554 (2.3 μmol) dissolved in Buffer B, diluted with a solution of $EuCl_3 \times 6H_2O$ which was treated with Condition B. In the purification step 'Purification B' was employed to yield 3.1 mg of the pure title compound (83% yield). HPLC: $R_t$=5.9 min. LC/TOF-MS: exact mass 1617.541 (calculated 1617.536). $C_{67}H_{96}EuN_{13}O_{18}S_3$ (MW=1619.721).

J. Copper(II)-Complex of Hex-[Cys(tMeBn(DOTA-AET))-Pro-Pro-Thr-Gln-Phe-Cys]-OH (3BP-4293)

The complex was prepared starting from 18 mg peptide 3BP-3554 (12.2 μmol) dissolved in Buffer A, diluted with a solution of Cu(OAc) 2 which was treated with Condition A. In the purification step 'Purification B' was employed to yield 16.5 mg of the pure title compound (88% yield). HPLC: $R_t$=6.5 min. LC/TOF-MS: exact mass 1530.553 (calculated 1530.553). $C_{67}H_{97}CuN_{13}O_{18}S_3$ (MW=1532.310).

K. Zinc-Complex of Hex-[Cys(tMeBn(DOTA-AET))-Pro-Pro-Thr-Gln-Phe-Cys]-OH (3BP-4343)

The complex was prepared starting from 20 mg peptide 3BP-3554 (13.6 μmol) dissolved in Buffer A, diluted with a solution of $ZnCl_2$ which was treated with Condition A. In the purification step 'Purification B' was employed to yield 16.1 mg of the pure title compound (77% yield). HPLC: $R_t$=6.4 min. LC/TOF-MS: exact mass 1531.553 (calculated 1531.553). $C_{67}H_{97}N_{13}O_{18}S_3Zn$ (MW=1534.160).

Example 5: Plasma Stability Assay

In order to determine the stability of selected compounds of the invention in human and mouse plasma, a plasma stability assay was carried out. Such plasma stability assay measures degradation of compounds of the present invention in blood plasma. This is an important characteristic of a compound as compounds, with the exception of pro-drugs, which rapidly degrade in plasma, generally show poor in vivo efficacy. The results show that those compounds are highly stable in human and mouse plasma. The stability is sufficient for the diagnostic, therapeutic and theragnostic use of these compounds according to the present invention.

The plasma stability samples were prepared by spiking 50 μl plasma aliquots (all K2EDTA) with 1 μl of a 0.5 mM compound stock solution in DMSO. After vortexing the samples were incubated in a Thermomixer at 37° C. for 0, 4 and 24 hours. After incubation the samples were stored on ice until further treatment. All samples were prepared in duplicates.

A suitable internal standard was added to each sample (1 μl of a 0.5 mM stock solution in DMSO). Protein precipitation was performed using two different methods depending on the compound conditions as indicated in Table 5.

A) 250 μl of acetonitrile containing 1% trifluoroacetic acid was added. After incubation at room temperature for 30 min the precipitate was separated by centrifugation and 150 μl of the supernatant was diluted with 150 μl of 1% aqueous formic acid.

B) 150 μl of a zinc sulphate precipitation agent containing 78% 0.1 M zinc sulphate and 22% acetonitrile was added. After incubation at room temperature for 30 min the precipitate was separated by centrifugation. To 100 μl of the supernatant 10 μl of 1% formic acid was added followed by further incubation at 60° C. for 10 min to complete the formation of the zinc chelate, if the compound contains a free DOTA moiety.

The determination of the analyte in the clean sample solutions was performed on an Agilent 1290 UHPLC system coupled to an Agilent 6530 Q-TOF mass spectrometer. The chromatographic separation was carried out on a Phenomenex BioZen XB-C18 HPLC column (50×2 mm, 1.7 μm particle size) with gradient elution using a mixture of 0.1% formic acid in water as eluent A and acetonitrile as eluent B (2% B to 41% in 7 min, 800 μl/min, 40° C.). Mass spectrometric detection was performed in positive ion ESI mode by scanning the mass range from m/z 50 to 3000 with a sampling rate of 2/sec.

From the mass spectrometric raw data, the ion currents for the double or triple charged monoisotopic signal was extracted for both, the compound and the internal standard.

Quantitation was performed by external matrix calibration with internal standard using the integrated analyte signals.

Additionally, recovery was determined by spiking a pure plasma sample that only contained the internal standard after treatment with a certain amount of the compound.

Carry-over was evaluated by analysis of a blank sample (20% acetonitrile) after the highest calibration sample.

The results of this assay performed on some of the compounds according to the present invention are given in the following Table 5. The result is stated as "% intact compound remaining after 24 h" and means that from the amount of material at the start of the experiment the stated percentage is detected as unchanged material at the end of the experiment by LC-MS quantification. Since all compounds are more than 50% intact after at least 24 h they are considered as stable enough for diagnostic and therapeutic applications.

TABLE 5

Results of the plasma stability assay

| Compound | Protein precipitation method | % intact compound remaining after 24 h incubation | | |
|---|---|---|---|---|
| | | Human plasma | Mouse plasma | Rat plasma |
| 3BP-3407 | A | 100% | 79% | 100% |
| 3BP-3554 | B | 100% | 85% | 100% |
| 3BP-3590 | B | 94% | 100% | 100% |
| 3BP-3623 | B | 100% | 100% | 100% |
| 3BP-3624 | B | 100% | 100% | 100% |

Example 6: FACS Binding Assay

In order to determine binding of compounds according to the present invention to FAP-expressing cells, a competitive FACS binding assay was established.

FAP-expressing human WI-38 fibroblasts (ECACC) were cultured in EMEM including 15% fetal bovine serum, 2 mM L-Glutamine and 1% Non-essential amino acids. Cells were detached with Accutase (Biolegend, #BLD-423201) and washed in FACS buffer (PBS including 1% FBS). Cells were diluted in FACS buffer to a final concentration of 100.000 cells per ml and 200 μl of the cell suspension are transferred to a u-shaped non-binding 96-well plate (Greiner). Cells were washed in ice-cold FACS buffer and incubated with 3 nM of Cy5-labeled compound (H-Met-[Cys(3MeBn)-Pro-Pro-Thr-Glu-Phe-Cys]-Asp-His-Phe-Arg-Asp-Ttds-Lys (Cy5SO3)-NH2) in the presence of increasing concentrations of peptides at 4° C. for 1 hour. Cells were washed twice with FACS buffer and resuspended in 200 μl FACS buffer. Cells were analyzed in an Attune N×T flow cytometer. Median fluorescence intensities (Cy5 channel) was calculated by Attune N×T software and plotted against peptide concentrations. Four parameter logistic (4PL) curve fitting and pIC50 calculations were performed using ActivityBase software. The results of this assay as well as the ones of the FAP protease activity assay as subject to Example 7 for each compound according to the present invention are presented in Table 6 (shown in Example 7). pIC50 category A stands for pIC50 values >8.0, category B for pIC50 values between 7.1 and 8.0, category C for pIC50 values between 6.1 and 7.0 and category D for pIC50 values ≤6.0.

Example 7: FAP Protease Activity Assay

In order to determine the inhibitory activity of the peptides of example 6, a FRET-based FAP protease activity assay was established.

Recombinant human FAP (R&D systems, #3715-SE) was diluted in assay buffer (50 mM Tris, 1 M NaCl, 1 mg/mL BSA, pH 7.5) to a concentration of 3.6 nM. 25 μl of the FAP solution was mixed with 25 μl of a 3-fold serial dilution of the test compounds and incubated for 5 min in a white 96-well ProxiPlate (Perkin Elmer). As specific FAP substrate the FRET-peptide HiLyteFluor™ 488-VS(D-)P SQG K(QXL® 520)-NH2 was used (Bainbridge, et al., Sci Rep, 2017, 7:12524). 25 μL of a 30 μM substrate solution, diluted in assay buffer, was added. All solutions were equilibrated at 37° C. prior to use. Substrate cleavage and increase in fluorescence (excitation at 485 nm and emission at 538 nm) was measured in a kinetic mode for 5 minutes at 37° C. in a SPECTRAmax M5 plate reader. RFU/sec was calculated by SoftMax Pro software and plotted against peptide concentration. Four parameter logistic (4PL) curve fitting and pIC50 calculations were performed using ActivityBase software. The results of this assay for each compound according to the present invention are given in Table 6 (Example 6). pIC50 category A stands for pIC50 values >8.0, category B for pIC50 values between 7.1 and 8.0, category C for pIC50 values between 6.1 and 7.0 and category D for pIC50 values ≤6.0.

As evident from Table 6, the compounds of the present invention show surprisingly superior results in both the FACS Binding assay and the FAP protease activity assay.

TABLE 6

Compound ID, sequence, exact calculated mass, exact mass found, retention time in minutes as determined by HPLC and pIC50 category of FACS binding and FAP activity assay

| ID | Sequence | Exact Mass (calc) | Exact Mass (found) | $R_t$ (HPLC) | pIC50 Category | pIC50 Category |
|---|---|---|---|---|---|---|
| 3BP-3407 | Hex-[Cys(tMeBn(DOTA-PP))-Pro-Pro-Thr-Gln-Phe-Cys]-Asp-NH2 | 1592.737 | 1592.737 | 5.70 | A | A |
| 3BP-3554 | Hex-[Cys(tMeBn(DOTA-AET))-Pro-Pro-Thr-Gln-Phe-Cys]-OH | 1469.639 | 1469.640 | 5.89 | A | A |
| 3BP-3590 | Hex-[Cys(tMeBn(InDOTA-PP))-Pro-Pro-Thr-Gln-Phe-Cys]-Asp-NH2 | 1702.617 | 1702.622 | 5.59 | A | A |
| 3BP-3591 | Hex-[Cys(tMeBn(LuDOTA-PP))-Pro-Pro-Thr-Gln-Phe-Cys]-Asp-NH2 | 1764.654 | 1764.654 | 5.65 | A | A |
| 3BP-3592 | Hex-[Cys(tMeBn(GaDOTA-PP))-Pro-Pro-Thr-Gln-Phe-Cys]-Asp-NH2 | 1658.639 | 1658.644 | 5.75 | A | A |
| 3BP-3623 | Hex-[Cys(tMeBn(InDOTA-AET))-Pro-Pro-Thr-Gln-Phe-Cys]-OH | 1579.520 | 1579.524 | 5.75 | A | A |
| 3BP-3624 | Hex-[Cys(tMeBn(LuDOTA-AET))-Pro-Pro-Thr-Gln-Phe-Cys]-OH | 1641.557 | 1641.560 | 5.81 | A | A |
| 3BP-3661 | Hex-[Cys(tMeBn(EuDOTA-PP))-Pro-Pro-Thr-Gln-Phe-Cys]-Asp-NH2 | 1740.633 | 1740.636 | 5.72 | A | A |
| 3BP-3662 | Hex-[Cys(tMeBn(EuDOTA-AET))-Pro-Pro-Thr-Gln-Phe-Cys]-OH | 1617.540 | 1617.541 | 5.83 | A | A |
| 3BP-3949 | Hex-[Cys(tMeBn(GaDOTA-AET))-Pro-Pro-Thr-Gln-Phe-Cys]-OH | 1535.541 | 1535.541 | 6.58 | A | A |

TABLE 6-continued

| Compound ID, sequence, exact calculated mass, exact mass found, retention time in minutes as determined by HPLC and pIC50 category of FACS binding and FAP activity assay | | | | | | |
|---|---|---|---|---|---|---|
| ID | Sequence | Exact Mass (calc) | Exact Mass (found) | $R_t$ (HPLC) | pIC50 Category | pIC50 Category |
| 3BP-4293 | Hex-[Cys-(tMeBn(CuDOTA-AET))-Pro-Pro-Thr-Gln-Phe-Cys]-OH | 1530.553 | 1530.562 | 6.5 | A | A |
| 3BP-4343 | Hex-[Cys-(tMeBn(ZnDOTA-AET))-Pro-Pro-Thr-Gln-Phe-Cys]-OH | 1531.553 | 1531.558 | 6.4 | A | A |

Example 8: Surface Plasmon Resonance Assay

Surface plasmon resonance studies were performed using a Biacore™ T200 SPR system. Briefly, polarized light is directed towards a gold-labeled sensor surface, and minimum intensity reflected light is detected. The angle of reflected light changes as molecules bind and dissociate. The gold-labeled sensor surface is loaded with FAP antibodies bearing FAP target proteins, whereby antibody binding does not occur at the substrate-binding site of FAP. Test compounds are contacted with the loaded surface, and a real-time interaction profile with the FAP ligand is recorded in a sensorgram. In real-time, the association and dissociation of a binding interaction is measured, enabling calculation of association and dissociation rate constants and the corresponding affinity constants. Importantly, a background response is generated due to the difference in the refractive indices of the running and sample buffers, as well as unspecific binding of the test compounds to the flow cell surface. This background is measured and subtracted by running the sample on a control flow cell coated with the same density of capture antibody in the absence of immobilized FAP. Furthermore, baseline drift correction of the binding data is performed, which is caused by slow dissociation of the captured FAP from the immobilized antibody. This drift is measured by injecting running buffer through a flow cell with the antibody and FAP immobilized to the sensor surface.

Biacore™ CM5 sensor chips were used. Human anti-FAP antibody (MAB3715, R&D systems) was diluted in 10 mM acetate buffer, pH 4.5, to a final concentration of 50 μg/mL. A 150 μL aliquot was transferred into plastic vials and placed into the sample rack of the Biacore™ T200 instrument. Amine Coupling Kit Reagent solutions were transferred into plastic vials and placed into the sample rack: 90 μL of 0.4 M 1-ethyl-3-(3-dimethylaminopropyl)carbodiimide (EDC), and 90 μL of 0.1 M N-hydroxysuccinimide (NHS). A 130 μL aliquot of 1 M ethanolamine-HCl, pH 8.5, was transferred into plastic vials and placed into the sample rack. The Biacore™ liquid system was set-up as follows: Separate bottles containing distilled water (1 L), Running Buffer (500 mL), as well as an empty bottle for waste were placed onto the buffer tray. A preinstalled program for immobilization was used, with an immobilization level of 7000 RU. Immobilization was performed at 25° C. The immobilization procedure of anti-FAP antibodies was performed, as described in the Table 7.

TABLE 7

| Immobilization protocol for anti-FAP antibodies used on the CM5 sensor chip. | | | |
|---|---|---|---|
| Step | Injected solution | Contact time | Flow rate |
| Surface conditioning | 50 mM NaOH | 300 s | 10 μL/min |
| Surface activation | EDC/NHS | 420 s | 10 μL/min |
| Washing | Ethanolamine | 90 s | 10 μL/min |
| Ligand binding | Human/mouse antibodies diluted in acetate buffer | 420 s | 10 μL/min |
| Washing | Running Buffer | 40 s | 10 μL/min |
| Deactivation of reactive, non-ligand bound surface | 1M ethanolamine | 420 s | 10 μL/min |
| Washing | Running Buffer | 30 s | 10 μL/min |

Human recombinant FAP was diluted in Running Buffer to a final concentration of 20 μg/mL. A 100 μL aliquot of human FAP-Working-Solution was transferred into plastic vials and placed into a sample rack. A 0.5 mM Compound-Stock-Solution was prepared by dissolving each compound in DMSO. For each test compound, Compound-Stock-Solutions were diluted in Running Buffer (HBST) at 500 nM and further diluted with HBST-DMSO Buffer (0.1% DMSO). SPR binding analyses for binary complexes were performed in SCK mode at 25° C. Table 8 describes the protocol for capturing and assessment of the binding kinetics. Following three SCK measurements, a baseline drift was assessed by injecting running buffer through a flow cell, with the antibody and FAP immobilized to the sensor surface.

TABLE 8

| Protocol for assessing the binding kinetics. | | | |
|---|---|---|---|
| Step | Injected solution | Contact time | Flow rate |
| Startup cycle as a triple run: | HBST-DMSO Buffer | 60 s | 30 μL/min |
| Washing & surface regeneration | 10 mM glycine, pH 2 | 5 s | |
| Binding target protein FAP (capturing) | 20 μg/mL rhFAP or 4 μg/mL rmFAP | 600 s | 5 μL/min |
| Washing (removal of unbound FAP) | HBST-DMSO-Buffer | 2700 s | 30 μL/min |
| 1. Binding kinetics of test compound | Dilution no. 5 (0.19 nM) | 120 s | 30 μL/min |
| 2. Binding kinetics of test compound | Dilution no. 4 (0.78 nM) | 120 s | 30 μL/min |
| 3. Binding kinetics of test compound | Dilution no. 3 (3.125 nM) | 120 s | 30 μL/min |

TABLE 8-continued

Protocol for assessing the binding kinetics.

| Step | Injected solution | Contact time | Flow rate |
|---|---|---|---|
| 4. Binding kinetics of test compound | Dilution no. 2 (12.5 nM) | 120 s | 30 μL/min |
| 5. Binding kinetics of test compound | Dilution no. 1 (50 nM) | 120 s | 30 μL/min |
| Dissociation cycle | HBST-DMSO Buffer | 1800 s | 30 μL/min |
| Regeneration | 10 mM glycine, pH 2 | 7 s | 30 μL/min |

For each test compound, SPR raw data in the form of resonance units (RU) were plotted as sensorgrams using the Biacore™ T200 control software. The signal from the blank sensorgram was subtracted from that of the test compound sensorgram (blank corrected). The blank corrected sensorgram was corrected for baseline drift by subtracting the sensorgram of a SCK run without the test compound (running buffer only). The association rate ($k_{on}$), dissociation rate ($k_{off}$), dissociation constant ($K_D$), and $t_{1/2}$ were calculated from Blank-normalized SPR data using the 1:1 Langmuir binding model from the Biacore™ T200 evaluation software. Raw data and fit results were imported as text files in IDBS. The $pK_D$ value (negative decadic logarithm of dissociation constant) was calculated in the IDBS excel template.

The results of this assay for a selection of compounds according to the present invention are presented in Table 9. Category A stands for $pK_D$ values >8.0, category B for $pK_D$ values between 7.1 and 8.0, category C for $pK_D$ values between 6.1 and 7.0.

TABLE 9

Compound ID, sequence and pkD category of Biacore assay

| ID | Sequence | $pK_D$ Category |
|---|---|---|
| 3BP-3407 | Hex--[C(tMeBn(DOTA--PP))-PPTQFC]D-NH2 | A |
| 3BP-3554 | Hex--[C(tMeBn(DOTA--AET))-PPTQFC]-OH | A |
| 3BP-3590 | Hex--C([tMeBn(InDOTA--PP))-PPTQFC]D-NH2 | A |
| 3BP-3591 | Hex--C([tMeBn(LuDOTA--PP))-PPTQFC]D-NH2 | A |
| 3BP-3592 | Hex--C([tMeBn(GaDOTA--PP))-PPTQFC]D-NH2 | A |
| 3BP-3623 | Hex--C([tMeBn(InDOTA--AET))-PPTQFC]-OH | A |
| 3BP-3624 | Hex--C([tMeBn(LuDOTA--AET))-PPTQFC]-OH | A |
| 3BP-3949 | Hex--[C(tMeBn(GaDOTA--AET))-PPTQFC]-OH | A |

Example 9: PREP and DPP4 Protease Activity Assay

In order to test selectivity of FAP binding peptides toward both PREP and DPP4, protease activity assays were performed analogues to the FAP activity assay described above with following exceptions.

PREP activity was measured with recombinant human PREP (R&D systems, #4308-SE). As substrate 50 μM Z-GP-AMC (Bachem, #4002518) was used. The DPP4 activity assay was performed in DPP assay buffer (25 mM Tris, pH 8.0). Recombinant human DPP4 was purchased from R&D systems (#9168-SE). 20 μM of GP-AMC (Santa Cruz Biotechnology, #115035-46-6) was used as substrate.

Fluorescence of AMC (excitation at 380 nm and emission at 460 nm) after cleavage was measured in a kinetic mode for 5 minutes at 37° C. in a SPECTRAmax M5 plate reader. RFU/sec was calculated by SoftMax Pro software and plotted against peptide concentration. Four parameter logistic (4PL) curve fitting and pIC50 calculations were performed using ActivityBase software. The results of this assay for some of the compounds according to the present invention are given in the following Table 10.

TABLE 10

Results (pIC50 values) of PREP and DPP4 activity assays

| ID | pIC50 (PREP) | pIC50 (DPP4) |
|---|---|---|
| 3BP-3407 | <6 | <6 |
| 3BP-3554 | <6 | <6 |

Example 10: Specificity Screen

The specificity screening was carried out in order to early identify significant off-target interactions of compounds of the present invention. The specificity was tested using a standard battery of assays ("SafetyScreen44™ Panel") comprising 44 selected targets and compounds binding thereto (referred to as "reference compounds", Ref. Compounds), recommended by Bowes et al. (Bowes, et al., *Nat Rev Drug Discov*, 2012, 11:909). The reference compounds served as positive controls for the respective assays, therefore inhibition is expected to be detected with these reference compounds. The compounds of the invention, however, were not expected to show inhibition in these assays. These binding and enzyme inhibition assays were performed by Eurofins Cerep SA (Celle l'Evescault, France).

3BP-3407 and 3BP-3554 were tested at 10 μM. Compound binding was calculated as % inhibition of the binding of a radioactively labeled ligand specific for each target ("% Inhibition of Specific Binding" (3BP-3407) or (3BP-3554), respectively. Compound enzyme inhibition effect was calculated as % inhibition of control enzyme activity.

Results showing an inhibition or stimulation higher than 50% are considered to represent significant effects of the test compounds. Such effects were not observed at any of the receptors studied which are listed in the following Table 11. The results of this assay are summarized in the following Table 11.

TABLE 11

Results of the specificity screening (SafetyScreen44 ™ Panel) for 10 μM 3BP-3407 and 10 μM 3BP-3554

| Assay | % Inhibition of Specific Binding (3BP-3407) | (3BP-3554) | Ref Compound | Ki Ref [M] | Cerep Catalog Ref | Literature Reference |
|---|---|---|---|---|---|---|
| A2A (h) (agonist radioligand) | −4 | −16 | NECA | 2.90E−08 | 4 | (Luthin, et al., *Mol Pharmacol*, 1995, 47: 307) |
| alpha 1A (h) (antagonist radioligand) | 2 | −12 | WB 4101 | 2.40E−10 | 2338 | (Schwinn, et al., *J Biol Chem*, 1990, 265: 8183) |
| alpha 2A (h) (antagonist radioligand) | −9 | 2 | yohimbine | 2.40E−09 | 13 | (Langin, et al., *Eur J Pharmacol*, 1989, 167: 95) |
| beta 1 (h) (agonist radioligand) | 4 | −13 | atenolol | 3.40E−07 | 18 | (Levin, et al., *J Biol Chem*, 2002, 277: 30429) |
| beta 2 (h) (antagonist radioligand) | 4 | 8 | ICI 118551 | 1.60E−10 | 20 | (Joseph, et al., *Naunyn Schmiedebergs Arch Pharmacol*, 2004, 369: 525) |
| BZD (central) (agonist radioligand) | −9 | 5 | diazepam | 8.10E−09 | 28 | (Speth, et al., *Life Sci*, 1979, 24: 351) |
| CB1 (h) (agonist radioligand) | 5 | −7 | CP 55940 | 2.10E−09 | 36 | (Rinaldi-Carmona, et al., *J Pharmacol Exp Ther*, 1996, 278: 871) |
| CB2 (h) (agonist radioligand) | 2 | −5 | WIN 55212-2 | 1.60E−09 | 37 | (Munro, et al., *Nature*, 1993, 365: 61) |
| CCK1 (CCKA) (h) (agonist radioligand) | 24 | 16 | CCK-8s | 4.90E−11 | 39 | (Bignon, et al., *J Pharmacol Exp Ther*, 1999, 289: 742) |
| D1 (h) (antagonist radioligand) | 0 | 7 | SCH 23390 | 2.00E−10 | 44 | (Zhou, et al., *Nature*, 1990, 347: 76) |
| D2S (h) (agonist radioligand) | 15 | −7 | 7-OH-DPAT | 1.30E−09 | 1322 | (Grandy, et al., *Proc Natl Acad Sci USA*, 1989, 86: 9762) |
| ETA (h) (agonist radioligand) | −18 | 6 | endothelin-1 | 1.50E−11 | 54 | (Buchan, et al., *Br J Pharmacol*, 1994, 112: 1251) |
| NMDA (antagonist radioligand) | 9 | 1 | CGS 19755 | 1.40E−07 | 66 | (Sills, et al., *Eur J Pharmacol*, 1991, 192: 19) |
| H1 (h) (antagonist radioligand) | 11 | 4 | pyrilamine | 1.10E−09 | 870 | (Smit, et al., *Br J Pharmacol*, 1996, 117: 1071) |
| H2 (h) (antagonist radioligand) | −5 | −16 | cimetidine | 4.30E−07 | 1208 | (Leurs, et al., *Br J Pharmacol*, 1994, 112: 847) |
| MAO-A (antagonist radioligand) | −5 | −25 | clorgyline | 7.30E−10 | 443 | (Cesura, et al., *Mol Pharmacol*, 1990, 37: 358) |
| M1 (h) (antagonist radioligand) | 6 | 8 | pirenzepine | 2.90E−08 | 91 | (Dorje, et al., *J Pharmacol Exp Ther*, 1991, 256: 727) |
| M2 (h) (antagonist radioligand) | −4 | 7 | Methoctramine | 4.80E−08 | 93 | (Dorje, et al., *J Pharmacol Exp Ther*, 1991, 256: 727) |
| M3 (h) (antagonist radioligand) | 10 | 1 | 4-DAMP | 8.00E−10 | 95 | (Peralta, et al., *Embo J*, 1987, 6: 3923) |

TABLE 11-continued

Results of the specificity screening (SafetyScreen44 ™ Panel) for 10 µM 3BP-3407 and 10 µM 3BP-3554

| Assay | % Inhibition of Specific Binding (3BP-3407) | (3BP-3554) | Ref Compound | Ki Ref [M] | Cerep Catalog Ref | Literature Reference |
|---|---|---|---|---|---|---|
| N neuronal alpha 4beta 2 (h) (agonist radioligand) | −8 | −2 | nicotine | 1.20E−09 | 3029 | (Gopalakrishnan, et al., *J Pharmacol Exp Ther*, 1996, 276: 289) |
| delta (DOP) (h) (agonist radioligand) | 0 | 1 | DPDPE | 1.20E−09 | 114 | (Simonin, et al., *Mol Pharmacol*, 1994, 46: 1015) |
| kappa (h) (KOP) (agonist radioligand) | 7 | 10 | U50488 | 4.50E−10 | 4461 | (Simonin, et al., *Proc Natl Acad Sci USA*, 1995, 92: 7006) |
| mu (MOP) (h) (agonist radioligand) | 2 | −10 | DAMGO | 3.70E−10 | 118 | (Wang, et al., *FEBS Lett*, 1994, 338: 217) |
| 5-HT1A (h) (agonist radioligand) | −3 | −5 | 8-OH-DPAT | 2.20E−10 | 131 | (Mulheron, et al., J *Biol Chem*, 1994, 269: 12954) |
| 5-HT1B(h) (antagonist radioligand) | −11 | 8 | Serotonine | 6.60E−08 | 4376 | (Maier, et al., *J Pharmacol Exp Ther*, 2009, 330: 342) |
| 5-HT2A (h) (agonist radioligand) | −2 | 4 | (±)DOI | 2.10E−10 | 471 | (Bryant, et al., *Life Sci*, 1996, 59: 1259) |
| 5-HT2B (h) (agonist radioligand) | 2 | 3 | (±)DOI | 4.20E−09 | 1333 | (Choi, et al., *FEBS Lett*, 1994, 352: 393) |
| 5-HT3 (h) (antagonist radioligand) | 2 | 4 | MDL 72222 | 6.50E−09 | 411 | (Hope, et al., *Br J Pharmacol*, 1996, 118: 1237) |
| GR (h) (agonist radioligand) | −2 | 0 | Dexamethasone | 1.90E−09 | 469 | (Clark, et al., *Invest Ophthalmol Vis Sci*, 1996, 37: 805) |
| AR (h) (agonist radioligand) | 3 | −5 | Testosterone | 2.00E−09 | 933 | (Zava, et al., *Endocrinology*, 1979, 104: 1007) |
| V1a (h) (agonist radioligand) | 16 | 1 | [d(CH2)51, Tyr(Me)2]-AVP | 1.10E−09 | 159 | (Tahara, et al., *Br J Pharmacol*, 1998, 125: 1463) |
| Ca2+ channel (L, dihydropyridine site) (antagonist radioligand) | 42 | 54 | nitrendipine | 1.40E−10 | 161 | (Gould, et al., *Proc Natl Acad Sci USA*, 1982, 79: 3656) |
| Potassium Channel hERG (human)- [3H] Dofetilide | 2 | 6 | Terfenadine | 4.40E−08 | 4094 | (Huang, et al., *Assay Drug Dev Technol*, 2010, 8: 727) |
| KV channel (antagonist radioligand) | −5 | 4 | alpha - dendrotoxin | 9.70E−11 | 166 | (Sorensen, et al., *Mol Pharmacol*, 1989, 36: 689) |
| Na+ channel (site 2) (antagonist radioligand) | −7 | 14 | veratridine | 1.20E−05 | 169 | (Brown, *J Neurosci*, 1986, 6: 2064) |
| norepinephrine transporter (h) (antagonist radioligand) | −8 | −5 | protriptyline | 2.30E−09 | 355 | (Pacholczyk, et al., *Nature*, 1991, 350: 350) |
| dopamine transporter (h) (antagonist radioligand) | 12 | 7 | BTCP | 6.80E−09 | 52 | (Pristupa, et al., *Mol Pharmacol*, 1994, 45: 125) |
| 5-HT transporter (h) (antagonist radioligand) | −3 | −8 | imipramine | 1.40E−09 | 439 | (Tatsumi, et al., *Eur J Pharmacol*, 1999, 368: 277) |
| COX1(h) | 10 | 8 | Diclofenac | 1.30E−08 | 4173 | (Vanachayangkul, et al., *Enzyme Res*, 2012, 2012: 416062) |

TABLE 11-continued

Results of the specificity screening (SafetyScreen44™ Panel) for 10 μM 3BP-3407 and 10 μM 3BP-3554

| Assay | % Inhibition of Specific Binding (3BP-3407) | (3BP-3554) | Ref Compound | Ki Ref [M] | Cerep Catalog Ref | Literature Reference |
|---|---|---|---|---|---|---|
| COX2(h) | −14 | −22 | NS398 | 5.40E−08 | 4186 | (Vanachayangkul, et al., *Enzyme Res*, 2012, 2012: 416062) |
| PDE3A (h) | −3 | −37 | milrinone | 1.00E−06 | 4072 | (Maurice, et al., *Nat Rev Drug Discov*, 2014, 13: 290) |
| PDE4D2 (h) | −5 | −4 | Ro 20-1724 | 2.30E−07 | 4077 | (Maurice, et al., *Nat Rev Drug Discov*, 2014, 13: 290) |
| Lck kinase (h) | 10 | −4 | Staurosporine | 2.30E−08 | 2906 | (Park, et al., *Anal Biochem*, 1999, 269: 94) |
| Acetylcholinesterase (h) | −6 | 1 | Galanthamine | 7.00E−07 | 363 | (Ellman, et al., *Biochem Pharmacol*, 1961, 7: 88) |

Additionally, a specificity screen for proteases was performed by BPS Biosciences to further determine the specificity of the compounds of the invention (Turk, *Nat Rev Drug Discov,* 2006, 5:785; Overall, et al., *Nat Rev Cancer,* 2006, 6:227; Anderson, et al., *Handb Exp Pharmacol,* 2009, 189:85).

3BP-3407 and 3BP-3554 were tested at 1 μM and 10 μM in duplicates. In the absence of the compound, the fluorescent intensity (Ft) in each data set was defined as 100% activity. In the absence of the enzyme, the background fluorescent intensity (Fb) in each data set was defined as 0% activity. The percent activity in the presence of each compound was calculated according to the following equation: % activity=(F−Fb)/(Ft−Fb), where F=the fluorescent intensity in the presence of the compound. Percentage inhibition was calculated according to the following formula: % inhibition=100%−% activity. Results showing an inhibition higher than 50% are considered to represent significant effects of the tested compound. The results of this assay are given in the following Table 12.

TABLE 12

Results of the specificity protease screening for 1 μM and 10 μM 3BP-3407 and 1 μM and 10 μM 3BP-3554

| Enzyme | Percentage inhibition (%) 3BP-3407 1 μM | 3BP-3407 10 μM | 3BP-3554 1 μM | 3BP-3554 10 μM | Reference |
|---|---|---|---|---|---|
| Activated Protein C | 5 | 8 | −11 | 1 | 74 (20 μM Dabigatran) |
| Beta secretase | −8 | −5 | 1 | 7 | 84 (150 nM Verubecestat) |
| Caspase-3 | 1 | −2 | −2 | −1 | 89 (100 nM Caspase 3/7 Inhibitor I) |
| Caspase-6 | 1 | −1 | 6 | −3 | 94 (1 μM Caspase 8 Inhibitor I) |
| Caspase-7 | −3 | −3 | −1 | −7 | 92 (1 μM Caspase 3/7 Inhibitor I) |
| Caspase-8 | 0 | 0 | 0 | −3 | 87 (100 nM Caspase 8 Inhibitor I) |
| Caspase-9 | 5 | 8 | −1 | −2 | N/A |
| Cathepsin B | 26 | 36 | 1 | 2 | 97 (100 nM E-64) |
| Cathepsin F | −3 | −24 | −23 | −25 | 74 (1 μM Cystatin C) |
| Cathepsin L | 3 | 6 | 0 | −6 | 97 (1 μM E-64) |
| Cathepsin S | 3 | 18 | −10 | −23 | 91 (100 nM E-64) |
| Cathepsin V | 1 | −18 | −1 | −1 | 83 (100 nM E-64) |

TABLE 12-continued

Results of the specificity protease screening for 1 μM and 10 μM 3BP-3407 and 1 μM and 10 μM 3BP-3554

| | Percentage inhibition (%) | | | | |
|---|---|---|---|---|---|
| | 3BP-3407 | | 3BP-3554 | | |
| Enzyme | 1 μM | 10 μM | 1 μM | 10 μM | Reference |
| A20 | 2 | −4 | 1 | 0 | 99 (1 μM Ub-Aldehyde) |
| Ataxin3 | 1 | 10 | 2 | −1 | 77 (10 μM Ub-Aldehyde) |
| Deubiquitinase OTUD6B | 2 | 15 | 0 | 0 | 97 (1 μM Ub-Aldehyde) |
| Ubiquitin carboxy-terminal hydrolase L1 | −2 | 4 | −4 | 4 | 92 (100 nM Ub-Aldehyde) |
| Ubiquitin carboxy-terminal hydrolase L3 | −1 | 14 | 0 | 0 | 95 (10 nM Ub-Aldehyde) |
| Ubiquitin carboxyl-terminal hydrolase 2 | 3 | 7 | 0 | −1 | 91 (1 μM Ub-Aldehyde) |
| Ubiquitin carboxyl-terminal hydrolase 5 | 3 | 46 | −4 | −2 | 84 (1 μM Ub-Aldehyde) |
| Ubiquitin carboxyl-terminal hydrolase 7 | 5 | 5 | 1 | 1 | 95 (1 μM Ub-Aldehyde) |
| Ubiquitin carboxyl-terminal hydrolase 8 | −3 | 6 | 2 | 1 | 73 (1 μM Ub-Aldehyde) |
| Ubiquitin carboxyl-terminal hydrolase 10 | −2 | 5 | 1 | −1 | 82 (1 μM Ub-Aldehyde) |
| Ubiquitin carboxyl-terminal hydrolase 14 | −1 | 5 | 1 | 2 | 96 (100 nM Ub-Aldehyde) |
| DPP3 | ND | ND | 2 | −1 | (100 nM Spinorphin) |
| DPP7 | 2 | −3 | −1 | −7 | 83 (200 μM KR62436) |
| DPP8 | 1 | 5 | 1 | 11 | 96 (200 μM KR62436) |
| DPP9 | −1 | 0 | −1 | −5 | 99 (200 μM KR62436) |
| FAP | 98 | 99 | 97 | 99 | 100 (100 nM SP-13786) |
| serine protease NS3 (a.a. 3-181) from Hepatitis C virus genotype 1a (mutant D168V) | 1 | 68 | −39 | −372 | 94 (100 nM Denoprevir) |
| serine protease NS3 (a.a. 3-181) from Hepatitis C virus genotype 1b | 1 | 5 | −5 | −9 | 100 (100 nM Denoprevir) |
| serine protease NS3 (a.a. 3-181) from Hepatitis C virus genotype 1b (mutant D168V) | 1 | −6 | −2 | −17 | 99 (100 nM Denoprevir) |
| serine protease NS3 (a.a. 3-181) from Hepatitis C virus genotype 1b (mutant R155K) | −2 | 5 | −1 | 0 | 90 (100 nM Denoprevir) |

TABLE 12-continued

Results of the specificity protease screening for 1 μM and 10 μM 3BP-3407 and 1 μM and 10 μM 3BP-3554

| | Percentage inhibition (%) | | | | |
|---|---|---|---|---|---|
| | 3BP-3407 | | 3BP-3554 | | |
| Enzyme | 1 μM | 10 μM | 1 μM | 10 μM | Reference |
| serine protease NS3 (a.a. 3-181) from Hepatitis C virus genotype 1b (mutant R155Q) | 0 | 2 | 0 | −5 | 99 (1 μM Denoprevir) |
| serine protease NS3 (a.a. 3-181) from Hepatitis C virus genotype 2a | 0 | −2 | −13 | −40 | 98 (100 nM Denoprevir) |
| Matrix metalloprotease 1 | −1 | 2 | 1 | −7 | 87 (1 μM NNGH) |
| Matrix metalloprotease 2 | 3 | 3 | −1 | −2 | 95 (100 nM NNGH) |
| Matrix metalloprotease 9 (mutant Q279R) | 3 | 2 | 3 | 2 | 92 (100 nM NNGH) |
| Renin | −1 | 3 | 0 | −1 | 99 (30 nM Aliskiren) |

Example 11: $^{111}$In- and $^{177}$Lu-Labeling of Selected Compounds

In order to serve as a diagnostically, therapeutically, or theragnostically active agent, a compound needs to be labeled with a radioactive isotope. The labeling procedure needs to be appropriate to ensure a high radiochemical yield and purity of the radiolabeled compound of the invention. This example shows that the compounds of the present invention are appropriate for radiolabeling and can be labeled in high radiochemical yield and purity.

30-100 MBq of $^{111}InCl_3$ (in 0.02 M HCl) were mixed with 1 nmol of compound (200 μM stock solution in 0.1 M HEPES pH 7) per 30 MBq and buffer (1 M sodium acetate buffer pH 5 or 1 M sodium acetate/ascorbic acid buffer pH 5 containing 25 mg/ml methionine) at a final buffer concentration of 0.1-0.2 M. The mixture was heated to 80° C. for 20-30 min. After cooling down, DTPA and TWEEN-20 were added at a final concentration of 0.2 mM and 0.1%, respectively.

0.2-2.0 GBq $^{177}LuCl_3$ (in 0.04 M HCl) were mixed with 1 nmol of compound (200 μM stock solution in 0.1 M HEPES pH 7) per 45 MBq and buffer (1 M sodium acetate/ascorbic acid buffer pH 5 containing 25 mg/ml methionine) at a final buffer concentration of ~0.4 M. The mixture was heated to 90° C. for 20 min.

The labeling efficiency was analyzed by thin layer chromatography (TLC) and HPLC. For TLC analysis, 1-2 μl of diluted labeling solution was applied to a strip of iTLC-SG chromatography paper (Agilent, 7.6×2.3 mm) and developed in citrate-dextrose solution (Sigma). The iTLC strip was then cut into 3 pieces and associated radioactivity was measured with a gamma-counter. The radioactivity measured at the solvent front represents free radionuclide and colloids, whereas the radioactivity at the origin represents radiolabeled compound. For HPLC, 5 μl of diluted labeling solution was analyzed with a Poroshell SB-C18 2.7 μm (Agilent). Eluent A: MeCN, eluent B: $H_2O$, 0.1% TFA, gradient from 5% B to 70% B within 15 min, flow rate 0.5 ml/min; detector: NaI (Raytest), DAD 230 nm. The peak eluting with the dead volume represents free radionuclide, the peak eluting with the peptide-specific retention time as determined with an unlabeled sample represents radiolabeled compound.

Figure 2:
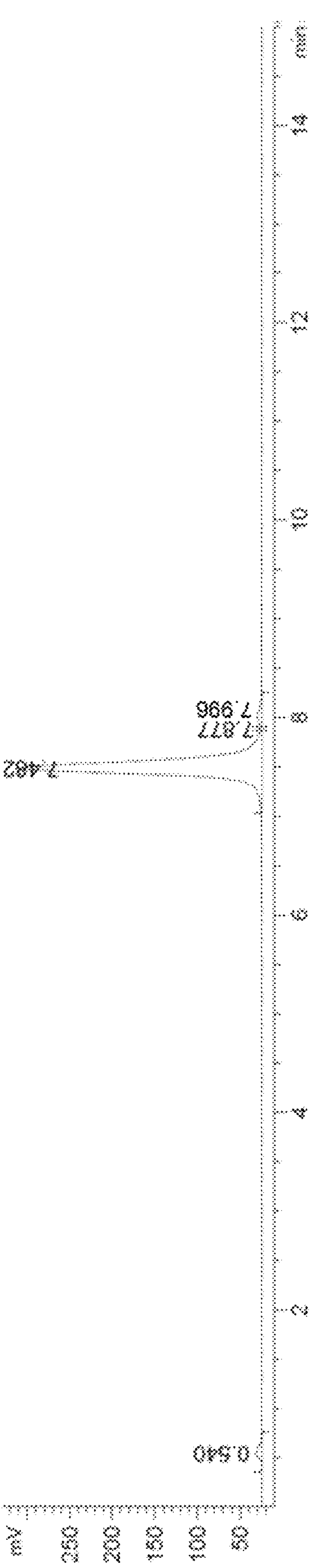
FIG. 2 shows a radiochromatogram of $^{177}$Lu-3BP-3407 in formulation buffer containing 100 mg/mL ascorbate and 5 mg/mL L-methionine analyzed six days after synthesis.
Figure 3:
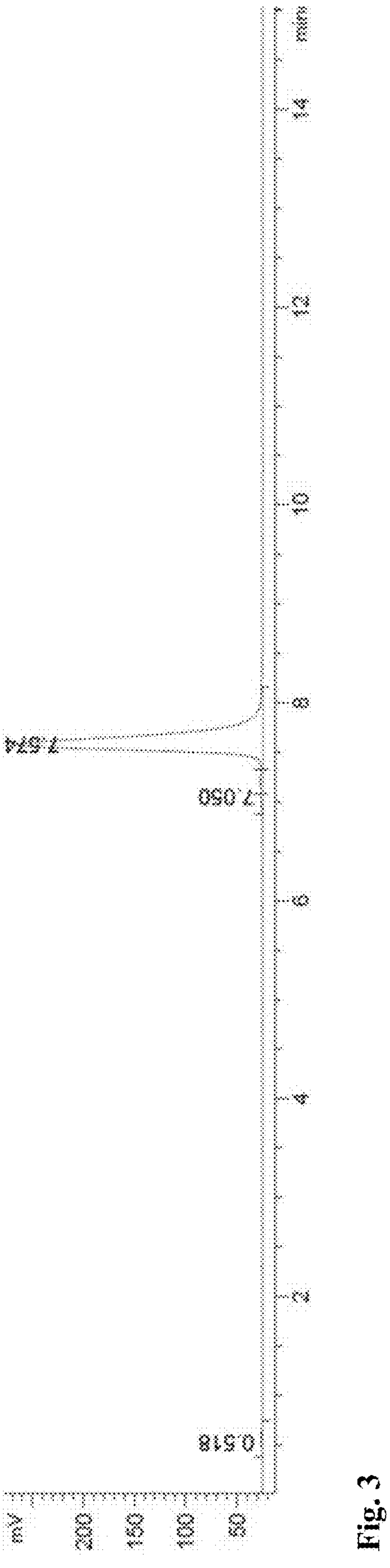
FIG. 3 shows a radiochromatogram of $^{177}$Lu-3BP-3554 in formulation buffer containing 100 mg/mL ascorbate and 5 mg/mL L-methionine analyzed immediately after synthesis.
Figure 4:
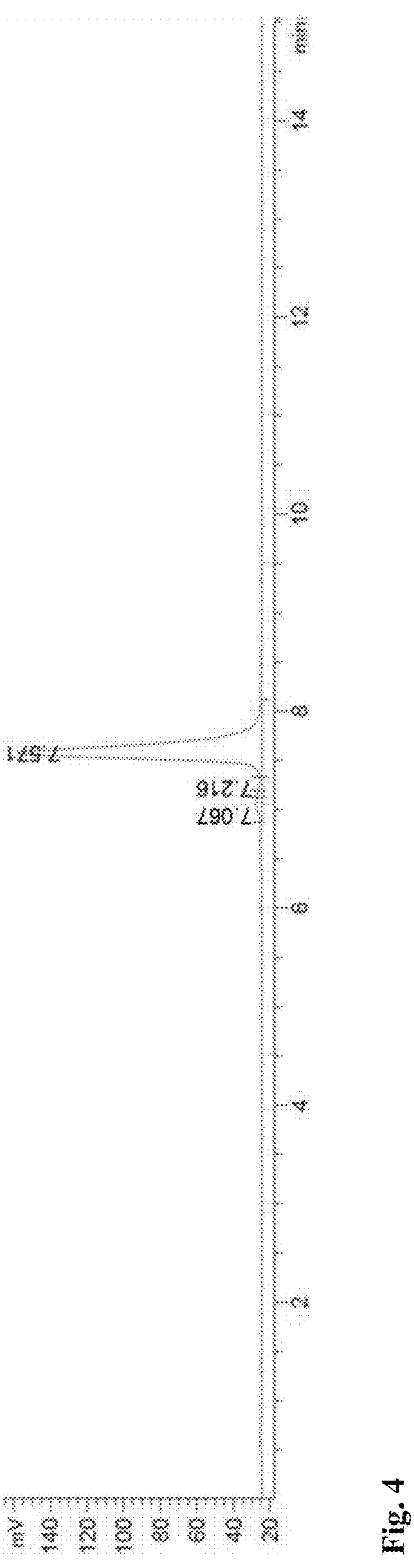
FIG. 4 shows a radiochromatogram of $^{177}$Lu-3BP-3554 in formulation buffer containing 100 mg/mL ascorbate and 5 mg/mL L-methionine analyzed six days after synthesis.

Radionuclidic incorporation yield was ≥95% and radiochemical purity ≥90% at end of synthesis. Exemplary radiochemical purities for $^{111}$In-labeled compounds are shown in Table 13. $^{177}$Lu-labeled compounds in formulations suitable for human use maintained a radiochemical purity of >90% up to 6 days post synthesis (Table 14). The radiochromatograms for selected compounds are shown in FIGS. 1 to 4, whereby FIG. 1 shows a radiochromatogramm of $^{177}$Lu-3BP-3407 in formulation buffer containing 100 mg/mL ascorbate and 5 mg/mL L-methionine analyzed immediately upon end of synthesis, FIG. 2 shows a radiochromatogramm of $^{177}$Lu-3BP-3407 in formulation buffer containing 100 mg/mL ascorbate and 5 mg/mL L-methionine analyzed six days post end of synthesis, FIG. 3 shows a radiochromatogramm of $^{177}$Lu-3BP-3554 in formulation buffer containing 100 mg/mL ascorbate and 5 mg/mL L-methionine analyzed immediately upon end of synthesis, and FIG. 4 shows a radiochromatogram of $^{177}$Lu-3BP-3554 in formulation buffer containing 100 mg/mL ascorbate and 5 mg/mL L-methionine analyzed six days post end of synthesis.

TABLE 13

| Radiochemical purity by HPLC of $^{111}$In-labeled compounds. | | | |
|---|---|---|---|
| | HPLC retention time [min] | HPLC Area % at end of synthesis | HPLC Area % appr. 4 h post end of synthesis |
| $^{111}$In-3BP-3407 | 7.3 | 97.6 | 95.4 |
| $^{111}$In-3BP-3554 | 7.5 | 95.6 | 96.2 |

TABLE 14

| Radiochemical purity by HPLC of $^{177}$Lu-labeled compounds in a formulation buffer containing 100 mg/mL ascorbate and 5 mg/mL L-methionine analyzed on day 0 and day 6 post end of synthesis. | | | |
|---|---|---|---|
| | HPLC retention time [min] | HPLC Area % Day 0 | HPLC Area % Day 6 |
| $^{177}$Lu-3BP-3407 | 7.5 | 95.7 | 94.0 |
| $^{177}$Lu-3BP-3554 | 7.6 | 97.2 | 95.6 |

Example 12: Imaging and Biodistribution Studies

Radioactively labeled compounds can be detected by imaging methods such as SPECT and PET. Furthermore, the data acquired by such techniques can be confirmed by direct measurement of radioactivity contained in the individual organs prepared from an animal injected with a radioactively labeled compound of the invention. Thus, the biodistribution (the measurement of radioactivity in individual organs) of a radioactively labeled compound can be determined and analyzed. This example shows that the compounds of the present invention show a biodistribution appropriate for diagnostic imaging and therapeutic treatment of tumors.

All animal experiments were conducted in compliance with the German animal protection laws. Male SCID beige (6- to 8-week-old, Charles River, Sulzfeld, Germany) were inoculated with $5\times10^6$ HEK-FAP (embryonic human kidney 293 cells genetically engineered to express high levels of FAP) cells in one shoulder. When tumors reached a size of >150 mm$^3$ mice received ~30 MBq $^{111}$In-labelled compounds of the invention (diluted to 100 μL with PBS) administered intravenously via the tail vein. Images were obtained on a NanoSPECT/CT system (Mediso Medical Imaging Systems, Budapest, Hungary) using exemplarily the following acquisition and reconstruction parameters (Table 15).

TABLE 15

| Acquisition and reconstruction parameters of NanoSPECT/CT imaging | |
|---|---|
| Acquistion parameters SPECT | |
| System | NanoSPECT/CT ™ |
| Scan range | whole body, 3-bed holder (mouse hotel) |
| Time per projection | 60 s |
| Aperture model, pinhole diameter | Aperture #2, 1.5 mm |
| Reconstruction parameters | |
| Method | HiSPECT (Scivis), iterative reconstruction |
| Smoothing | 35% |
| Iterations | 9 |
| Voxel size | 0.15 mm × 0.15 mm × 0.15 mm |

TABLE 15-continued

| Acquisition and reconstruction parameters of NanoSPECT/CT imaging | |
|---|---|
| Acquisition parameters CT | |
| System | NanoSPECT/CT ™ |
| Scan range | whole body, 3-bed holder (mouse hotel) |
| Scan duration | 7 minutes |
| Tube voltage | 45 kVp |
| Exposure time | 500 ms |
| Number of projections | 240 |

Imaging data were saved as DICOM files and analysed using VivoQuant™ software (Invicro, Boston, USA). Results are expressed as a percentage of injected dose per gram of tissue (% ID/g). For biodistribution studies, animals were sacrificed by cervical dislocation at 24 h or 48 h post injection and then dissected. Different organs and tissues were collected and weighed, and the radioactivity was determined by γ-counting. Two animals were used per time point. Results are expressed as a percentage of injected dose per gram of tissue (% ID/g).

Figure 5:
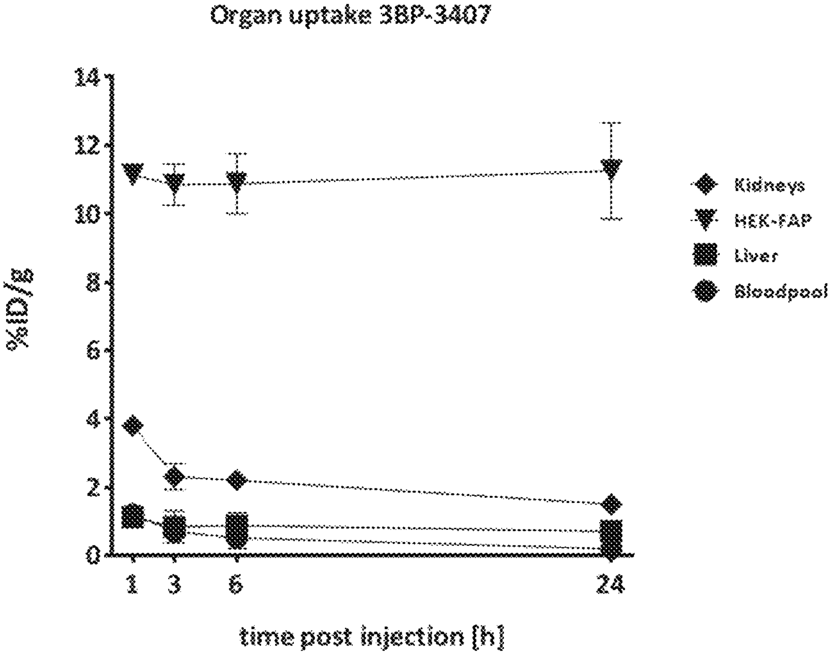
FIG. 5 shows the percentage of injected dose per gram of tissue (% ID/g) uptake in the kidney, liver, bloodpool, and HEK-FAP tumor as determined by SPECT-imaging of $^{111}$In-3BP-3407 1 h, 3 h, 6 h and 24 h post injection into the mouse model.
Figure 6:
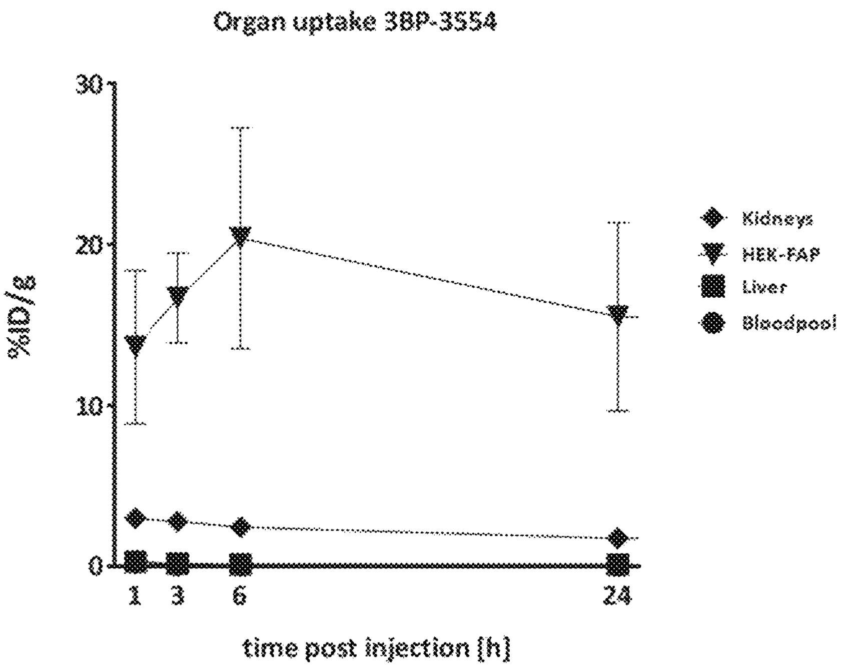
FIG. 6 shows the % ID/g uptake in kidney, liver, bloodpool, and HEK-FAP tumor as determined by SPECT-imaging of $^{111}$In-3BP-3554 1 h, 3 h, 6 h and 24 h post injection into the mouse model.

The results of the imaging and biodistribution studies for selected compounds are shown in FIGS. 5-7.

Example 13: Efficacy Study-HEK-FAP

Radioactively labeled compounds can be used for therapeutic and diagnostic application in various diseases, especially cancer. This example shows that the compounds of the present invention have anti-tumor activity suitable for the therapeutic treatment of tumors.

All animal experiments were conducted in compliance with the German animal protection laws. Female swiss nude mice (7- to 8-week-old, Charles River Laboratories, France) were inoculated with 5×106 HEK-FAP cells in one shoulder, and treatments were administered when the tumors reached a mean tumor volume of 160±44 mm3. Mice were divided into 4 different groups of 10 animals/group: Group 1-vehicle control, Group 2-cold compound natLu-3BP-3554, Group 3-30 MBq 177Lu-3BP-3554 (low dose), and Group 4-60 MBq 177Lu-FAP-3554 (high dose). Treatments were administered on Day 0 by intravenous injection into the tail vein at 4 mL/kg (100 μL/mouse). Tumor volume and body weights were measured on Day 0 (i.e. the first day of radiotracer administration) and then thrice weekly until completion of the study.

The tracer distribution in mice injected with 177Lu-labeled 3BP-3554 was determined by SPECT imaging in three mice per dosing group. Subsequently, following SPECT, a CT scan was done for anatomical information. Imaging was performed 3 h, 24 h, 48 h and 120 h post injection with a NanoSPECT/CT system (Mediso Medical Imaging Systems, Budapest, Hungary) using exemplarily the following acquisition and reconstruction parameters (Table 16).

TABLE 16

| Acquisition and reconstruction parameters of NanoSPECT/CT imaging | |
|---|---|
| Acquistion parameters SPECT | |
| System | NanoSPECT/CT ™ |
| Scan range | whole body, 3-bed holder (mouse hotel) |
| Time per projection | 60 s or 120 s |
| Aperture model, pinhole diameter | Aperture #2, 1.5 mm |
| Reconstruction parameters | |
| Method | HiSPECT (Scivis), iterative reconstruction |
| Smoothing | 35% |
| Iterations | 9 |
| Voxel size | 0.15 mm × 0.15 mm × 0.15 mm |
| Acquisition parameters CT | |
| System | NanoSPECT/CT ™ |
| Scan range | whole body, 3-bed holder (mouse hotel) |
| Scan duration | 7 minutes |
| Tube voltage | 45 kVp |
| Exposure time | 500 ms |
| Number of projections | 240 |

Imaging data were saved as DICOM files and analysed using VivoQuant™ software (Invicro, Boston, USA). Results are expressed as a percentage of injected dose per gram of tissue (% ID/g).

Figure 9A:
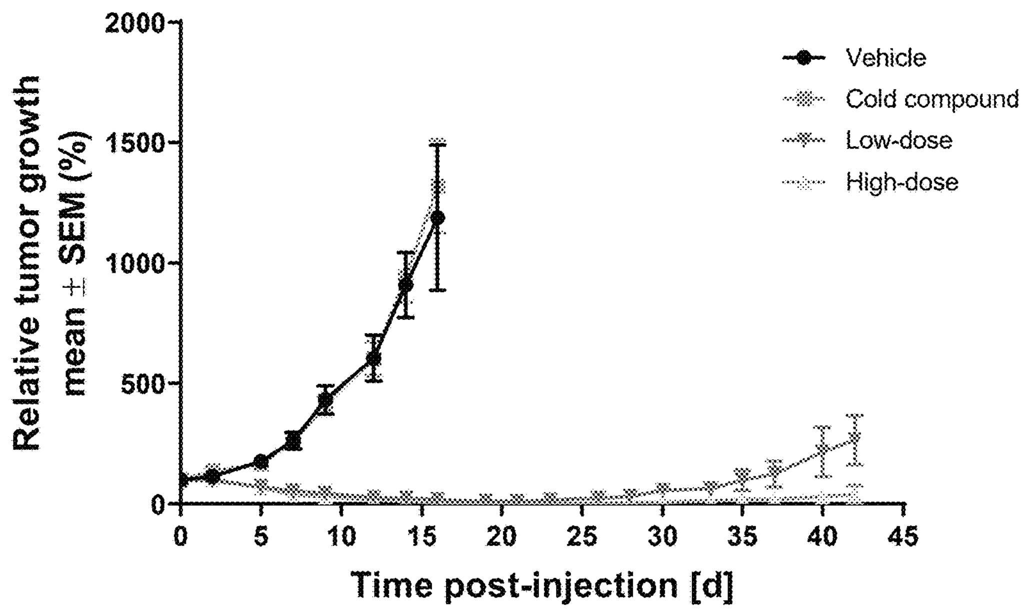
FIG. 9A shows tumor growth over time in mice with HEK-FAP tumors treated with vehicle, cold compound $^{nat}$Lu-3BP-3554, 30 MBq (low dose) $^{177}$Lu-3BP-3554, and 60 MBq (high dose) $^{177}$Lu-3BP-3554.
Figure 9B:
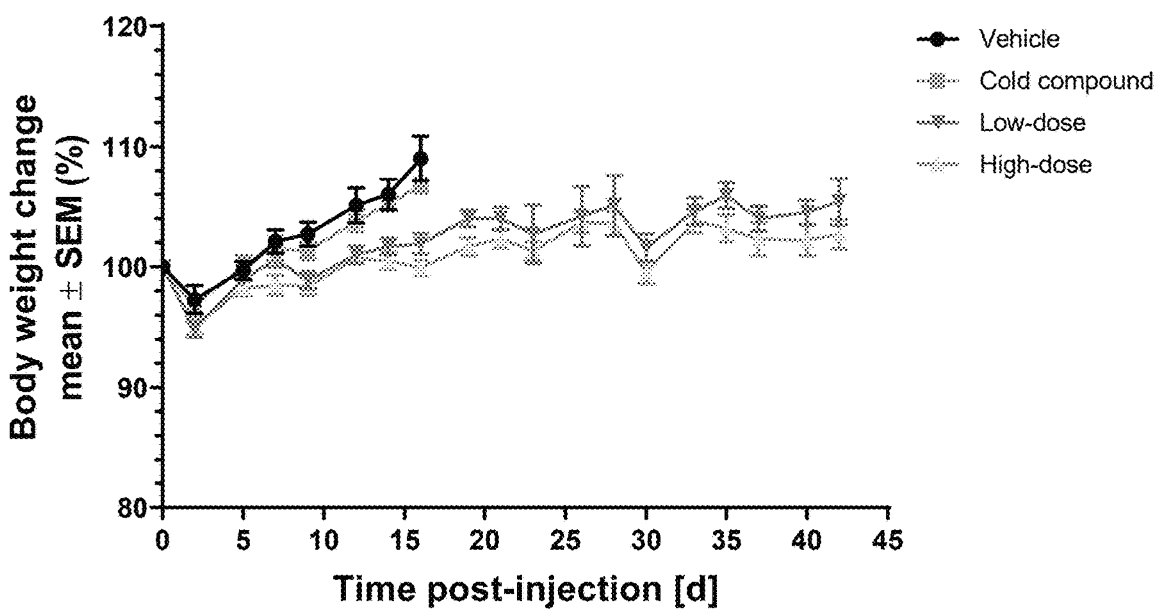
FIG. 9 B shows percent body weight changes over time in mice with HEK-FAP tumors treated with vehicle, cold compound $^{nat}$Lu-3BP-3554, 30 MBq $^{177}$Lu-3BP-3554, and 60 MBq $^{177}$Lu-3BP-3554.

Tumors in vehicle and cold compound $^{nat}$Lu-3BP-3554-treated mice reached a mean tumor volume (MTV) of 1338±670 mm$^3$ and 1392±420 mm$^3$ on day 14, respectively (FIG. 9 A). Statistically significant (P<0.01) anti-tumor activity was observed in mice of both treatment groups. Tumor growth inhibition (TGI) at day 14 was 111% and 113% in mice treated with a single dose of 30 or 60 MBq $^{177}$Lu-3BP-3554, respectively, relative to the vehicle-treated group. The MTV in all mice treated with $^{177}$Lu-3BP-3554 was reduced to ≤70 mm$^3$ on day 14. Tumors were monitored for regrowth and on day 42 (which represents the end of the study), three of ten and nine of ten mice treated with 30 or 60 MBq $^{177}$Lu-3BP-3554, respectively, were tumor-free (<10 mm$^3$), suggesting a potential dose-response in this model. No treatment-related body weight loss was observed throughout the study (FIG. 9 B). After a 3-5% decrease in body weight observed in all groups on Day 2, the body weight of the animals increased over time.

Figure 10A:
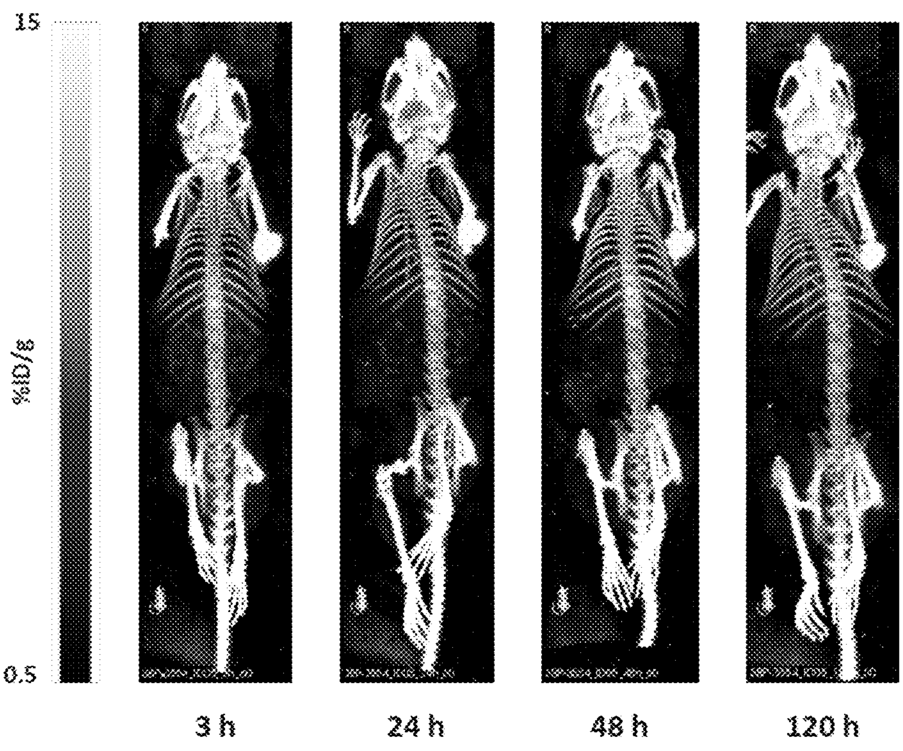
FIG. 10A shows representative SPECT/CT images over time of the biodistribution of 60 MBq $^{177}$Lu-3BP-3554 in mice with HEK-FAP tumors.
Figure 10B:
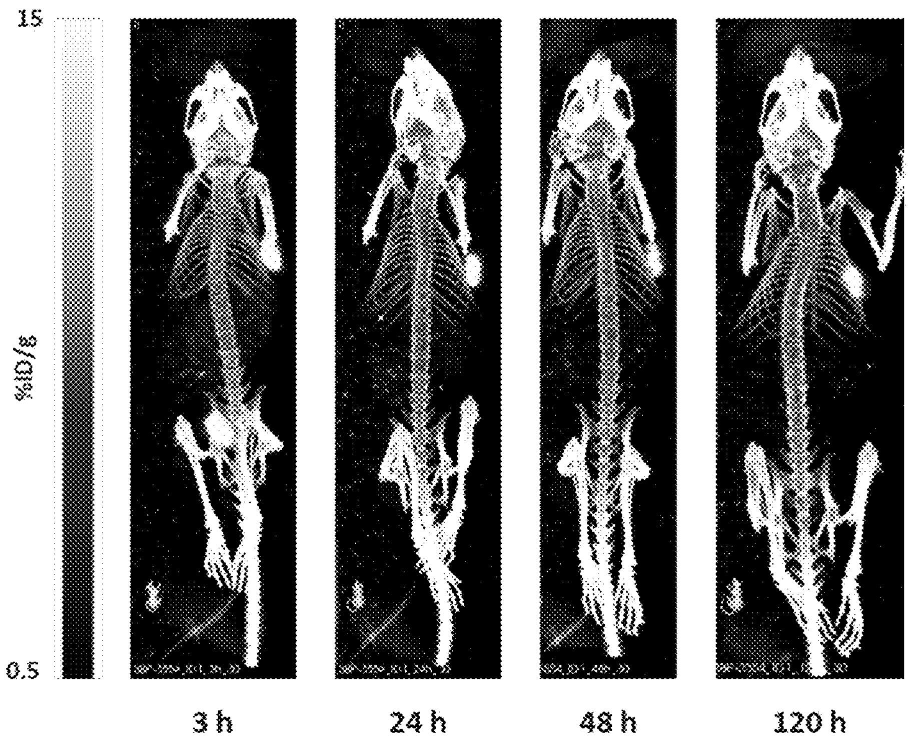
FIG. 10 B shows representative SPECT/CT images over time of the biodistribution of 30 MBq $^{177}$Lu-3BP-3554 in mice with HEK-FAP tumors.

SPECT/CT imaging of 3 animals of both $^{177}$Lu-labeled treatment groups showed high tumor-to-background contrast during all examined time points (3-120 h post-injection (p.i.)). High tumor retention up to 120 h was observed. The organ with the highest non-target uptake was the kidney, with tumor-to-kidney ratios of 8.6±0.6 and 8.0±1.6 at 3 h p.i. in mice treated with 30 or 60 MBq $^{177}$Lu-3BP-3554, respectively. These ratios increased over time, attaining the highest value at 120 h with 40±7.9 and 32±7.4 tumor-to-kidney ratios in mice treated with 30 or 60 MBq $^{177}$Lu-3BP-3554, respectively. An exemplary panel of SPECT/CT images for mouse 5 which is a high-dose animal is shown in FIG. 10A and for mouse 1 which is a low-dose animal is shown in FIG. 10 B.

Example 14: Imaging Study—Sarcoma PDX Models

Sarcoma tumors have been reported to express FAP, and imaging of four different sarcoma patient-derived xenograft (PDX) tumor models was performed to evaluate 3BP-3554 uptake. The Sarc4183, Sarc4605, Sarc4809 and Sarc12616 PDX models were derived from patients with rhabdomyosarcoma, osteosarcoma, undifferentiated sarcoma and undifferentiated pleiomorphic sarcoma, respectively (Experimental Pharmacology & Oncology Berlin-Buch, Germany). Tumor fragments were transplanted subcutaneously in the left flank of 8-week-old NMRI nu/nu mice (Janvier Labs, France). All animal experiments were conducted in compliance with the German animal protection laws. 47 days (Sarc4183, Sarc4809) or 46 days (Sarc4605, Sarc12616) after transplantation, 2-3 mice per model were imaged 3 hours after a single intravenous injection of 30 MBq of $^{111}$In-3BP-3554. Imaging was performed as described in Example 12.

Figure 11A:
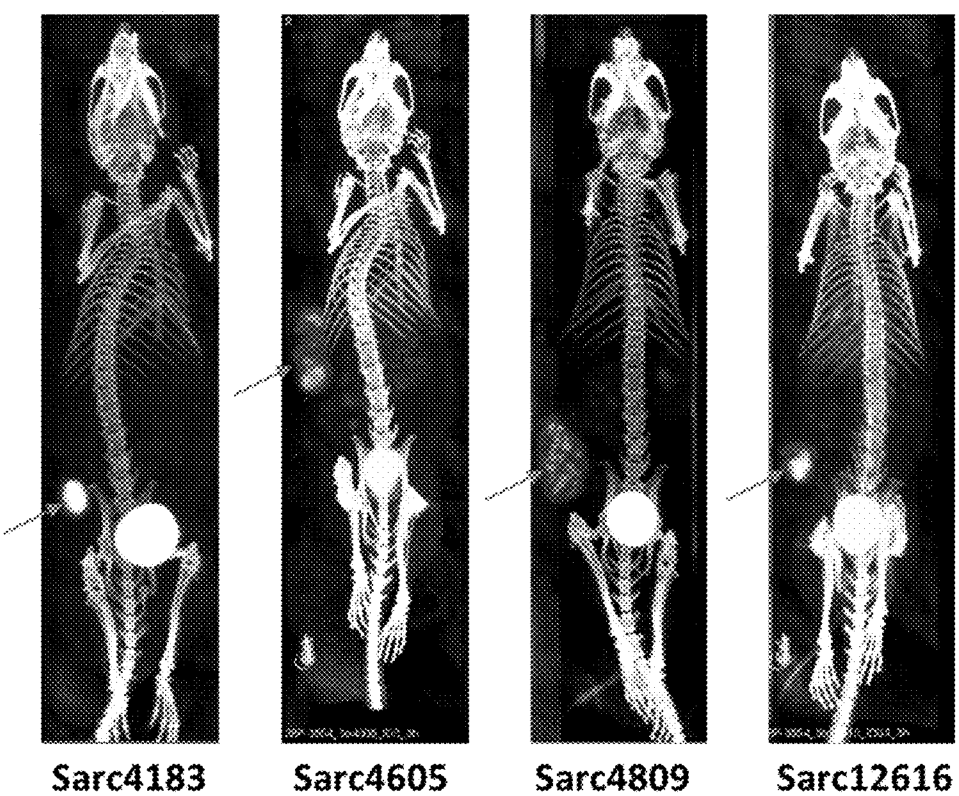
FIG. 11 A shows representative SPECT/CT images of four different sarcoma PDX models 3 h after $^{111}$In-3BP-3554 administration.
Figure 11B:
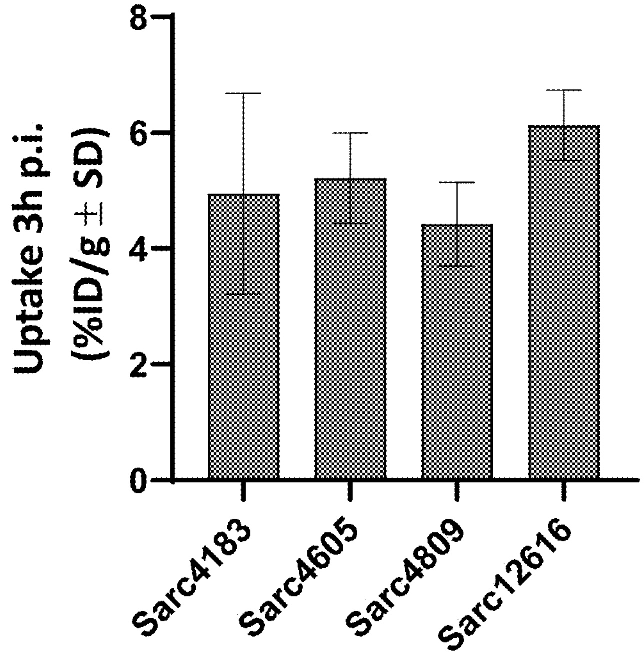

The imaging results with $^{111}$In-3BP-3554 showed high tumor uptake 3 h p.i. and a high tumor-to-background contrast. Representative SPECT/CT images are shown in FIG. 11 A. Quantification of tumor uptake of two (Sarc4605, Sarc12616) or three (Sarc4183, Sarc4809) PDX-bearing mice, respectively, revealed % ID/g values of 4.9±1.7 (Sarc4183), 5.2±0.8 (Sarc4605), 4.4±0.7 (Sarc4809) and 6.1±0.6 (Sarc 12616) as shown in FIG. 11 B. These results demonstrate $^{111}$In-3BP-3554 uptake in all 4 sarcoma models. Tumor-to-kidney ratios were 4.7±1.2 (Sarc4183), 3.2±0.4 (Sarc4605) 4.1±0.7 (Sarc4809) and 4.3±1.2 (Sarc12616).

Example 15: Efficacy Study-Sarcoma Sarc4809 PDX Model

The efficacy of $^{177}$Lu-3BP-3554 was investigated in the human sarcoma PDX tumor model Sarc4809. This model of an undifferentiated sarcoma demonstrates $^{111}$In-3BP-3554 uptake (Example 14) and was also shown to express FAP by immunohistochemistry.

All animal experiments were conducted in compliance with the German animal protection laws. Sarc4809 tumor fragments were transplanted subcutaneously at the left flank of 8-week-old NMRI nu/nu mice (Janvier Labs, France) Treatment started 23 days after transplantation at a mean tumor volume of 187.08±123.8 mm$^3$. Mice were split into four groups of 10 animals/group: Group 1—vehicle control, Group 2—cold compound $^{nat}$Lu-FAP-3554, Group 3-30 MBq $^{177}$Lu-3BP-3554, Group 4-60 MBq $^{177}$Lu-FAP-3554. Treatments were administered on Day 0 by intravenous injection into the tail vein at 4 mL/kg (100 μL/mouse). Tumor volume and body weight were determined at Day 0 (i.e. the first day of radiotracer administration) and then thrice weekly until completion of the study.

Figure 12A:
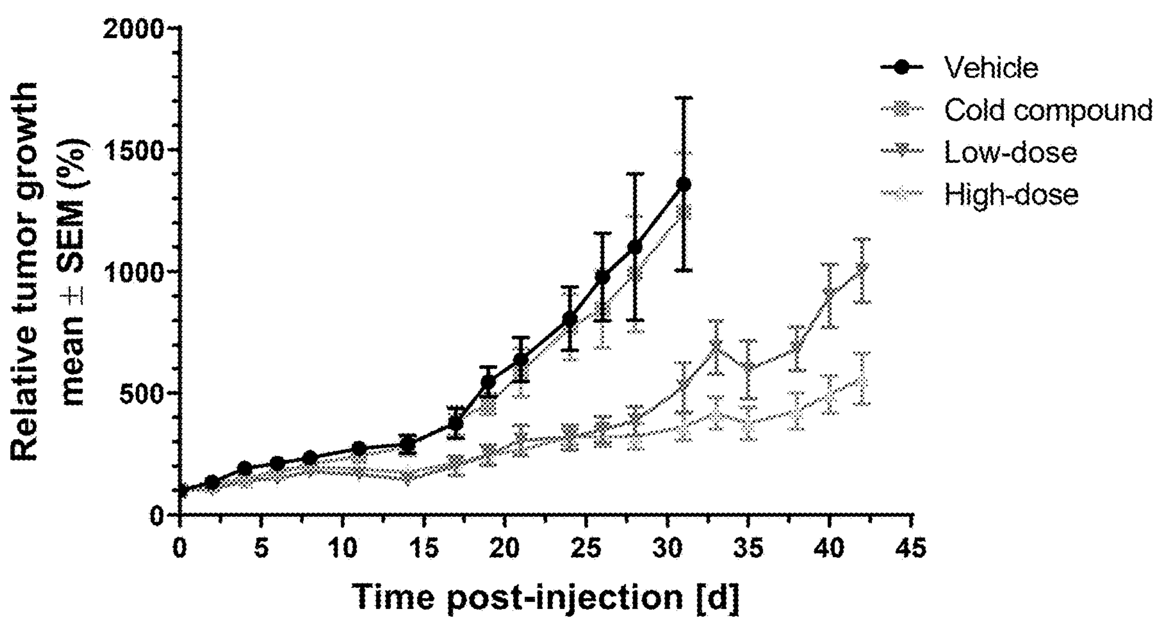
FIG. 12 A shows tumor growth over time in mice with sarcoma Sarc4809 PDX tumors treated with vehicle, cold compound $^{nat}$Lu-3BP-3554, 30 MBq $^{177}$Lu-3BP-3554, or 60 MBq $^{177}$Lu-3BP-3554.
Figure 12B:
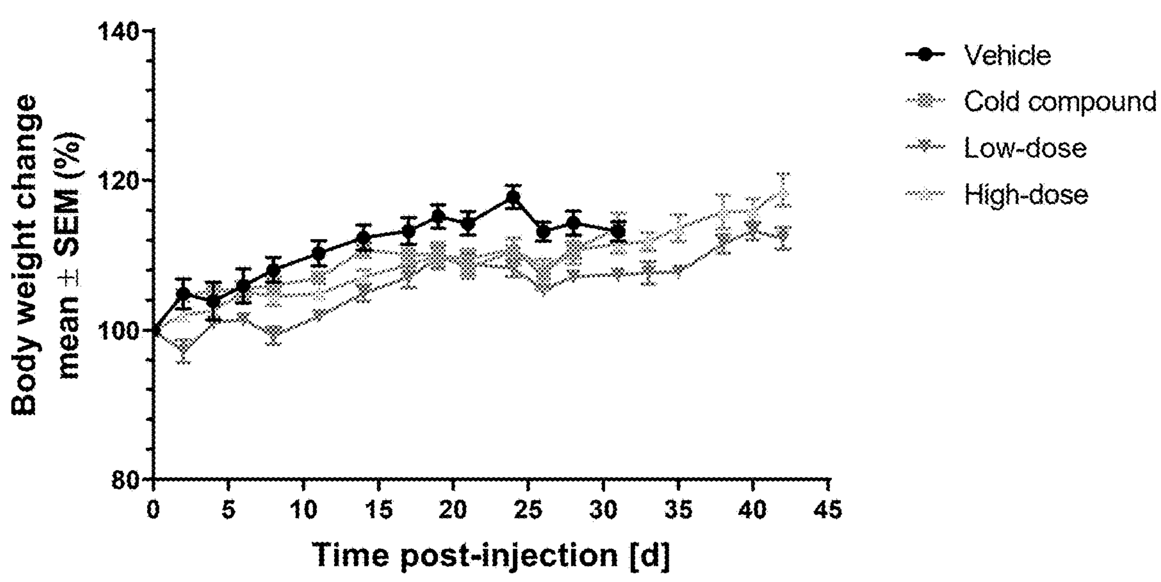

All tumors continuously grew throughout the follow-up period of the study until day 42. Tumors in vehicle and $^{nat}$Lu-3BP-3554 treated mice (control groups) reached an MTV of 894±610 mm$^3$ and 1225±775 mm$^3$ on day 31 (the last day on which at least 50% mice per group were still alive), respectively. Tumors in mice treated with a single dose of 30 or 60 MBq $^{177}$Lu-3BP-3554 reached an MTV of 635±462 and 723±391 mm$^3$ on day 31, respectively (FIG. 12A). Statistically significant (P<0.05) anti-tumor activity was observed in mice of both treatment groups. Tumor growth inhibition (TGI) at day 31 was 61% and 73% in mice treated with a single dose of 30 or 60 MBq $^{177}$Lu-3BP-3554, respectively, relative to the vehicle-treated group. No treatment-related body weight loss (BWL) was observed throughout the study. In all groups body weight increased during study follow-up (FIG. 12B)

Example 16: Pharmacokinetic Studies

The pharmacokinetic behavior of selected compounds was assessed in mice and rats. This characterization of the pharmacokinetic behavior of a compound enables new insights into distribution and elimination of the compound and the calculation of the exposure.

Different amounts of the compounds were stable formulated in PBS. The formulations were applied intravenous with a dose of 4 nmol/kg, 40 nmol/kg and 400 nmol/kg in mice and 2 nmo/kg, 20 nmol/kg and 200 nmol/kg (3BP-3554) or 40 nmol/kg and 400 mol/kg (3BP-3623) in rats. Assuming an allometric translation factor of 12.3 from human to mouse, and 6.2 from human to rats (Nair A B, Jacob S. Journal of Basic and Clinical Pharmacy, 2016, 7 (2): 27-31), the applied doses represent a human dose range of 0.325 nmol/kg to 32.5 nmol/kg.

Blood samples were collected after different times (5 min, 15 min, 30 min, 1 h, 2 h, 4 h, 6 h, 8 h) from tail vein (rats) or retrobulbar (mice).

After separation of the blood cells from the blood plasma by centrifugation, the compounds were quantified in the prepared plasma samples were subjected to a protein precipitation procedure. 150 μl of a zinc sulphate precipitation agent containing 78% 0.1 M zinc sulphate and 22% acetonitrile was added. After incubation at room temperature for 30 min the precipitate was separated by centrifugation. To 100 μl of the supernatant 10 μl of 1% formic acid was added followed by further incubation at 60° C. for 10 min to complete the formation of the zinc chelate, if the compound contains a free DOTA moiety.

The determination of the analyte in the clean sample solutions was performed on an Agilent 1290 UHPLC system coupled to an Agilent 6470 triple quadrupole mass spectrometer. The chromatographic separation was carried out on a Phenomenex BioZen Peptide XB-C18 HPLC column (50×2 mm, 1.7 μm particle size) at 40° C. with gradient elution using a mixture of 0.1% formic acid in water as eluent A and acetonitrile as eluent B (isocratic at 5% B for 1 min followed by a linear gradient to 43% B in 4 min, 500 μl/min).

Mass spectrometric detection was performed in positive ion ESI mode by multiple reaction monitoring (MRM).

TABLE 17

Mass spectrometric detection parameters

| Compound | Fragmentor | | Precursor | Product | Collision energy |
|---|---|---|---|---|---|
| 3BP-4343 | 190 V | Quantifier | 767.0 | 683.2 | 24 V |
| | | Qualifier | 767.0 | 542.9 | 38 V |
| 3BP-3623 | 110 V | Quantifier | 791.8 | 777.6 | 21 V |
| | | Qualifier | 791.8 | 708.2 | 19 V |

Quantitation of test items was accomplished using the Quantitative Analysis software of the Agilent MassHunter software suite. A quadratic regression was performed with a weighting factor of 1/x.

The plasma level were subjected to a non-compartmental analysis (NCA) with following results: initial concentration of the compound ($C_0$), volume of distribution at steady state ($V_{ss}$), volume of distribution in the terminal phase ($V_z$), terminal half-life ($t_{1/2}$), clearance (CL) and area under the curve extrapolated to infinity ($AUC_{inf}$). A summary of NCA parameters of 3BP-3554 are presented in Table 18 for 3BP-3554 in mouse plasma and in Table 19 for 3BP-3554 in rat plasma, and of NCA parameters of 3BP-3623 in Table 20 for 3BP-3623 in mouse plasma and in Table 21 for 3BP-3623 in rat plasma.

TABLE 18

Summary of NCA parameters of 3BP-3554 in mouse plasma

| PK parameter | 4 nmol/kg | 40 nmol/kg | 400 nmol/kg |
|---|---|---|---|
| $C_0$ | 25.6 nM | 177 nM | 4970 nM |
| $V_{ss}$ | 0.21 L/kg | 0.32 L/kg | 0.10 L/kg |
| $V_z$ | 0.26 L/kg | 1.02 L/kg | 0.21 L/kg |
| $AUC_{inf}$ | 8.3 nM h | 56 nM h | 961 nM h |
| $t_{1/2}$ | 23 min | 59 min | 40 min |
| CL | 0.482 L/kg h | 0.711 L/kg h | 0.482 L/kg h |

TABLE 19

Summary of NCA parameters of 3BP-3554 in rat plasma

| PK parameter | 2 nmol/kg | 20 nmol/kg | 200 nmol/kg |
|---|---|---|---|
| $C_0$ | 10.3 nM | 111 nM | 1480 nM |
| $V_{ss}$ | 0.28 L/kg | 0.30 L/kg | 0.17 L/kg |
| $V_z$ | 0.32 L/kg | 0.35 L/kg | 0.42 L/kg |
| $AUC_{inf}$ | 8.1 nMh | 69 nM h | 726 nM h |
| $t_{1/2}$ | 54 min | 50 min | 63 min |
| CL | 0.248 L/kg h | 0.291 L/kg h | 0.275 L/kg h |

TABLE 20

Summary of NCA parameters of 3BP-3623 in mouse plasma

| PK parameter | 4 nmol/kg | 40 nmol/kg | 400 nmol/kg |
|---|---|---|---|
| $C_0$ | 17.6 nM | 228 nM | 2134 nM |
| $V_{ss}$ | 0.36 L/kg | 0.31 L/kg | 0.20 L/kg |
| $V_z$ | 0.44 L/kg | 0.53 L/kg | 0.64 L/kg |
| $AUC_{inf}$ | 7.7 nM h | 55 nM h | 532 nM h |
| $t_{1/2}$ | 35 min | 30 min | 35 min |
| CL | 0.518 L/kg h | 0.722 L/kg h | 0.752 L/kg h |

TABLE 21

Summary of NCA parameters of 3BP-3623 in rat plasma

| PK parameter | 40 nmol/kg | 400 nmol/kg |
|---|---|---|
| $C_0$ | 127 nM | 1408 nM |
| $V_{ss}$ | 0.48 L/kg | 0.32 L/kg |
| $V_z$ | 0.58 L/kg | 0.93 L/kg |
| $AUC_{inf}$ | 74 nM h | 738 nM h |
| $t_{1/2}$ | 45 min | 71 min |
| CL | 0.541 L/kg h | 0.542 L/kg h |

The results indicate distribution mainly in the blood and interstitial fluids and a clearance typical for peptides with terminal half-lifes between 23 min and 59 min in mice and between 45 min and 71 min in rats. Exposure as described by the AUC correlates almost linear to the injected dose and the clearance is constant for all applied doses in a particular animal model. These observations suggest no significant non-linearity of the pharmacokinetic behavior that need to be considered for first-in-human dose calculation.

The features of the present invention disclosed in the specification, the claims, the sequence listing and/or the drawings may both separately and in any combination thereof be material for realizing the invention in various forms thereof.

REFERENCES

The disclosure of each and any document recited herein is incorporated by reference.

What is claimed is:

1. A compound, which is:

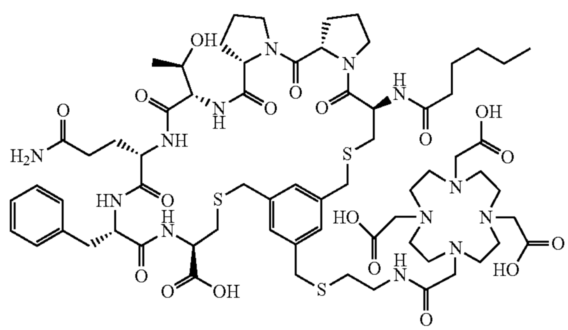 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(=O)O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

or a pharmaceutically acceptable salt thereof, or a solvate thereof, wherein $^{68}$Ga is complexed to 1,4,7,10-tetraazacyclododecane-1,4,7,10-tetraacetic acid (DOTA) chelator of the compound.

2. The compound of claim 1, wherein the solvate is a hydrate.

3. A compound:

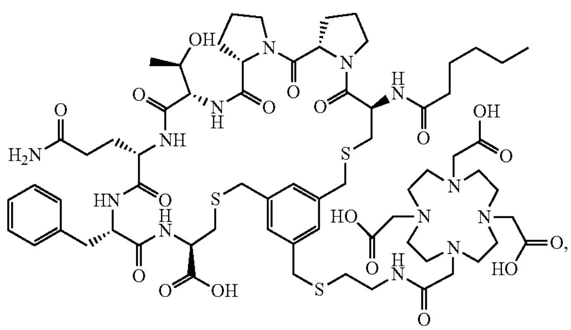 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(=O)O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

wherein $^{68}$Ga is complexed to 1,4,7,10-tetraazacyclododecane-1,4,7,10-tetraacetic acid (DOTA) chelator of the compound.

4. A composition comprising the compound of claim 1 and a pharmaceutically acceptable excipient.

5. A composition comprising the compound of claim 3 and a pharmaceutically acceptable excipient.

6. A method of preparing the compound of claim 1, comprising radiolabeling

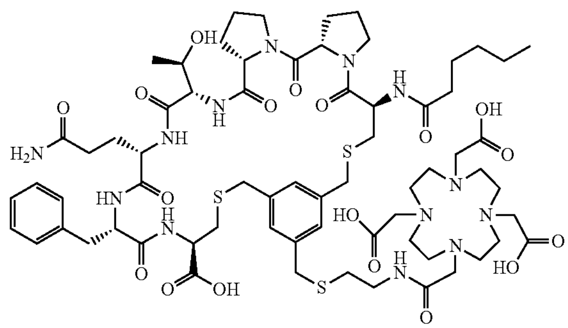 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(=O)O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

or the pharmaceutically acceptable salt thereof, or the solvate thereof, with $^{68}$Ga.

7. A method of preparing the compound of claim 3, comprising radiolabeling

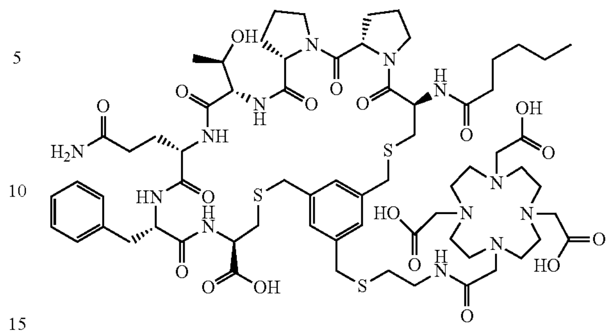

with $^{68}$Ga.

8. A method of diagnosing a cancer in a patient in need thereof, comprising administering to the patient in need thereof a diagnostically effective amount of the compound of claim 1.

9. The method of claim 8, further comprising imaging the patient.

10. The method of claim 9, wherein the imaging is performed using Positron Emission Tomography (PET) or a combination of PET with CT (PET/CT).

11. A method of diagnosing a tumor in a patient in need thereof, comprising administering to the patient in need thereof a diagnostically effective amount of the compound of claim 1.

12. The method of claim 11, further comprising imaging the patient.

13. The method of claim 12, wherein the imaging is performed using Positron Emission Tomography (PET) or a combination of PET with CT (PET/CT).

14. A method of diagnosing a disease in a patient in need thereof, comprising administering to the patient in need thereof a diagnostically effective amount of the compound of claim 1, wherein the disease is selected from the group consisting of bladder cancer, breast cancer, cervical cancer, colorectal cancer, cholangiocarcinoma, endometrial cancer, esophageal cancer, gastric cancer, gastrointestinal stromal tumors, head and neck cancer, liver cancer, lung cancer, melanoma, mesothelioma, neuroendocrine tumors and carcinomas, ovarian cancer, pancreatic cancer, prostate cancer, renal cell carcinoma, salivary carcinoma, sarcoma, squamous cell carcinoma, and thyroid cancer.

15. A method of diagnosing a cancer in a patient in need thereof, comprising administering to the patient in need thereof a diagnostically effective amount of the compound of claim 3.

16. The method of claim 15, further comprising imaging the patient.

17. The method of claim 16, wherein the imaging is performed using Positron Emission Tomography (PET) or a combination of PET with CT (PET/CT).

18. A method of diagnosing a tumor in a patient in need thereof, comprising administering to the patient in need thereof a diagnostically effective amount of the compound of claim 3.

19. The method of claim 18, further comprising imaging the patient.

20. The method of claim 19, wherein the imaging is performed using Positron Emission Tomography (PET) or a combination of PET with CT (PET/CT).

21. The method of claim 18, wherein the tumor is a solid tumor.

22. The method of claim 18, wherein the tumor is an epithelial tumor.

23. A method of diagnosing a disease in a patient in need thereof, comprising administering to the patient in need thereof a diagnostically effective amount of a compound:

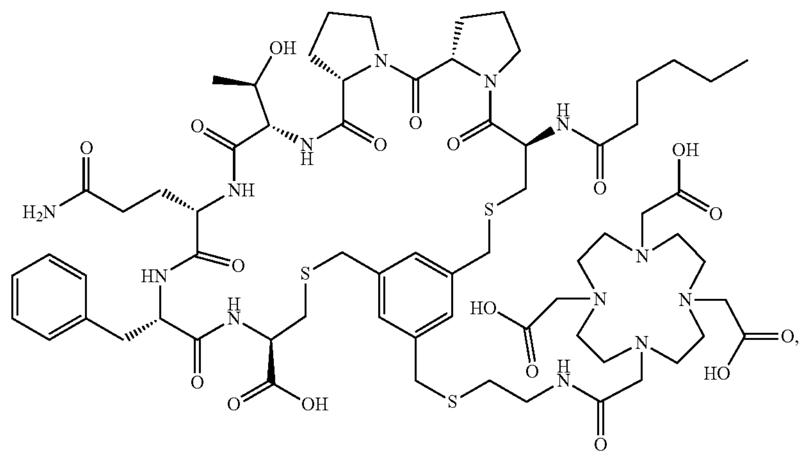

wherein $^{68}Ga$ is complexed to 1,4,7,10-tetraazacyclododecane-1,4,7,10-tetraacetic acid (DOTA) chelator of the compound, and wherein the disease is breast cancer, non-small cell lung cancer, pancreatic cancer, or bladder cancer.

24. The method of claim 23, wherein the disease is breast cancer.

25. The method of claim 23, wherein the disease is non-small cell lung cancer.

26. The method of claim 23, wherein the disease is pancreatic cancer.

27. The method of claim 23, wherein the disease is bladder cancer.

28. The method of claim 23, further comprising imaging the patient.

29. The method of claim 28, wherein the imaging is performed using Positron Emission Tomography (PET) or a combination of PET with CT (PET/CT).

30. A kit comprising:

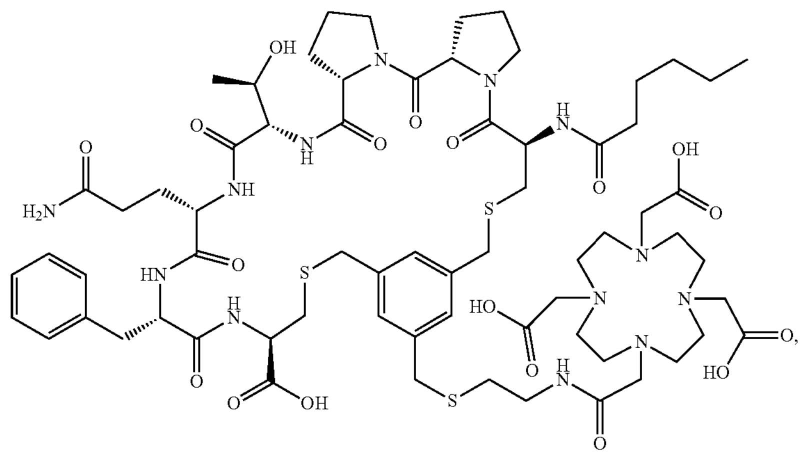 [SMILES: CCCCCC(=O)N[C@H]1CSCc2cc(CSCCNC(=O)CN3CCN(CC(=O)O)CCN(CC(=O)O)CCN(CC(=O)O)CC3)cc(c2)CSC[C@@H](C(=O)O)NC(=O)[C@H](Cc2ccccc2)NC(=O)[C@H](CCC(N)=O)NC(=O)[C@H]([C@@H](C)O)NC(=O)[C@@H]2CCCN2C(=O)[C@@H]2CCCN2C1=O]

or a pharmaceutically acceptable salt thereof; and instructions to label with $^{68}Ga$ for preparation of the compound of claim 1.

* * * * *